United States Patent
Wu et al.

(10) Patent No.: US 10,513,514 B2
(45) Date of Patent: Dec. 24, 2019

(54) PIPERIDINE COMPOUNDS AS PCSK9 INHIBITORS

(71) Applicant: SHENZHEN SALUBRIS PHARM CO LTD, Shenzhen (CN)

(72) Inventors: Chengde Wu, Shanghai (CN); Jie Yan, Shenzhen (CN); Wenjie Xu, Shenzhen (CN); Tao Yu, Shanghai (CN); Ning Li, Shanghai (CN); Shuhui Chen, Shanghai (CN)

(73) Assignee: SHENZHEN SALUBRIS PHARM CO LTD., Shenzhen, Guangdong (CN)

( * ) Notice: Subject to any disclaimer, the term of this patent is extended or adjusted under 35 U.S.C. 154(b) by 0 days.

(21) Appl. No.: 15/958,192

(22) Filed: Apr. 20, 2018

(65) Prior Publication Data
US 2018/0305346 A1    Oct. 25, 2018

(30) Foreign Application Priority Data

Apr. 21, 2017 (CN) .......................... 2017 1 0266732

(51) Int. Cl.
    *C07D 413/12*      (2006.01)
    *C07D 413/14*      (2006.01)
    *A61P 9/00*      (2006.01)
    *C07D 471/04*      (2006.01)
    *C07D 491/048*      (2006.01)

(52) U.S. Cl.
    CPC ......... *C07D 413/14* (2013.01); *C07D 413/12* (2013.01); *C07D 471/04* (2013.01); *C07D 491/048* (2013.01); *A61P 9/00* (2018.01)

(58) Field of Classification Search
    CPC .......................... C07D 413/12; C07D 413/14
    See application file for complete search history.

(56) References Cited

U.S. PATENT DOCUMENTS

| | | |
|---|---|---|
| 9,227,956 B2 | 1/2016 | Darout et al. |
| 2014/0315928 A1 | 10/2014 | Darout et al. |
| 2016/0058768 A1 | 3/2016 | Darout et al. |
| 2016/0102074 A1 | 4/2016 | Darout et al. |

FOREIGN PATENT DOCUMENTS

| | | |
|---|---|---|
| WO | WO 2014/170786 A1 | 10/2014 |
| WO | WO 2016/055901 A1 | 4/2016 |

OTHER PUBLICATIONS

Seidah, Expert Opinion on Therapeutic Targets, 13:1, 19-28. (Year: 2009).*
Chaudhary et al. World J Cardiol Feb. 26, 2017; 9(2): 76-91. (Year: 2017).*
Lintner, N., et al, "Selective stalling of human translation through small-molecule engagement of the ribosome nascent chain," PLoS Biol 15(3): e2001882, Mar. 21, 2017.
Full Prescribing Information (PRALUENT™), Revised Jul. 2015 (47 pages).
Full Prescribing Information (REPATHA™), Revised Aug. 2015 (34 pages).

* cited by examiner

*Primary Examiner* — Emily A Bernhardt
(74) *Attorney, Agent, or Firm* — Leason Ellis LLP

(57) ABSTRACT

One aspect of the invention relates to a series of new PCSK9 inhibitor compounds comprising piperidine ring structures, including compounds of formula (I) and/or pharmaceutically acceptable salts thereof. Another aspect of the invention relates to methods of treating PCSK9 receptor related diseases comprising administration of one or more compounds of formula (I) or a pharmaceutically acceptable salt thereof.

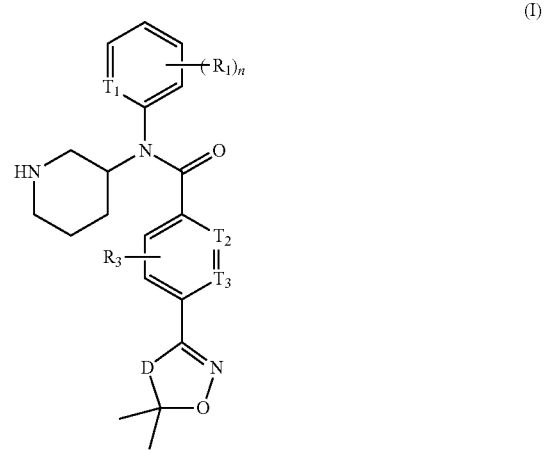

28 Claims, No Drawings

PIPERIDINE COMPOUNDS AS PCSK9 INHIBITORS

PRIORITY

The present application claims priority under 35 U.S.C. § 119 to Chinese Patent Application No. 201710266732.9, filed on Apr. 21, 2017, the entire contents of which are hereby incorporated by reference.

FIELD

The disclosure pertains to a series of new PCSK9 inhibitor compounds comprising piperidine ring structures, including compounds of formula (I), and/or pharmaceutically acceptable salts thereof.

BACKGROUND

Low density lipoprotein cholesterin (LCL-C) level of plasma is closely related to the occurrence of cardiovascular diseases risk, and the low density lipoprotein receptor (LDL-R) expressed on liver cell surface is one key factor deciding the level of LDL-C. The PCSK9 in blood can specifically bind to LDL-R on cell surface to form complex compound which is transferred to lysosome and accelerate the degradation of LDL-R, and increase the level of LDL-C. Numerous basic researches and clinical trial results show that removal of low density lipoprotein (LDL) in plasma can be accelerated after exogenous interventions inhibit the activity of PCSK9 thus to have a good lipid-lowering effect. Therefore, PCSK9 inhibitor will be probably a new generation of drugs for the treatment of dyslipidemia and relevant cardiovascular diseases.

The following chemical compound PF-06446846 and similar chemical compounds are reported in WO2014170786.

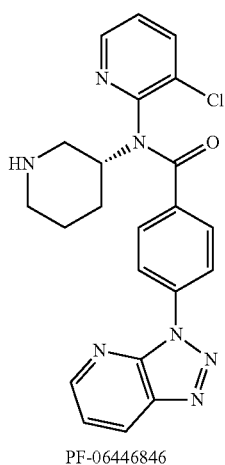 [SMILES: O=C(c1ccc(-n2nnc3cccnc32)cc1)N(c1ncccc1Cl)[C@@H]1CCCNC1]

PF-06446846

DETAILED DESCRIPTION OF THE DISCLOSURE

In some embodiments, the disclosure pertains to compounds of formula (I), and/or pharmaceutically acceptable salts thereof,

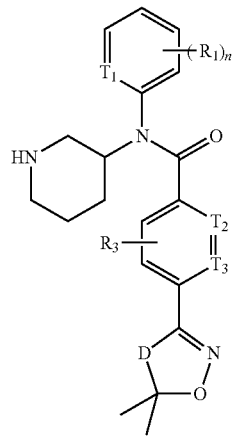

(I)

Wherein,
$T_1$ is chosen from N and CH;
$T_2$ is chosen from CH and N;
$T_3$ is chosen from CH and N;
D is chosen from

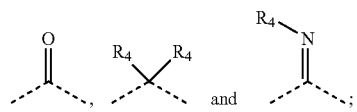

N is chosen from 0, 1, 2 and 3;
Each $R_1$ is independently chosen from halogen, OH and $NH_2$, or chosen from a $C_{1-3}$ alkyl, $C_{1-3}$ heteroalkyl, $C_{3-6}$ cycloalkyl, phenyl, and 5 or 6 membered heteroaryl group, any of which is optionally substituted by one, two or three R groups;
or, two adjacent $R_1$s are connected together to form a 5 or 6 membered ring which is optionally substituted by one, two or three R groups;
$R_3$ is chosen from H, halogen, OH and $NH_2$, or chosen from a $C_{1-3}$ alkyl group that is optionally substituted by one, two or three R groups;
Each $R_4$ is independently chosen from H and OH, or chosen from a $C_{1-3}$ alkyl group and a $C_{1-3}$ alkoxy group, either of which is optionally substituted by one, two or three R groups;
R is chosen from F, Cl, Br, I, OH, $NH_2$, $NH(CH_3)$, $N(CH_3)_2$, Me and

wherein each of said $C_{1-3}$ heteroalkyl and 5 or 6 membered heteroaryl independently comprises 1, 2, or 3 heteroatom groups independently chosen from —NH—, N, —O—, and —S—.

In one embodiment of this disclosure, each above-mentioned $R_1$ is independently chosen from F, Cl, Br, I, OH and $NH_2$, or is chosen from a $C_{1-3}$ alkyl and a $C_{1-3}$ alkoxy group, either of which is optionally substituted by one, two or three R groups.

In one embodiment of this disclosure, each above-mentioned $R_1$ is independently chosen from F, Cl, Br, I, OH and $NH_2$, or is chosen from Me, Et,

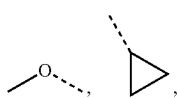

phenyl, and pyridyl groups, any of which is optionally substituted by one, two or three R groups.

In one embodiment of this disclosure, each above-mentioned $R_1$ is independently chosen from F, Cl, Br, I, OH, $NH_2$, Me, Et,

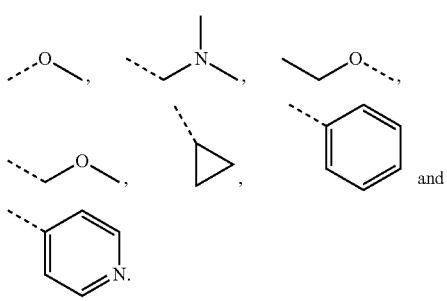

and

In one embodiment of this disclosure, above-mentioned structural unit

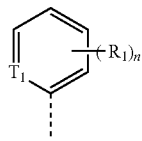

is chosen from

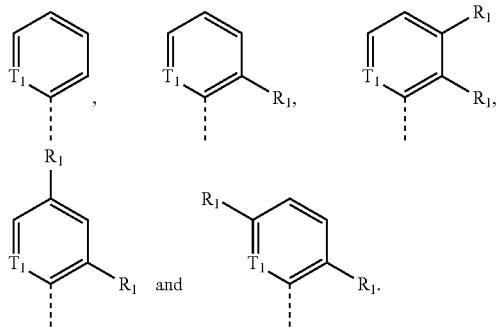

In one embodiment of this disclosure, above-mentioned structural unit

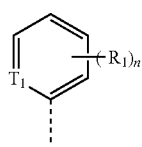

is chosen from

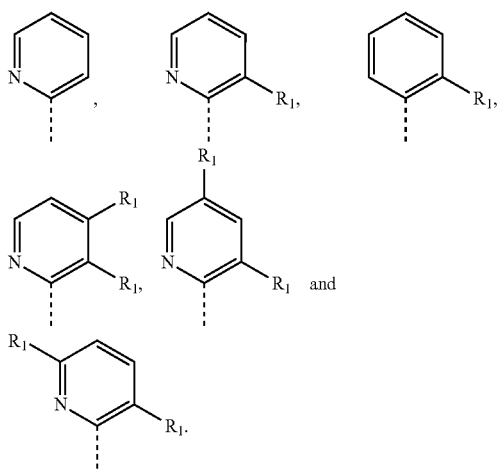

In one embodiment of this disclosure, above-mentioned structural unit

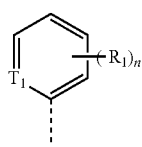

is chosen from

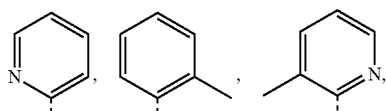

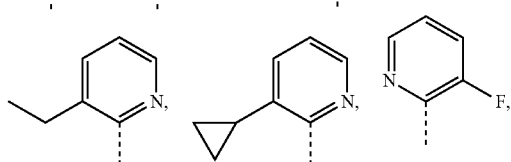

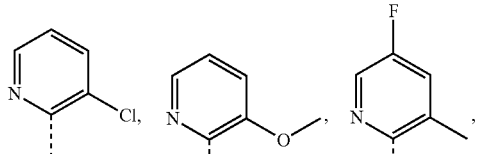

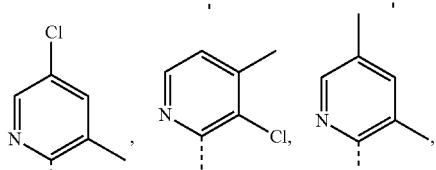

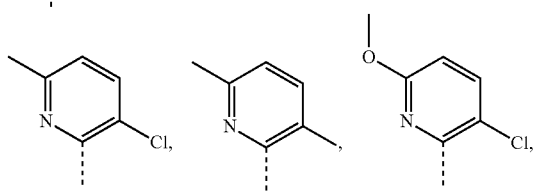

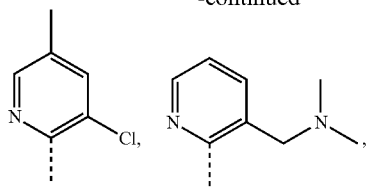 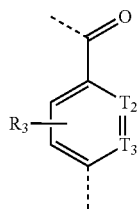

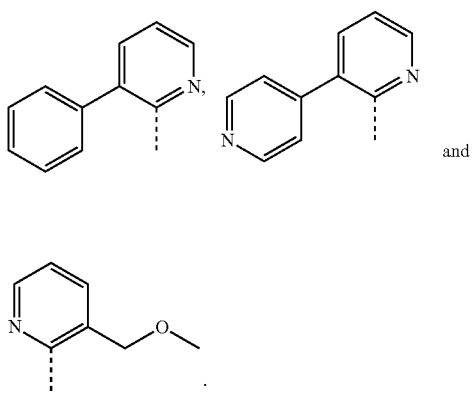

In one embodiment of this disclosure, two above-mentioned adjacent $R_1$ groups are connected together to form a nitrogen-contained 5-membered ring, oxygen-contained 5-membered ring, or a benzene ring, any of which is optionally substituted by one, two, or three R groups.

In one embodiment of this disclosure, above-mentioned structural unit

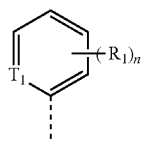

is chosen from

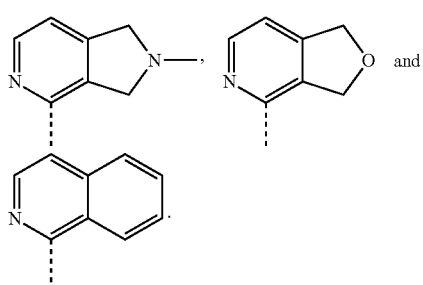

In one embodiment of this disclosure, above-mentioned $R_3$ is chosen from H, F, Cl, Br, I, OH and $NH_2$, or chosen from Me and Et, either of which is optionally substituted by one, two or three R groups.

In one embodiment of this disclosure, above-mentioned $R_3$ is chosen from H, F, Cl, Br, I, OH, $NH_2$, Me and Et.

In one embodiment of this disclosure, above-mentioned structural unit

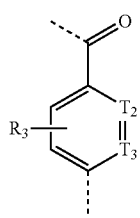

is chosen from

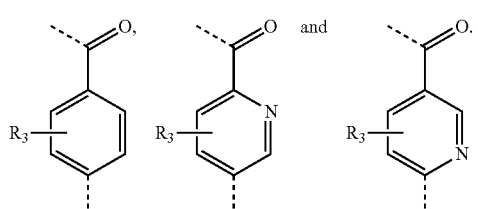

In one embodiment of this disclosure, above-mentioned structural unit is chosen from

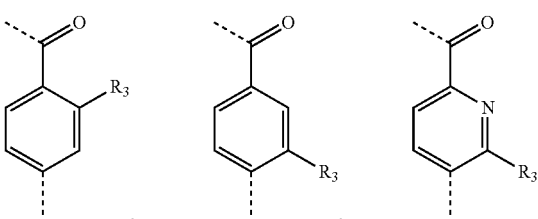

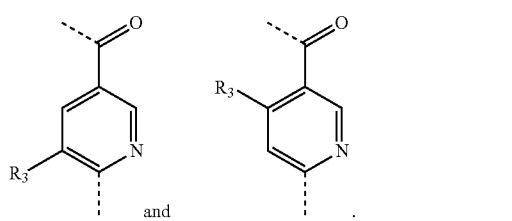

In one embodiment of this disclosure, above-mentioned structural unit

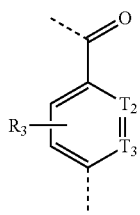

is chosen from

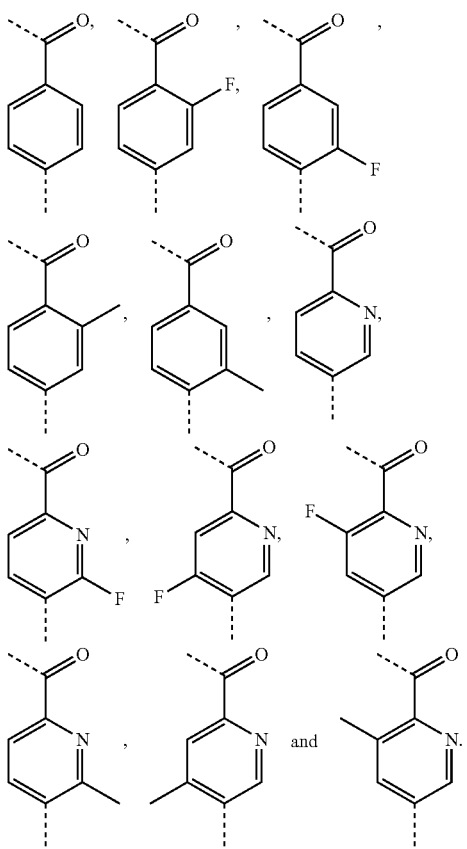

In one embodiment of this disclosure, above-mentioned each $R_4$ is independently chosen from H and OH, or chosen from Me, Et,

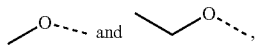

any of which is optionally substituted by one, two or three R groups.

In one embodiment of this disclosure, above-mentioned each $R_4$ is independently chosen from H, OH, Me,

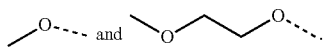

In one embodiment of this disclosure, above-mentioned structural unit

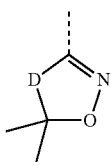

is chosen from

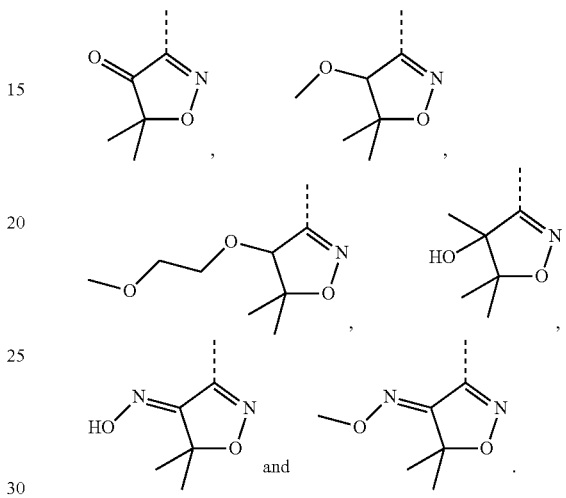

In one embodiment of this disclosure, above-mentioned $R_1$ is chosen from F, Cl, Br, I, OH and $NH_2$, or chosen from a $C_{1-3}$ alkyl group and a $C_{1-3}$ alkoxy group, either of which is optionally substituted by one, two or three R groups, and other variables are defined as above.

In one embodiment of this disclosure, above-mentioned $R_1$ is chosen from F, Cl, Br, I, OH and $NH_2$, or from Me, Et,

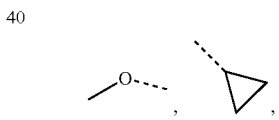

phenyl and pyridyl, any of which is optionally substituted by one, two or three R groups, and other variables are defined as above.

In one embodiment of this disclosure, above-mentioned $R_1$ is chosen from F, Cl, Br, I, OH, $NH_2$, Me, Et,

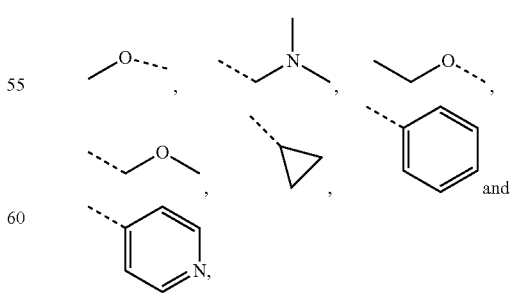

and other variables are defined as above.

In one embodiment of this disclosure, above-mentioned structural unit

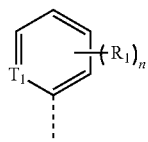

is chosen from

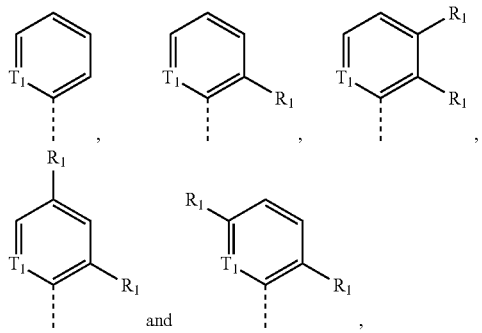

and other variables are defined as above.

In one embodiment of this disclosure, above-mentioned structural unit

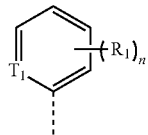

is chosen from

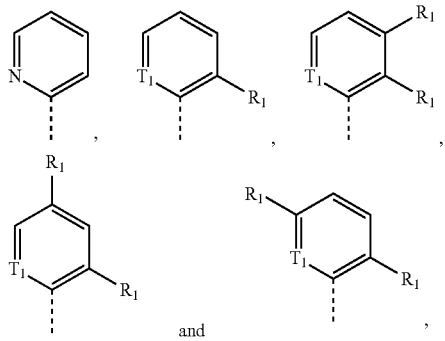

and other variables are defined as above.

In one embodiment of this disclosure, above-mentioned structural unit

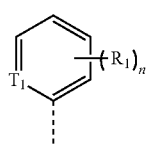

is chosen from

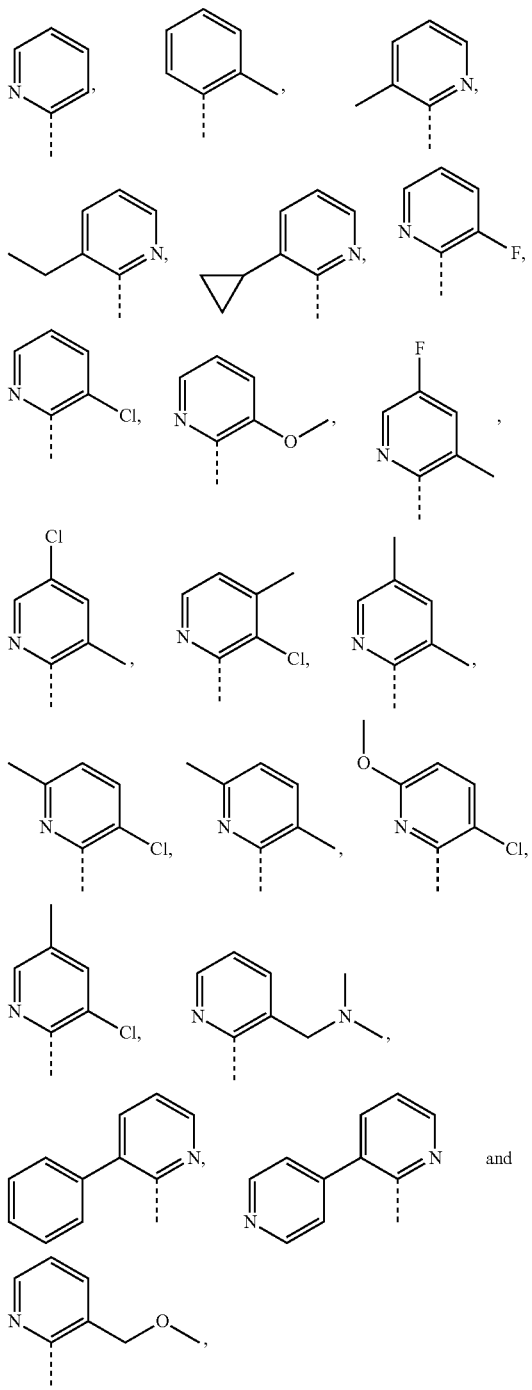

and other variables are defined as above.

In one embodiment of this disclosure, two above-mentioned adjacent $R_1$s are connected together to form a nitrogen-containing 5-membered ring, oxygen-containing 5-membered ring or benzene ring, any of which is optionally substituted by one, two or three R groups, and other variables are defined as above.

In one embodiment of this disclosure, above-mentioned structural unit

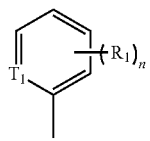

is chosen from

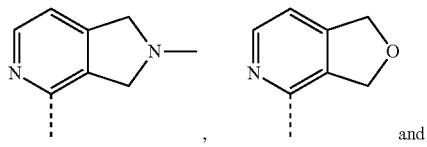

and other variables are defined as above.

In one embodiment of this disclosure, above-mentioned $R_3$ is chosen from H, F, Cl, Br, I, OH and $NH_2$, or chosen from Me and Et, either of which is optionally substituted by one, two or three R groups, and other variables are defined as above.

In one embodiment of this disclosure, above-mentioned $R_3$ is chosen from H, F, Cl, Br, I, OH, $NH_2$, Me and Et, and other variables are defined as above.

In one embodiment of this disclosure, above-mentioned structural unit

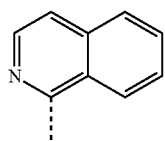

is chosen from

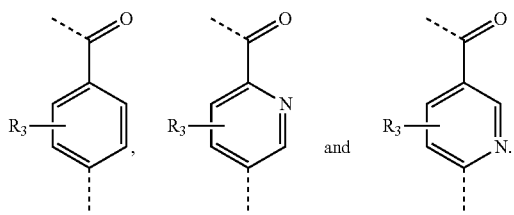

In one embodiment of this disclosure, above-mentioned structural unit

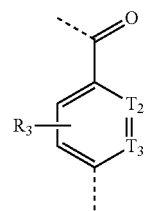

is chosen from

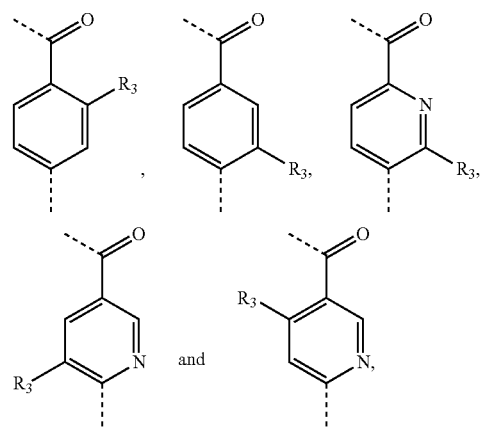

and other variables are defined as above.

In one embodiment of this disclosure, above-mentioned structural unit

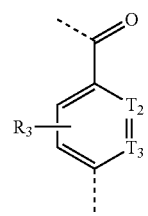

is chosen from

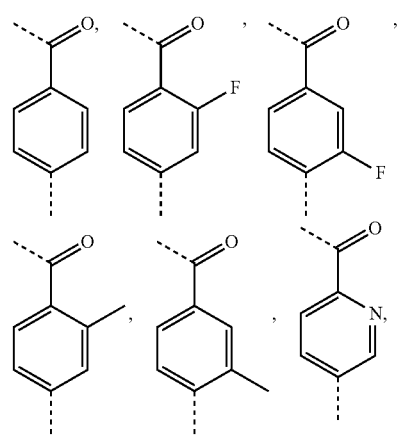

-continued

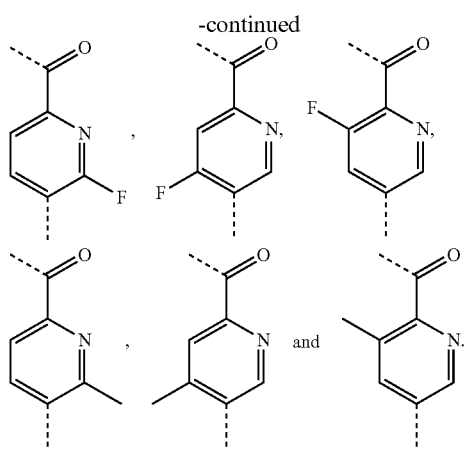

and other variables are defined as above.

In one embodiment of this disclosure, each above-mentioned $R_4$ is independently chosen from H or OH, or from Me, Et,

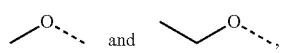

any of which is optionally substituted by one, two or three R groups, and other variables are defined as above.

In one embodiment of this disclosure, each above-mentioned $R_4$ is independently chosen from H, OH, Me,

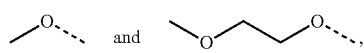

and other variables are defined as above.

In one embodiment of this disclosure, above-mentioned structural unit

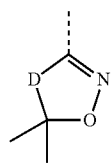

is chosen from

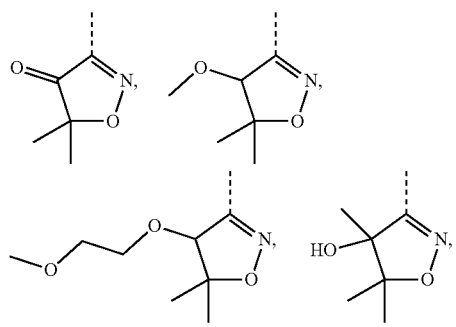

-continued

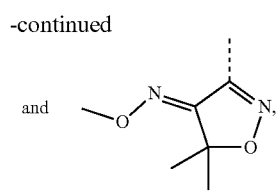

and other variables are defined as above.

In one embodiment of this disclosure, above-mentioned compound or the pharmaceutically acceptable salt is chosen from:

(I-1)

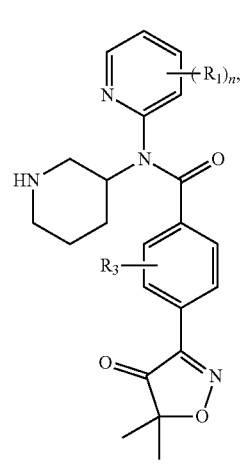

(I-2)

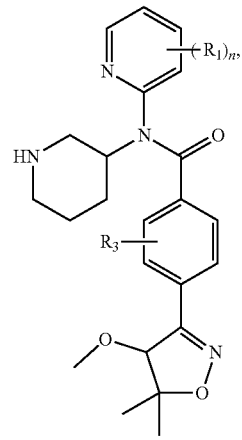

(I-3)

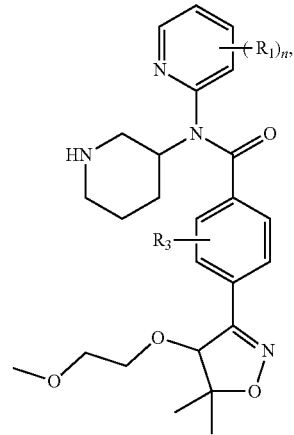

-continued

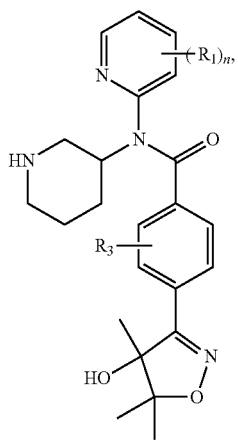
(I-4)

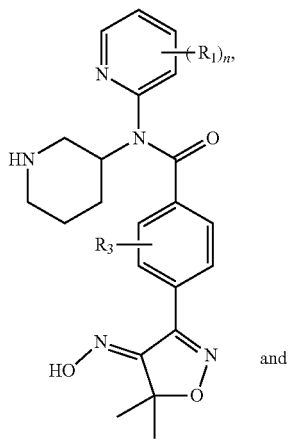
(I-5)

and

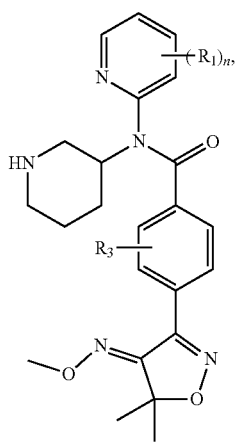
(I-6)

Where, R₁, R₃ and n are defined as above.

Further, in some embodiments, the compound of formula (I) is chosen from the structural formulas (IA) and (IB) below,

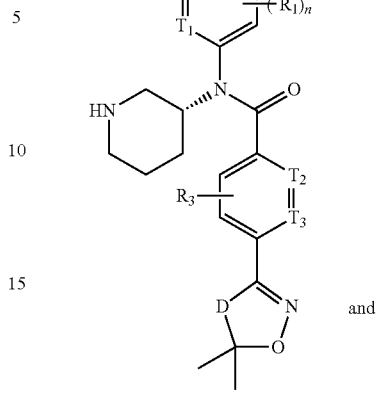
(IA)

and

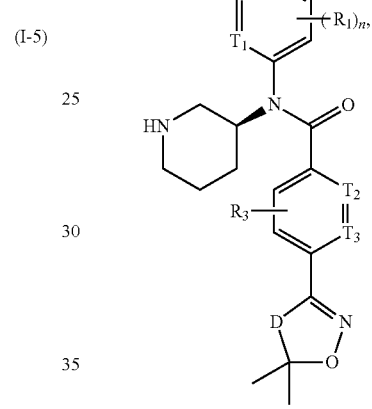
(IB)

comprising substituent groups as defined above.

In some embodiments, compounds and/or pharmaceutically acceptable salts thereof of this disclosure comprise combinations of the above-described variables.

In some embodiments, the compound and/or pharmaceutically acceptable salt thereof of this disclosure is chosen from:

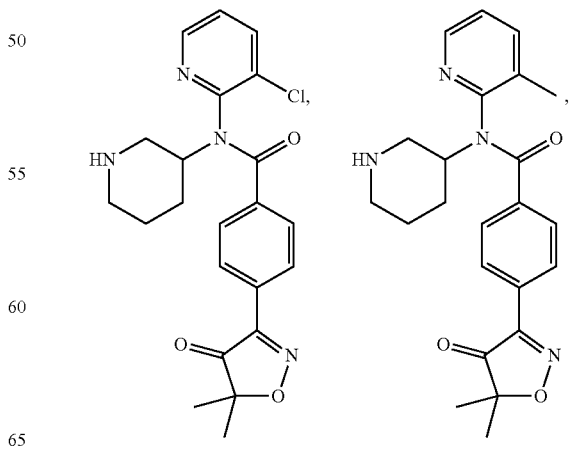

-continued
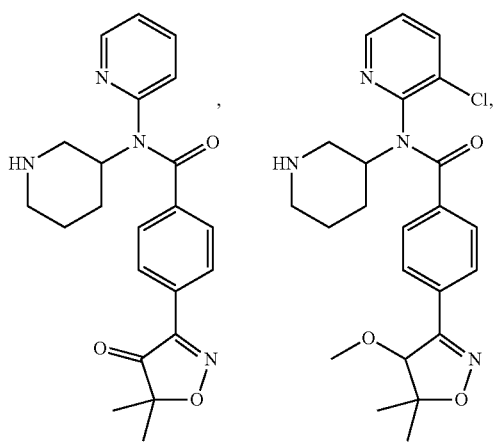
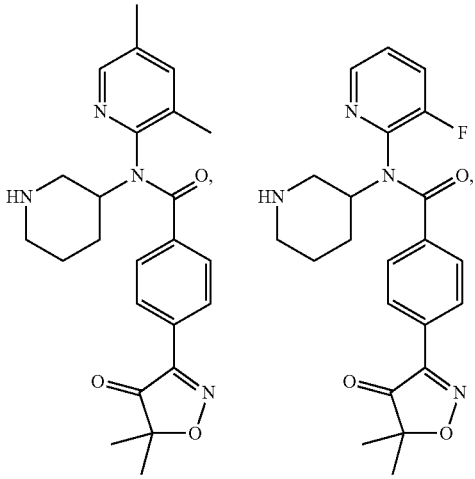
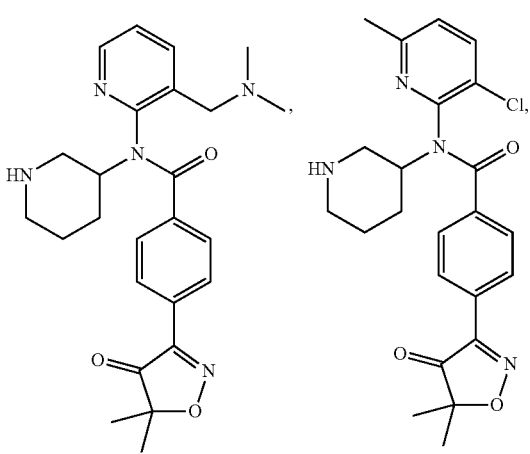

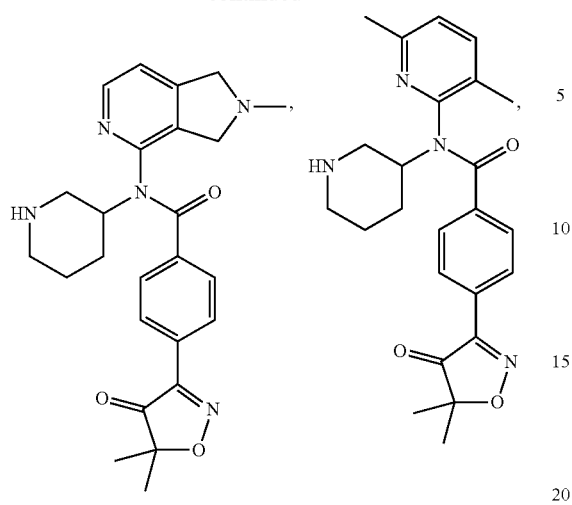
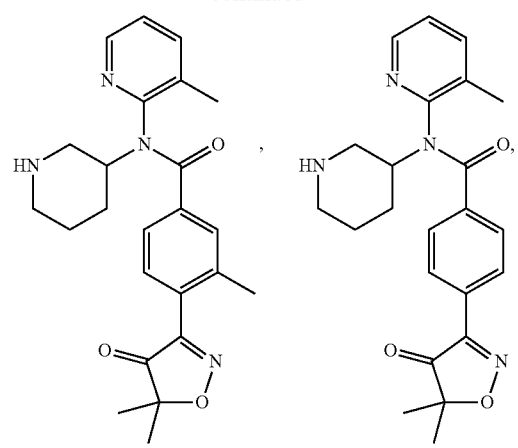
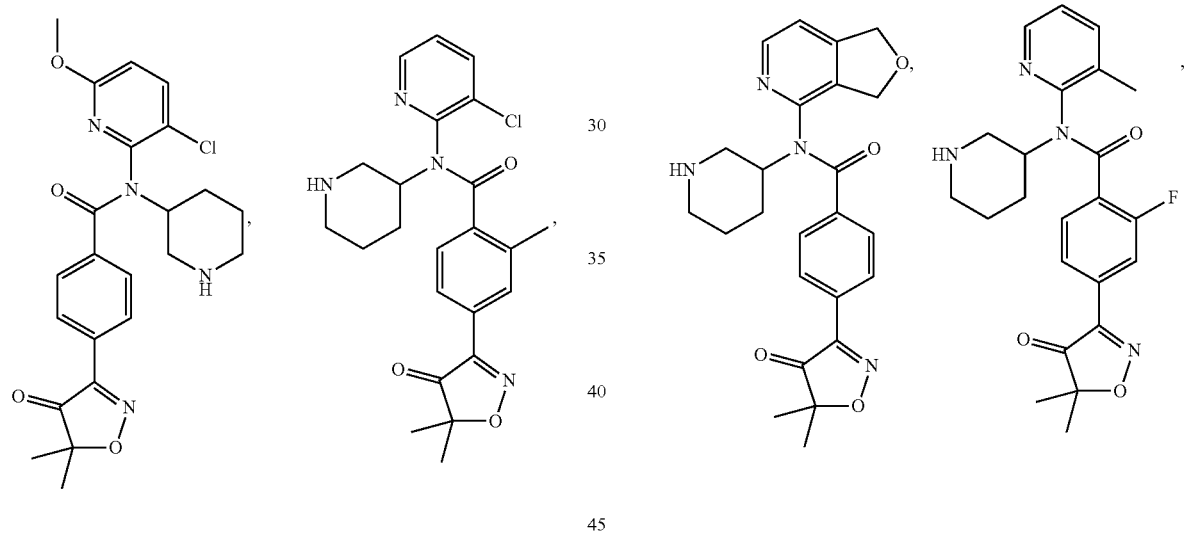
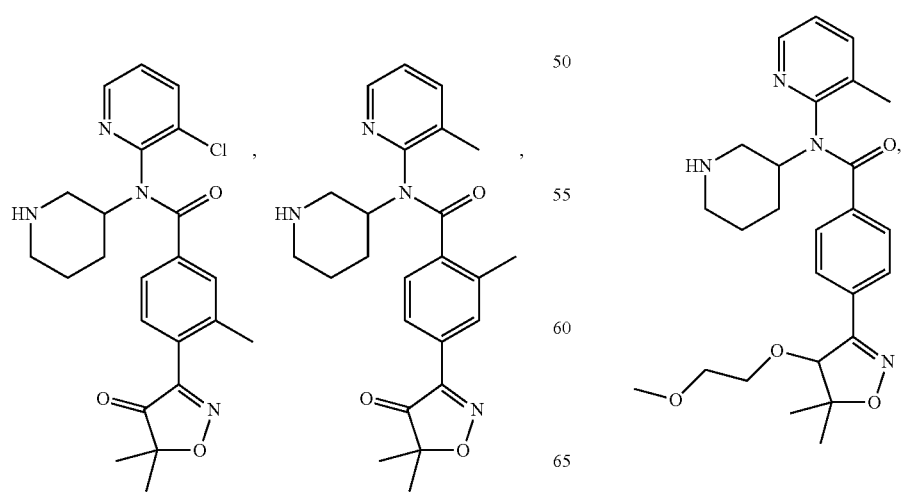

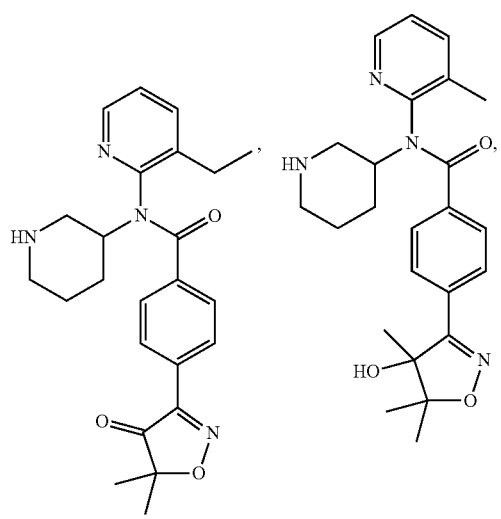
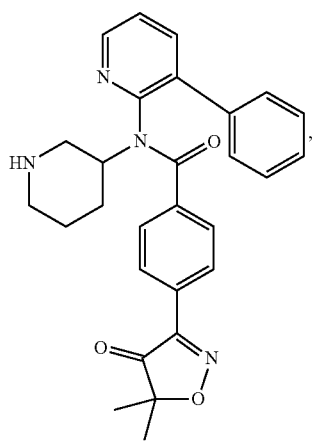

23
-continued
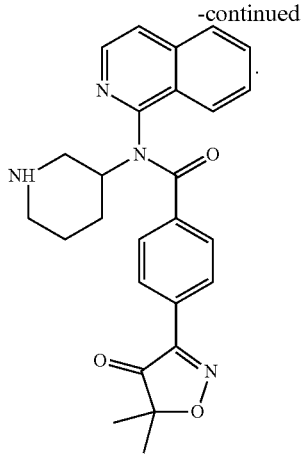
24
-continued
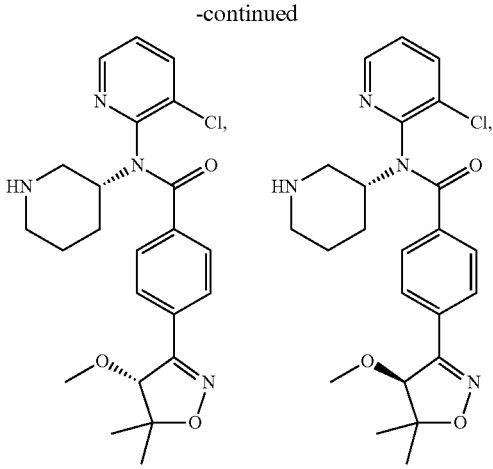
In one embodiment of this disclosure, the above-mentioned compound and/or the pharmaceutically acceptable salt thereof is chosen from:
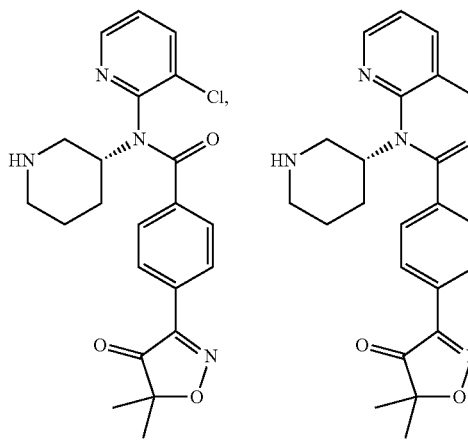
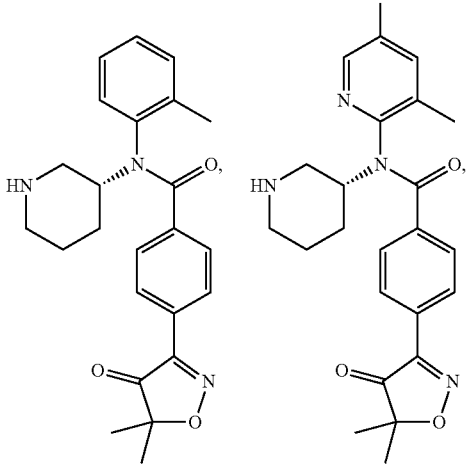
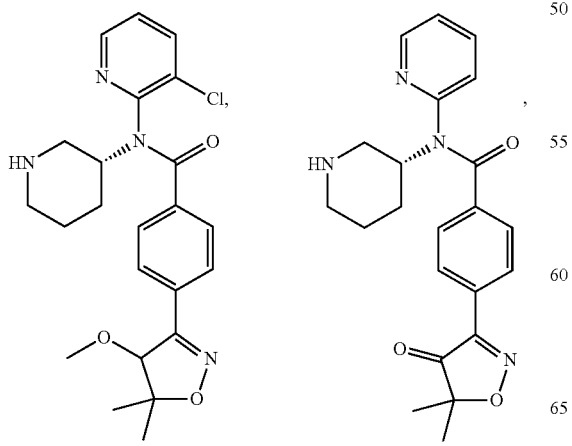
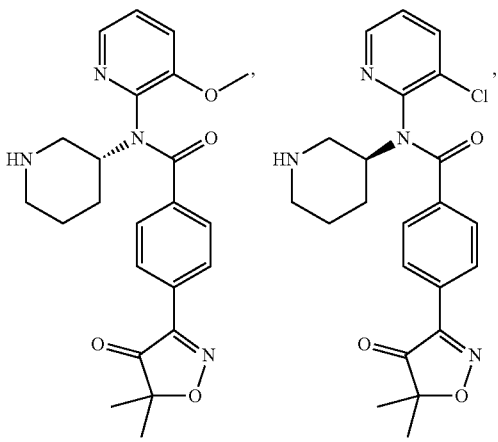

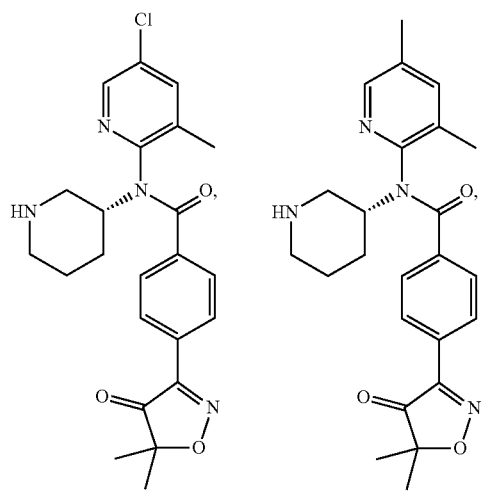
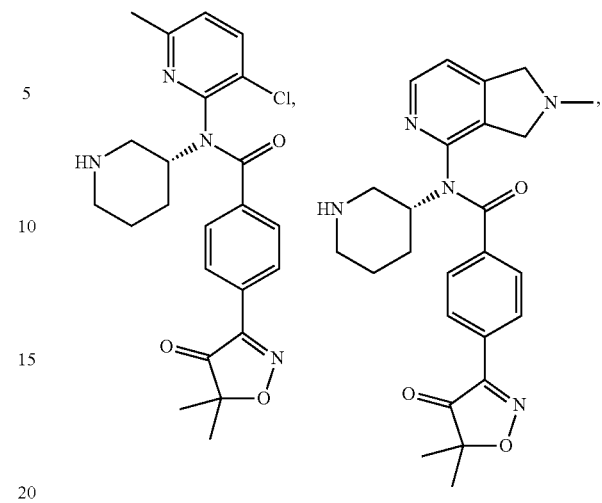
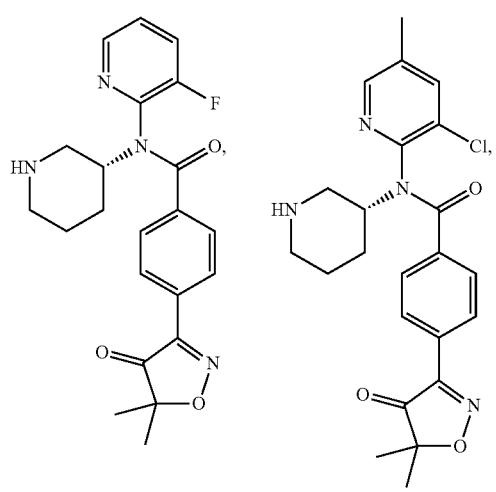
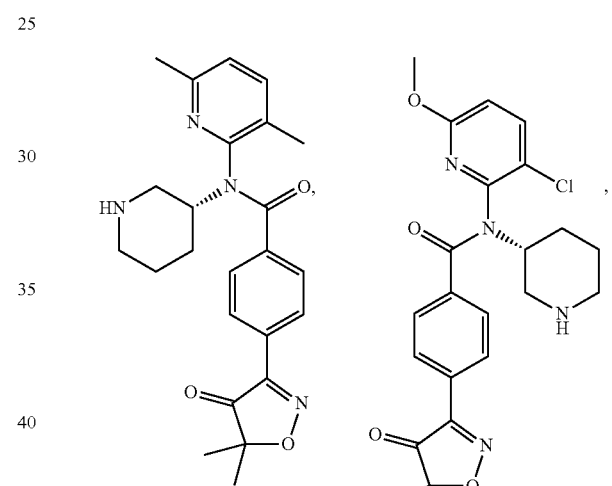
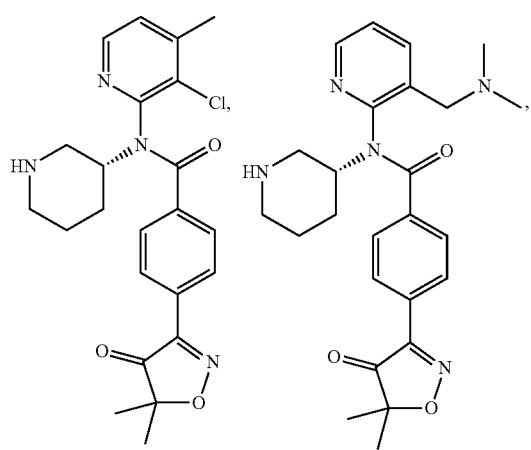
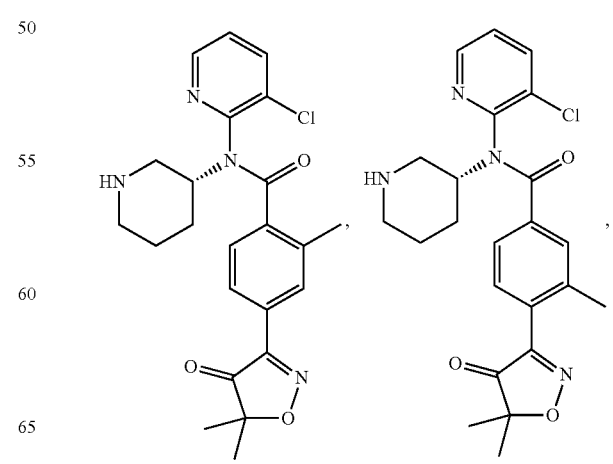

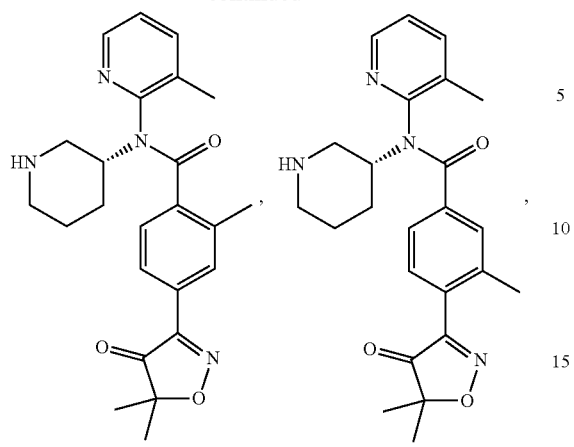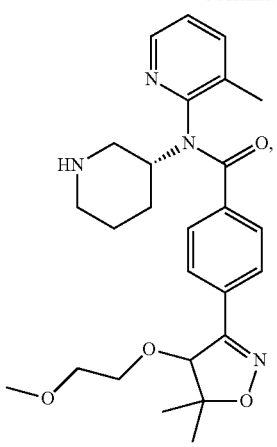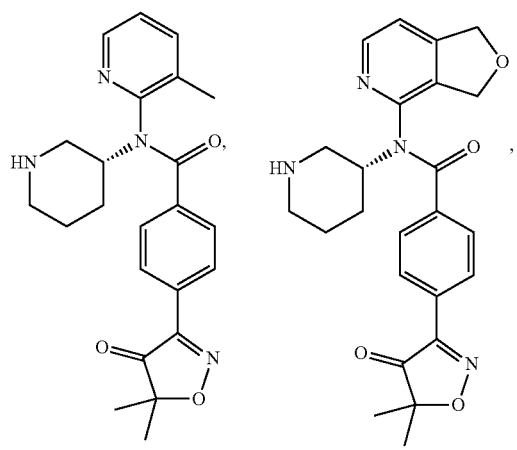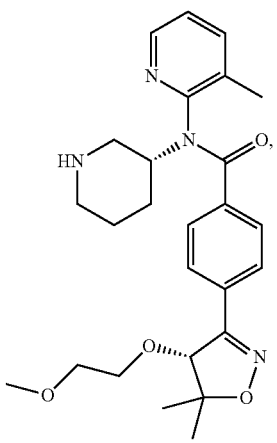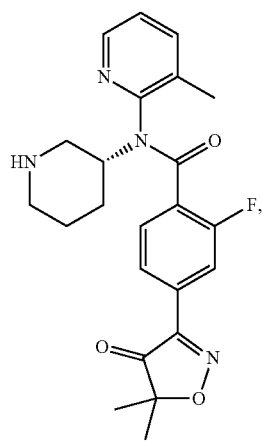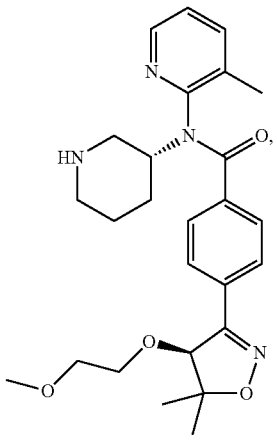

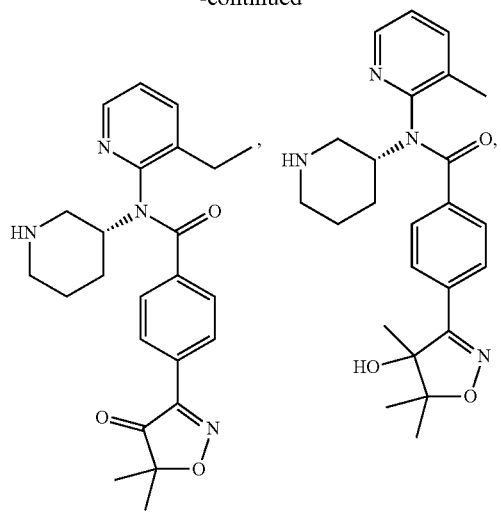
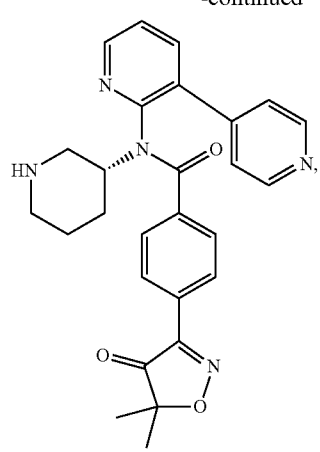
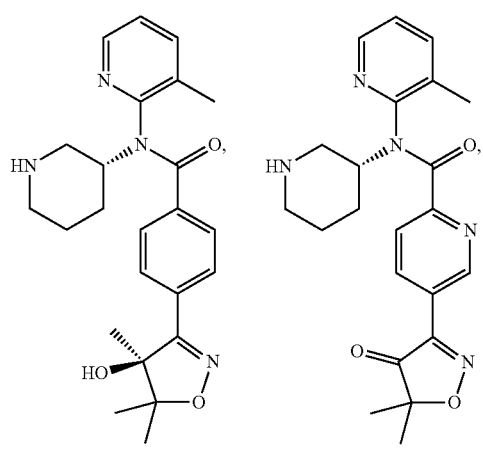
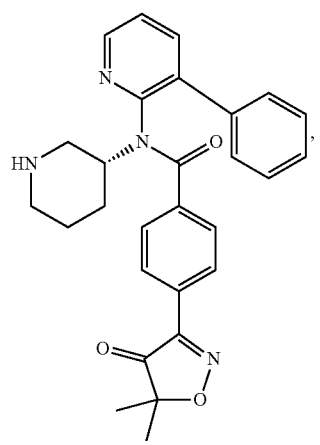
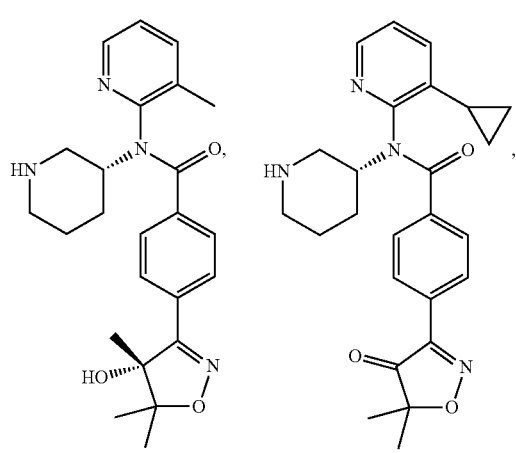
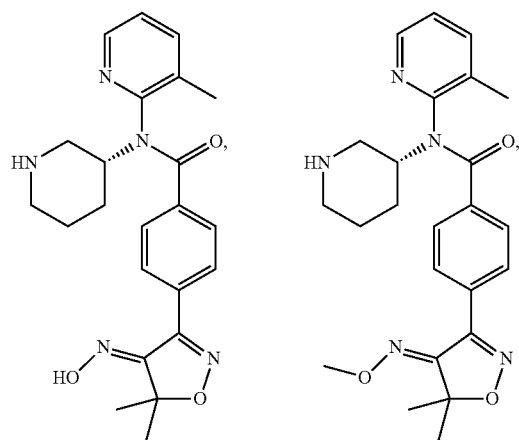

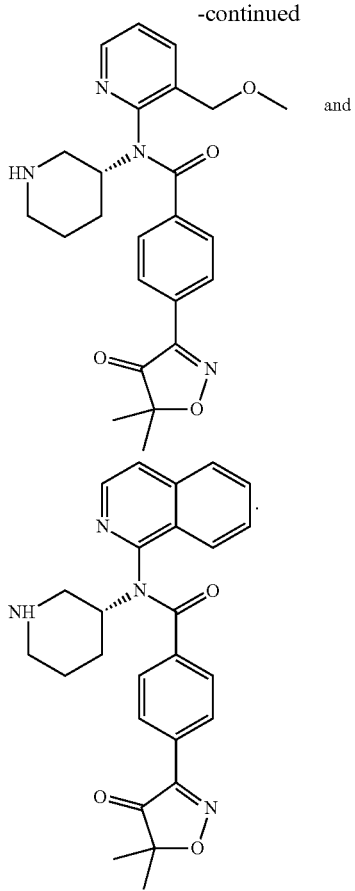

and

In some embodiments of this disclosure, a compound of this disclosure and/or a pharmaceutically acceptable salt thereof is used in the preparation of a medicament for treating one or more PCSK9 receptor related diseases.

Definition and Terms

Unless otherwise specified, the following terms and phrases used in this text have the following meanings. A specific term or phrase shall not be considered uncertain or unclear in the absence of a specific definition, and shall be understood according to the common meaning. The trade name, if occurring in this text, is intended to refer to its corresponding commodity or active ingredients. The term "pharmaceutically acceptable salt" used herein is specific to those compounds, materials, compositions and/or dosage forms which are suitable for contacting the tissues of human and animals within the range of reliable medical judgement, but have no excessive toxicity, stimulate allergic reactions, or create other problems or complications, matching with reasonable benefit/risk ratio.

The term "pharmaceutically acceptable salt" means a salt of a compound of this disclosure, which is prepared by the compound's specific substituent group with a relatively nontoxic acid or alkali. The compound in this disclosure, if containing relatively acidic functional groups, can obtain alkaline addition salt by using a sufficient quantity of alkali to yield the neutral form of such compound in pure solution or suitable inert solvent. Pharmaceutically acceptable alkali addition salts include the sodium, potassium, calcium, ammonia, organic ammonia, magnesium salts or similar salts. The compound in this disclosure, if containing relatively alkaline functional groups, can obtain acid addition salt by using enough quantity of acid to yield the neutral form of such compound in pure solution or suitable inert solvent. Examples of pharmaceutically acceptable acid addition salts include inorganic acid salts, wherein inorganic acids include hydrochloric acid, hydrobromic acid, nitric acid, carbonic acid, bicarbonate radical, phosphoric acid, mono hydrogen phosphate radical, dihydrogen phosphate radical, sulfuric acid, hydrogen sulfate radical, hydroiodic acid, phosphorous acid, etc.; organic acid salts, wherein organic acids include acetic acid, propionic acid, isobutyric acid, maleic acid, malonic acid, benzoic acid, succinic acid, octanedioic acid, fumaric acid, lactic acid, mandelic acid, phthalic acid, benzenesulfonic acid, p-toluenesulfonic acid, citric acid, tartaric acid, methanesulfonic acid, and other similar acids; salts of amino acids (such as arginine, etc.), and salts of organic acids (such as glucuronic acid) (See Berge et al., "Pharmaceutical Salts", Journal of Pharmaceutical Science 66: 1-19 (1977)). As some specific compounds in this disclosure contain alkaline and acid functional groups, they can be converted into any alkali or acid addition salts. Preferably, the salt contacts with an alkali or acid conventionally, and then separates the parent compound to produce the neutral form of compound. The parent form of compound and its various salts are different in certain physical properties, for example, they have different solubilities in the polar solvent.

The term "pharmaceutically acceptable salt" as used in this text refers to a derivative of a compound of this disclosure, wherein, the described parent compound is modified to yield an acid or alkaline addition salt. Examples of pharmaceutically acceptable salts include but are not limited to those comprising basic groups, such as inorganic acid or organic acid salts of amines, and those comprising acid radicals, such as alkali metal or organic salt of carboxylic acid. The pharmaceutically acceptable salts include regular non-toxic salts of quaternary ammonium salts of parent compounds, such as the salt formed using a non-toxic inorganic acid or organic acid. Regular non-toxic salts include but are not limited to the salts derived from inorganic acids and organic acid, in which the described inorganic acids or organic acids are chosen from 2-acetoxybenzoic acid, acetic acid, ascorbic acid, benzenesulfonic acid, benzoic acid, hydrosulphuric acid, carbonic acid, citric acid, edetic acid, ethane disulfonic acid, ethane sulfonic acid, fumaric acid, glucoheptonic acid, gluconic acid, glutamic acid, glycolic acid, hydrobromic acid, hydrochloric acid, hydroiodic acid, hydroxyl naphthalic acid, isethionic acid, lactic acid, lactobionic acid, dodecyl sulfonic acid, maleic acid, malic acid, mandelic acid, methane sulfonic acid, nitric acid, oxalic acid, pamoic acid, pantothenic acid, phenylacetic acid, phosphoric acid, polygalacturonic acid, propionic acid, salicylic acid, stearic acid, acetic acid, succinic acid, sulfamic acid, sulfanilic acid, sulfuric acid, tannic acid, tartaric acid and p-toluenesulfonic acid.

The pharmaceutically acceptable salts in this disclosure can be synthesized from parent compounds containing acid radical or basic group using conventional methods. Generally, the preparation of such salts comprises reaction of these compounds in the form of free acid or alkali with stoichiometric amounts of suitable acid or alkali in water or organic solvent or mixture of both. Generally, ether, ethyl acetate, ethyl alcohol, isopropanol or acetonitrile and other non-aqueous media are preferred.

In addition to salt forms, compounds provided in this disclosure can also be present as prodrugs. Prodrugs of compounds described in this text can easily undergo chemical changes under physiological conditions and thus be converted into the compounds described in this disclosure. In addition, the prodrugs can be converted into the compounds described in this disclosure by chemical or biochemical method in internal environment (e.g., in vivo). Some compounds in this disclosure can exist in solvated or unsolvated forms, including in hydrated forms. Generally, the solvated and unsolvated forms are equivalent and are included in the scope of this disclosure. Unless otherwise specified, wedge-shaped full line bond ( ⫽ ) and wedge-shaped dotted line bond ( ⫽ ) are used to represent the absolute configuration of a stereocenter, wavy line ( ⫽ ) is used to represent wedge-shaped full line bond ( ⫽ ) or wedge-shaped imaginary line bond ( ⫽ ), and straight full line bond ( ⫽ ) and straight dotted line bond ( ⫽ ) are used to represent the relative configuration of a stereocenter. If the compounds described in this text contain olefinic double-bonds or other geometric asymmetry centers, unless otherwise specified, E and Z geometrical isomers are included. Similarly, all tautomeric forms are included in the scope of this disclosure. The compounds described in this disclosure can have specific geometric isomers or stereoisomeric forms. All such compounds are considered in this disclosure, including cis and trans isomers, (−)- and (+)-enantiomers, (R)- and (S)-enantiomers, diastereoisomers, (D)-isomers, (L)-isomers, racemic mixtures and other mixtures, such as mixtures enriched in enantiomers or diastereomers, and all these mixtures are included in the scope of this disclosure. Alkyl and other substituent groups can have other unsymmetrical carbons. All these isomers and their mixtures are included in the scope of this disclosure.

(R)- and (S)-isomers, or D and L isomers with optical activity can be prepared by chiral synthesis or using chiral reagents or using other routine techniques. A desired enantiomer of certain compound in this disclosure can be prepared by asymmetric synthesis or by derivatization using chiral auxiliaries, separating the mixture of diastereomers, and removing the auxiliary group to obtain the required pure enantiomer. Or, when the molecules contain alkaline functional groups (such as amino) or acidic functional groups (such as carboxyl), they can be reacted with suitable optically active acids or alkalis to form the salt of diastereoisomer, followed by separation of the diastereoisomer by conventional methods well known in the field of this disclosure, to obtain the pure enantiomer by recovery. In addition, the separation between enantiomer and diastereoisomer is usually completed by chromatography which uses a chiral stationary phase and optionally combines with chemical derivation method (for example, from amine to generate carbaminate).

The compounds described in this disclosure can contain non-naturally proportional atomic isotopes on one or more atoms constituting such compounds. For example, radioisotopes can be used to label compound, such as tritium ($^3$H), iodine-125 ($^{125}$I) or C-14 ($^{14}$C). All isotope-comprising forms of compounds described in this disclosure, whether radioactive or not, are included in the scope of this disclosure.

The term "pharmaceutically acceptable carrier" means any preparation carrier or medium which can deliver an effective quantity of active substances without interfering with the biological activity of active substances, and have no toxic or side effects on a host or patient. Representative carriers include water, oils, vegetable and mineral substance, cream bases, lotion bases, ointment bases, etc. These matrixes include suspending agent, tackifier, transdermal accelerant, etc. Their preparations are well known by those skilled in cosmetic fields or topical drug fields. For other information regarding pharmaceutically acceptable carriers, refer to Remington: The Science and Practice of Pharmacy, 21st Ed., Lippincott, Williams & Wilkins (2005), the contents of which are incorporated by reference.

The term "excipient" usually means the carrier, diluent and/or medium used for preparing the effective pharmaceutical compositions.

For the pharmaceutical or pharmacological ingredients, the term "effective quantity" or "therapeutically effective quantity" means enough dosage of drug or medicament which is non-toxic, but can achieve the desired effect. For the oral dosage forms in this disclosure, the "effective quantity" of an active substance in the composition means the dosage required for achieving desired effect when used in combination with another active substance in this composition. The effective quantity varies from person to person, is subject to the age and general condition of patient, as well as the specific active substance, and appropriate effective quantities in individual cases can be determined according to routine tests by technical staff in the field.

The term "active ingredient", "therapeutic agent", "active substance" or "activator" means a chemical entity which can effectively cure target disorders, diseases or conditions.

"Optional" or "optionally" means that the events or conditions described subsequently may occur but are not necessary, and this description includes the circumstances that the events or conditions described occur, as well as the circumstances that the events or conditions described do not occur.

The term "substituted" means that one or more hydrogen atoms on specific atom are substituted by a substituent group, e.g., a hydrogen atom can be replaced by a heavy hydrogen so long as the valence state of a specific atom is normal and the post-substitution compound is stable. If the substituent group is keto group (that is, =O), it means that two hydrogen atoms are substituted. Ketone substitution never occurs on aryl. The term "optionally substituted" means that a group can be substituted or unsubstituted. Unless otherwise specified, the type and number of said substituent groups can be arbitrarily selected in the chemical field.

When a variable (such as R) occurs more than once in the composition or structure of compound, its definition in each case is independent from other occurrence(s). Therefore, if a group is substituted by 0-2 Rs, the groups described can be optionally substituted by two Rs at most, and the R in each case is independently chosen. The combination of substituent group(s) and/or variant(s) thereof is permitted only under the circumstances that such combination produces a stable compound.

When the number of a linking group is 0, such as —(CRR)$_0$—, it means that this linking connection is a single bond.

When a variable is chosen from a single bond, it means that the two groups linked are linked directly. For example, when L represents a single bond in A-L-Z, it means that this structure is actually A-Z.

When a substituent group is absent, it means that this substituent group is non-existent, for example, when X is absent in A-X, it means that this structure is actually A.

If a substituent group can be linked to more than one atoms on a ring, it means that this substituent group can be bonded to any atom on this ring. For example, the structural units

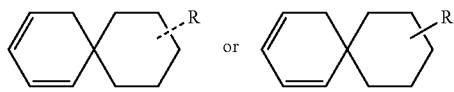

show that substituent group R can have substitution in any position on cyclohexyl or cyclohexadiene. If it does not indicate that the substituent group enumerated is linked to a group substituted by a specific atom, then this substituent group can be bonded by any atom. For example, pyridyl can be linked to the substituted group by any one carbon atom. If the linking direction of the linking group enumerated is not indicated, its linking direction is arbitrary, for example, when the linking group L in

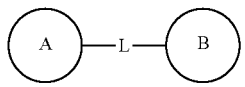

is -M-W—, the rings A and B can be linked by -M-W— to either form

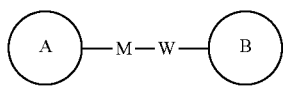

in the direction the same as reading order from left to right, or form

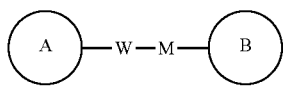

in the direction opposite to the reading order from left to right.

The combination of linking group(s), substituent group(s) and/or variants thereof is permitted only under the circumstances that such combination produces a stable compound.

Unless otherwise specified, the term "hetero" represents a heteroatom or a hetero-radical (namely, a radical containing heteroatoms), including atoms except carbon (C) and hydrogen (H), and including radicals containing these heteroatoms, such as oxygen (O), nitrogen (N), sulphur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the optionally substituted —C(=O)N(H)—, —N(H)—, —C(=NH)—, —S(=O)$_2$N(H)— or —S(=O)N(H)—.

Unless otherwise specified, a "ring" represents a substituted or unsubstituted cycloalkyl, hetero-cycloalkyl, cycloalkenyl, hetero-cycloalkenyl, cycloalkynyl, hetero-cycloalkynyl, aryl or hetero-aryl. The term "ring" includes a monocyclic ring, a linking ring, a spiral ring, a fused ring or a bridge ring. The number of atoms on a ring is usually defined as the membered number of this ring, for example, "a "5-7 membered ring" means that 5-7 atoms are arranged in an encircling way. In some embodiments of a 5-7 membered ring, a 5- or 6-membered ring is preferred. Unless otherwise specified, this ring optionally includes 1-3 heteroatoms. Therefore, "5-6 membered ring" includes phenyl, pyridine and piperidyl alternatively, the term "5-6 membered heterocycloalkyl" includes pyridyl and piperidyl, but excludes phenyl. The term "ring" also includes a ring system containing at least one ring, wherein each "ring" is independently chosen in accordance with the above-mentioned definition.

Unless otherwise specified, the term "heterocyclic ring" or "heterocyclic radical" means a stable monocyclic ring, dicyclic ring or tricyclic ring containing a heteroatom or a hetero-radical, which is saturated, partly unsaturated, or unsaturated (aromatic), contains at least one carbon atom and one, two, three or four cyclo-heteroatoms which are independently chosen from N, O and S, wherein any above-mentioned heterocyclic ring can be fused to a benzene ring to form a dicyclic compound. Nitrogen and sulfur heteroatoms can be optionally oxidized (namely, NO and S(O)p, wherein p is 1 or 2). A nitrogen-atom can be substituted or unsubstituted (namely, N or NR, in which R is H or a substituent group as defined in this text). The heterocyclic ring can be attached to the side-chain group of any heteroatom or carbon atom to form a stable structure. If the compound so-produced is stable, a heterocyclic ring described in this text can have substitution on carbon or on nitrogen. The nitrogen atom in the heterocyclic ring is optionally quaternized. In some embodiments, the total number of S and O atoms in a heterocyclic ring is more than 1, and these atoms are not adjacent to each other. In some embodiments, the total number of S and O atoms in the heterocyclic ring is not more than 1. As used in this text, the term "aromatic heterocyclic group" or "heteroaryl" means an aromatic 5-, 6-, or 7-membered monocyclic ring or bicyclic ring, or an aromatic 5-, 6- 7-, 8-, 9- or 10 membered bicyclic heterocyclic radical which contains carbon atoms and 1, 2, 3 or 4 cyclic-heteroatoms which are independently chosen from N, O and S. A nitrogen atom can be substituted or unsubstituted (for example, being N or NR, wherein R is H or a substituent group as defined in this text). In some embodiments, the total number of S and O atoms on aromatic heterocyclic ring is not more than 1. The bridge ring is also included in the definition of "heterocycle." The bridge ring is formed when one or more atoms (for example, C, O, N or S) link to two nonadjacent carbon atoms or nitrogen atoms. In some embodiments, bridge rings include but are not limited to one carbon atom, two carbon atoms, one nitrogen atom, two nitrogen atoms and one carbon-nitrogen base. It is noteworthy that a bridge always converts a monocycle into a tricycle. Substitutions on the ring can also occur on the bridge in the bridge ring.

Examples of heterocyclic compounds include but are not limited to acridinyl, azocinyl, benzimidazolyl, benzofuryl, benzo-sulfhydryl furyl, benzo-sulfhydryl phenyl, benzoxazolyl, benzo-oxazolinyl, benzothiazolyl, benzotriazolyl, benzo-tetrazyl, benzo-isoxazolyl, benzo-thiazolyl, benzo-imidazolinyl, carbazolyl, 4aH-carbazolyl, carbolinyl, benzo-dihydropyranyl, chromene, cinnolinyl-decahydroquinolinyl, 2H,6H-1,5,2-dithiazinyl, dihydrofuran-[2,3-b]tetrahydrofuranyl, furyl, furazyl, imidazolidinyl, imidazolyl, 1H-indazolyl, indolenyl, indolinyl, indolizinyl, indolyl, 3H-indolyl, isobenzofuryl, isoindolyl, isoindolinyl, isoquinolyl, isothiazolyl, isoxazolyl, methylenedioxy phenyl, morpholinyl, naphthyridinyl, octahydro-isoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidyl, phenanthridinyl, phenanthrolinyl, azophenylene, phenothiazine, benzo-xanthinyl, phenoxazinyl, phthalazinyl, piperazinyl, piperidyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridino-oxazole, pyridino-imidazole, pyridino-thiazole, pyridyl, pyrrolidyl, pyrrolinyl, 2H-pyrrolyl, pyrrolyl, quinazolinyl, quinolyl, 4H-quinolizidinyl, quinoxalinyl, quinuclidinyl, tetrahydrofuranyl, tetrahydroisoquinolinyl, tetrahydroquinolinyl, tetrazyl, 6H-1,2,5-thiadiazinyl, 1,2,3-thiadiazinyl, 1,2,4-thiadiazinyl, 1,2,5-thiadiazinyl, 1,3,4-thiadiazolyl, thiadiazolyl, thianthrenyl, thiazolyl, isothiazolithiophenyl, thieno-oxazolyl, thieno-thiazolyl, thieno-imidazolyl, thienyl, triazinyl, 1H-1,2,3-thiazolyl, 2H-1,2,3-thiazolyl, 4H-1,2,4-triazoly, and xanthenyl. Fused rings and spiro compounds are also included.

Unless otherwise specified, the term "hydrocarbyl" and related terms (such as alkyl, alkenyl, alkynyl, and aryl) whether recited on their own or as a part of another substituent group, represent straight-chain, branched-chain, or cyclic hydrocarbon radicals, or combinations thereof, any of which can be completely saturated (as in alkyl), mono-membered or multi-membered unsaturated (as in alkenyl, alkynyl, or aryl), mono-substituted or poly-substituted, monovalent (as in methyl), divalent (as in methylene) or multi-valent (as in methine), can include divalent or multivalent radicals and can comprise a specified number of carbon atoms (wherein, for example, $C_1$-$C_{12}$ means 1-12 carbons, $C_{1-12}$ is chosen from $C_1$, $C_2$, $C_3$, $C_4$, $C_5$, $C_6$, $C_7$, $C_8$, $C_9$, $C_{10}$, $C_{11}$ and $C_{12}$; and $C_{3-12}$ is chosen from $C_3$, $C_4$, $C_5$, $C_6$, $C_7$, $C_8$, $C_9$, $C_{10}$, $C_{11}$ and $C_{12}$). "Alkyl" includes but is not limited to aliphatic hydrocarbyl and aromatic hydrocarbyl, wherein aliphatic hydrocarbyl includes but is not limited to straight-chain and cyclic alkyl, alkenyl and alkynyl, and aromatic hydrocarbyl includes but is not limited to 6-12 membered aromatic hydrocarbyls, such as benzene and naphthalene. In some examples, the term "hydrocarbyl" represents straight-chain or branched-chain radicals or their combinations which can be completely saturated, mono-membered or multi-membered unsaturated, and can include divalent or multivalent radicals. Non-limiting examples of saturated hydrocarbon radicals include but are not limited to methyl, ethyl, n-propyl, isopropyl, n-butyl, tertiary butyl, isobutyl, sec-butyl, cyclohexyl, (cyclohexyl)methyl, cyclopropyl methyl, and the homologues or isomers of n-amyl, n-hexyl, n-heptyl, n-octyl and other radicals. An unsaturated hydrocarbyl comprises one or more double bonds or triple bonds and includes but is not limited to ethenyl, 2-propenyl, butenyl, crotyl, 2-isopentenyl, 2-(butadienyl), 2,4-pentadienyl, 3-(1,4-pentadienyl), acetenyl, 1- and 3-propinyl, 3-butynyl, and more advanced homologues and isomers.

Unless otherwise specified, the term "hetero-hydrocarbyl" and related terms (such as hetero-alkyl, hetero-alkenyl, hetero-alkynyl, hetero-aryl) whether recited on their own or as part of another term represent stable straight-chain, branched-chain or cyclic hydrocarbon radicals or combinations thereof, any of which comprise a certain number of carbon atoms and at least one heteroatom. In some embodiments, the term "hetero-hydrocarbyl" whether used by itself or in combination with another term represents stable straight-chain or branched-chain hydrocarbon radicals or combinations thereof that comprise a certain number of carbon atoms and at least one heteroatom. In a typical embodiment, a heteroatom is chosen from O, N and S, wherein said N or S atoms are optionally oxidized, and said nitrogen heteroatom is optionally quaternized. The heteroatom or hetero-radical can be located in any position of a hetero-hydrocarbyl, including embodiments wherein this hydrocarbyl attaches to a position of another part of a molecule, while the terms "alkoxy", "alkyl amino" and "alkyl sulphanyl" (or sulfo-alkoxy) are understood to respectively mean that the alkyl groups link to other parts of a molecule by a oxygen atom, amino or sulphur atom. Such examples include but are not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. At least two heteroatoms can be continuous, such as —$CH_2$—NH—$OCH_3$.

Unless otherwise specified, the term "cyclo-hydrocarbyl", "heterocyclic hydrocarbyl" and related terms (such as aryl, hetero-aryl, cycloalkyl, heterocycloalkyl, cycloalkenyl, hetero-cycloalkenyl, cycloalkynyl, hetero-cycloalkynyl) whether used on their own or in combination with other terms respectively represents a cyclized "hydrocarbyl" or "hetero-hydrocarbyl". In addition, for hetero-hydrocarbyl or hetero-cyclohydrocarbyl (such as heteroalkyl or heterocycloalkyl), the heteroatom can be located in a position wherein the heterocycle attaches to the rest of a molecule. Such examples of cyclohydrocarbyl include but are not limited to cyclopentyl, cyclohexyl, 1-cyclohexenyl, 3-cyclohexenyl, cycloheptyl, etc. Non-limiting examples of heterocyclic radicals include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuran-indol-3-yl, triophane-2-yl, triophane-3-yl, 1-piperazinyl and 2-piperazinyl.

Unless otherwise specified, the term "alkyl" means a straight-chain or branched-chain saturated hydrocarbyl which can be mono-substituted (such as —$CH_2F$) or poly-substituted (such as —$CF_3$), monovalent (such as methyl, divalent (such as methylene) or multivalent (such as methenyl). Such examples of alkyl include methyl (Me), ethyl (Et), propyl (such as n-propyl and isopropyl), butyl (such as n-butyl, isobutyl, s-butyl, t-butyl), amyl (such as n-amyl, isoamyl, neo-amyl), etc.

Unless otherwise specified, "alkenyl" means an alkyl that comprises one or more carbon-carbon double bonds at any site of a chain that can be mono-substituted or poly-substituted, and monovalent, divalent or multivalent. Such examples of alkenyl include ethenyl, propenyl, butenyl, pentenyl, hexenyl, butadienyl, pentadienyl, hexadienyl, etc.

Unless otherwise specified, "alkynyl" means an alkyl that comprises one or more carbon-carbon triple bonds at any site of a chain that can be mono-substituted or poly-substituted, and monovalent, divalent or multivalent. Such examples of alkynyl include acetenyl, propinyl, butynyl, pentynyl, etc.

Unless otherwise specified, cycloalkyl include any stable cyclic or polycyclic hydrocarbyl, wherein all carbon atoms are saturated which can be mono-substituted or poly-substituted, and monovalent, divalent or multivalent. Examples of these cycloalkyls include but are not limited to cyclopropyl, norborneol alkyl, [2.2.2] biocyclooctane, [4.4.0] biocyclodecane, etc.

Unless otherwise specified, cycloalkenyl includes any stable cyclic or polycyclic hydrocarbyl comprising one or more unsaturated carbon-carbon double bonds at any site of a ring that can be mono-substituted or poly-substituted, and monovalent, divalent or multivalent. Such examples of cycloalkenyl include but are not limited to cyclopentenyl, cyclohexenyl, etc.

Unless otherwise specified, cycloalkynyl includes any stable cyclic or polycyclic hydrocarbyl comprising one or more unsaturated carbon-carbon triple bonds at any site of a ring that can be mono-substituted or poly-substituted, and monovalent, divalent or multivalent.

Unless otherwise specified, the term "halogen" whether used by itself or as a part of another substituent group, represents a fluorine, chlorine, bromine or iodine atom. In addition, the term "halogenated alkyl" includes monohalogenated alkyl and polyhalogenated alkyl. For example, the term "halogenated ($C_1$-$C_4$) alkyl" includes but is not limited to trifluoromethyl, 2,2,2-trifluoroethyl, 4-chlorobutyl and 3-brominepropyl, etc. Unless otherwise specified, such examples of halogenated alkyl include but are not limited to trifluoromethyl, trichloromethyl, pentafluoromethyl and pentachloromethyl.

"Alkoxy" means an alkyl as defined elsewhere herein comprising a specific number of carbon atoms and linked by an oxygen bridge. Unless otherwise specified, $C_{1-6}$ alkoxy includes the alkoxies of $C_1$, $C_2$, $C_3$, $C_4$, $C_5$ and $C_6$. Such examples of alkoxy include but are not limited to methoxy, ethyoxy, n-propoxy, isopropoxy, n-butoxy, sec-butoxy, tert-butoxy, n-amoxy and S-amoxyl.

Unless otherwise specified, the term "aryl" refers to a polyunsaturated aromatic hydrocarbon substituent group that can be mono-substituted or poly-substituted, monovalent, divalent or multivalent, and monocyclic or polycyclic (such as comprising 1-3 rings; wherein, at least one ring is aromatic) that is fused or covalently linked. The term "heteroaryl" means an aryl (or aromatic ring) containing 1-4 heteroatoms. In a representative example, the heteroatoms are chosen from B, N, O and S, wherein, said N and S atoms are optionally oxidized, and said nitrogen atom is optionally quaternized. A heteroaryl can be linked to the rest of a molecule by a heteroatom. The non-limiting examples of aryl or heteroaryl include phenyl, naphthyl, biphenyl, pyrrolyl, pyrazolyl, imidazolyl, pyrazinyl, oxazolyl, phenyloxazolyl, isoxazolyl, thiazolyl, furyl, thienyl, pyridyl, pyrimidyl, benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. All of the above-mentioned substituent groups on aryl or heteroaryl ring systems can be chosen from the acceptable substituent groups described elsewhere herein.

Unless otherwise specified, aryl, if used in conjunction with other terms (such as in aryloxy, arsulfenyl, aralkyl), includes aryl and heteroaryl as defined as above. Therefore, the term "aralkyl" is intended to include radicals (such as benzyl, phenethyl, pyridylmethyl) in which an aryl attaches to an alkyl, including alkyls, such as phenoxyl-methyl, 2-pyridine-oxymethyl, 3-(1-naphthoxy) propyl, wherein a carbon atom (such as methylene) has been substituted by, for example, an oxygen atom.

The term "leaving group" means a functional groups or atom(s) that can be substituted by another functional group or atom by a substitution reaction (such as a nucleophilic substitution reaction). For example, representative leaving groups include triflate; chlorine, bromine, iodine; sulphonate, such as methanesulfonate, Cis-tritosylate, parabromobenzenesulfonate, tosylate; and acyloxy, such as acetoxyl, trifluoroacetyl.

The term "protecting group" includes but is not limited to "amino-protecting group", "hydroxy-protecting group" or "sulfhydryl-protecting group". The term "amino-protecting group" means protecting groups that are suitably used for preventing side reactions at an amino nitrogen site. Representative amino-protecting groups include but are not limited to formyl; acyl, such as alkylacyl (such as acetyl, trichloroacetyl or trifluoroacetyl); alkoxycarbonylphenyl, such as tert-butoxycarbonyl (Boc); arylmethoxycarbonyl, such as carbobenzoxy (Cbz) and 9-fluorenylmethoxycarbonyl (Fmoc); arylmethyl, such as benzyl (Bn), trityl (Tr) and 1,1-bis-(4'-methoxyphenyl) methyl; silyl, such as trimethylsilyl (TMS) and tert-butyldimethylsilicyl (TBS). The term "hydroxy-protecting group" means protecting groups that are suitably used for preventing the side reaction of hydroxy. Representative hydroxy-protecting groups include but are not limited to alkyl, such as methyl, ethyl and tertiary butyl; acyl, such as alkylacyl (such as acetyl); arylmethyl, such as benzyl (Bn), p-methoxybenzyl (PMB), 9-fluorenylmethyl (Fm) and diphenylmethyl (benzhydryl, DPM); silyl, such as trimethylsilyl (TMS) and tert-butyldimethylsilicyl (TBS).

The compounds described in this disclosure can be prepared by many synthetic methods well known by those skilled in the art, including the methods described below, such methods used in combination with other chemical synthetic methods, or the other modes well known by those skilled in the art, and the preferred methods include but are not limited to the methods in this disclosure.

The solvents used in this disclosure are available commercially. The following abbreviations are used in this disclosure: aq represents water; HATU represents O-(7-azabenzotriazole-1-yl)-N,N,N',N'-tetramethylureahexafluorophosphate; EDC represents N-(3-dimethylaminopropyl)-N'-ethylcarbodiimide hydrochloride; m-CPBA represents 3-chloroperoxybenzoic acid; eq represents equivalent; CDI represents carbonyldiimidazole; DCM represents dichloromethane; THF represents tetrahydrofuran; PE represents petroleum ether; DIAD represents diisopropyl azodicarboxylate; DMF represents N,N-dimethylformamide; DMSO represents dimethylsulfoxide; EtOAc or EA represents ethyl acetate; EtOH represents ethyl alcohol; MeOH represents methyl alcohol; CBz represents carbobenzoxy which is an amino-protecting group; Boc represents t-butyloxycarboryl which is an amino-protecting group; HOAc represents acetic acid; $NaCNBH_3$ represents sodium cyanoborohydride; r.t. represents room temperature; O/N represents staying overnight; THF represents tetrahydrofuran; $Boc_2O$ represents di-tert-butyl dicarbonate; TFA represents trifluoroacetic acid; DIPEA represents N-di(isopropyl)ethylamine; $SOCl_2$ represents sulfoxide chloride; $CS_2$ represents carbon disulfide; TsOH represents p-toluenesulfonic acid; NCS represents 1-chlorine pyrrolidine-2,5-diketone; LDA represents lithium diisopropylamide; tBuXPhos Pd G3 represents methylsulphonicacid (2-di-tert-butylphosphine-2',4',6'-triisopropyl-1,1'-biphenyl)(2'-amino-1,1'-biphenyl-2-yl) palladium(II); $Pd_2(dba)_3$ represents tris(dibenzylideneacetone) dipalladium; Xantphos represents 4,5-bis diphenylphosphine-9,9-dimethyl oxanthene; Pd (dppf) $ClCH_2Cl$ represents [1,1'-di(phenylphosphine) ferrocene] palladium dichloride dichloromethane complex; MTBE represents methyl tertiary butyl ether; $Pd(PPh_3)_4$ represents tetrakis (triphenylphosphine) palladium; XPHOS-PD-G2 represents chlorine (2-dicyclohexylphosphine-2',4',6'-triisopropyl-1,1'-biphenyl) [2-(2'-amino-1,1'-biphenyl)] palladium (II); TEA represents triethylamine; sPHOS-PD-G2 represents chlorine (2-triisopropyl dicyclohexylphosphine-2',6'-dimethoxy-1,1'-biphenyl)(2'-amino-1,1'-biphen-2-yl) palladium (II). The compounds are named manually or using ChemDraw®, and commercially available compounds are referred to using the names in the catalog provided by the corresponding supplier.

EXAMPLES

The examples below described the disclosure, but do not restrict it. The disclosure has been described in this text, and various changes and improvements associated with the disclosure are apparent to those skilled in the art without departing from the spirit and scope of this disclosure.

Fragment WXBB-1

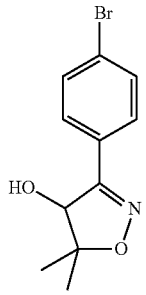

Synthetic Route:

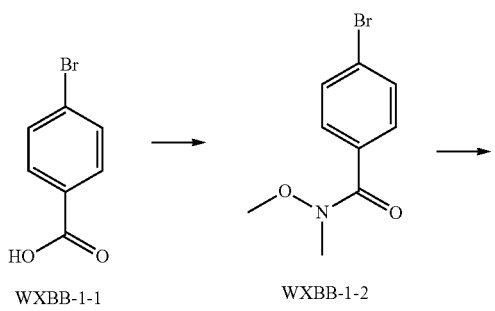

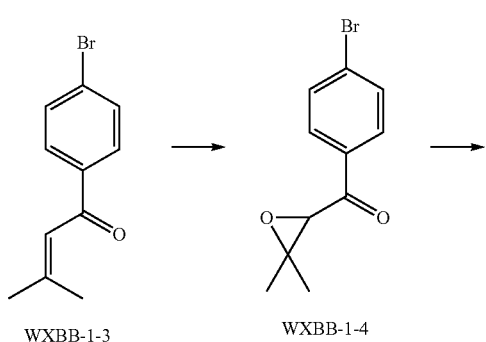

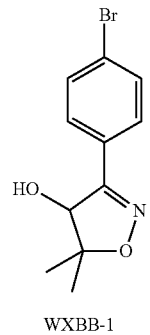

WXBB-1

Step 1: Synthesis of Compound WXBB-1-2

WXBB-1-1 (10.00 g, 49.75 mmol, 1.00 eq.) was added to anhydrous dichloromethane (100.00 mL), and then N,O-dimethylhydroxylamine hydrochloride (4.85 g, 49.75 mmol, 1.00 eq.), triethylamine (10.07 g, 99.50 mmol, 13.79 mL, 2.00 eq.), 1-ethyl-(3-dimethylaminopropyl) carbonyl dimethylamine hydrochloride (10.49 g, 54.73 mmol, 1.10 eq.) and 1-hydroxybenzotriazole (7.39 g, 54.73 mmol, 1.10 eq.) were added in order. The mixture was stirred at 20° C. for 3 h. After reaction, the reaction liquid was diluted with dichloromethane (100 mL), and then washed with hydrochloric acid (50 mL, 0.5N), saturated sodium bicarbonate solution (50 mL), and saturated sodium chloride solution (50 mL) in order. The organic phase was dried with anhydrous sodium sulfate, filtered and dried by rotary evaporation to obtain the compound WXBB-1-2. $^1$H NMR (400 MHz, CDCl$_3$): δ ppm: 7.61-7.48 (m, 4H), 3.52 (s, 3H), 3.34 (s, 3H).

Step 2: Synthesis of Compound WXBB-1-3

Under nitrogen condition, the compound WXBB-1-2 (2.00 g, 8.19 mmol, 1.00 eq.) was added to anhydrous tetrahydrofuran (20.00 mL), the resulting solution was cooled to −10° C., and then (2-methacrylonitrile-1-yl) magnesium bromide (0.5 M, 19.66 mL, 1.20 eq.) was added. The mixture was warmed to 30° C. and stirred for 4 h. After reaction, the reaction liquid was cooled to 0° C., the saturated ammonia chloride solution (10 mL) was slowly added, and then water (50 mL) and ethyl acetate (100 mL) were added. The mixture was layered. The organic phase was taken and dried with anhydrous sodium sulfate, then filtered and dried by rotary evaporation to obtain the crude. The crude was purified by column chromatography (ethyl acetate/petroleum ether=1~5%) to obtain the compound WXBB-1-3. $^1$H NMR (400 MHz, CDCl$_3$): δ ppm: 7.79 (d, J=8.5 Hz, 2H), 7.58 (d, J=8.5 Hz, 2H), 6.69 (s, 1H), 2.21 (s, 3H), 2.02 (s, 3H).

Step 3: Synthesis of Compound WXBB-1-4

Under nitrogen condition, the compound WXBB-1-3 (4.20 g, 17.57 mmol, 1.00 eq.) was added to anhydrous tetrahydrofuran (20.00 mL), the resulting solution was cooled to 0° C., and then added with meta-chloroperoxybenzoic acid (18.00 g, 83.46 mmol, 80% purity, 4.75 eq.). The mixture was stirred for 20 h at 20° C. After reaction, the reaction liquid was slowly poured into saturated sodium sulfite solution (100 mL). The mixture was layered. The organic phase was taken, washed with saturated sodium chloride solution (50 mL), dried with anhydrous sodium sulfate, filtered and dried to obtain the crude. $^1$H NMR (400 MHz, CDCl$_3$) δ=7.85 (d, J=8.5 Hz, 2H), 7.65 (d, J=8.5 Hz, 2H), 4.03-3.93 (m, 1H), 1.61-1.55 (m, 3H), 1.26-1.20 (m, 3H).

Step 4: Synthesis of Compound WXBB-1-4

Compound WXBB-1-4 (3.20 g, 12.54 mmol, 1.00 eq.) and hydroxylamine hydrochloride (3.49 g, 50.16 mmol, 4.00 eq.) were added to the mixed solution of methanol (50.00 mL) and pyridine (30.00 mL), and then the mixture was stirred at 80° C. for 20 h. After reaction, the crude obtained by concentrating the reaction solution was dissolved in water (100 mL). The pH was adjusted as 3-4 with acetic acid, and the mixture was then extracted with ethyl acetate (30 mL*3). The organic phase was washed with water (100 mL) and saturated chloride solution (100 mL) in order. The organic phase was dried with anhydrous sodium sulfate, filtered and dried by rotary evaporation to obtain the crude. The crude was purified by column chromatography (ethyl acetate/petroleum ether=1~5%) to obtain the compound WXBB-1. $^1$H NMR (400 MHz, CDCl$_3$) δ ppm: 7.64 (d, J=8.5 Hz, 2H), 7.50 (d, J=8.5 Hz, 2H), 4.77 (br. s., 1H), 2.63 (br. s., 1H), 1.54-1.46 (m, 3H), 1.35-1.28 (m, 3H).

Fragment WXBB-2

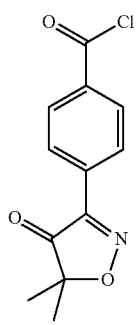 [SMILES: CC1(C)ON=C(c2ccc(C(=O)Cl)cc2)C1=O]

Synthetic Route:

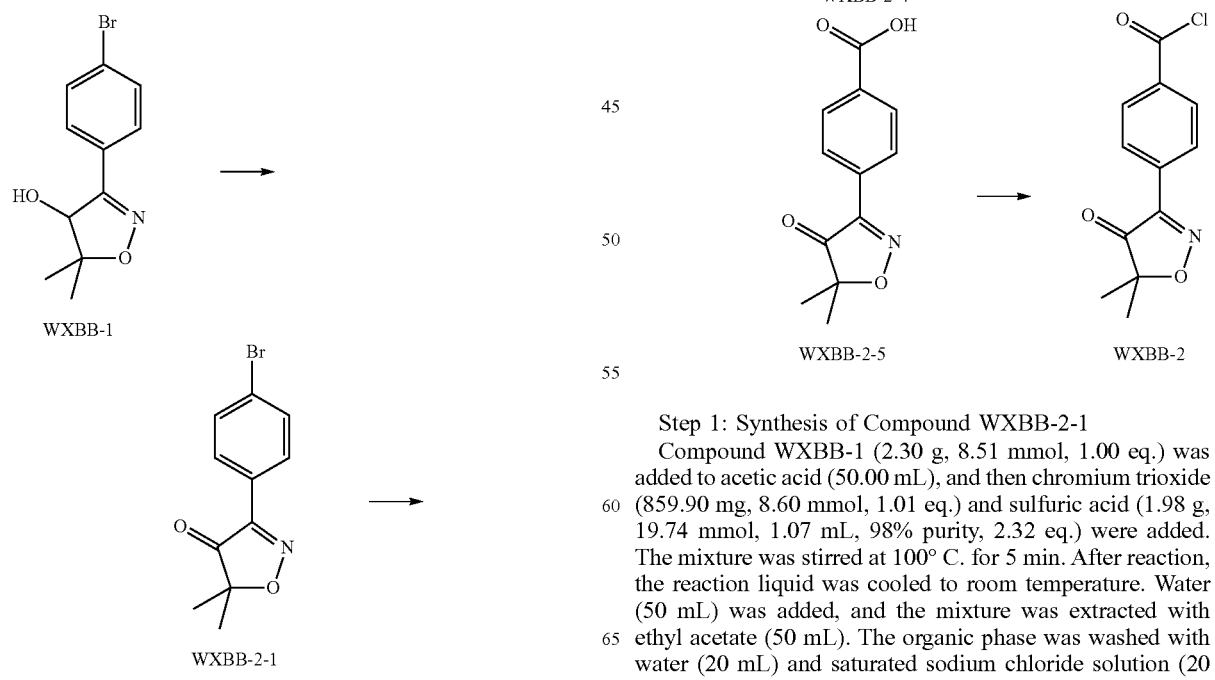

Step 1: Synthesis of Compound WXBB-2-1

Compound WXBB-1 (2.30 g, 8.51 mmol, 1.00 eq.) was added to acetic acid (50.00 mL), and then chromium trioxide (859.90 mg, 8.60 mmol, 1.01 eq.) and sulfuric acid (1.98 g, 19.74 mmol, 1.07 mL, 98% purity, 2.32 eq.) were added. The mixture was stirred at 100° C. for 5 min. After reaction, the reaction liquid was cooled to room temperature. Water (50 mL) was added, and the mixture was extracted with ethyl acetate (50 mL). The organic phase was washed with water (20 mL) and saturated sodium chloride solution (20 mL) in order. The organic phase was dried with anhydrous sodium sulfate, filtered and dried by rotary evaporation to obtain the compound WXBB-2-1. H NMR (400 MHz, CDCl$_3$) δ ppm: 7.99 (d, J=8.5 Hz, 2H), 7.60 (d, J=8.5 Hz, 2H), 1.47 (s, 6H)

Step 2: Synthesis of Compound WXBB-2-2

Compound WXBB-2-1 (1.00 g, 3.73 mmol, 1.00 eq.) was added to the mixed solution of N,N-dimethylformamide (20.00 mL) and methanol (60.00 mL), then triethylamine (1.13 g, 11.19 mmol, 1.55 mL, 3.00 eq.) and tetrakis (triphenylphosphine) palladium (431.00 mg, 373.00 μmol, 0.10 eq.) were added. The reaction liquid was stirred under CO (50 psi) condition at 80° C. for 20 h. After reaction, the reaction liquid was concentrated to obtain the green crude. The crude was purified by column chromatography (ethyl acetate/petroleum ether=1~5%) to obtain the compound WXBB-2-2. $^1$H NMR (400 MHz, CDCl$_3$) δ ppm: 8.24-8.17 (m, 2H), 8.16-8.09 (m, 2H), 3.95 (s, 3H), 1.49 (s, 6H).

Step 3: Synthesis of Compound WXBB-2-3

Compound WXBB-2-2 (900.00 mg, 3.64 mmol, 1.00 eq.) was added to anhydrous tetrahydrofuran (10.00 mL), then sodium borohydride (413.11 mg, 10.92 mmol, 3.00 eq.) was added. The mixture was stirred at 20° C. for 1.5 h. After reaction, acetone (5 mL) was added to reaction liquid, and the crude obtained by concentration was dissolved in ethyl acetate (50 mL). The mixture was washed with water (20 mL) and saturated sodium chloride solution (30 mL) in order. The organic phase was dried with anhydrous sodium sulfate, filtered and dried by rotary evaporation to obtain the compound WXBB-2-3. $^1$H NMR (400 MHz, CDCl$_3$) δ ppm: 8.03 (d, J=8.3 Hz, 2H), 7.86 (d, J=8.3 Hz, 2H), 4.85 (s, 1H), 3.94 (s, 3H), 1.53 (s, 3H), 1.34 (s, 3H).

Step 4: Synthesis of Compound WXBB-2-4

Compound WXBB-2-3 (900.00 mg, 3.61 mmol, 1.00 eq.) and lithium hydroxide monohydrate (757.52 mg, 18.05 mmol, 5.00 eq.) were added to the mixed solution of anhydrous tetrahydrofuran (20.00 mL) and water (10.00 mL) in order. The mixture was stirred at 20° C. for 2 h. After reaction, the reaction liquid was concentrated to about 5 mL, and then used for the next reaction without further processing. 5 mL (theoretical weight 849 mg) reaction liquid was obtained for direct use in the next reaction.

Step 5: Synthesis of Compound WXBB-2-5

Compound WXBB-2-4 (840.00 mg, 3.57 mmol, 1.00 eq.) was dissolved in acetic acid (30.00 mL). Chromium trioxide (357.05 mg, 3.57 mmol, 1.00 eq.), water (5.00 mL) and sulfuric acid (821.96 mg, 8.21 mmol, 446.72 μL, 98% purity, 2.30 eq.) were added in order. The mixture was stirred at 100° C. for 5 min. After reaction, the reaction liquid was cooled to room temperature, and then added with water (150 mL) (there was precipitation of solid) and filtered. The filter cake was washed with water (20 mL), dissolved in the mixed solution of dichloromethane:methanol=20:1 (30 mL), dried with anhydrous sodium sulfate, filtered and dried by rotary evaporation to obtain the compound WXBB-2-5. $^1$H NMR (400 MHz, CDCl$_3$) δ ppm: 8.28-8.17 (m, 4H), 1.51 (s, 6H).

Step 6: Synthesis of Compound WXBB-2

Under nitrogen condition, compound WXBB-2-5 (200.00 mg, 857.56 μmol, 1.00 eq.), oxalyl chloride (163.28 mg, 1.29 mmol, 112.61 μL, 1.50 eq.) and N,N-dimethylformamide (6.27 mg, 85.76 μmol, 6.60 μL, 0.10 eq.) were added to anhydrous dichloromethane (10.00 mL) in order. The mixture was stirred at 20° C. for 1.5 h. After reaction, the reaction liquid was concentrated to obtain the crude, then was dissolved in methylbenzene (5 mL), vacuumed to spined out the solvent by rotary evaporation completely, and the procedure was repeated three times. Compound WXBB-2 was obtained.

Fragment WXBB-3

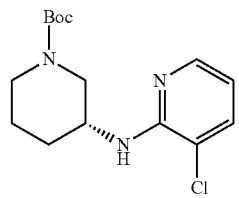 [SMILES: CC(C)(C)OC(=O)N1CCC[C@@H](Nc2ncccc2Cl)C1]

Synthetic Route:

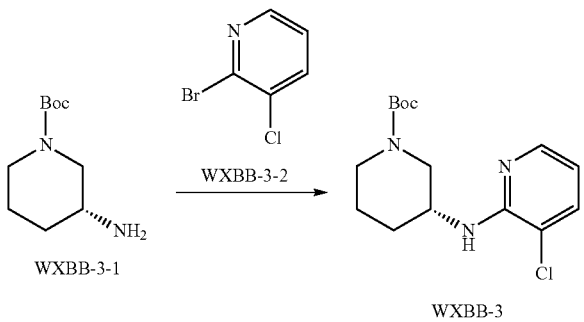 [SMILES: CC(C)(C)OC(=O)N1CCC[C@@H](N)C1 ; Clc1cccnc1Br ; CC(C)(C)OC(=O)N1CCC[C@@H](Nc2ncccc2Cl)C1]

Step 1: Synthesis of Compound WXBB-3

WXBB-3-1 (10.41 g, 51.96 mmol, 1.00 eq), sodium tert-butoxide (9.99 g, 103.92 mmol, 2.00 eq), (±)-2,2'-bis-diphenyl phosphino-1,1'-dinaphthyl(4.85 g, 7.79 mmol, 0.15 eq) and tris (dibenzylideneacetone) dipalladium (4.76 g, 5.20 mmol, 0.10 eq) were added to the solution mixture of anhydrous methylbenzene (150.00 mL) of WXBB-3-2 (10.00 g, 51.96 mmol, 1.00 eq). Under nitrogen condition, the mixture was stirred at 90° C. for 12 h. After reaction, the mixture was concentrated under vacuum. The residue was dissolved in ethyl acetate (500 mL), washed with water (200 mL*3) and saturated sodium chloride solution (500 mL) in order. The organic phase was dried with anhydrous sodium sulfate, filtered, and concentrated under vacuum to obtain the crude. The crude was purified by column chromatography (petroleum ether:ethyl acetate=100:0-5:1) to obtain the compound WXBB-3. $^1$H NMR (400 MHz, CDCl$_3$) δ ppm: 1.41 (s, 9H), 1.61 (br, s, 1H), 1.76-1.73 (m, 2H), 1.97-1.92 (m, 1H), 3.67-3.40 (br, m, 4H), 4.12 (br, 1H), 5.06 (br, 1H), 6.55-6.52 (m, 1H), 7.45 (d, J=7.6 Hz, 1H), 8.03 (d, J=4.8 Hz, 1H). MS m/z: 312.1 [M+H]$^+$.

Implementation 001: WX001

Synthetic Route:

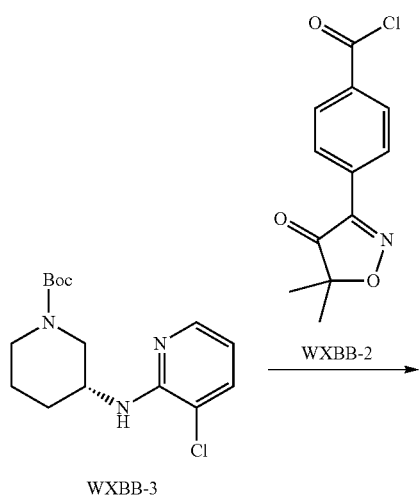

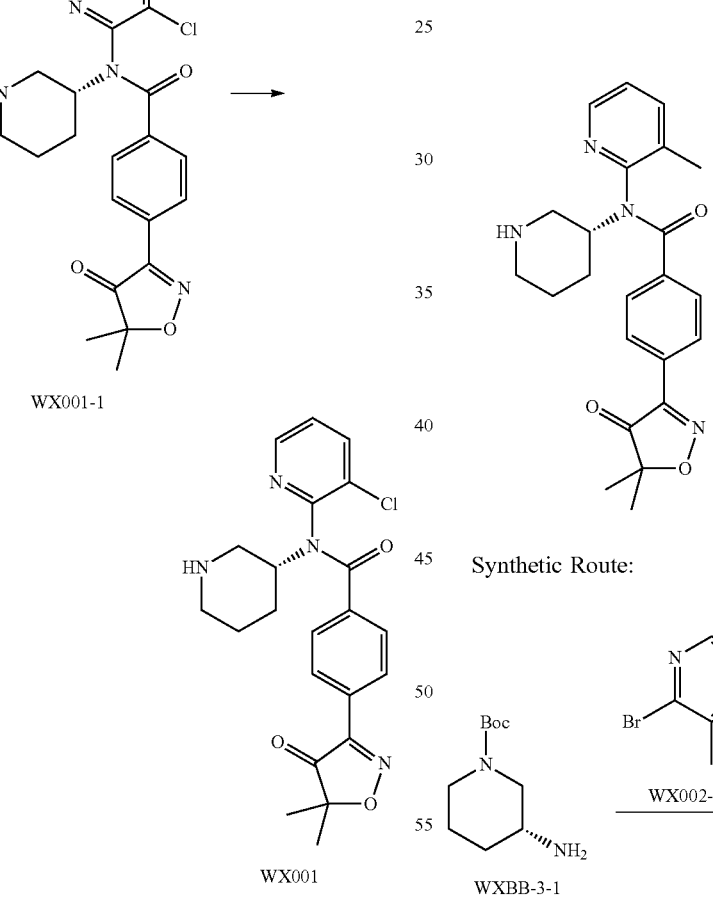

Step 1: Synthesis of Compound WX001-1

At 0° C., hexamethylenediamine lithium (1 M, 768.86 μL, 0.90 eq.) was added to the anhydrous tetrahydrofuran (5.00 mL) of WXBB-3 (213.10 mg, 683.43 μmol, 0.80 eq.) The reaction liquid was stirred for 1 h at 0° C., and then WXBB-2 (215.00 mg, 854.29 μmol, 1.00 eq.) was added. The mixture was reacted at 20° C. for 18 h under nitrogen condition. After reaction, the reaction liquid was quenched with water (30 mL) and extracted with ethyl acetate (30 mL*3). The organic phase was combined, dried with anhydrous sodium sulfate, filtered, and concentrated under vacuum to obtain the crude. The crude was purified by chromatographic column (petroleum ether:ethyl acetate=100:1-2:1) to obtain the yellow oily compound WX001-1. $^1$H NMR (400 MHz, CDCl3) δ ppm: 8.53 (br, 1H), 7.98 (d, J=8.03 Hz, 2H), 7.61 (br, 1H), 7.50 (d, J=8.03 Hz, 2H), 7.15-7.28 (m, 1H), 4.29-4.79 (br m, 2H), 4.23-3.95 (br m, 0.5H) 3.94-4.15 (br m, 1H), 3.40 (br m, 0.5H), 2.63 (br m, 1H), 1.91-2.46 (m, 1H), 1.91-2.09 (m, 1H), 1.67-1.88 (m, 2H), 1.45-1.60 (m, 15H). MS m/z: 471.1 [M-56+H]$^+$.

Step 2: Synthesis of Compound WX001

Hydrochloric acid/methanol solution (4 M, 1.00 mL, 35.13 eq.) was added to the methanol (5.00 mL) solution of WX001-1 (60.00 mg, 113.85 μmol, 1.00 eq.). The mixture was stirred at 20° C. for 1 h. After reaction, the reaction liquid was concentrated under vacuum to obtain the product WX001. $^1$H NMR (400 MHz, MeOD) δ ppm: 8.61-8.50 (m, 1H), 7.93 (d, J=8.0 Hz, 2H), 7.86-7.76 (m, 1H), 7.48-7.36 (m, 3H), 5.15-5.01 (m, 1H), 3.83-3.72 (m, 1H), 3.60 (t, J=12.0 Hz, 1H), 3.39 (br., 1H), 2.96-2.86 (m, 1H), 2.03 (m, 2H), 1.91 (m, 1H), 1.48 (m, 1H), 1.42 (s, 6H). MS m/z=427.1 [M+H]$^+$.

Implementation 002: WX002

Synthetic Route:

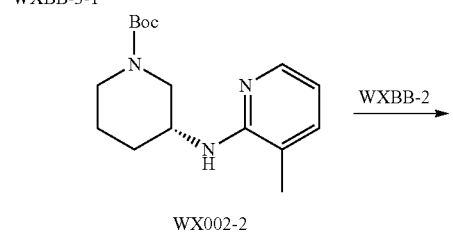

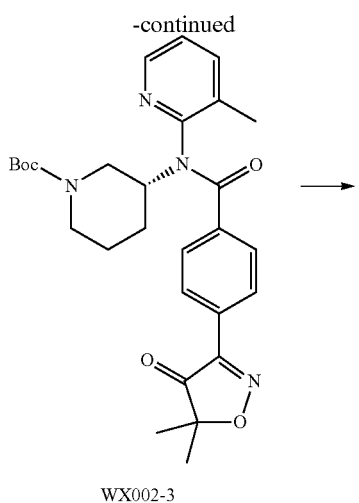

WX002-3

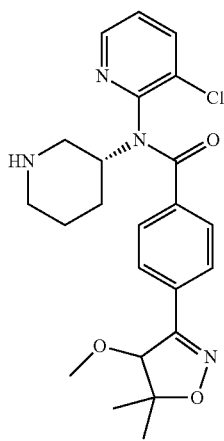

WX002

Step 1: Synthesis of Compound WX002-2

WXBB-3-1 (10.00 g, 49.93 mmol, 1.00 eq), WX002-1 (8.59 g, 49.93 mmol, 5.58 mL, 1.00 eq), sodium tert-butoxide (9.60 g, 99.86 mmol, 2.00 eq), (±)-2,2'-bis-diphenyl phosphino-1,1'-binaphthyl(4.66 g, 7.49 mmol, 0.15 eq) and tris(dibenzylideneacetone) dipalladium (4.57 g, 4.99 mmol, 0.10 eq) were placed in methylbenzene (20.00 mL). The mixture was displaced with nitrogen three times, and was then stirred at 90° C. for 16 h under nitrogen condition. After reaction, the reaction liquid was concentrated under vacuum to remove methylbenzene. Then residue was added with water (200 mL), extracted with ethyl acetate (200 mL*3). The organic phase was combined. The saturated sodium chloride solution (200 mL) was washed, dried with anhydrous sodium sulfate, and then filtered. The filtrate was concentrated under vacuum. The residue was purified by chromatographic column (petroleum ether:ethyl acetate=20/1-1:1) to obtain the compound WX002-2. $^1$H NMR (400 MHz, CDCl$_3$) δ ppm: 1.38 (s, 9H), 1.58 (br, s, 1H), 1.90-1.70 (m, 4H), 2.05 (s, 3H), 3.35-3.29 (m, 1H), 3.51 (br, 2H), 3.64-3.61 (m, 1H), 4.14-4.08 (m, 1H), 6.50 (t, J=6 Hz, 1H), 7.20 (d, J=6.8 Hz, 1H), 7.99 (d, J=4.8 Hz, 1H). MS m/z: 292.0 [M+H]$^+$.

Step 2: Synthesis of Compound WX002-3

At 0° C., hexamethylenediamine lithium (1 M, 2.38 mL, 3.00 eq) was dropwise added to tetrahydrofuran (10.00 mL) solution of WX002-2 (231.57 mg, 794.69 μmol, 1.00 eq), and the mixture was stirred at 0° C. for 1.5 h. Then tetrahydrofuran (5.00 mL) solution of WXBB-2 (200.00 mg, 794.69 μmol, 1.00 eq) and triethylamine (146.35 mg, 1.45 mmol, 200.48 μL, 1.82 eq) were added. The mixture was stirred at 20° C. for 14 h. After reaction, the reaction liquid was concentrated under vacuum, water (100 mL) was added to the residue, ethyl acetate (50 mL*3) was used for extraction. The organic phase was combined, washed with saturated sodium chloride solution (20 mL*2), dried with anhydrous sodium sulfate and filtered. The filtrate was concentrated under vacuum. The residue was purified by preparative chromatoplate (petroleum ether:ethyl acetate=1:1) to obtain the compound WX002-3. $^1$H NMR (400 MHz, CDCl$_3$) δ ppm: 8.35 (br s, 1H), 7.80 (br d, J=7.8 Hz, 2H), 7.34-7.21 (m, 3H), 7.08-6.98 (m, 1H), 4.44 (br d, J=11.7 Hz, 1H), 4.00 (br d, J=10.8 Hz, 1H), 3.44-3.25 (m, 1H), 2.65-2.21 (m, 2H), 1.95 (br d, J=15.3 Hz, 3H), 1.69 (br s, 2H), 1.62-1.50 (m, 2H), 1.43-1.34 (m, 15H). MS m/z: 507.2 [M+H]$^+$ Step 3: Synthesis of Compound WX002

At 0-10° C., hydrochloric acid/ethyl acetate (4 M, 1.00 mL) was added to the ethyl acetate (1.00 mL) solution of WX002-3 (30.00 mg, 56.85 μmol, 1.00 eq). The mixture was stirred at 20° C. for 1 h. After reaction, the filtrate was concentrated under vacuum, and the residue was purified by preparative high performance liquid chromatography (HPLC) to obtain the product WX002. H NMR (400 MHz, CDCl$_3$) δ: 9.33 (br s, 0.5H), 8.97 (br s, 0.5H), 8.38 (br s, 1H), 7.83-7.71 (m, 2H), 7.31 (br d, J=7.3 Hz, 1H), 7.19 (s, 2H), 7.14 (br s, 1H), 5.05 (br s, 4H), 4.02-3.06 (m, 2.5H), 2.82 (br s, 0.5H), 1.98 (br s, 1H), 1.87 (br s, 3H), 1.72 (br s, 1H), 1.35 (s, 6H). MS m/z: 407.1 [M+H]$^+$.

Implementation 003: WX003, WX004, WX005

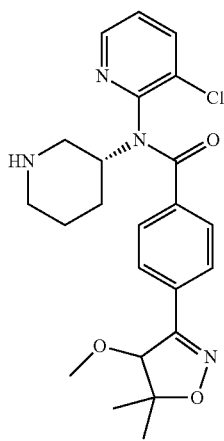

WX003

51
-continued
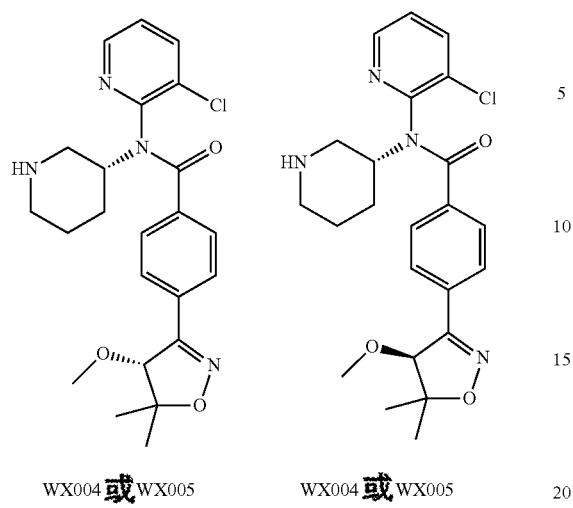
Synthetic Route:
52
-continued
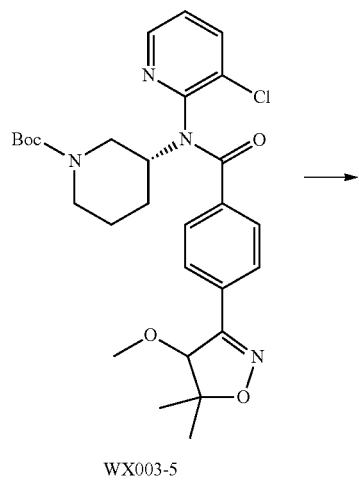
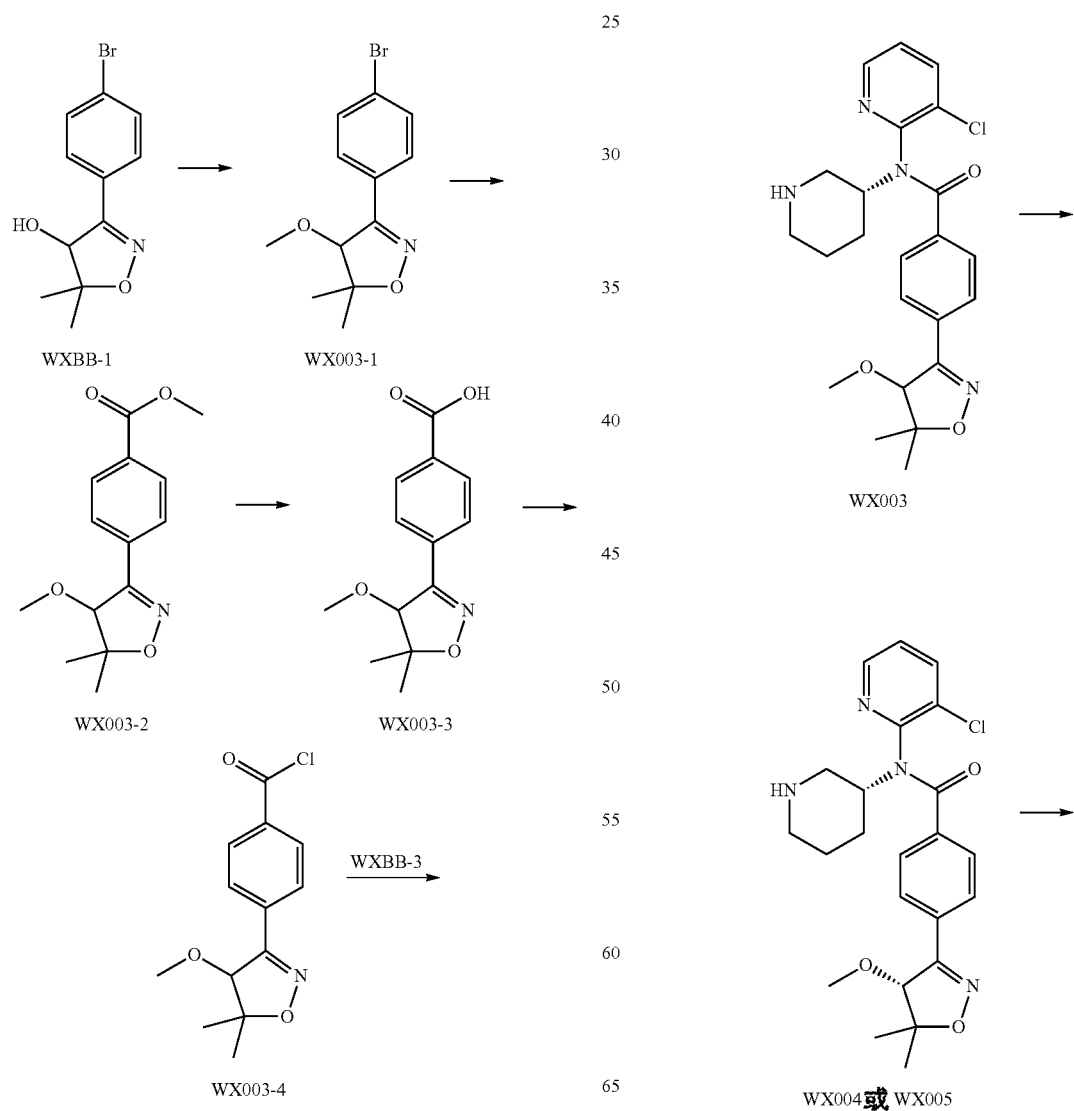

-continued

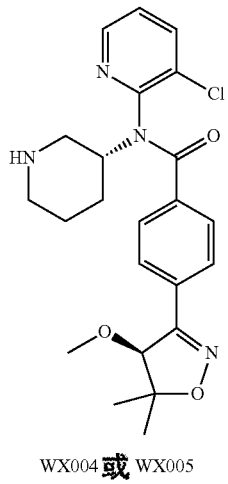

WX004 或 WX005

Step 1: Synthesis of Compound WX003-1

At 0° C., sodium-hydrogen (500.00 mg, 12.50 mmol, 60% purity, 1.21 eq) was repeatedly added to the tetrahydrofuran (60.00 mL) solution of compound WXBB-1 (2.80 g, 10.37 mmol, 1.00 eq). The mixture was stirred at this temperature for half an hour. Then, iodomethane (2.06 g, 14.52 mmol, 903.81 μL, 1.40 eq) was added to the reaction liquid which was then continuously stirred at 20° C. for 2 h. The mixture was quenched with saturated ammonia chloride (60 mL) and extracted with ethyl acetate (100 mL) for two times. The organic phase was combined, the mixture was dried by rotary evaporation and purified by column (petroleum ether: ethyl acetate=1:0-40:1) to obtain the compound WX003-1. H NMR (400 MHz, CDCl$_3$) δ ppm: 7.51-7.58 (m, 2H) 7.44-7.50 (m, 2H) 4.45 (s, 1H) 3.28-3.42 (m, 3H) 1.46 (s, 3H) 1.21-1.36 (m, 3H). MS m/z: 286.0 [M+H+2]$^+$ Step 2: Synthesis of Compound WX003-2

Compound WX003-1 (2.30 g, 8.00 mmol, 1.00 eq, 98.82%) was dissolved in the mixed solution of N,N-dimethylformamide (50.00 mL) and methanol (150.00 mL), and then triethylamine (2.43 g, 24.00 mmol, 3.33 mL, 3.00 eq) and tetrakis (triphenylphosphine) palladium (1.00 g, 865.38 μmol, 0.11 eq) were added. The mixture was reacted under carbon monoxide at 80° C. and stirred in a hydrogenation bottle under 50 psi for 40 h. The reaction liquid was concentrated to obtain the crude, and the crude was purified by chromatographic column (petroleum ether:ethyl acetate=1:0-5:1) to obtain the compound WX003-2. MS m/z: 263.9 [M+H]$^+$.

Step 3: Synthesis of Compound WX003-3

Lithium hydroxide monohydrate (1.49 g, 35.45 mmol, 5.00 eq) was added to the mixed solution of tetrahydrofuran (50.00 mL) and water (25.00 mL) of compound WX003-2 (2.00 g, 7.09 mmol, 1.00 eq, 93.33%). The reaction liquid was stirred at 20° C. for 16 h. Most of tetrahydrofuran in the reaction liquid was removed by rotary evaporation. The reaction liquid was neutralized with 1 mol aqueous hydrochloric acid solution to pH=4-6, and there were a lot of precipitations of solid. They were filtered and dried by rotary evaporation to obtain the compound WX003-3. $^1$H NMR (400 MHz, DMSO-d6) δ ppm: 8.07 (d, J=8.53 Hz, 2H) 7.89 (d, J=8.53 Hz, 2H) 4.88 (s, 1H) 3.50 (s, 4H) 1.50 (s, 3H) 1.34 (s, 3H). MS: m/z: 250.0 [M+H]$^+$.

Step 4: Synthesis of Compound WX003-4

Oxalyl chloride (188.50 mg, 1.49 mmol, 130.00 μL, 1.24 eq) and N,N-dimethylformamide (9.50 mg, 129.98 μmol, 10.00 μL, 0.11 eq) were added to the mixture of dichloromethane (5.00 mL) of WX003-3 (300.00 mg, 1.20 mmol, 1.00 eq), and the reaction liquid was stirred at 20° C. for 2 h. After reaction, the reaction liquid was dry-spined under vacuum. Methylbenzene (10 mL) was added to the residue, then the mixture was spined dry under vacuum with oil pump at 50° C., the operation was repeated three times to obtain WX003-4.

Step 5: Synthesis of Compound WX003-5

At 0° C., hexamethylenediamine lithium (1 M, 1.80 mL, 1.50 eq) was added to the mixture of WXBB-3 (415.00 mg, 1.20 mmol, 1.00 eq) and tetrahydrofuran (5.00 mL), and the reaction liquid was stirred at 0° C. for 1 h. WX003-4 (320.00 mg, 1.20 mmol, 1.00 eq) was added to the reaction liquid. The reaction solution was stirred at 25° C. for 18 h. After reaction, the reaction liquid was added with water (20 mL), and then extracted with dichloromethane (20 mL*3). The organic phase was washed with saturated sodium chloride solution (50 mL), dried with anhydrous sodium sulfate and filtered. The filtrate was vacuumed with water pump at 50° C. and dried to obtain the crude by rotary evaporation. The crude was purified by column chromatography (petroleum ether:ethyl acetate=1:0-1:1) to obtain the product WX003-5. $^1$H NMR (400 MHz, CDCl$_3$) δ 8.38 (br s, 1H), 7.44 (br d, J=7.78 Hz, 3H), 7.31 (br d, J=7.78 Hz, 2H), 6.99-7.15 (m, 1H), 3.90-4.68 (m, 4H), 3.32 (br s, 4H), 2.48 (br s, 1H), 1.98 (s, 2H), 1.56-1.75 (m, 2H), 1.33-1.47 (m, 12H), 1.24 (s, 3H). MS m/z: 487.1[M-56+H]$^+$.

Step 6: Synthesis of Compound WX003

Hydrochloric acid/methanol solution (4 M, 5.00 mL, 36.20 eq) was added to the ethyl acetate (5.00 mL) solution of WX003-5 (300.00 mg, 552.44 μmol, 1.00 eq). The reaction liquid was reacted at 25° C. for 2 h. After reaction, the reaction liquid was dried by rotary evaporation under vacuum to obtain WX003.

$^1$H NMR (400 MHz, MeOD) δ 8.38-8.69 (m, 1H), 7.77 (br d, J=7.78 Hz, 1H), 7.54 (br d, J=7.78 Hz, 2H), 7.19-7.44 (m, 3H), 5.04 (br s, 1H), 4.61 (s, 1H), 3.65-3.84 (m, 1H), 3.56 (br t, J=11.80 Hz, 1H), 3.42 (br d, J=6.02 Hz, 3H), 3.35 (br s, 1H), 2.87 (br t, J=11.92 Hz, 1H), 1.72-2.39 (m, 3H), 1.44 (s, 4H), 1.27 (s, 3H). MS m/z: 443.2[M+H]$^+$

Step 6: Synthesis of compounds WX004, WX005

250 mg of WX003 250 mg was separated by SFC (column: AD (250 mm*30 mm, 5 μm); mobile phase: [0.1% NH$_3$ water ETOH]; B %: 35%-35%, min), and two compounds WX004 and WX005 were obtained by chiral separation.

WX004:

Prepeak, Rt=4.300, $^1$H NMR (400 MHz, MeOD-d4) δ 8.44-8.68 (m, 1H), 7.78 (br d, J=8.03 Hz, 1H), 7.54 (br d, J=8.03 Hz, 2H), 7.23-7.43 (m, 3H), 4.99-5.16 (m, 1H), 4.61 (s, 1H), 3.64-3.85 (m, 1H), 3.48-3.62 (m, 1H), 3.43 (s, 3H), 3.34 (br d, J=13.80 Hz, 1H), 2.80-2.99 (m, 1H), 2.80-2.99 (m, 1H), 1.75-2.45 (m, 4H), 1.44 (s, 3H), 1.27 (s, 3H). MS m/z: 443.2 [M+H]$^+$.

WX005:

Postpeak, Rt=4.432, $^1$H NMR (400 MHz, MeOD) δ ppm: 8.61-8.50 (m, 1H), 7.93 (m, 1H), 7.86-7.76 (d, J=8.0 Hz, 2H), 7.48-7.36 (m, 3H), 5.15-5.01 (m, 1H), 4.62 (s, 1H), 3.83-3.72 (m, 1H), 3.60 (t, J=12.0 Hz, 1H), 3.42 (s, 3H), 3.39 (br. s., 1H), 2.96-2.86 (m, 1H), 2.03 (d, J=12.0 Hz, 2H), 1.91 (d, J=13.6 Hz, 1H), 1.45 (s, 4H), 1.27 (s, 3H). MS m/z: 443.2 [M+H]$^+$.

Implementation 004: WX006

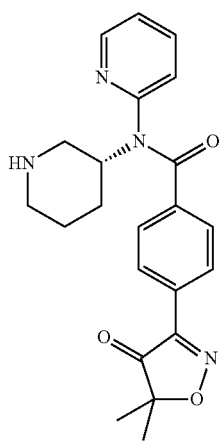 [SMILES: CC1(C)ON=C(c2ccc(C(=O)N(c3ccccn3)[C@@H]3CCCNC3)cc2)C1=O]

Synthetic Route:

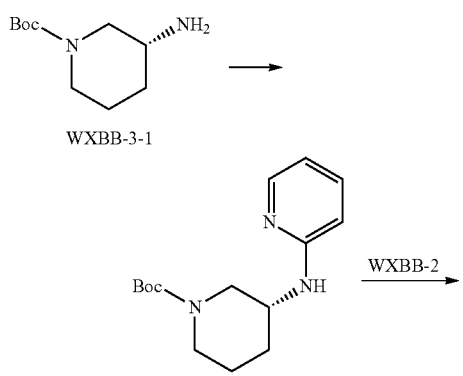

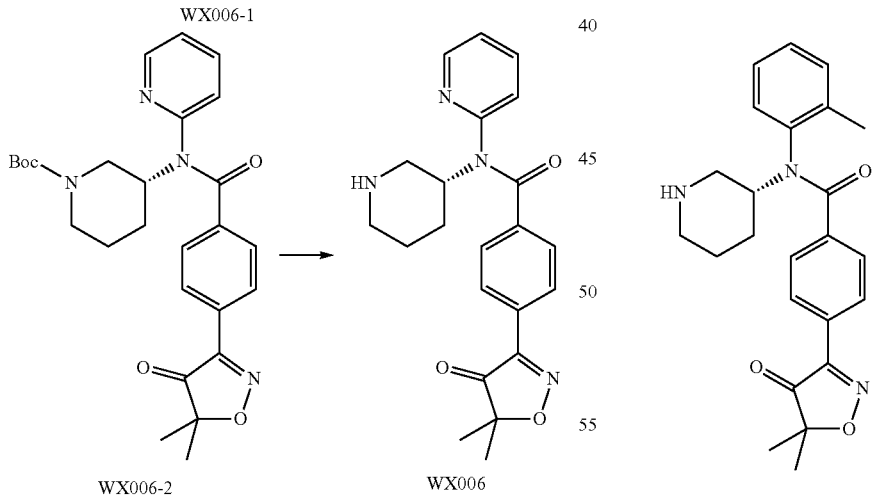

Step 1: Synthesis of Compound WX006-1

WXBB-3-1 (1.27 g, 6.33 mmol, 1.00 eq) and 2-bromopyridine (1.00 g, 6.33 mmol, 602.41 µL, 1.00 eq) were dissolved in methylbenzene (20.00 mL). The mixture was placed in a 50 mL single-mouth round-bottom flask, which was then added with tris(dibenzylideneacetone)dipalladium (579.65 mg, 633.00 µmol, 0.10 eq), (±)-2,2'-bis-diphenyl phosphino-1,1'-binaphthyl(591.23 mg, 949.50 µmol, 0.15 eq) and potassium tert-butoxide (1.48 g, 13.17 mmol, 2.08 eq). The mixture was stirred at 90° C. for 16 h under nitrogen condition. After reaction, the mixture was concentrated, then was added with water (30 mL) and extracted with dichloromethane (20 mL*3), The organic phase was dried with sodium sulfate, filtered, and concentrated. The crude was purified by chromatographic column (petroleum ether:ethyl acetate=30:1-1:1), and further purified by preparative HPLC to obtain WX006-1. $^1$H NMR (400 MHz, CDCl$_3$) δ ppm: 8.07 (d, J=4 Hz, 1H), 7.44-7.40 (m, 1H), 6.59-6.56 (m, 1H), 6.43 (d, J=8.4 Hz, 1H), 4.52 (br, 1H), 4.00-2.8 (br m, 4H), 2.01-1.97 (m, 1H), 1.77-1.71 (m, 1H), 1.60- 1.56 (m, 2H), 1.43 (s, 9H). MS m/z: 278.1 [M+H]$^+$.

Step 2: Synthesis of Compound WX006-2

WX006-1 (200.00 mg, 721.08 µmol, 1.00 eq) was dissolved in 2 mL of tetrahydrofuran, then hexamethylenediamine lithium (1 M, 1.10 mL, 1.53 eq) was added. The mixture was stirred for 0.5 h. The tetrahydrofuran (8 mL) solution of WXBB-2 (199.62 mg, 793.19 µmol, 1.10 eq) was added, and the mixed solution was stirred at 25° C. for 20 h. After reaction, the reaction liquid was concentrated. The crude was purified by preparative HPLC (petroleum ether: ethyl acetate=1:1) to obtain WX006-2. MS m/z: 493.2 [M+H]$^+$.

Step 3: Synthesis of Compound WX006

WX006-2 (91.00 mg, 102.50 µmol, 1.00 eq) was dissolved in ethyl acetate (3.00 mL), and hydrochloric acid/ ethyl acetate solution (4 M, 5.00 mL, 195.12 eq) was added. The mixture was stirred at 25° C. for 2 h. After reaction, the reaction liquid was concentrated to obtain the crude, and the crude was purified by preparative HPLC to obtain WX006. $^1$H NMR (400 MHz, CDCl$_3$) δ ppm: 8.53 (d, J=3.6 Hz, 1H), 7.93 (d, J=8.4 Hz, 2H), 7.50-7.47 (m, 1H), 7.33 (d, J=8.4 Hz, 2H), 7.19-7.16 (m, 1H), 6.77 (d, J=8.0 Hz, 1H) 5.05 (br, 1H), 3.78-3.76 (m, 1H), 3.68-3.62 (m, 1H), 3.43-3.40 (m, 1H), 2.96 (br, 1H), 2.05 (br, 1H), 1.98-1.90 (m, 3H), 1.46 (s, 6H). MS m/z: 393.1 [M+H]$^+$.

Implementation 005: WX007

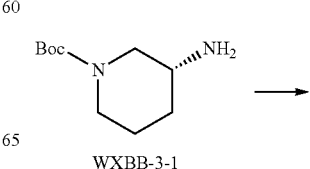

Synthetic Route:

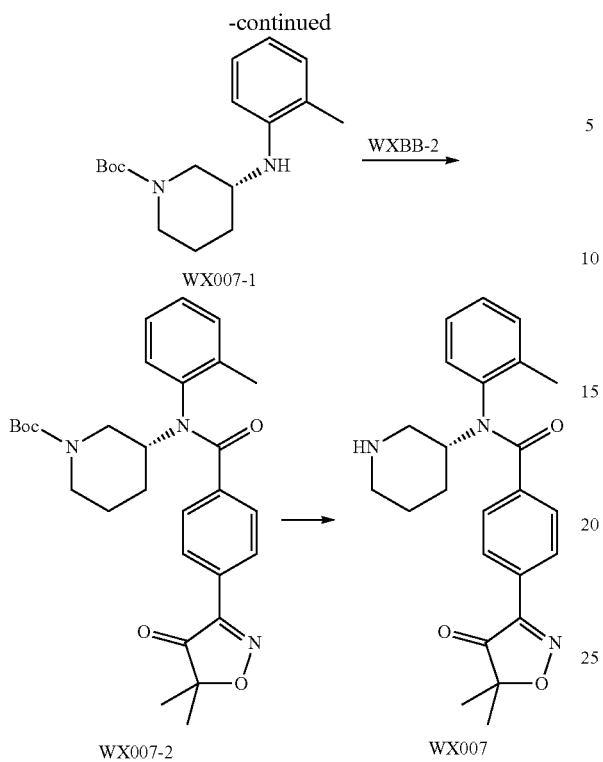

Step 1: Synthesis of Compound WX007-1

Under nitrogen condition, WXBB-3-1 (1.16 g, 5.81 mmol, 1.00 eq) and 2-bromotoluene (994.00 mg, 5.81 mmol, 700.00 µL, 1.00 eq) were dissolved in methylbenzene (20.00 mL), then the mixture was placed in a 50 mL single-mouth round-bottom flask. Tris (dibenzylideneacetone) dipalladium (532.00 mg, 581.00 µmol, 0.10 eq), 1,1'-binaphthyl-2,2'-bis (diphenylphosphino) (542.66 mg, 871.50 µmol, 0.15 eq) and potassium tert-butoxide (1.36 g, 12.08 mmol, 2.08 eq) were added. The mixture solution was stirred at 90° C. for 18 h. After reaction, the reaction liquid was concentrated, then diluted with water (30 mL) and extracted with dichloromethane (3*30 mL). The organic phase was combined and dried with anhydrous sodium sulfate, filtered and concentrated. The crude was purified by column chromatography (ethyl acetate/petroleum ether=1~20%) to obtain the compound WX007-1. H NMR (400 MHz, CDCl$_3$) δ ppm: 7.14-7.05 (m, 2H), 6.71-6.64 (m, 2H), 3.89-3.65 (m, 1H), 3.64-3.45 (m, 3H), 3.32-3.17 (m, 1H), 3.30-2.99 (m, 1H), 2.12 (s, 3H), 1.98 (br, 1H), 1.85-1.75 (min, 1H), 1.59-1.56 (m, 1H), 1.45 (s, 10H). MS m/z: 291.1 [M+H]$^+$ Step 2: Synthesis of Compound WX007-2

Under nitrogen condition, the compound WX007-1 (200.00 mg, 688.71 µmol, 1.00 eq) was dissolved in tetrahydrofuran (2 mL), lithium bis (trimethylsilyl) amide (1 M, 1.00 mL, 1.45 eq) was added. The mixture was stirred at 20° C. for 0.5 h. Then, the tetrahydrofuran solution (5 mL) of WXBB-2 (190.00 mg, 754.96 µmol, 1.10 eq) was added. The mixture solution was stirred at 20° C. for 16 h. After reaction, the reaction liquid was quenched with water (10 mL), and extracted with ethyl acetate. The organic phase was combined and dried with anhydrous sodium sulfate, filtered, and concentrated. The crude was purified by Prep-TLC (petroleum ether:ethyl acetate=3:1) to obtain WX007-2. MS m/z: 506.2 [M+H]$^+$ Step 3: Synthesis of Compound WX007

Compound WX007-2 (30.00 mg, 59.33 µmol, 1.00 eq) was dissolved in ethyl acetate (3.00 mL), and hydrochloric acid/ethyl acetate solution (4 M, 3.00 mL, 202.26 eq) was added. The mixture was stirred at room temperature (28° C.) for 2 h. After reaction, the reaction liquid was concentrated to obtain the crude, and the crude was purified by preparative HPLC to obtain WX007. H NMR (400 MHz, CDCl$_3$) δ ppm: 7.90 (d, J=8.4 Hz, 2H), 7.42 (d, J=8.4 Hz, 2H), 7.38-7.33 (m, 1H), 7.24-7.22 (m, 2H), 7.17-7.15 (m, 1H), 4.6-4.7 (m, 1H), 3.89-3.65 (m, 1H), 3.39-3.36 (m, 1H), 3.05-3.2 (m, 0.5H), 2.94-2.88 (m, 1H), 2.3-2.45 (m, 0.5H), 2.19-1.15 (m, 3H), 2.05-1.85 (m, 3H), 1.59-1.56 (m, 1H), 1.41 (s, 6H). MS m/z: 406.1 [M+H]$^+$ Implementation 006: WX008

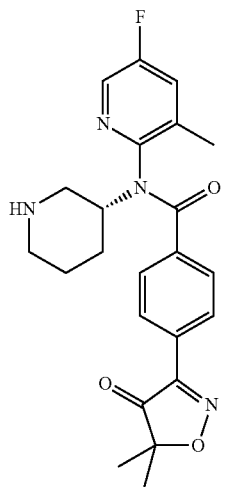 [SMILES: Cc1cc(F)cnc1N(C(=O)c1ccc(C2=NOC(C)(C)C2=O)cc1)[C@@H]1CCCNC1]

Synthetic Route:

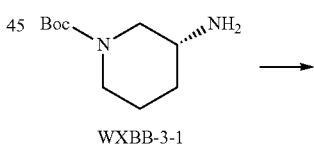

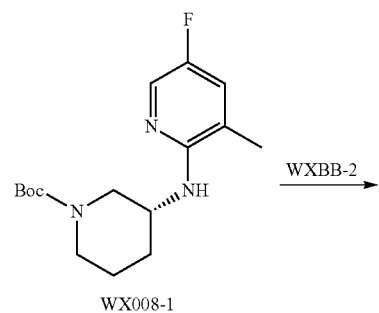

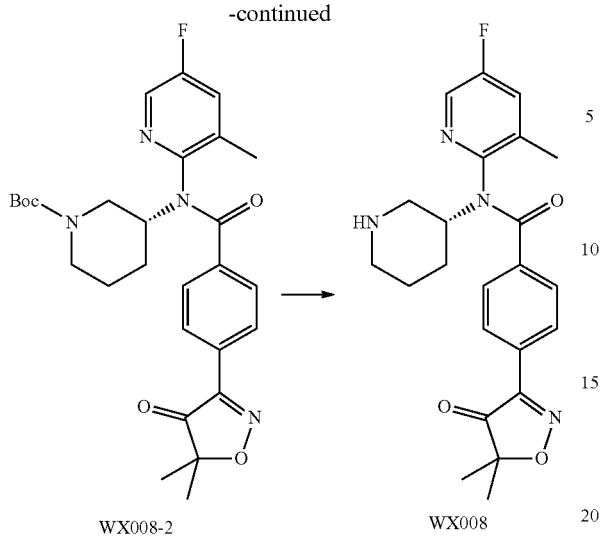

reaction, the solvent was spined out by rotary evaporation. The crude was purified by prep-TLC (dichloromethane: methanol=10:1) to obtain WX008. $^1$H NMR (400 MHz, MeOD) δ ppm: 1.18-1.33 (m, 1H), 1.40 (s, 6H), 1.59-1.87 (m, 3H), 2.01-2.14 (m, 3H), 2.24-2.58 (m, 2H), 2.98 (br d, J=10.04 Hz, 1H), 3.15 (br t, J=11.42 Hz, 1H), 3.47 (br d, J=11.80 Hz, 1H), 4.47-4.80 (m, 1H), 7.34 (br d, J=7.53 Hz, 3H), 7.91 (br d, J=8.03 Hz, 2H), 8.21-8.44 (m, 1H).

Implementation 007: WX009

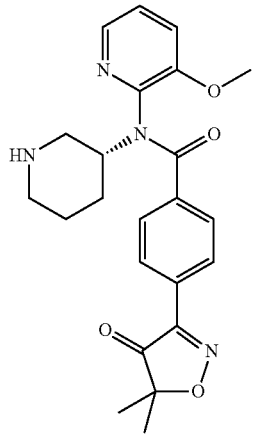 [SMILES: COc1cccnc1N(C(=O)c1ccc(C2=NOC(C)(C)C2=O)cc1)[C@@H]1CCCNC1]

Step 1: Synthesis of Compound WX008-1

Under nitrogen condition, 2-bromine-5-fluorine-3-methylpyridine (1.00 g, 5.26 mmol, 1.00 eq), WXBB-3-1 (1.05 g, 5.26 mmol, 1.00 eq), sodium tert-butoxide (1.01 g, 10.53 mmol, 2.00 eq), 1,1'-binaphthyl-2,2'-bis (diphenylphosphino) (492.00 mg, 790.15 μmol, 0.15 eq) and tris (dibenzylideneacetone) dipalladium (482.00 mg, 526.36 μmol, 0.10 eq) were added in methylbenzene (20.00 mL). The mixture was stirred at 90° C. for 16 h. After reaction, the reaction liquid was added with water and then extracted with ethyl acetate (3*20 mL). The organic phase was washed with saturated sodium chloride solution (20 mL), dried with anhydrous magnesium sulfate, filtered, and concentrated to obtain the crude. The crude was purified by column chromatography (ethyl acetate:petroleum ether=5~20%) to obtain WX008-1. $^1$H NMR (400 MHz, CDCl$_3$) δ ppm: 1.40 (br s, 9H), 1.60 (br s, 1H), 1.66-1.81 (m, 2H), 1.91 (br s, 1H), 2.08 (s, 3H), 3.31-3.40 (m, 1H), 3.41-3.54 (m, 2H), 3.65 (br d, J=12.80 Hz, 1H), 4.07 (br s, 1H), 7.06 (br d, J=8.28 Hz, 1H), 7.86 (d, J=2.76 Hz, 1H).

Step 2: Synthesis of Compound WX008-2

Under nitrogen condition, WX008-1 (211.00 mg, 682.01 μmol, 0.80 eq) was added to anhydrous tetrahydrofuran (5.00 mL). Lithium bis (trimethylsilyl) amide (1 M, 682.00 μL, 0.80 eq) was added at 0° C. The mixture was stirred for 1 h, then added with WXBB-2 (215.00 mg, 854.29 μmol, 1.00 eq), warmed to 25° C. and stirred for 18 h. After reaction, the reaction liquid was added with water (10 mL) and extracted with ethyl acetate (3*12 mL). The organic phase was washed with saturated sodium chloride solution (10 mL), dried with anhydrous sodium sulfate, filtered and concentrated. The crude was purified by column chromatography (ethyl acetate:petroleum ether=5~30%) to obtain WX008-2. $^1$H NMR (400 MHz, CDCl$_3$) δ ppm: 0.87 (br d, J=11.04 Hz, 2H), 1.26-1.27 (m, 2H), 1.45 (s, 9H), 1.49 (br s, 6H), 2.03-2.08 (m, 3H), 2.28-2.68 (m, 1H), 3.34 (br s, 1H), 4.00-4.18 (m, 2H), 4.46-4.67 (m, 1H), 7.05 (br s, 1H), 7.36 (br d, J=6.53 Hz, 2H), 7.91 (br d, J=8.03 Hz, 2H), 8.26 (br s, 1H).

Step 3: Synthesis of Compound WX008

Compound WX008-2 (65.00 mg, 123.91 μmol, 1.00 eq) was added to hydrochloric acid/ethyl acetate (4 M, 1.55 mL, 50.00 eq). The mixture was stirred at 25° C. for 16 h. After Synthetic Route:

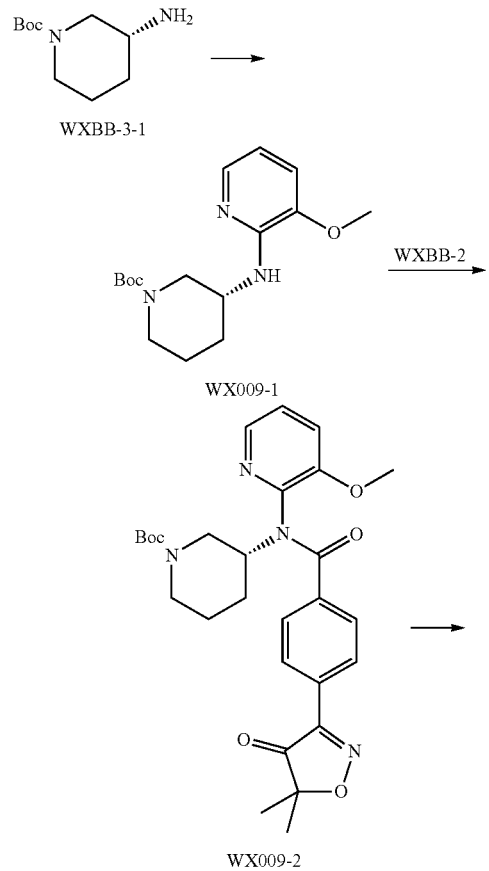

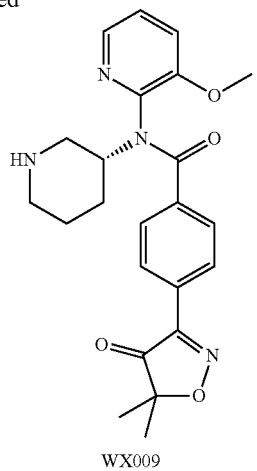

WX009

Step 1: Synthesis of Compound WX009-1

Under nitrogen condition, sodium tert-butoxide (1.02 g, 10.64 mmol, 2.00 eq), 1,1'-binaphthyl-2,2'-bis (diphenylphosphino) (497.00 mg, 798.00 μmol, 0.15 eq) and tris (dibenzylideneacetone)dipalladium (487.00 mg, 532.00 μmol, 0.10 eq) were added in methylbenzene (25.00 mL), then 2-bromine-3-methoxypyridine (1.00 g, 5.32 mmol, 1.00 eq) and WXBB-3-1 (1.07 g, 5.32 mmol, 1.00 eq) were added. The mixture was stirred at 90° C. for 16 h. After reaction, the reaction liquid was added with water (50 mL) and extracted with ethyl acetate (3*50 mL). The organic phase was washed with saturated sodium chloride solution (40 mL), dried with anhydrous magnesium sulfate, filtered, and concentrated. The crude was purified by column chromatography (ethyl acetate:petroleum ether=5~20%) to obtain WX009-1. $^1$H NMR (400 MHz, CDCl$_3$) δ ppm: 1.31 (br s, 9H), 1.42-1.92 (m, 5H), 3.24-3.62 (m, 3H), 3.73 (s, 3H), 3.98-4.07 (m, 1H), 4.89 (br d, J=7.78 Hz, 1H), 6.44 (dd, J=7.65, 5.14 Hz, 1H), 6.70-6.77 (m, 1H), 7.62 (dd, J=5.14, 1.38 Hz, 1H).

Step 2: Synthesis of Compound WX009-2

Under nitrogen condition, compound WX009-1 (269.00 mg, 682.59 μmol, 0.80 eq) was added to tetrahydrofuran (5.00 mL), lithium bis(trimethylsilyl)amide (1 M, 853.00 μL, 1.00 eq) was added at 0° C. The mixture was stirred for 1 h, and WXBB-2 (215.00 mg, 854.29 μmol, 1.00 eq) was added. Then, the mixture was warmed to 25° C. The mixture was stirred for 16 h. After reaction, the reaction liquid was added with water (10 mL), extracted with ethyl acetate (3*12 mL). The organic phase was washed with saturated sodium chloride solution (10 mL), dried with anhydrous sodium sulfate, filtered, and concentrated. The crude was purified by column chromatography (methanol:dichloromethane=1~5%) to obtain WX009-2. m/z=523.2 [M+1].

Step 3: Synthesis of Compound WX009

Compound WX009-2 (235.00 mg, 449.68 μmol, 1.00 eq) was added in hydrochloric acid/ethyl acetate solution (4 M, 4.50 mL, 40.00 eq). The mixture was stirred at 25° C. for 16 h. After reaction, the solvent was spined out. pH was adjusted with saturated sodium bicarbonate solution to pH≈7. The mixture solution was extracted with ethyl acetate (3*10 mL). The organic phase was washed with saturated sodium chloride solution (10 mL), dried with anhydrous magnesium sulfate, filtered and concentrated. The crude was separated by prep-TLC (dichloromethane:methyl alcohol=10:1) to obtain WX009. $^1$H NMR (400 MHz, MeOD) δ ppm: 1.20-1.34 (m, 2H), 1.39 (s, 6H) 1.54-1.92 (m, 3H), 2.15-2.49 (m, 2H), 2.88-3.04 (m, 2H), 3.59-3.73 (m, 3H), 4.51-4.73 (m, 1H), 7.21- 7.31 (m, 2H), 7.35 (br d, J=8.03 Hz, 2H), 7.87 (d, J=8.28 Hz, 1H), 7.85-7.91 (m, 1H), 8.02-8.11 (m, 1H).

Implementation 008: WX010

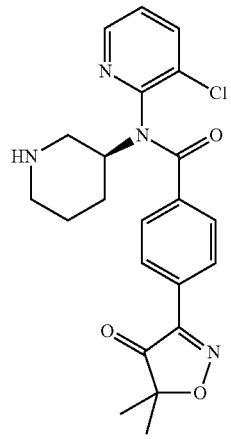 [SMILES: CC1(C)ON=C(c2ccc(C(=O)N(c3ncccc3Cl)[C@H]3CCCNC3)cc2)C1=O]

Synthetic Route:

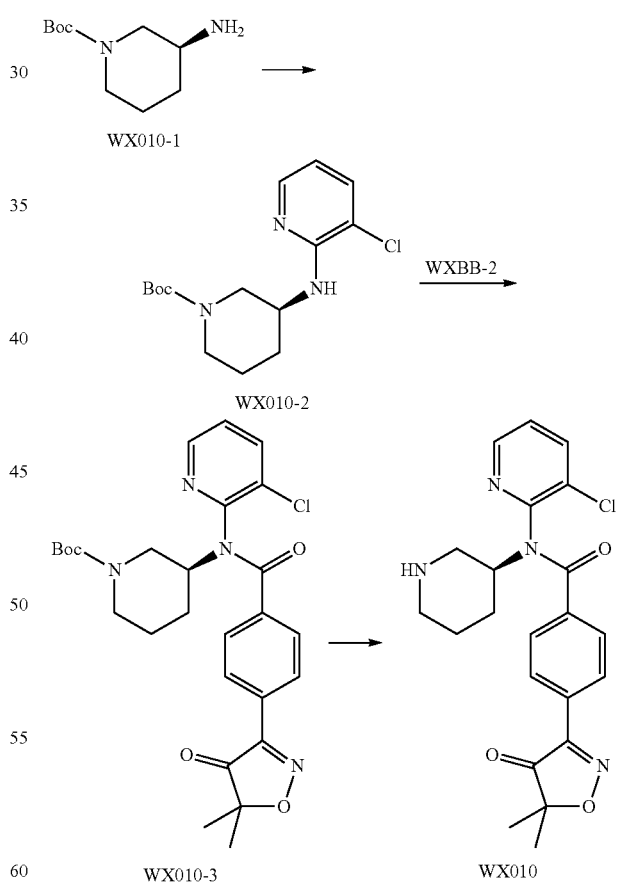

Step 1: Synthesis of Compound WX010-2

Under nitrogen atmosphere, 2,3-dichloropyridine (100.00 mg, 675.72 μmol, 1.00 eq), WX010-1 (148.87 mg, 743.29 μmol, 1.10 eq), sodium tert-butoxide (129.87 mg, 1.35 mmol, 2.00 eq), 1,1'-binaphthyl-2,2'-bis (diphenylphosphino) (84.15 mg, 135.14 μmol, 0.20 eq) and tris(dibenzylideneacetone) dipalladium (61.88 mg, 67.57 μmol, 0.10 eq) were dissolved in methylbenzene (5.00 mL). The reaction liquid was then agitated for 12 h at 90° C. After reaction, it was filtered through the diatomite. The filter cake was washed with dichloromethane (20 mL). The filtrate was dried by rotary evaporation for crude which was then purified by prep-TLC (petroleum ether:ethyl acetate=8:1) for WX010-2. $^1$H NMR (400 MHz, CDCl$_3$) δ ppm: 8.05 (d, J=4.90 Hz, 1H), 7.47 (d, J=4.90 Hz, 1H), 6.55 (dd, J=7.48 Hz, 1H), 5.07 (br s, 1H), 4.18-4.07 (m, 1H), 3.75-3.35 (m, 3H), 2.03-1.93 (m, 1H), 1.83-1.71 (m, 2H), 1.69-1.66 (m, 2H), 1.43 (s, 9H).

Step 2: Synthesis of Compound WX010-3

Under nitrogen condition, WX010-2 (139.76 mg, 448.21 μmol, 0.80 eq) was dissolved in anhydrous tetrahydrofuran (5.00 mL), and lithium bis(trimethylsilyl)amide (1 M, 504.23 μL, 0.90 eq) was added at 0° C. to reaction liquid. The reaction liquid was stirred at 0° C. for 1 h, and then WXBB-2 (141.00 mg, 560.26 μmol, 1.00 eq) was added to reaction liquid at 0° C. The reaction liquid was stirred at 25° C. for 12 h. After reaction, the reaction liquid was added to 10 mL of ice water, and then extracted with ethyl acetate (10 mL*3). The organic phase was washed with saturated sodium chloride solution (10 mL), dried with anhydrous sodium sulfate, filtered, and dried by rotary evaporation to obtain the crude. The crude was purified by preparative thin-layer chromatography (petroleum ether/ethyl acetate=3:1) to obtain WX010-3. $^1$H NMR (400 MHz, CDCl$_3$) δ ppm: 8.52-8.43 (m, 1H), 7.97-7.88 (m, 2H), 7.61-7.51 (m, 1H), 7.49-7.40 (m, 2H), 7.21-7.12 (m, 1H), 4.73-4.45 (m, 2H), 4.40-3.95 (m, 2H), 3.41-3.25 (m, 1H), 2.75-2.45 (m, 1H), 2.35-1.90 (m, 1H), 1.53-1.4 (m, 11H), 1.46 (s, 6H).

Step 3: Synthesis of Compound WX010

WX010-3 (80.00 mg, 151.80 μmol, 1.00 eq) was dissolved in methanol (4.00 mL), and then hydrochloric acid/methanol solution (4 M, 2.00 mL) was added. Under nitrogen condition, the reaction liquid was stirred for 1 h at 25° C. After reaction, the reaction liquid was directly dried by rotary evaporation to obtain the target product WX010. $^1$H NMR (400 MHz, MeOD) δ ppm: 8.62-8.50 (m, 1H), 7.93 (d, J=8.16 Hz, 2H), 7.86-7.75 (m, 1H), 7.51-7.36 (m, 3H), 5.14-5.01 (m, 1H), 3.85-3.70 (m, 1H), 3.65-3.55 (m, 1H), 3.41-3.35 (m, 1H), 2.96- 2.85 (m, 1H), 2.19-1.98 (m, 2H), 1.96-1.83 (m, 1H), 1.53-1.44 (m, 1H), 1.42 (s, 6H).

Implementation 009: WX011

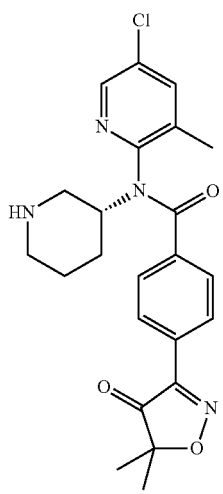 [SMILES: Cc1cc(Cl)cnc1N(C(=O)c1ccc(C2=NOC(C)(C)C2=O)cc1)[C@@H]1CCCNC1]

Synthetic Route:

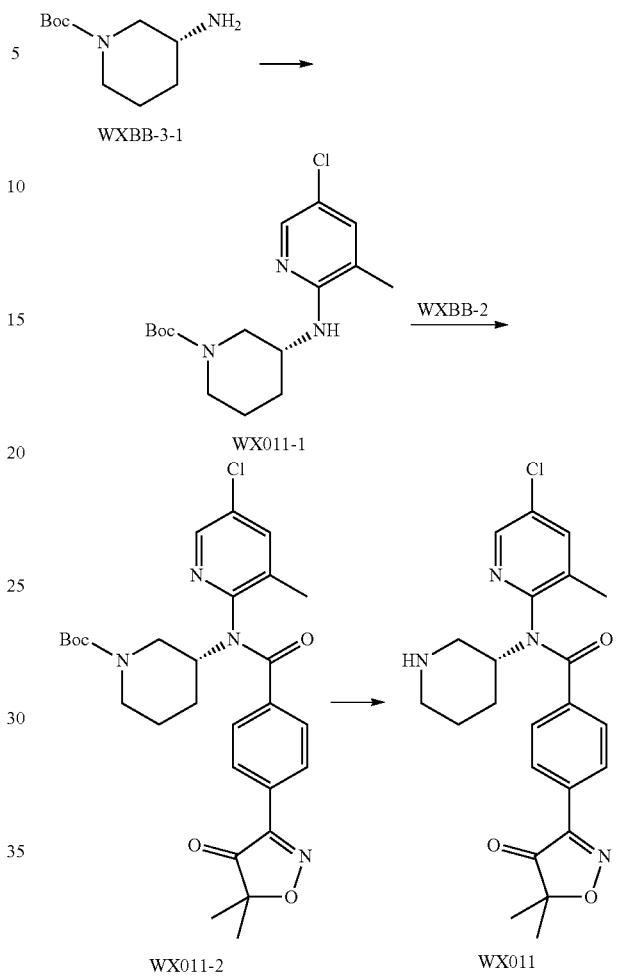

Step 1: Synthesis of Compound WX011-1

Under nitrogen condition, 2-bromine-3-methyl-5-chloropyridine (400.00 mg, 1.94 mmol, 1.00 eq), WXBB-3-1 (465.61 mg, 2.32 mmol, 1.20 eq), sodium tert-butoxide (372.35 mg, 3.87 mmol, 2.00 eq), 1,1'-binaphthyl-2,2'-bis(diphenylphosphino) (241.26 mg, 387.47 μmol, 0.20 eq) and tris(dibenzylideneacetone)dipalladium (177.40 mg, 193.73 μmol, 0.10 eq) were dissolved in anhydrous methylbenzene (10.00 mL). The mixture was stirred at 90° C. for 12 h. After reaction, the reaction liquid was dried by rotary evaporation to obtain the crude. The crude was purified by column chromatography (ethyl acetate: petroleum ether=1~20%) to obtain WX011-1. $^1$H NMR (400 MHz, CDCl$_3$) δ ppm: 7.96 (d, J=2.00 Hz, 1H), 7.22 (s, 1H), 4.17-4.06 (m, 1H), 3.68-3.61 (m, 1H), 3.58-3.46 (m, 2H), 3.41-3.31 (m, 1H), 2.07 (s, 3H), 1.99- 1.86 (m, 1H), 1.84-1.67 (m, 2H), 1.65-1.60 (m, 1H), 1.59 (s, 9H).

Step 2: Synthesis of Compound WX011-2

Under nitrogen condition, WX011-1 (207.15 mg, 635.75 μmol, 0.80 eq) was dissolved in anhydrous tetrahydrofuran (10.00 mL), and lithium bis(trimethylsilyl)amide (1 M, 715.22 μL, 0.90 eq) was added in reaction liquid at 0° C. The reaction liquid was stirred at 0° C. for 1 h, and then WXBB-2 (200.00 mg, 794.69 μmol, 1.00 eq) was added in reaction liquid at 0° C. The reaction liquid was stirred at 25° C. for 12 h. After reaction, the reaction liquid was quenched with water (10 mL), extracted with ethyl acetate (15 mL*3), and washed with saturated sodium chloride solution (10 mL*1). The organic phase was dried with anhydrous sodium sulfate, filtered and dried by rotary evaporation to obtain the crude. The crude was purified by preparative thin-layer chromatography (petroleum ether/ethyl acetate=3:1) to obtain the pure product WX011-2. $^1$H NMR (400 MHz, CDCl$_3$) δ ppm: 8.40-8.36 (m, 1H), 7.99-7.90 (m, 2H), 7.43-7.32 (m, 3H), 4.73-4.45 (m, 1H), 4.20-3.95 (m, 2H), 3.41-3.25 (m, 1H), 2.75-2.45 (m, 1H), 2.10-1.90 (m, 3H), 1.85-1.65 (m, 2H), 1.52-1.44 (m, 16H), 1.35-1.23 (m, 1H).

Step 3: Synthesis of Compound WX011

WX011-2 (110.00 mg, 203.31 μmol, 1.00 eq) was dissolved in methanol (4.00 mL), and hydrochloric acid/methanol solution (4 M, 2.00 mL) was added. The reaction liquid was stirred at 25° C. for 1 h. After reaction, the reaction liquid was directly dried by rotary evaporation to obtain WX011. $^1$H NMR (400 MHz, MeOD-d4) δ ppm: 8.49-8.39 (m, 1H), 7.93 (d, J=8.16 Hz, 2H), 7.68-7.60 (m, 1H), 7.36 (d, J=8.16 Hz, 2H), 5.12-5.01 (m, 1H), 3.81-3.72 (m, 1H), 3.65-3.51 (m, 1H), 3.41-3.32 (m, 1H), 2.95-2.82 (m, 1H), 2.17-2.09 (m, 1H), 2.02 (s, 3H), 1.98-1.84 (m, 2H), 1.41 (s, 6H), 1.38-1.28 (m, 1H).

Implementation 010: WX012

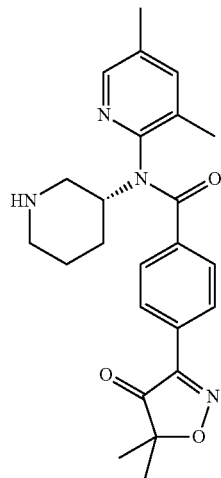 [SMILES: Cc1cnc(N(C(=O)c2ccc(C3=NOC(C)(C)C3=O)cc2)[C@@H]2CCCNC2)c(C)c1]

Synthetic Route:

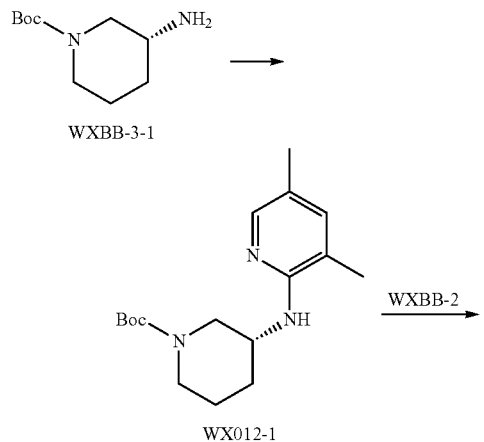

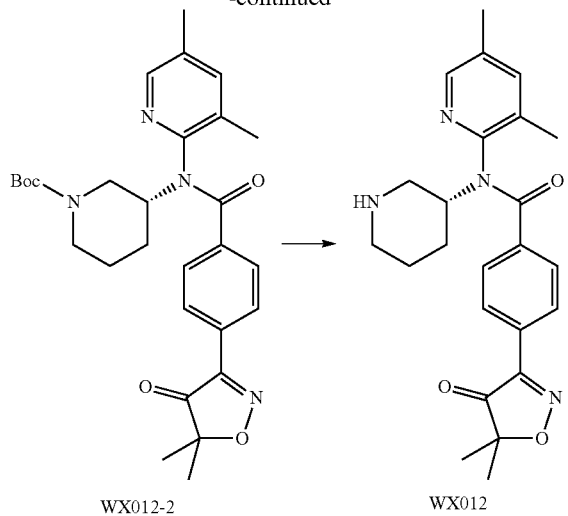

Step 1: Synthesis of Compound WX012-1

Under nitrogen condition, 2-bromine-3,5-dimethyl pyridine (500.00 mg, 2.69 mmol, 1.00 eq) and WXBB-3-1 (592.07 mg, 2.96 mmol, 1.10 eq) were dissolved in methylbenzene (25 ml). Tris(dibenzylideneacetone)dipalladium (246.10 mg, 269.00 μmol, 0.10 eq), sodium tert-butoxide (387.40 mg, 4.04 mmol, 1.50 eq) and 1,1'-binaphthyl-2,2'-bis (diphenylphosphino) (335.00 mg, 538.00 μmol, 0.20 eq) were added. The mixture was stirred at 90° C. for 18 h. After reaction, the reaction liquid was filtered through diatomite to remove the palladium catalyst, the filter cake was washed with ethyl acetate (10 ml), the solvent was dried by rotary evaporation under vacuum, and ethyl acetate (30 ml) was added. Then the resulting mixture was washed with water (10 ml), the methyl acetate phase was dry-spined under vacuum, and the crude was purified by column chromatography (ethyl acetate:petroleum ether=1~20%) to obtain WX012-1 (Rf=0.5). $^1$H NMR (400 MHz, CDCl$_3$) δ ppm: 7.74 (s, 1H), 6.99 (s, 1H), 4.08-4.02 (m, 1H), 3.98 (br, s, 1H), 3.60-3.57 (m, 1H), 3.30-3.38 (m, 2H), 3.29-3.24 (m, 1H), 2.07 (s, 3H), 1.97 (s, 3H), 1.84-1.82 (m, 1H), 1.71-1.60 (m, 2H), 1.49-1.43 (m, 1H), 1.33 (s, 9H).

Step 2: Synthesis of Compound WX012-2

Under nitrogen condition, WX012-1 (150.48 mg, 492.71 μmol, 0.80 eq) was dissolved in tetrahydrofuran (6.00 mL), lithium bis(trimethylsilyl)amide (1 M, 554.30 μL, 0.90 eq) was dropwise added in ice bath. The mixture was stirred at 0° C. for 1 h, then WXBB-2 (155.00 mg, 615.89 μmol, 1.00 eq) was added and the reaction liquid was stirred at 25° C. for 2 h, After reaction, water (10 mL) and ethyl acetate (20 mL) were added to reaction liquid. The liquid was separated. The aqueous phase was extracted with ethyl acetate (20 mL), the combined organic phases was concentrated under vacuum to obtain the crude, and the crude was purified by prep-TLC (petroleum ether:ethyl acetate=2:1) to obtain WX012-2. $^1$H NMR (400 MHz, CDCl$_3$) δ ppm: 8.22 (s, 1H), 7.88 (d, J=8.00 Hz, 2H), 7.38 (d, J=8.00 Hz, 2H), 7.12 (s, 1H), 4.64-4.02 (m, 4H), 3.49-3.38 (m, 1H), 2.55-2.29 (m, 1H), 2.27 (s, 3H), 1.92-1.188 (m, 3H), 1.78-1.63 (m, 3H), 1.48-1.44 (m, 15H).

Step 3: Synthesis of Compound WX012

WX012-2 (80.00 mg, 153.66 μmol, 1.00 eq) was dissolved in methanol (2.00 mL), then hydrochloric acid/ethyl acetate solution (4 M, 5.00 mL) was added. The mixture was stirred at 25° C. for 1 h. After reaction, the reaction liquid was directly dried by rotary evaporation to obtain the target product WX012. ¹H NMR (400 MHz, MeOD-d4) δ ppm: 8.29 (s, 1H), 7.82 (s, 2H), 7.53 (s, 1H), 7.33 (s, 2H), 3.75-3.72 (m, 1H), 3.56-3.54 (m, 1H), 3.29-3.22 (m, 2H), 2.82 (br, s, 1H), 2.25 (s, 4H), 2.17 (s, 3H), 2.02 (br, s, 2H), 1.40-1.36 (m, 1H), 1.18 (s, 6H).

Implementation 011: WX013

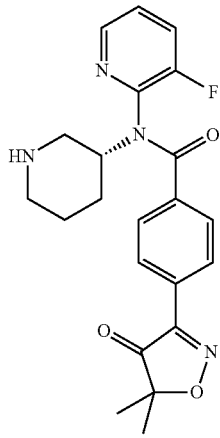 [SMILES: CC1(C)ON=C(c2ccc(C(=O)N(c3ncccc3F)[C@@H]3CCCNC3)cc2)C1=O]

Synthetic Route:

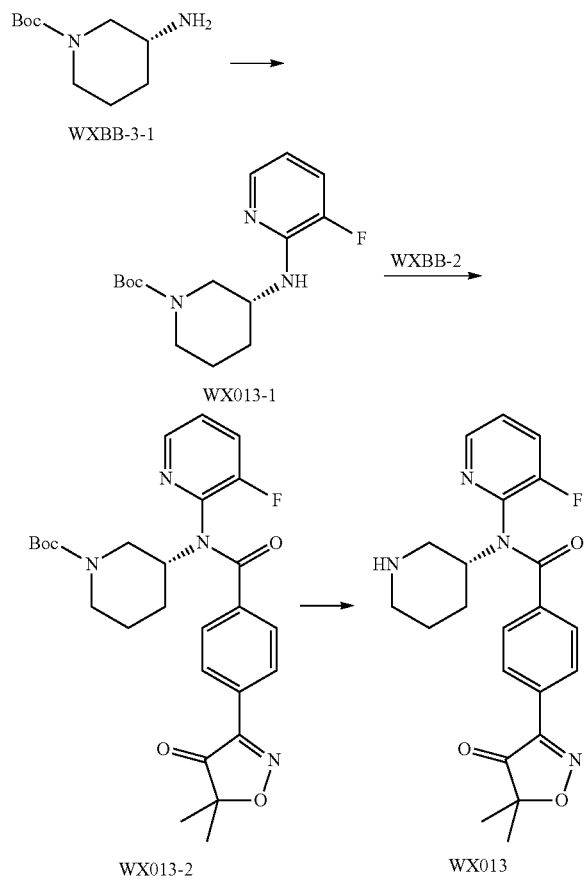

Step 1: Synthesis of Compound WX013-1

Under nitrogen condition, 2-bromine-3-fluoropyridine (1.00 g, 5.68 mmol, 1.00 eq) and WXBB-3-1 (1.25 g, 6.25 mmol, 1.10 eq) were dissolved in anhydrous methylbenzene (50 mL), tris(dibenzylideneacetone)dipalladium (520.33 mg, 568.00 μmol, 0.10 eq), sodium tert-butoxide (819.08 mg, 8.52 mmol, 1.50 eq) and 1,1'-binaphthyl-2,2'-bis (diphenylphosphino) (707.35 mg, 1.14 mmol, 0.20 eq) were added. The mixture was stirred at 90° C. for 18 h. After reaction, the reaction liquid was filtered through diatomite, and the filtrate was dried by rotary evaporation to obtain the crude. The crude was dissolved with ethyl acetate (100 mL), washed with water (20 mL) and dried with anhydrous sodium. The filtrate was filtered and dried by rotary evaporation under vacuum. The crude was purified by column chromatography (ethyl acetate:petroleum ether=(1~20%) to obtain WX013-1. ¹H NMR (400 MHz, CDCl₃) δ ppm: 7.80 (d, J=5.20 Hz, 1H), 7.05 (dd, J=8.00 Hz, 10.40 Hz, 1H), 6.46-6.42 (m, 1H), 4.59-4.58 (m, 1H), 4.04-4.02 (m, 1H), 3.72-3.52 (m, 1H), 3.49-3.21 (m, 2H), 1.92-1.85 (m, 1H), 1.65 (br, s, 2H), 1.54-1.50 (m, 1H), 1.33 (s, 9H).

Step 2: Synthesis of Compound WX013-2

Under nitrogen condition, WX013-1 (200.00 mg, 677.16 μmol, 0.80 eq) was dissolved in anhydrous tetrahydrofuran (10.00 mL), and lithium bis(trimethylsilyl)amide (1 M, 761.81 μL, 0.90 eq) was dropwise added to the reaction liquid at 0° C. The reaction liquid was stirred at 0° C. for 1 h, and then WXBB-2 (213.03 mg, 846.45 μmol, 1.00 eq) was added to the reaction liquid at 0° C. The reaction liquid was stirred at 25° C. for 11 h. After reaction, the reaction liquid was quenched with water (10 mL), then extracted with ethyl acetate (10 mL*3). The organic phase was washed with saturated sodium chloride solution (10 mL), dried with anhydrous sodium sulfate, filtered and dried by rotary evaporation to obtain the crude. The crude was purified by pre-TLC (petroleum ether/ethyl acetate=3:1) to obtain WX013-2. ¹H NMR (400 MHz, CDCl₃) δ ppm: 8.37-8.33 (m, 1H), 7.94 (d, J=8.28 Hz, 2H), 7.42 (d, J=8.28 Hz, 2H), 7.27-7.17 (m, 1H), 4.74-4.59 (m, 1H), 4.48-4.35 (m, 1H), 4.20-4.01 (m, 1H), 2.64-2.45 (m, 1H), 1.78-1.63 (m, 2H), 1.85-1.65 (m, 2H), 1.49 (s, 9H), 1.46 (s, 6H), 1.44-1.41 (m, 1H), 1.31-1.26 (m, 1H).

Step 3: Synthesis of Compound WX013

WX013-2 (110.00 mg, 215.45 μmol, 1.00 eq) was dissolved in methanol (4.00 mL), and hydrochloric acid/methanol solution (4 M, 4.00 mL) was added. The reaction liquid was stirred at 25° C. for 1 h. After reaction, the reaction liquid was directly dried by rotary evaporation to obtain WX013. ¹H NMR (400 MHz, MeOD-d4) δ ppm: 8.42 (d, J=4.30 Hz, 1H), 7.95 (d, J=8.28 Hz, 2H), 7.57-7.50 (m, 1H), 7.47-7.38 (m, 3H), 5.15-4.95 (m, 1H), 3.83-3.73 (m, 1H), 3.43-3.35 (m, 1H), 3.31-3.27 (m, 1H), 2.95-2.85 (m, 1H), 2.11-2.01 (m, 2H), 1.98- 1.85 (m, 1H), 1.42 (s, 6H), 1.40-1.35 (m, 1H).

Implementation 012: WX014

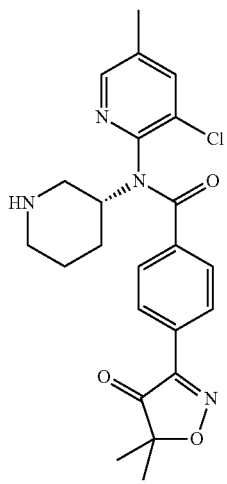 [SMILES: Cc1cnc(N(C(=O)c2ccc(C3=NOC(C)(C)C3=O)cc2)[C@@H]2CCCNC2)c(Cl)c1]

Synthetic Route:

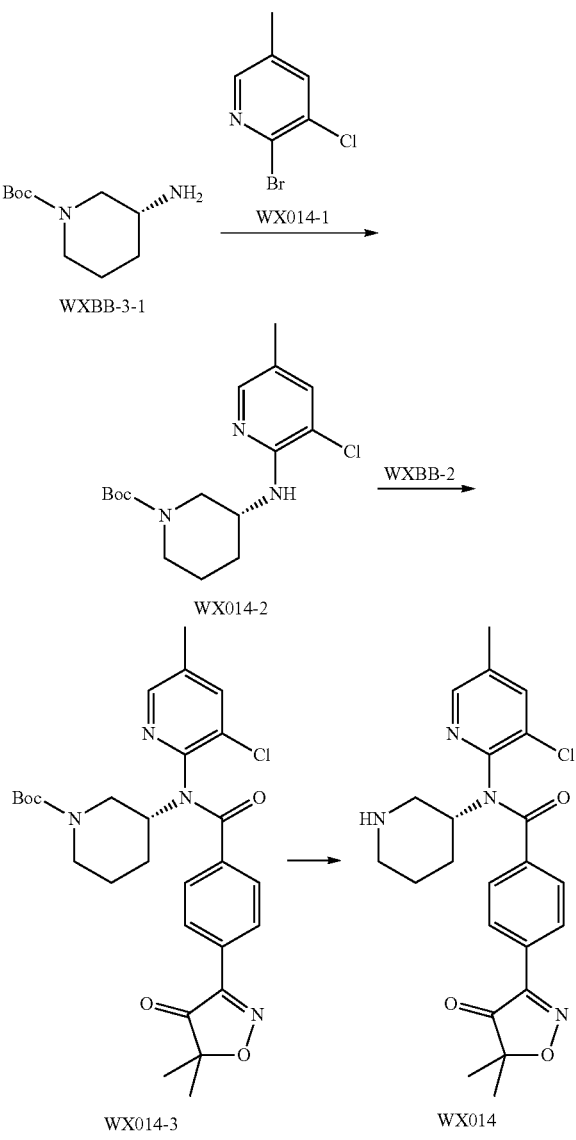

Step 1: Synthesis of Compound WX014-2

WX014-1 (500.00 mg, 2.42 mmol, 1.00 eq) and compound WXBB-3-1 (533.51 mg, 2.66 mmol, 1.10 eq) were dissolved in methylbenzene (25 ml). Tris(dibenzylideneacetone)dipalladium (221.76 mg, 242.00 μmol, 0.10 eq), sodium tert-butoxide (349.08 mg, 3.63 mmol, 1.50 eq) and binaphthyl (BINAP) (301.37 mg, 484.00 μmol, 0.20 eq) were added. The mixture was reacted at 90° C. for 18 h. After reaction, the reaction liquid was filtered through diatomite, the filtrate was washed with ethyl acetate (10 ml), and dried by rotary evaporation under vacuum. Ethyl acetate (50 ml) was added to residue. The resulting mixture was washed with water (10 ml), the organic phase was dried by rotary evaporation under vacuum, and the crude was purified by column chromatography (petroleum ether:ethyl acetate=30:1-10:1) to obtain the compound WX014-2. $^1$H NMR (400 MHz, CDCl$_3$) δ ppm: 7.76 (s, 1H), 7.22 (s, 1H), 4.79 (d, J=4.00 Hz, 1H), 3.98 (br, s, 1H), 3.30 (br, s, 3H), 2.09 (s, 3H), 1.87-1.82 (m, 2H), 1.65-1.58 (m, 3H), 1.33 (s, 9H).

Step 2: Synthesis of Compound WX014-3

WX014-2 (150.18 mg, 460.92 μmol, 0.80 eq) was dissolved in tetrahydrofuran (6.00 mL), LHMDS (11 M, 518.54 μL, 0.90 eq) was dropwise added. The mixture was reacted at 0° C. for 1 h. Then WXBB-2 (145.00 mg, 576.15 μmol, 1.00 eq) was added, and the reaction liquid was stirred at 25° C. for 2 h, After reaction, water (10 mL) and ethyl acetate (20 mL) was added to reaction liquid, the liquid was separated, the aqueous phase was extracted with ethyl acetate (20 mL) and the combined organic phases was concentrated under vacuum to obtain the crude. The crude was purified by prep-TLC (petroleum ether:ethyl acetate=2:1) to obtain WX014-3. $^1$H NMR (400 MHz, CDCl$_3$ δ ppm: 8.19 (s, 1H), 7.83 (d, J=8.00 Hz, 2H), 7.35 (d, J=7.60 Hz, 2H), 7.27 (br, s, 1H), 4.43-4.20 (m, 2H), 4.06-4.02 (m, 1H), 3.41-3.30 (m, 1H), 2.50 (br, s, 1H), 2.22 (s, 3H), 1.62-1.52 (m, 4H), 1.41 (s, 6H), 1.36 (s, 9H). MS: m/z=485.1 [M-55].

Step 3: Synthesis of Compound WX014

WX014-3 (100.00 mg, 184.83 μmol, 1.00 eq) was dissolved in methanol (2.00 mL), then hydrochloric acid-methanol solution (4 M, 5.00 mL) was added. The mixture was reacted at 25° C. for 1 h. After reaction, the reaction liquid was directly dried by rotary evaporation to obtain WX014. $^1$H NMR (400 MHz, MeOD-d4) δ ppm: 8.42 (s, 1H), 7.92 (d, J=8.40 Hz, 2H), 7.63 (s, 1H), 7.44 (d, J=8.40 Hz, 2H), 5.12-5.01 (m, 1H), 3.79-3.77 (m, 1H), 3.57-3.52 (m, 1H), 3.38-3.35 (m, 1H), 2.92-2.82 (m, 1H), 2.34 (s, 3H), 2.08-2.00 (m, 2H), 1.91-1.88 (m, 1H), 1.48-1.45 (m, 1H), 1.42 (s, 6H). MS: m/z=441.2, [M+1].

Implementation 013: WX015

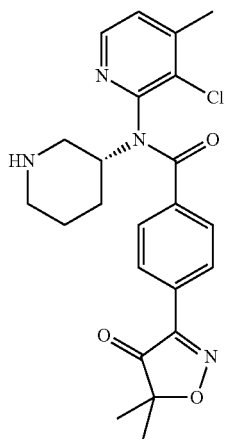 [SMILES: Cc1ccnc(N(C(=O)c2ccc(C3=NOC(C)(C)C3=O)cc2)[C@@H]2CCCNC2)c1Cl]

Synthetic Route:

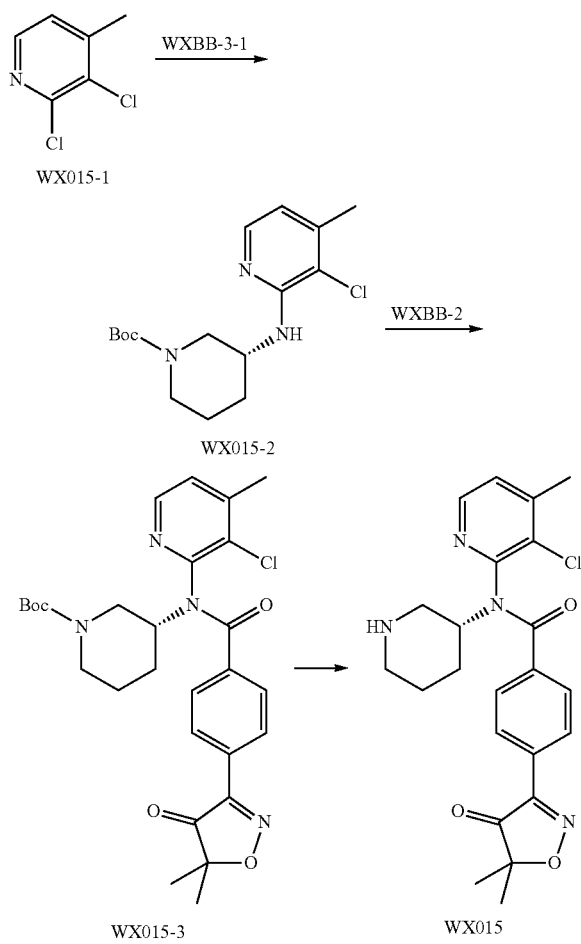

Step 1: Synthesis of Compound WX015-2

WXBB-3-1 (300.00 mg, 1.50 mmol, 1.00 eq), WX015-1 (243.03 mg, 1.50 mmol, 1.00 eq), tris(dibenzylideneacetone)dipalladium (137.36 mg, 150.00 μmol, 0.10 eq), BINAP (186.80 mg, 300.00 μmol, 0.20 eq) and sodium tert-butoxide (216.23 mg, 2.25 mmol, 1.50 eq) were dissolved in anhydrous methylbenzene (20.00 mL). The reaction liquid was stirred at 90° C. for 1 h under nitrogen condition. After reaction, the reaction liquid was filtered through diatomite, the filter cake was washed with dichloromethane (20 mL), and the filtrate was dried by rotary evaporation to obtain the crude. The crude was dissolved with ethyl acetate (30 mL), water (30 mL) was added, the pH was adjusted with aqueous hydrochloric acid solution (2M) to 1-2, the liquid was separated, the pH of aqueous phase was adjusted with solid sodium bicarbonate to 7-8. Ethyl acetate (30 mL*2) was used for extracted. The organic phase was washed with saturated sodium chloride solution (30 mL), dried with anhydrous sodium sulfate, filtered and dried by rotary evaporation to obtain the target product. $^1$H NMR (400 MHz, CDCl$_3$) δ ppm: 7.90 (d, J=5.02 Hz, 1H), 6.48 (dd, J=5.02 Hz, 1H), 5.18-5.05 (m, 1H), 4.17-4.05 (m, 1H), 3.75-3.30 (m, 3H), 2.32 (s, 3H), 2.00-1.92 (m, 1H), 1.83-1.68 (m, 2H), 1.66-1.56 (m, 1H), 1.42 (s, 9H). MS: m/z=326.1 [M+1]

Step 2: Synthesis of Compound WX015-3

Compound WX015-2 (200.00 mg, 613.82 μmol, 0.80 eq) was dissolved in anhydrous tetrahydrofuran (10.00 mL), then LHMDS (1 M, 690.54 μL, 0.90 eq) was dropwise added at 0° C. The mixture was stirred at 0° C. for half an hour, then compound WXBB-2 (193.10 mg, 767.27 μmol, 1.00 eq) was added, and the reaction liquid was stirred at 25° C. for 1.5 h. After reaction, the reaction liquid was quenched with water (10 mL), extracted with ethyl acetate (10 mL*2). The organic phase was washed with saturated sodium chloride solution (10 mL). The organic phase was dried with anhydrous sodium sulfate, filtered and dried by rotary evaporation to obtain the crude. The crude was purified by prep-TLC (petroleum ether:ethyl acetate=2:1) to obtain WX015-3. $^1$H NMR (400 MHz, CDCl$_3$) δ ppm: 8.30-8.22 (m, 1H), 7.87 (d, J=7.72 Hz, 2H), 7.42 (d, J=7.50 Hz, 2H), 7.04 (s, 1H), 4.61-4.37 (m, 2H), 4.30-4.19 (m, 1H), 3.41-3.22 (m, 1H), 2.65-2.45 (m, 1H), 2.21 (s, 3H), 1.69-1.59 (m, 1H), 1.57-1.52 (m, 1H), 1.50-1.48 (m, 17H). MS: m/z=485.2 [M-56].

Step 3: Synthesis of Compound WX015

Compound WX015-3 (192.00 mg, 354.87 μmol, 1.00 eq) in methanol (5.00 mL) was dissolved, hydrochloric acid-methanol solution (4 M, 4.00 mL) was added, and the reaction liquid was stirred at 25° C. for 1 h. After reaction, the reaction liquid was directly dried by rotary evaporation to obtain compound WX015. $^1$H NMR (400 MHz, MeOD-d4) δ ppm: 8.46-8.35 (m, 1H), 7.92 (d, J=8.16 Hz, 2H), 7.43 (d, J=8.16 Hz, 2H), 7.35 (d, J=4.64 Hz, 1H), 5.11-5.00 (m, 1H), 3.83-3.71 (m, 1H), 3.64-3.54 (m, 1H), 3.41-3.35 (m, 1H), 2.98-2.85 (m, 1H), 2.26 (s, 3H), 2.15-1.85 (m, 3H), 1.51-1.45 (m, 1H), 1.42 (s, 6H). MS: m/z=441.1 [M+1].

Implementation 014: WX016

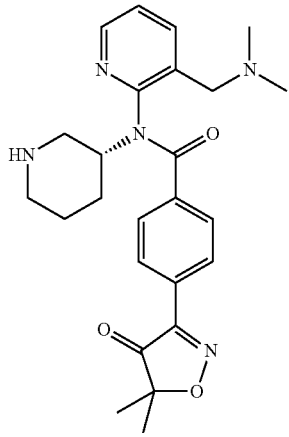 [SMILES: CN(C)Cc1cccnc1N(C(=O)c1ccc(C2=NOC(C)(C)C2=O)cc1)[C@@H]1CCCNC1]

Synthetic Route:

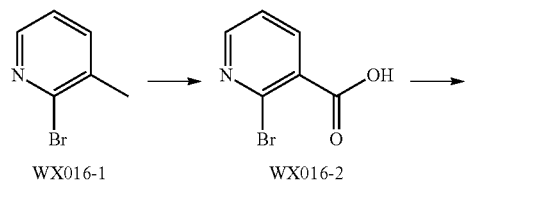

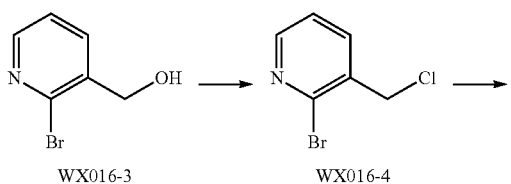

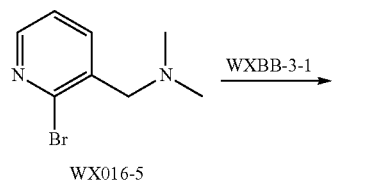

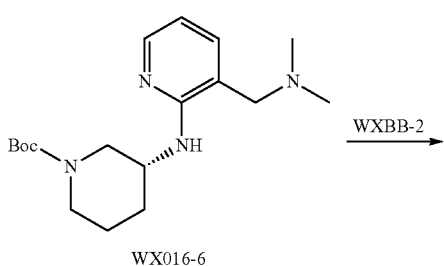

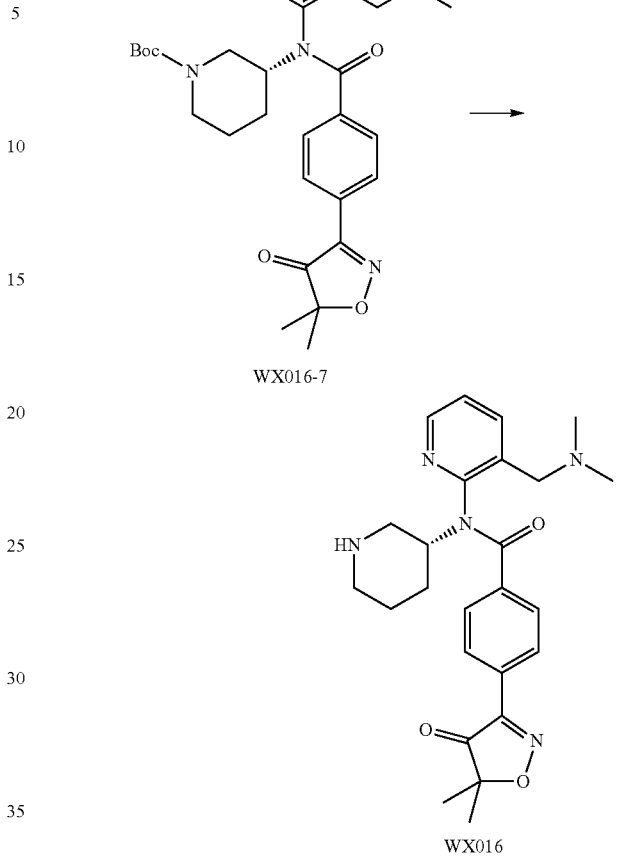

Step 1: Synthesis of Compound WX016-2

Under 15° C., potassium permanganate (9.46 g, 59.87 mmol, 1.03 eq) was added to the water (200.00 mL) solution of WX016-1 (10.00 g, 58.13 mmol, 6.49 mL, 1.00 eq) and the mixture was stirred at 100° C. for 1 h. Potassium permanganate (9.46 g, 59.87 mmol, 1.03 eq) was added and the mixture was stirred for 15 h. Then potassium permanganate (9.46 g, 59.87 mmol, 1.03 eq) was added and continuously stirred for 24 h. After reaction, the mixture was filtered to remove the undissolved substances. The reaction liquid was added with water. pH was adjusted with hydrochloric acid (4M) to 3-4. Ethyl acetate was used for extraction three times (200 mL each time). The organic phase was washed with saturated sodium chloride solution (200 mL), dried with anhydrous sodium sulfate, filtered, and concentrated to obtain WX016-2. $^1$H NMR (400 MHz, MeOD-d4) δ ppm: 7.50 (dd, J=7.53, 5.02 Hz, 1H), 8.18 (dd, J=7.53, 2.01 Hz, 1H), 8.45 (dd, J=5.02, 2.01 Hz, 1H).

Step 2: Synthesis of Compound WX016-3

Under $N_2$ condition, borane-tetrahydrofuran (1 M, 80.00 mL, 1.47 eq) was added to the anhydrous tetrahydrofuran (20.00 mL) solution (0° C.) of WX016-2 (11.00 g, 54.45 mmol, 1.00 eq). The mixture was warmed to 15° C. and stirred for 16 h. Borane-tetrahydrofuran solution (1 M, 40.00 mL, 0.73 eq) was added and the mixture solution was continuously stirred for 24 h. After reaction, water (100 mL) was slowly added to the reaction liquid to quench the reaction. The solvent tetrahydrofuran was spined out by rotary evaporation, and ethyl acetate was used for extraction three times (100 mL each time). The organic phase was washed with saturated sodium chloride solution (100 mL), dried with anhydrous sodium sulfate, filtered and concentrated to obtain WX016-3. $^1$H NMR (400 MHz, CDCl$_3$) δ ppm: 4.76 (s, 2H), 7.32 (dd, J=7.53, 4.77 Hz, 1H), 7.83-7.88 (m, 1H), 8.30 (dd, J=4.77, 2.01 Hz, 1H).

Step 3: Synthesis of Compound WX016-4

Under N$_2$ condition, thionyl chloride (9.84 g, 82.71 mmol, 6.00 mL, 15.55 eq) and pyridine (50.00 µL) were added to the anhydrous dichloromethane (20.00 mL) solution of WX016-3 (1.00 g, 5.32 mmol, 1.00 eq) in order. The mixture was stirred at 15° C. for 5 h. After reaction, water (50 mL) was slowly added to the reaction liquid to quench the reaction. Dichloromethane was used for extraction three times (50 mL each time). The organic phase was washed with saturated sodium chloride solution (50 mL), dried with anhydrous sodium sulfate, filtered and concentrated to obtain WX016-4. $^1$H NMR (400 MHz, CDCl$_3$) δ ppm: 4.69 (s, 2H), 7.33 (dd, J=7.53, 5.02 Hz, 1H), 7.84 (dd, J=7.53, 2.01 Hz, 1H), 8.35 (dd, J=4.77, 1.76 Hz, 1H).

Step 4: Synthesis of Compound WX016-5

WX016-4 (940.00 mg, 4.55 mmol, 1.00 eq), dimethylamine (1.87 g, 13.66 mmol, 2.10 mL, 3.00 eq) (33% of aqueous solution), and NaOH (275.00 mg, 6.88 mmol, 1.51 eq) were added to the mixed solvent of water (10.00 mL) and anhydrous tetrahydrofuran (10.00 mL). The mixture was stirred for 16 h at 15° C. Dimethylamine (890.00 mg, 6.52 mmol, 1.00 mL, 1.43 eq) (33% of aqueous solution) and NaOH (100.00 mg, 2.50 mmol, 0.55 eq) were added. The resulting mixture was continuously stirred for 5 h. After reaction, the solvent was spined out. Water (20 mL) was added to the reaction liquid. Ethyl acetate was used for extraction three times (30 mL each time). The organic phase was washed with saturated sodium chloride solution (30 mL), dried with anhydrous sodium sulfate, filtered, and concentrated to obtain WX016-5. $^1$H NMR (400 MHz, CDCl$_3$) δ ppm: 2.32 (s, 6H), 3.52 (s, 2H), 7.27 (s, 1H), 7.78 (dd, J=7.53, 2.01 Hz, 1H), 8.27 (dd, J=4.77, 1.76 Hz, 1H).

Step 5: Synthesis of Compound WX016-6

Under N$_2$ condition, WX016-5 (770.00 mg, 3.58 mmol, 1.00 eq) and WXBB-3-1 (717.00 mg, 3.58 mmol, 1.00 eq) were added to anhydrous methylbenzene (20.00 mL). Then NaOBu-t (691.00 mg, 7.19 mmol, 2.01 eq), BINAP (334.00 mg, 536.40 µmol, 0.15 eq) and Pd$_2$(dba)$_3$ (327.00 mg, 357.10 µmol, 0.10 eq) were added. The mixture was stirred at 90° C. for 16 h. After reaction, water (20 mL) was added to the reaction liquid. Ethyl acetate was used for extraction three times (20 mL each time). The organic phase was combined, washed with saturated sodium chloride solution (20 mL), dried with anhydrous magnesium sulfate, filtered, and concentrated. The crude was dissolved in water/ethyl acetate (1:1) (20 mL), and the pH was adjusted with hydrochloric acid (4M) to pH=2-3. The aqueous phase was taken out. The pH was adjusted with Na$_2$CO$_3$ to 9-10. Ethyl acetate (3*20 mL) was used for extraction. The organic phase was washed with saturated sodium chloride solution (20 mL), dried with anhydrous magnesium sulfate, filtered, and concentrated. The crude was purified by prep-TLC to obtain WX016-6. $^1$H NMR (400 MHz, CDCl$_3$) δ ppm: 1.14-1.53 (m, 9H), 1.54-1.80 (m, 3H), 1.87-2.02 (m, 1H), 2.14-2.31 (m, 6H), 3.14-3.84 (m, 6H), 3.94-4.23 (m, 1H), 6.42-6.48 (m, 1H), 7.13 (m, 2H), 8.00-8.07 (m, 1H).

Step 6: Synthesis of Compound WX016-7

Under N$_2$ condition, LiHMDS (1 M, 780.00 µL, 0.80 eq) was added to the anhydrous tetrahydrofuran (4.00 mL) solution (0° C.) of WX016-6 (260.00 mg, 357.59 µmol, 0.37 eq) (purity 46%). WXBB-2 (245.00 mg, 973.50 µmol, 1.00 eq) was added after stirring for 1 h. When warmed to 15° C., the mixture was stirred for 16 h. After reaction, saturated NH$_4$Cl solution (20 mL) was added to the reaction liquid. The resulting solution was extracted with ethyl acetate three times (20 mL each time). The organic phase was washed with saturated sodium chloride solution (20 mL), dried with anhydrous sodium sulfate, filtered, and concentrated. The crude was dissolved in water/ethyl acetate (1:1) (20 mL), and the pH was adjusted with hydrochloric acid (4M) to 2-3. Organic phase was taken out, washed with saturated sodium chloride solution (10 mL), dried with anhydrous magnesium sulfate, filtered, and concentrated. The crude was separated by prep-TLC (dichloromethane:methanol=20:1) to obtain WX016-7. $^1$H NMR (400 MHz, MeOD-d$_4$) δ ppm: 1.29 (s, 1H), 1.40 (s, 6H), 1.44-1.47 (m, 9H), 1.65-1.91 (m, 3H), 2.06-2.17 (m, 6H), 2.33 (br s, 1H), 2.65 (br s, 1H), 3.38-3.53 (m, 1H), 3.95-4.23 (m, 1H), 4.45-4.72 (m, 3H), 7.36 (br d, J=7.53 Hz, 2H), 7.52-7.59 (m, 1H), 7.74-7.94 (m, 2H), 8.14-8.21 (m, 1H) 8.42-8.58 (m, 1H).

Step 7: Synthesis of Compound WX016

WX016-7 (110.00 mg, 154.10 µmol, 1.00 eq) (purity 77%) was added to HCl/methanol (4 M, 2.00 mL, 51.91 eq). The mixture was stirred at 15° C. for 16 h. After reaction, water (20 mL) and ethyl acetate (20 mL) were added to reaction liquid. The aqueous phase was taken out, adjusted with sodium bicarbonate to pH=8-9, extracted with ethyl acetate three times (20 mL each time), washed with saturated sodium chloride solution (20 mL), dried with anhydrous sodium sulfate, filtered, and concentrated. The crude was purified by prep-HPLC (column: Kromasil 150*25 mm*10 µm; mobile phase: [water (0.05% ammonia hydroxide v/v)-ACN]; B %: 35%-65%,8 min) to obtain WX016. $^1$H NMR (400 MHz, CDCl$_3$) δ ppm: 1.22-1.34 (m, 1H), 1.44 (s, 6H), 1.56-1.72 (m, 2H), 1.85 (br s, 2H), 2.06 (br s, 6H), 2.15-2.68 (m, 2H), 2.81-3.05 (m, 1H), 3.07-3.37 (m, 2H), 4.45-4.79 (m, 1H), 7.21 (br s, 1H), 7.37 (br s, 2H), 7.70-7.95 (m, 3H), 8.49 (br s, 1H).

Implementation 015: WX017

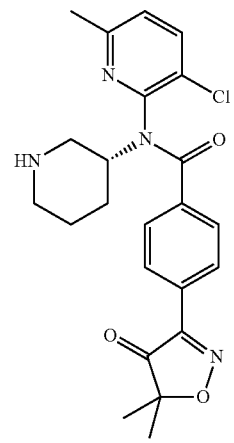 [SMILES: Cc1ccc(Cl)c(N(C(=O)c2ccc(C3=NOC(C)(C)C3=O)cc2)[C@@H]2CCCNC2)n1]

Synthetic Route:

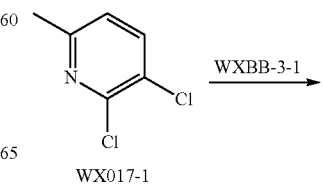

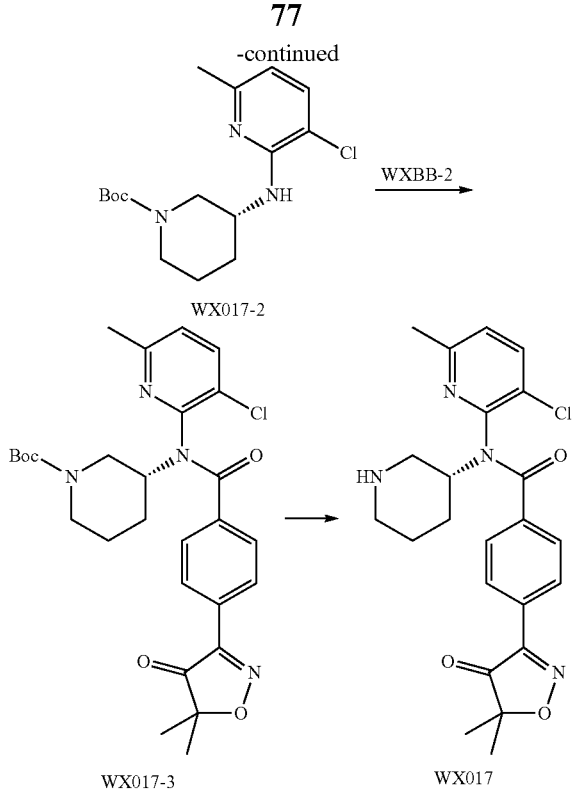

Step 1: Synthesis of Compound WX017-2

WX017-1 (300.00 mg, 1.85 mmol, 1.00 eq), WXBB-3-1 (389.39 mg, 1.94 mmol, 1.05 eq), sodium tert-butoxide (355.88 mg, 3.70 mmol, 2.00 eq), BINAP (230.59 mg, 370.00 μmol, 0.20 eq) and tris(dibenzylideneacetone)dipalladium (169.56 mg, 185.00 μmol, 0.10 eq) were added in a pre-dried reaction flask, then anhydrous methylbenzene (10.00 mL) was added in the reaction flask. The mixture was bubbled with nitrogen for 1 min. The reaction flask was placed in oil bath at 90° C. and the mixture was stirred for 12 h. After reaction, the reaction liquid was filtered and the filter cake was washed with dichloromethane (20 mL). The filtrate was collected and concentrated under vacuum to obtain yellow oily crude. The crude was diluted with 10 mL of ethyl acetate and 10 mL of water. The pH of aqueous phase was adjusted with aqueous hydrochloric acid solution (2M) to 1-2. The liquid was separated and the aqueous phase was collected. The aqueous phase was adjusted with solid sodium bicarbonate to pH=8, and extracted with ethyl acetate (10 mL*3). The organic phase was collected, washed with saturated sodium chloride solution (10 mL), dried with anhydrous sodium sulfate and filtered. The filtrate was concentrated to obtain WX017-2. H NMR (400 MHz, CDCl$_3$) δ ppm: 7.329-7.310 (d, 1H), 6.405-6.385 (d, 1H), 4.8-4.95 (br, 1H), 4.154-4.136 (m, 1H), 3.792-3.765 (d, 1H), 3.474-3.382 (m, 3H), 2.382 (s, 3H), 1.747 (m, 1H), 1.731 (m, 2H), 1.699 (s, 10H).

Step 2: Synthesis of Compound WX017-3

WX017-2 (110.00 mg, 337.60 μmol, 0.80 eq) and anhydrous tetrahydrofuran (10.00 mL) were added in a pre-dried reaction flask. Air was extracted and changed with nitrogen three times. LHMDS (1 M, 379.80 μL, 0.90 eq) was slowly dropwise added in the reaction system at 0° C., and the mixture was continuously stirred at OC for 1 h. WXBB-2 (106.20 mg, 422.00 μmol, 1.00 eq) was slowly added. The system was naturally warmed to 25° C. after WXBB-2 was added, and the mixture was stirred for 12 h. After reaction, the reaction system was cooled to 0° C., and 10 ml of water was slowly added to quench the reaction. The reaction liquid was extracted with ethyl acetate (10 mL*3). The organic phase was collected, washed with saturated sodium chloride solution (10 mL), dried with anhydrous sodium sulfate and filtered. The filtrate was concentrated to obtain yellow oily crude. The crude was purified by preparative thin layer plate (petroleum ether:ethyl acetate=2:1) to obtain WX017-3. MS: m/z=485.2 [M-56].

Step 3: Synthesis of Compound WX017

WX017-3 (110.00 mg, 203.31 μmol, 1.00 eq), anhydrous methanol (4.00 mL) and hydrochloric acid-methanol solution (4 M, 4.00 mL) were added in a reaction flask, and the reaction liquid was stirred at 25° C. for 2 h. After reaction, the reaction liquid was directly dried by rotary evaporation to obtain the crude. The crude was dissolved in 5 mL of water. The aqueous phase was adjusted with solid sodium bicarbonate to pH=8, and extracted with ethyl acetate (5 mL*6). The organic phase was collected, washed with saturated sodium chloride solution (5 mL), dried with anhydrous sodium sulfate and filtered. The filtrate was concentrated under vacuum to obtain the crude, and the crude was separated by prep-HPLC to obtain WX017. $^1$H NMR (400 MHz, MeOD) δ ppm: 7.93 (d, J=8.04 Hz, 2H), 7.62 (d, J=8.54 Hz, 1H), 7.43 (d, J=8.16 Hz, 2H), 7.26 (d, J=8.28 Hz, 1H), 5.11-4.98 (m, 1H), 3.84-3.71 (m, 1H), 3.64-3.52 (m, 1H), 3.44-3.35 (m, 1H), 2.98-2.86 (m, 1H), 2.62 (s, 3H), 2.14-1.98 (m, 2H), 1.96-1.83 (m, 1H), 1.55-1.45 (m, 1H), 1.43 (s, 6H). MS: m/z=441.2 [M+1].

Implementation 016: WX018

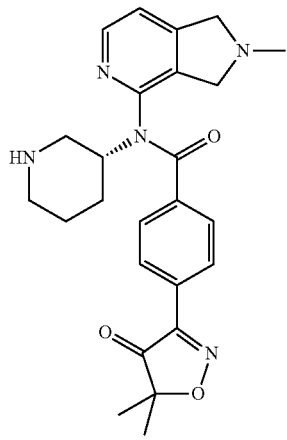 [SMILES: CN1Cc2ccnc(N(C(=O)c3ccc(C4=NOC(C)(C)C4=O)cc3)[C@@H]3CCCNC3)c2C1]

Synthetic Route:

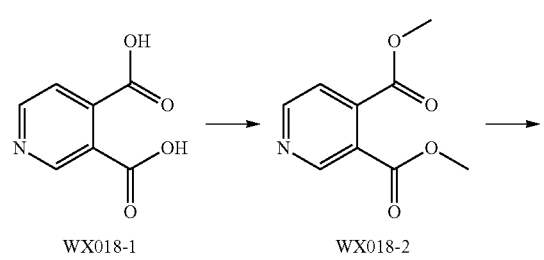

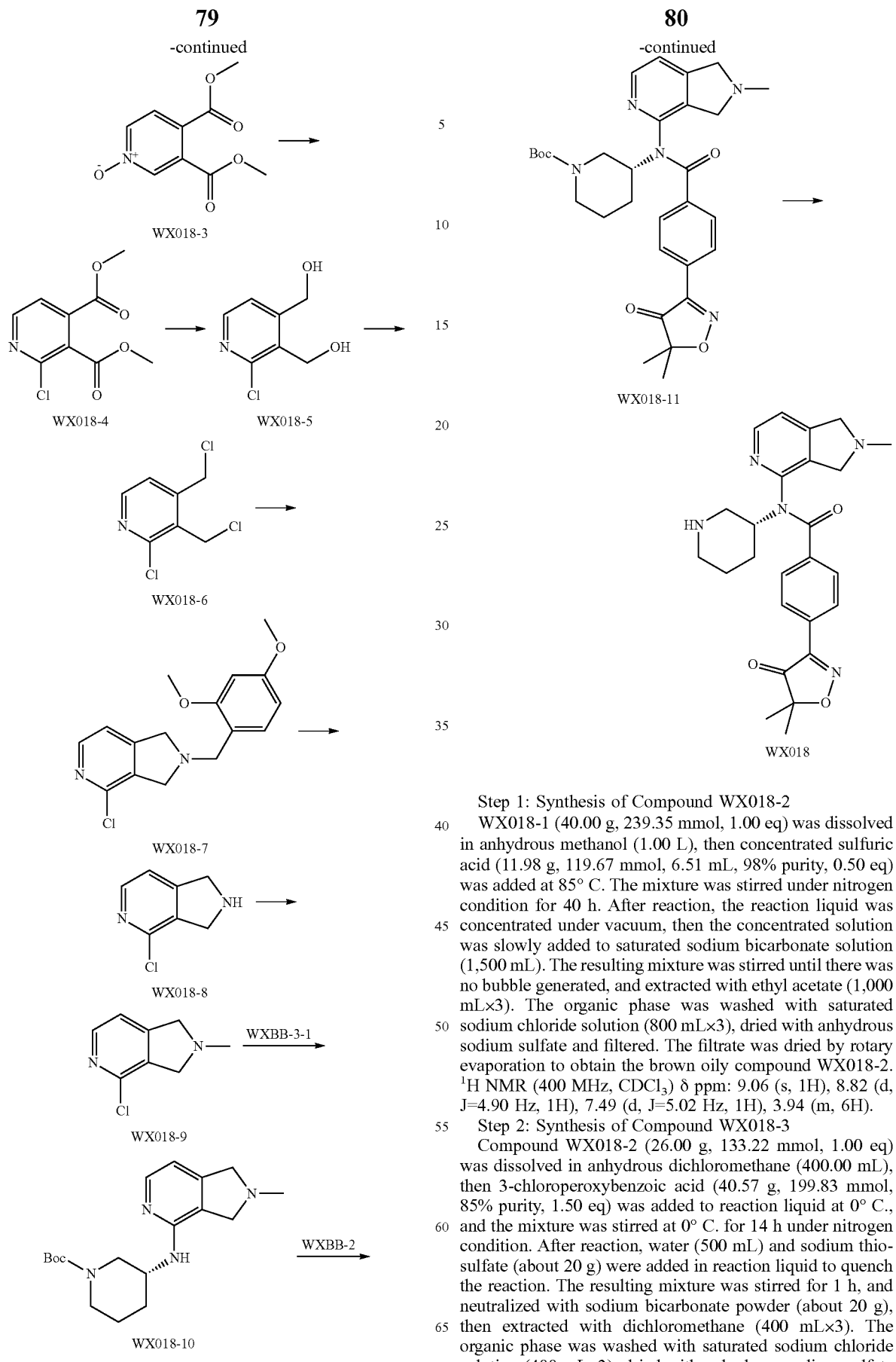

Step 1: Synthesis of Compound WX018-2

WX018-1 (40.00 g, 239.35 mmol, 1.00 eq) was dissolved in anhydrous methanol (1.00 L), then concentrated sulfuric acid (11.98 g, 119.67 mmol, 6.51 mL, 98% purity, 0.50 eq) was added at 85° C. The mixture was stirred under nitrogen condition for 40 h. After reaction, the reaction liquid was concentrated under vacuum, then the concentrated solution was slowly added to saturated sodium bicarbonate solution (1,500 mL). The resulting mixture was stirred until there was no bubble generated, and extracted with ethyl acetate (1,000 mL×3). The organic phase was washed with saturated sodium chloride solution (800 mL×3), dried with anhydrous sodium sulfate and filtered. The filtrate was dried by rotary evaporation to obtain the brown oily compound WX018-2. $^1$H NMR (400 MHz, CDCl$_3$) δ ppm: 9.06 (s, 1H), 8.82 (d, J=4.90 Hz, 1H), 7.49 (d, J=5.02 Hz, 1H), 3.94 (m, 6H).

Step 2: Synthesis of Compound WX018-3

Compound WX018-2 (26.00 g, 133.22 mmol, 1.00 eq) was dissolved in anhydrous dichloromethane (400.00 mL), then 3-chloroperoxybenzoic acid (40.57 g, 199.83 mmol, 85% purity, 1.50 eq) was added to reaction liquid at 0° C., and the mixture was stirred at 0° C. for 14 h under nitrogen condition. After reaction, water (500 mL) and sodium thiosulfate (about 20 g) were added in reaction liquid to quench the reaction. The resulting mixture was stirred for 1 h, and neutralized with sodium bicarbonate powder (about 20 g), then extracted with dichloromethane (400 mL×3). The organic phase was washed with saturated sodium chloride solution (400 mL×3), dried with anhydrous sodium sulfate and filtered. The filtrate was dried by rotary evaporation to obtain the crude. The crude was purified by column chromatography (petroleum ether:ethyl acetate=50:1-1:1) to obtain WX018-3. $^1$H NMR (400 MHz, CDCl$_3$) δ ppm: 8.35 (d, J=1.64 Hz, 1H), 8.25 (dd, J=6.78, 1.76 Hz, 1H), 7.70 (d, J=6.78 Hz, 1H), 3.96 (s, 3H), 3.93 (s, 3H).

Step 3: Synthesis of Compound WX018-4

Compound WX018-3 (4.00 g, 18.85 mmol, 1.00 eq) was dissolved in chloroform (80.00 mL), then phosphorus oxychloride (26.42 g, 172.29 mmol, 16.01 mL, 9.14 eq) was added to reaction liquid. The mixture was stirred at 80° C. for 60 h under nitrogen condition. After reaction, the reaction liquid was concentrated, and the concentrated solution was poured into saturated sodium bicarbonate solution (150 mL). Then dichloromethane (100 mL×3) was used for extraction. Organic phase was combined after liquid separation, washed with 250 mL of saturated sodium chloride solution, dried with anhydrous sodium sulfate and filtered. The filtrate was dried by rotary evaporation to obtain the brown oily crude. The crude was purified by column chromatography (petroleum ether/ethyl acetate=100/1-30/1) to obtain faint yellow solid compound WX018-4. $^1$H NMR (400 MHz, CDCl$_3$) δ ppm: 8.62-8.56 (m, 1H), 7.79 (dd, J=5.08, 0.70 Hz, 1H), 4.03-3.99 (m, 3H), 3.97-3.93 (m, 3H).

Step 4: Synthesis of Compound WX018-5

Compound WX018-4 (500.00 mg, 2.18 mmol, 1.00 eq) was dissolved in absolute ethyl alcohol (50.00 mL), sodium borohydride (500.59 mg, 13.23 mmol, 6.07 eq) was added to reaction liquid, and the reaction liquid was stirred at 25° C. for 2 h under nitrogen condition. After reaction, formic acid was dropwise added to reaction liquid to adjust pH to 5; the filtrate was filtered and evaporated by rotation to obtain the crude. The crude was dissolved in 100 mL of hydrochloric acid (2 M) and filtered. The aqueous phase was collected. The pH of aqueous phase was adjusted with sodium bicarbonate powder to 8. Then ethyl acetate (100 mL×5) was used for extraction. The organic phase was dried with anhydrous sodium sulfate and filtered. The filtrate was dried by rotary evaporation to obtain WX018-5. $^1$H NMR (400 MHz, CDCl$_3$) δ ppm: 8.36 (d, J=5.02 Hz, 1H), 7.35 (d, J=5.02 Hz, 1H), 4.94 (br d, J=3.50 Hz, 2H), 4.85 (br d, J=3.50 Hz, 2H).

Step 5: Synthesis of Compound WX018-6

Compound WX018-5 (1.90 g, 10.94 mmol, 1.00 eq) was dissolved in anhydrous dichloromethane (127.00 mL), thionyl chloride (207.74 g, 1.75 mol, 126.67 mL, 159.54 eq) was added to reaction liquid, and the reaction liquid was stirred at 25° C. for 14 h under nitrogen condition. After reaction, the reaction liquid was directly dried by rotary evaporation, the pH was adjusted with saturated sodium bicarbonate solution to 8. Then dichloromethane (20 mL×3) was used for extraction. The organic phase was collected, washed with saturated sodium chloride solution (50 mL), dried with anhydrous sodium sulfate and filtered. The filtrate was dried by rotary evaporation to obtain WX018-6. MS: m/z=210.1 [M+1].

Step 6: Synthesis of Compound WX018-7

WX018-6 (150.00 mg, 712.62 μmol, 1.00 eq), 2,4-dimethoxybenamine (375.35 mg, 2.24 mmol, 338.15 μL, 3.15 eq) and diisopropylethylamine (374.84 mg, 2.90 mmol, 506.54 μL, 4.07 eq) were dissolved in anhydrous dichloromethane (24.00 mL), and the reaction liquid was stirred at 25° C. for 40 h under nitrogen condition. After reaction, the reaction liquid was directly dried by rotary evaporation to obtain the crude. The crude was purified by Pre-TLC to obtain WX018-7. $^1$H NMR (400 MHz, CDCl$_3$) δ ppm: 8.13 (d, J=4.90 Hz, 1H), 7.15-7.21 (m, 1H), 6.99 (d, J=4.90 Hz, 1H), 6.45-6.39 (m, 2H), 3.94 (br d, J=3.01 Hz, 4H), 3.81 (s, 2H), 3.75 (d, J=5.66 Hz, 6H).

Step 7: Synthesis of Compound WX018-8

Compound WX018-7 (500.00 mg, 1.64 mmol, 1.00 eq) was dissolved in trifluoroacetic acid (5.00 mL), then triethylsilicon (95.35 mg, 820.00 μmol, 130.62 μL, 0.50 eq) was added to reaction liquid, and the reaction liquid was stirred at 63° C. for 4 h under nitrogen condition. After reaction, 10 mL of ethyl acetate was added, and then the reaction liquid was cooled to room temperature. Hydrochloric acid-ethyl acetate solution (10 mL) was added, The mixture solution was stirred for about 1 h at room temperature and filtered. The solid was washed with 20 mL of ethyl acetate to obtain WX018-8. $^1$H NMR (400 MHz, MeOD) δ ppm: 8.42 (d, J=5.02 Hz, 1H), 7.50 (d, J=5.02 Hz, 1H), 4.79 (s, 2H), 4.71 (s, 2H).

Step 8: Synthesis of Compound WX018-9

Compound WX018-8 (230.00 mg, 1.49 mmol, 1.00 eq) was dissolved in anhydrous methanol (20.00 mL), then paraformaldehyde (201.33 mg, 2.24 mmol, 1.50 eq), sodium borohydride acetate (473.69 mg, 2.24 mmol, 1.50 eq) and formic acid (7.16 mg, 149.00 μmol, 0.10 eq) were added to reaction liquid, and the liquid was stirred at 60° C. for 16 h under nitrogen condition. After reaction, the reaction liquid was dried by rotary evaporation, added with 100 mL of water, adjusted with sodium bicarbonate powder to pH=8, then extracted with dichloromethane (70 mL×3). The organic phase was washed with 150 mL of saturated sodium chloride solution, dried with anhydrous sodium sulfate and filtered. The filtrate was dried by rotary evaporation to obtain the crude. The crude was purified by Pre-TLC to obtain WX018-9. $^1$H NMR (400 MHz, CDCl$_3$) δ ppm: 8.25 (d, J=4.90 Hz, 1H), 7.11 (d, J=4.90 Hz, 1H), 3.99 (br d, J=3.14 Hz, 4H), 2.61 (s, 3H).

Step 9: Synthesis of Compound WX018-10

Compound WX018-9 (50.00 mg, 296.52 μmol, 1.00 eq), WXBB-3-1 (65.33 mg, 326.17 μmol, 1.10 eq), sodium tert-butoxide (56.99 mg, 593.04 μmol, 2.00 eq), BINAP (36.93 mg, 59.30 μmol, 0.20 eq) and tris(dibenzylideneacetone)dipalladium (27.15 mg, 29.65 μmol, 0.10 eq) were dissolved in anhydrous methylbenzene (3.00 mL). The mixture solution was stirred at 90° C. for 12 h under nitrogen condition. After reaction, the reaction liquid was diluted with 10 mL of methanol and filtered. The filter cake was washed with methanol (10 mL), and the filtrate was dried by rotary evaporation to obtain the crude. 10 mL of water was added to the crude. The pH of aqueous phase was adjusted with anhydrous hydrochloric acid solution (2M) to 1-2, the liquid was separated and the aqueous phase was collected. The aqueous phase was adjusted with solid sodium bicarbonate to pH=8, and extracted with ethyl acetate (10 mL×3). The organic phase was collected, washed with saturated sodium chloride solution (10 mL), dried with anhydrous sodium sulfate and filtered. The filtrate was concentrated under vacuum to obtain WX018-10. $^1$H NMR (400 MHz, CDCl$_3$) δ ppm: 7.99 (d, J=5.26 Hz, 1H), 6.52 (d, J=5.26 Hz, 1H), 4.12 (br, 1H), 3.92-3.84 (m, 2H), 3.77-3.64 (m, 3H), 3.48-3.31 (m, 3H), 2.59 (s, 3H), 1.93 (br s, 1H), 1.69 (br s, 2H), 1.43 (br s, 10H).

Step 10: Synthesis of Compound WX018-11

Compound WX018-10 (90.00 mg, 270.73 μmol, 0.80 eq) was dissolved in anhydrous tetrahydrofuran (7.00 mL), and LHMDS (1 M, 304.57 μL, 0.90 eq) was added to reaction liquid at 0° C. The reaction liquid was stirred at 0° C. for 1 h, then WXBB-2 (85.17 mg, 338.41 μmol, 1.00 eq) was added at 0° C., and the reaction liquid was stirred at 25° C.

for 12 h. After reaction, reaction liquid was added with water to quench the reaction, and extracted with ethyl acetate (40 mL×3). The organic phase was washed with saturated sodium chloride solution (40 mL), dried with anhydrous sodium sulfate, and dried by rotary evaporation to obtain the crude. The crude was separated and purified by HPLC to obtain WX018-11. MS: m/z=548.3 [M+1].

Step 11: Synthesis of Compound WX018

Compound WX018-11 (25.00 mg, 45.65 μmol, 1.00 eq) was dissolved in anhydrous methanol (5.00 mL), and hydrochloric acid-methanol solution (4 M, 5.00 mL) was added to reaction liquid. The reaction liquid was stirred at 25° C. for 1 h. After reaction, the reaction liquid was directly dried by rotary evaporation to obtain WX018. $^1$H NMR (400 MHz, MeOD) δ ppm: 8.61 (br, 1H), 8.01 (d, J=7.16 Hz, 2H), 7.49 (m, 3H), 4.75-4.5 (br, 1H), 3.55-3.8 (m, 1H), 3.25-3.45 (br, 1H), 2.90 (br, 5H), 2.03 (br, 2H), 1.89 (br, 2H), 1.41 (s, 6H). m/z=448.2 [M+1].

Implementation 017: WX019

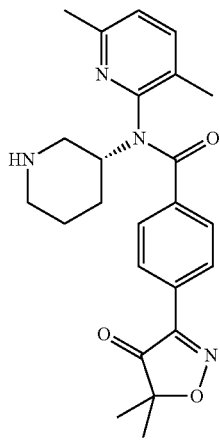

Synthetic Route:

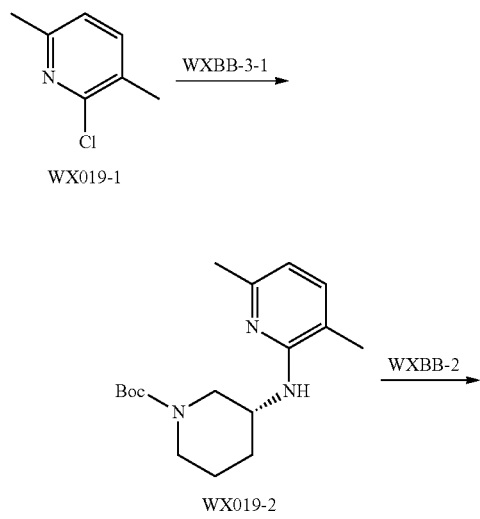

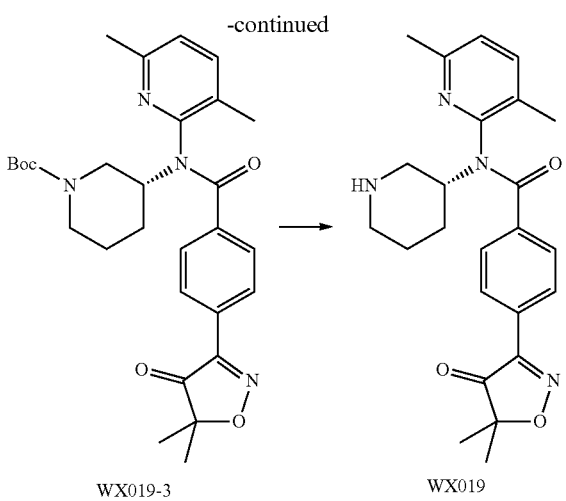

Step 1: Synthesis of Compound WX019-2

Compound WX019-1 (300.00 mg, 2.12 mmol, 1.00 eq), WXBB-3-1 (445.54 mg, 2.22 mmol, 1.05 eq), sodium tert-butoxide (407.20 mg, 4.24 mmol, 2.00 eq), BINAP (263.84 mg, 423.73 μmol, 0.20 eq) and tris(dibenzylideneacetone)dipalladium (194.01 mg, 211.86 μmol, 0.10 eq) were added in a 40 ml pre-dried reaction flask, then anhydrous methylbenzene (10.00 mL) was added in the reaction flask, The mixture was bubbled with nitrogen for 1 min. The reaction flask was placed in oil bath at 90° C., and the mixture was stirred for 12 h. After reaction, the reaction liquid was naturally cooled to room temperature, and then filtered through a five-hole funnel covered with diatomite. The filter cake was washed with dichloromethane (20 mL). The filtrate was combined and concentrated under vacuum with water pump at 40° C. to obtain the crude. The crude was diluted with 20 mL of ethyl acetate and 20 mL of water. The aqueous hydrochloric acid solution (2M) was dropwise added to the above-mentioned system to adjusted the pH of aqueous phase to 1-2. The liquid was separated and the aqueous phase was collected. The pH of aqueous phase was adjusted with solid sodium bicarbonate to 8, extracted with ethyl acetate (20 mL*3). The organic phase was combined after liquid separation, washed with saturated sodium chloride solution (10 mL), dried with anhydrous sodium sulfate, filtered, and concentrated under vacuum to obtain WX019-2. MS: m/z=306.3 [M+1].

Step 2: Synthesis of Compound WX019-3

WX019-2 (150.00 mg, 491.14 μmol, 0.80 eq) and anhydrous tetrahydrofuran (10.00 mL) were added in a 100 mL pre-dried three-mouth flask. LHMDS (1 M, 552.54 μL, 0.90 eq) was slowly dropwise added at 0° C. under nitrogen condition. The mixture was continuously stirred for 1 h, then added with WXBB-2 (154.51 mg, 613.93 μmol, 1.00 eq), naturally warmed to 25° C. The mixture was stirred for 2 h. After reaction, the reaction system was cooled to 0° C., 10 mL of water was slowly added to quench the reaction. Ethyl acetate (10 mL*3) was added in the system for extraction. The organic phase was combined, washed with saturated sodium chloride solution (10 mL), dried with anhydrous sodium sulfate, and filtered. The filtrate was concentrated under vacuum to obtain the crude, and the crude was purified by TLC silica gel plate (petroleum ether:ethyl acetate=2:1) to obtain yellow solid compound WX019-3. MS: m/z=521.3 [M+1].

Step 3: Synthesis of Compound WX019

Compound WX019-3 (150.00 mg, 288.12 μmol, 1.00 eq) and hydrochloric acid-methanol solution (4 M, 4.00 mL) were added in a pre-dried 50 ml reaction flask, then anhydrous methanol (4.00 mL) was added in the reaction flask, The mixture was bubbled with nitrogen for 1 min. The mixture was stirred at 25° C. for 2 h. After reaction, The reaction liquid was directly dried by rotary evaporation with water pump to obtain the crude, and 30 mL of ethyl acetate and 20 mL of water were added to obtain crude. The aqueous phase was adjusted with solid sodium bicarbonate to pH=8, extracted with ethyl acetate (30 mL*6). The organic phase was combined, washed with saturated sodium chloride solution (50 mL), dried with anhydrous sodium sulfate and filtered. The filtration was concentrated under vacuum to obtain WX019. $^1$H NMR (400 MHz, CDCl$_3$) δ ppm: 7.89 (d, J=8.28 Hz, 2H), 7.38 (d, J=7.78 Hz, 2H), 7.23-7.16 (m, 1H), 7.00-6.94 (m, 1H), 4.86-4.53 (m, 1H), 3.62-3.50 (m, 1H), 3.38-3.20 (m, 1H), 3.13-3.03 (m, 1H), 2.67-2.51 (m, 4H), 2.45-2.25 (m, 1H), 2.00-1.89 (m, 3H), 1.86-1.79 (m, 1H), 1.75-1.63 (m, 2H), 1.45 (s, 6H), 1.38-1.26 (m, 1H).

Implementation 018: WX020

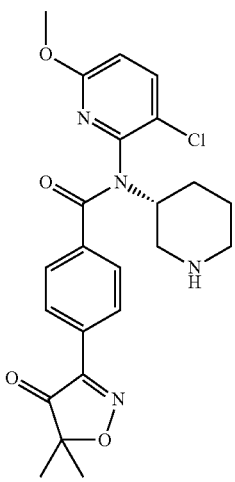 [SMILES: COc1ccc(Cl)c(N(C(=O)c2ccc(C3=NOC(C)(C)C3=O)cc2)[C@@H]2CCCNC2)n1]

Synthetic Route:

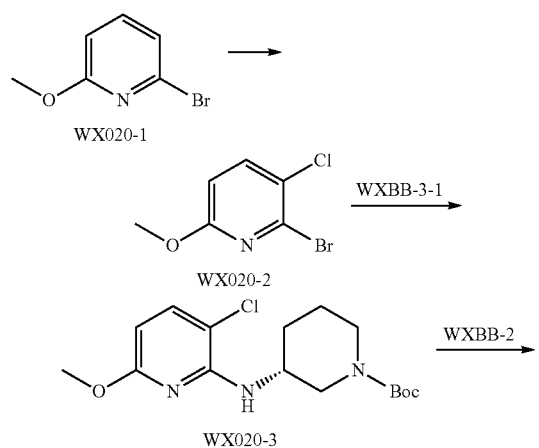

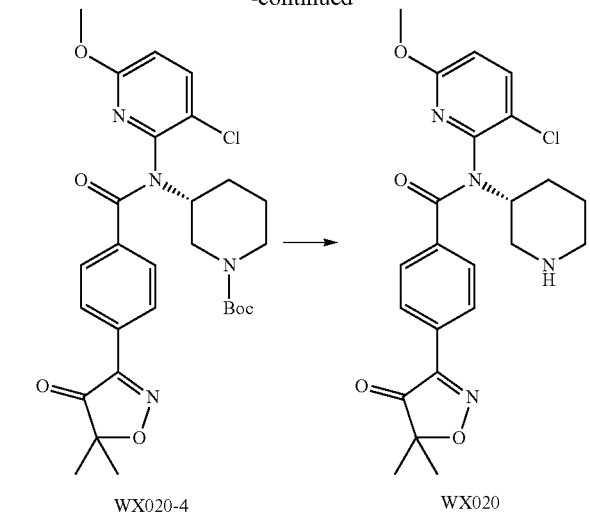

Step 1: Synthesis of Compound WX020-2

Compound WX020-1 (500.00 mg, 2.66 mmol, 326.80 μL, 1.00 eq) was added to a round-bottom flask containing anhydrous N,N-dimethylformamide (10.00 mL), and N-chlorosuccinimide (800.00 mg, 6.00 mmol, 2.26 eq) was added. After reaction, 25 mL of water was added. The mixture solution was extracted with 30 mL of ethyl acetate. The organic phase was washed with 20 mL of water, 25 mL of saturated sodium bicarbonate solution and 25 mL of saturated sodium chloride solution in order. The organic phase was dried with anhydrous sodium sulfate, and filtered. The filtrate was dried by rotary evaporation under vacuum to obtain WX020-2. $^1$H NMR (400 MHz, CDCl$_3$) δ ppm: 3.93 (s, 3H), 6.68 (d, J=8.78 Hz, 1H), 7.57 (d, J=8.53 Hz, 1H).

Step 2: Synthesis of Compound WX020-3

Compound WX020-2 (400.00 mg, 1.71 mmol, 1.00 eq) and WXBB-3-1 (360.00 mg, 1.80 mmol, 1.05 eq) were added to a round-bottom flask containing anhydrous methylbenzene (15.00 mL), then sodium tert-butoxide (340.00 mg, 3.54 mmol, 2.07 eq), BINAP (160.00 mg, 256.96 μmol, 0.15 eq) and tris(dibenzylideneacetone)dipalladium (160.00 mg, 174.73 μmol, 0.10 eq) were added, and the reaction liquid was stirred at 90° C. for 19 h under nitrogen condition. After reaction, the reaction liquid was dried by rotary evaporation, dissolved with 20 mL of dichloromethane, and washed with 20 mL of water. The organic phase was dried with anhydrous sodium sulfate, and filtered. The filtrate was dried by rotary evaporation under vacuum to obtain brown crude. The crude was purified by column chromatography (petroleum ether:ethyl acetate=19:1-7:3) to obtain WX020-3. $^1$H NMR (400 MHz, CDCl$_3$) δ ppm: 1.40 (br s, 9H), 1.53-1.60 (m, 1H), 1.62 (s, 4H), 1.68-1.81 (m, 2H), 1.91-2.00 (m, 1H), 3.45 (br s, 3H), 3.69 (br s, 1H), 3.87 (s, 3H), 4.05 (tt, J=6.96, 3.33 Hz, 1H), 5.99 (d, J=8.28 Hz, 1H), 7.33 (d, J=8.28 Hz, 1H).

Step 3: Synthesis of Compound WX020-4

Compound WX020-3 (500.00 mg, 1.36 mmol, 0.82 eq) was dissolved in anhydrous tetrahydrofuran (20.00 mL), LHMDS (1 M, 2.00 mL, 1.20 eq) was added at 0° C. under nitrogen condition. The mixture was stirred for 1 h, added with WXBB-2 (420.00 mg, 1.67 mmol, 1.00 eq), and then reacted at 20° C. for 18 h. After reaction, the reaction was quenched with 30 mL water, extracted with ethyl acetate (30 mL*3). The organic phase was collected, dried with anhydrous sodium sulfate, and filtered. The filtration was dried by rotary evaporation under vacuum to obtain brown solid, which was then separated and purified by column chromatography (petroleum ether:ethyl acetate=10:1-3:1) to obtain WX020-4. ¹H NMR (400 MHz, CDCl3) δ ppm: 1.45 (s, 9H), 1.49 (s, 6H), 1.70-1.83 (m, 2H), 1.92-2.03 (m, 1H), 2.19-2.82 (br, 2H), 3.09-3.62 (m, 2H), 3.81 (s, 1H), 3.90-3.99 (m, 3H), 4.50 (br, 1H), 6.60 (d, J=8.53 Hz, 1H), 7.35 (d, J=8.78 Hz, 1H), 7.45 (J=8.28 Hz, 2H), 7.93 (d, J=8.03 Hz, 2H).

Step 4: Synthesis of Compound WX020

Compound WX020-4 (200.00 mg, 262.73 μmol, 1.00 eq) was dissolved in anhydrous methanol (20.00 mL), hydrochloric acid-methanol solution (4 M, 3.10 mL, 47.20 eq) was added. The mixture was stirred at 20° C. for 2 h. After reaction, the reaction liquid was dried by rotary evaporation under vacuum to obtain yellow-green solid. The solid was dissolved with 20 mL water, adjusted with saturated sodium bicarbonate to pH=7-8, extracted with dichloromethane (20 mL*3), dried with anhydrous sodium sulfate, and filtered. The filtrate was dried by rotary evaporation under vacuum to obtain the yellow-green solid. The solid was purified by prep-TLC (dichloromethane:methanol=10:1) to obtain WX020. ¹H NMR (400 MHz, CDCl₃) δ ppm: 1.30 (br, 1H), 1.45 (s, 6H), 1.72-1.85 (m, 1H), 1.95 (br, 1H), 2.29-2.67 (m, 2H), 3.03-3.01 (m, 1H), 3.12-3.34 (m, 1H), 3.49-3.55 (m, 1H), 3.94-3.98 (m, 3H), 4.55-4.73 (br, 1H), 6.60 (d, J=8.53 Hz, 1H), 7.33 (d, J=8.78 Hz, 1H), 7.44 (d, J=7.78 Hz, 2H), 7.93 (d, J=8.03 Hz, 2H).

Implementation 019: WX021

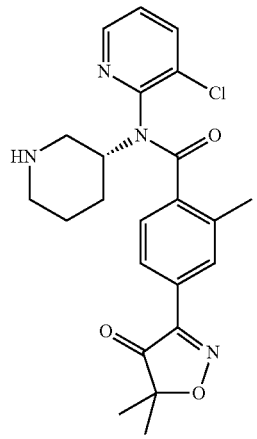

Synthetic Route:

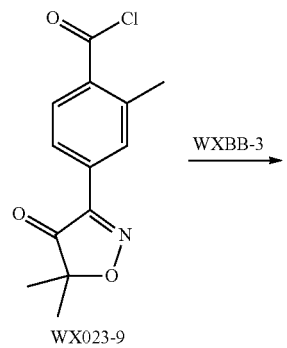

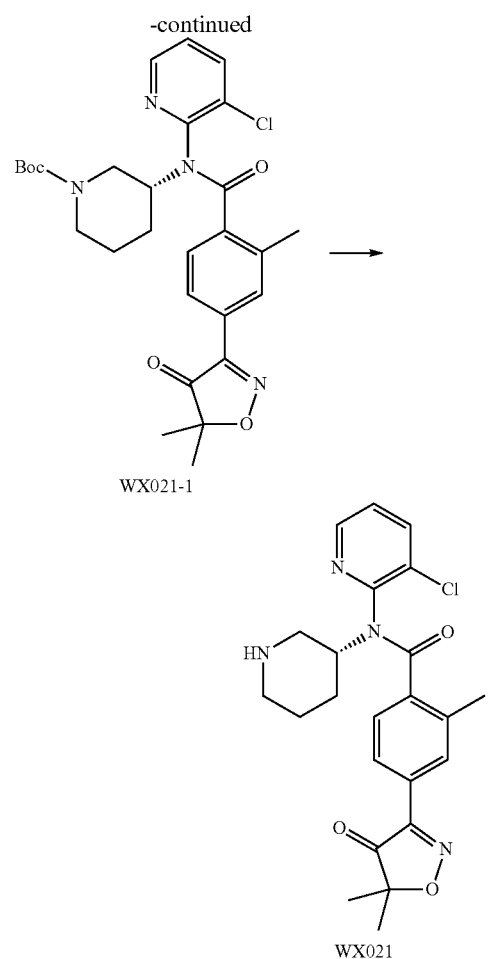

Step 1: Synthesis of Compound WX021-1

WXBB-3 (100.00 mg, 320.71 μmol, 0.80 eq) was dissolved in anhydrous tetrahydrofuran (10.00 mL). Air was extracted and changed with nitrogen three times. LiHMDS (1 M, 360.80 μL, 0.90 eq) was slowly dropwise added at 1-5° C. under nitrogen condition. The mixture was continuously stirred at 0° C. for 1 h after charging, then was slowly added with WX023-9 (106.51 mg, 400.89 μmol, 1.00 eq), gradually warmed to 25° C. The mixture was stirred for 1 h. After reaction, the reaction system was cooled to 0° C. 10 mL of water was slowly added to quench the reaction. The system was added with ethyl acetate (10 mL*3) for extraction. The organic phase was dried with anhydrous sodium sulfate, and filtered. The filtrate was concentrated under vacuum to obtain WX021-1.

Step 2: Synthesis of Compound WX021

WX021-1 (50.00 mg, 92.41 μmol, 1.00 eq) was dissolved in anhydrous methanol (4.00 mL), and then HCl/methanol (4 M, 6.40 mL) was added in the reaction flask. Air was extracted and changed with nitrogen three times, and the reaction flask was placed at 25° C. to stir for 2 h. After reaction, the reaction liquid was concentrated at 50° C. under vacuum to obtain WX021. ¹H NMR (400 MHz, MeOD) δ ppm: 8.46-8.44 (m, 1H), 7.81-7.76 (m, 2H), 7.60-7.58 (m, 1H), 7.32-7.30 (m, 1H), 7.18-7.14 (m, 1H), 4.99-4.97 (m, 1H), 3.83-3.81 (m, 1H), 3.57-3.56 (m, 1H), 3.34-3.33 (m, 1H), 2.85-2.88 (m, 1H), 2.47 (s, 3H), 2.01-1.96 (m, 3H), 1.39-1.36 (m, 7H).

Implementation 020: WX022

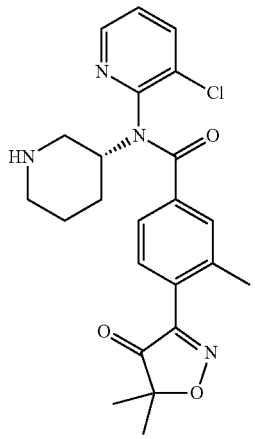 [SMILES: Cc1cc(C(=O)N(c2ncccc2Cl)[C@@H]2CCCNC2)ccc1C1=NOC(C)(C)C1=O]

Synthetic Route:

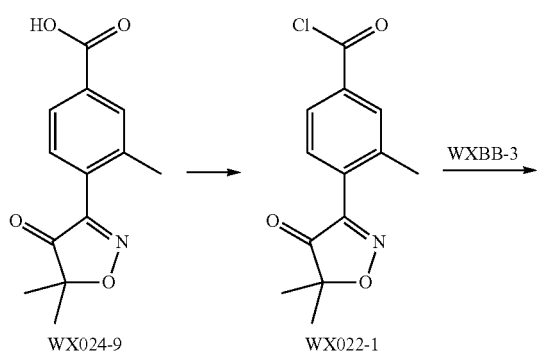

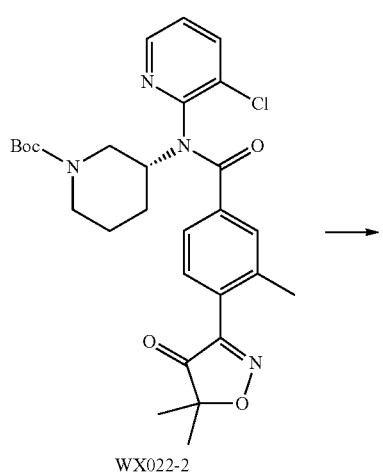

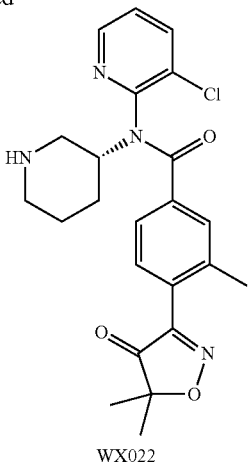

WX022

Step 1: Synthesis of Compound WX022-1

WX024-9 (200.00 mg, 808.90 μmol, 1.00 eq) and (COCl)$_2$ (203.00 mg, 1.60 mmol, 140.00 μL, 1.98 eq) were added to the solvents of anhydrous dichloromethane (2.00 mL) and DMF (50.00 μL). The mixture was stirred at 20° C. for 2 h. After reaction, the solvent was spined out by rotary evaporation. anhydrous methylbenzene (3*10 mL) was added to crude, and then spined out; the reaction liquid was concentrated with oil pump to obtain WX022-1.

Step 2: Synthesis of Compound WX022-2

Under N$_2$ condition, WXBB-3 (232.18 mg, 677.62 μmol, 0.80 eq) (purity 91%) was added to anhydrous tetrahydrofuran (5.00 mL). The mixture was cooled to 0° C., added with LiHMDS (1 M, 680.00 μL, 0.80 eq). The mixture was stirred for 1 h. Then WX022-1 (214.00 mg, 847.02 μmol, 1.00 eq) was added. The mixture was slowly warmed to 20° C. and stirred for 16 h. After reaction, water (10 mL) was added to reaction liquid, and ethyl acetate (3*12 mL) was used for extraction. The organic phase was washed with saturated sodium chloride solution (10 mL), dried with anhydrous sodium sulfate, filtered, and concentrated. The crude was purified by column chromatography (petroleum ether:ethyl acetate=1:0-4:1) to obtain WX022-2. $^1$H NMR (400 MHz, MeOD) δ ppm: 1.41 (s, 6H), 1.38-1.52 (m, 1H), 1.43-1.51 (m, 9H), 1.93-1.57 (m, 3H), 2.30 (s, 3H), 2.51-2.91 (m, 2H), 4.01 (br, 1H), 4.23-4.64 (m, 2H), 7.12-7.52 (m, 4H), 7.69-7.87 (m, 1H), 8.43-8.58 (m, 1H).

Step 2: Synthesis of Compound WX022

WX022-2 (65.00 mg, 108.13 μmol, 1.00 eq) (purity 90%) was added to HCl/EtOAc (4 M, 1.40 mL, 51.79 eq). The mixture was stirred at 15° C. for 20 h. After reaction, the mixture was adjusted with saturated sodium bicarbonate to pH≈7, and extracted with dichloromethane (3*10 mL). The organic phase was washed with saturated sodium chloride solution (10 mL), dried with anhydrous magnesium sulfate, filtered, and concentrated. The crude was purified by prep-TLC (dichloromethane:methanol=10:1) and prep-HPLC (column: Xtimate C18 150*25 mm*5 μm; mobile phase: [water (0.05% ammonia hydroxide v/v)-ACN]; B %: 40%-70%, 10 min) to obtain WX022. $^1$H NMR (400 MHz, MeOD) δ ppm: 1.18-1.36 (m, 1H), 1.41 (s, 6H), 1.61-1.98 (m, 3H), 2.29 (s, 3H), 2.37-2.62 (m, 1H), 2.96 (br d, J=12.80 Hz, 1H), 3.07-3.28 (m, 1H), 3.44 (br d, J=11.80 Hz, 1H), 4.46-4.78 (m, 1H), 7.20 (br s, 1H), 7.26-7.37 (m, 2H), 7.43 (br d, J=6.78 Hz, 1H), 7.75 (br d, J=8.03 Hz, 1H), 8.53 (br s, 1H).

Implementation 021: WX023
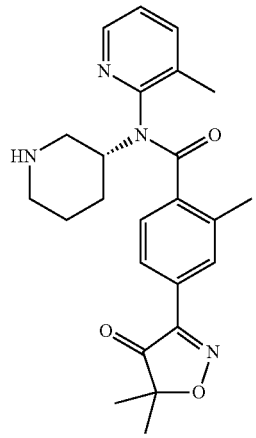 [SMILES: Cc1cc(C2=NOC(C)(C)C2=O)ccc1C(=O)N(c1ncccc1C)[C@@H]1CCCNC1]
Synthetic Route:
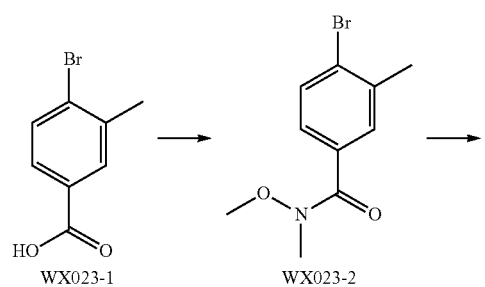
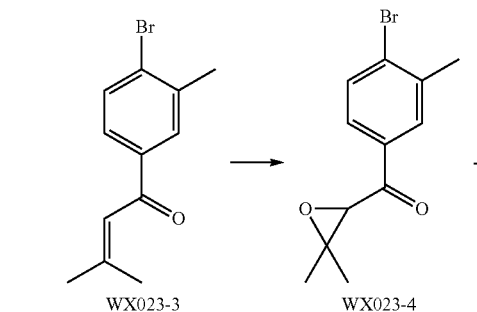
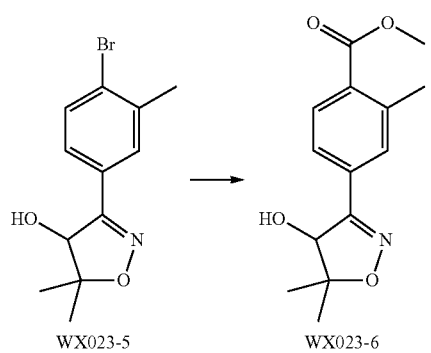
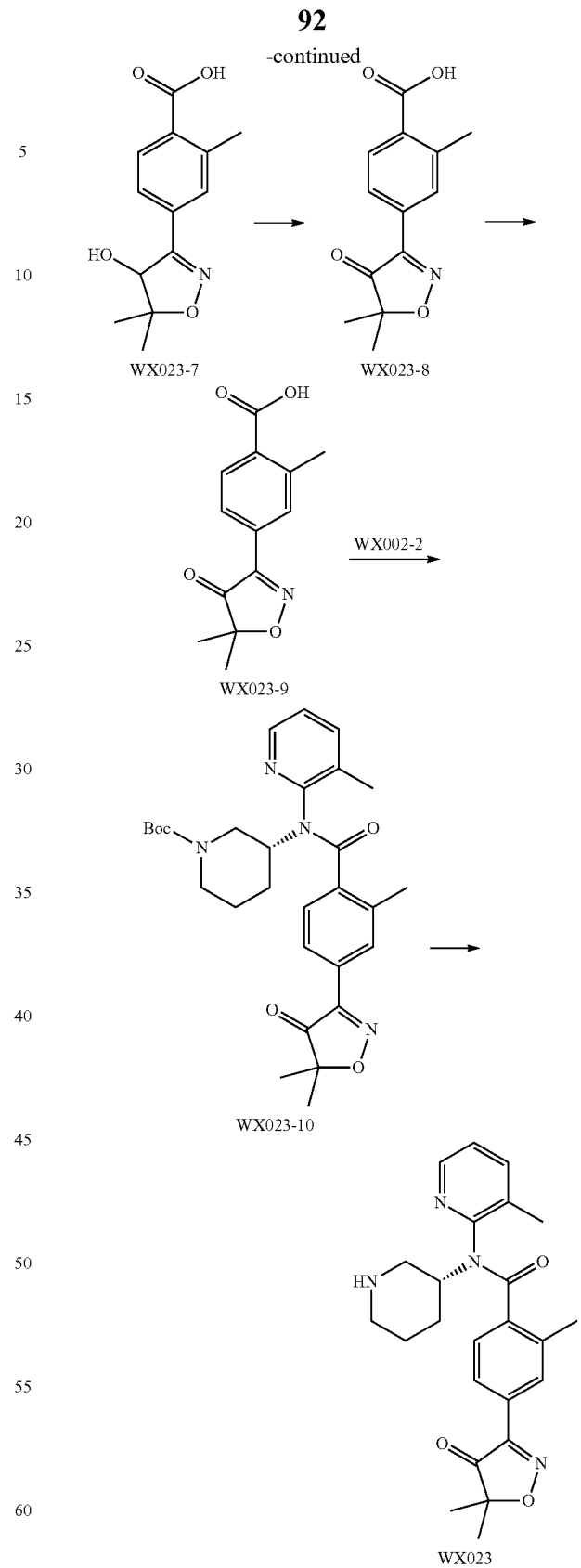
Step 1: Synthesis of Compound WX023-2
WX023-1 (50.00 g, 232.51 mmol, 1.00 eq), anhydrous dichloromethane (500.00 mL) and triethylamineethyl acetate (47.06 g, 465.02 mmol, 64.47 mL, 2.00 eq) were added to the reaction flask, then HOBt (34.56 g, 255.76 mmol, 1.10 eq), EDCI (49.03 g, 255.76 mmol, 1.10 eq), and N-methoxymethylamine (27.22 g, 279.01 mmol, 1.20 eq, HCl) were added to the reaction flask. Air was extracted and changed with nitrogen three times. The reaction flask was placed at 25° C., and the mixture was stirred for 3 h. After reaction, the reaction liquid was diluted with 300 ml of dichloromethane, washed with 0.5N HCl (800 ml) (there was white solid generated), and filtered. The filtration was separated. The aqueous phase was extracted with dichloromethane (300 ml*3). The combined organic phase was washed with saturated sodium bicarbonate (300 ml), dried with anhydrous sodium sulfate, filtered, and concentrated under vacuum to obtain WX023-2. $^1$H NMR (400 MHz, $CDCl_3$) δ ppm: 7.58-7.54 (m, 2H), 7.37 (dd, J=8.16, 1.76 Hz, 1H), 3.55 (s, 3H), 3.36 (s, 3H), 2.43 (s, 3H).

Step 2: Synthesis of Compound WX023-3

WX023-2 (10.00 g, 38.74 mmol, 1.00 eq) was added to anhydrous tetrahydrofuran (100.00 mL), Air was extracted and changed with nitrogen three times. 2-methyl-1-propenylmagnesium bromide (0.5 M, 116.22 mL, 1.50 eq) was slowly dropwise added at −10° C., and the reaction was terminated after 2-methyl-1-propenylmagnesium bromide was completely added. The reaction system was cooled to 0° C., and $NH_4Cl$ saturated solution (100 mL) was slowly added to quench the reaction. The reaction liquid was extracted with ethyl acetate (300 mL*3). The combined organic phase was dried with anhydrous sodium sulfate, and filtered. The filtrate was concentrated under vacuum, and the crude was purified by rapid column chromatography (mesh number of silica gel: 100-200 meshes; petroleum ether:ethyl acetate=100:1-20:1) to obtain WX023-3.

$^1$H NMR (400 MHz, $CDCl_3$) δ ppm: 7.79 (d, J=0.66 Hz, 1H), 7.64-7.56 (m, 2H), 6.72-6.68 (m, 1H), 2.46 (s, 3H), 2.22 (s, 3H), 2.03 (s, 3H).

Step 3: Synthesis of Compound WX023-4

WX023-3 (9.00 g, 35.55 mmol, 1.00 eq) was dissolved in dichloromethane (180.00 mL). Air was extracted and changed with nitrogen three times. Metachloroperbenzoic acid (34.29 g, 168.86 mmol, 85% purity, 4.75 eq) was added to the reaction flask in five bathes at 0° C. The mixture was gradually warmed to 25° C. and stirred for 20 h. After reaction, the reaction system was cooled to 0° C., slowly added $Na_2SO_3$ saturated solution (300 mL) to quench the reaction, and the mixture was stirred for 1 h. Sodium bicarbonate (30 g) was added to the reaction system, then the reaction liquid was stirred for 30 min and separated. The organic phase was washed with saturated sodium chloride solution (200 mL), dried with anhydrous sodium sulfate, and filtered. The filtrate was concentrated under vacuum to obtain WX023-4.

$^1$H NMR (400 MHz, $CDCl_3$) δ ppm 7.85 (d, J=1.32 Hz, 1H), 7.70-7.63 (m, 2H), 4.00 (s, 1H), 2.48 (s, 3H), 1.58 (s, 3H), 1.24 (s, 3H)

Step 4: Synthesis of Compound WX023-5

WX023-4 (8.70 g, 32.33 mmol, 1.00 eq) was dissolved in anhydrous methanol (130.00 mL) and pyridine (80.00 mL), then hydroxylamine hydrochloride (8.99 g, 129.32 mmol, 4.00 eq) was added. Air was extracted and changed with nitrogen. The reaction flask was placed in oil bath at 80° C., and the mixture was stirred for 16 h. After reaction, the reaction liquid was concentrated under vacuum, and the residuum was dissolved with water (500 mL). The glacial acetic acid was dropwise added to the system to pH=3-4. The system was added with ethyl acetate (500 mL*3) for extraction, and the organic phase was combined after liquid separation. The organic phase was washed with saturated sodium chloride solution (500 mL), dried with anhydrous sodium sulfate and filtered. The filtrate was concentrated under vacuum. The residue was washed with 80 ml of (petroleum ether:ethyl acetate=15:1) to obtain WX023-5. $^1$H NMR (400 MHz, $CDCl_3$) δ ppm: 7.69 (s, 1H), 7.59-7.56 (m, 1H), 7.52-7.47 (m, 1H), 4.81 (s, 1H), 2.43 (s, 3H), 1.52 (s, 3H), 1.33 (s, 3H).

Step 5: Synthesis of Compound WX023-6

WX023-5 (2.00 g, 7.04 mmol, 1.00 eq) was dissolved in anhydrous methanol (150.00 mL) and DMF (50.00 mL), then triethylamine (2.14 g, 21.12 mmol, 2.93 mL, 3.00 eq) and $Pd(PPh_3)_4$ (813.35 mg, 703.85 μmol, 0.10 eq) were added in order. Air was extracted and changed with carbon monoxide three times, and pressurized to 50 psi. The reaction container was placed in oil bath at 80° C., and the mixture was stirred for 140 h. After reaction, the reaction liquid was filtered, and the filtrate was concentrated under vacuum. The crude was purified by rapid column chromatography (petroleum ether:ethyl acetate=100:1-1:1) to obtain WX023-6. $^1$H NMR (400 MHz, $CDCl_3$) δ ppm: 7.95 (d, J=8.16 Hz, 1H), 7.72-7.62 (m, 2H), 4.85 (d, J=9.70 Hz, 1H), 3.92 (s, 3H), 2.63 (s, 3H), 1.53 (s, 3H), 1.34 (s, 3H).

Step 6: Synthesis of Compound WX023-7

WX023-6 (1.80 g, 6.84 mmol, 1.00 eq) was dissolved in anhydrous tetrahydrofuran (20.00 mL) and water (5.00 mL), then monohydrate LiOH (1.44 g, 34.20 mmol, 5.00 eq) was added in the reaction flask. Air was extracted and exchanged with nitrogen three times. The reaction flask was placed at 25° C. and the mixture was stirred for 2 h. After reaction, the 2N HCl reaction liquid was dropwise added to reaction system to pH=2-3. Ethyl acetate (10 mL*3) was added to the system for extraction, and the organic phase was concentrated under vacuum to obtain WX023-7. $^1$H NMR (400 MHz, $CDCl_3$) δ ppm: 8.03 (d, J=8.16 Hz, 1H), 7.71-7.66 (m, 2H), 4.84 (s, 1H), 2.67 (s, 3H), 1.56 (s, 3H), 1.34 (s, 3H).

Step 7: Synthesis of Compound WX023-8

WX023-7 (1.10 g, 4.41 mmol, 1.00 eq) was dissolved in AcOH (20.00 mL), then concentrated $H_2SO_4$ (600.00 μL), and water (2.00 mL) were added. Finally $CrO_3$ (529.51 mg, 5.29 mmol, 196.11 μL, 1.20 eq) was added to the reaction flask. The reaction flask was placed at 100° C. in oil bath, and the mixture was stirred for 2 h. After reaction, 50 mL of water was added in the reaction system (there was precipitation generated). The reaction liquid was filtered. The filtrate was added to the separating funnel and extracted with dichloromethane (100 mL*3). The residue was dissolved with dichloromethane:methanol=10:1 (150 mL), and washed with water (100 mL). The combined organic phase was dried with anhydrous sodium sulfate, and filtered. The filtrate was concentrated under vacuum to obtain WX023-8. $^1$H NMR (400 MHz, MeOD) δ ppm: 7.99-7.97 (m, 3H), 2.63 (s, 3H), 1.45 (s, 6H).

Step 8: Synthesis of Compound WX023-9

Substrate 8 (300.00 mg, 1.21 mmol, 1.00 eq) was dissolved with anhydrous dichloromethane (20.00 mL), then $(COCl)_2$ (230.38 mg, 1.81 mmol, 158.88 μL, 1.50 eq) and DMF (8.84 mg, 121.00 μmol, 9.31 μL, 0.10 eq) were added at 0° C., and the mixture was stirred for 2 h. After reaction, the reaction liquid was concentrated. The residue was added with anhydrous methylbenzene (10 mL*3), and then concentrated under vacuum to obtain WX023-9.

Step 9: Synthesis of Compound WX023-10

WX002-2 (100.00 mg, 343.18 μmol, 0.80 eq) was dissolved in anhydrous tetrahydrofuran (10.00 mL). Air was extracted and changed with nitrogen three times. The mixture was then cooled to 0° C., slowly dropwise added with LiHMDS (1 M, 386.08 μL, 0.90 eq) under nitrogen condition. The reaction liquid was continuously stirred at 0° C. for 1 h, added with WX023-9 (113.98 mg, 428.98 μmol, 1.00 eq), gradually warmed to 25° C. The mixture was stirred for 1 h. After reaction, the reaction system was cooled to 0° C., slowly added with 10 mL of water to quench the reaction. The mixture was extracted with ethyl acetate (10 mL*3), combined with the organic phase, dried with anhydrous sodium sulfate, and filtered. The filtrate was concentrated under vacuum to obtain WX023-10. $^1$H NMR (400 MHz, CDCl$_3$) δ ppm: 8.32-8.29 (m, 1H), 7.80 (m, 1H), 7.60-7.57 (m, 1H), 7.36-7.34 (m, 1H), 7.08-6.99 (m, 2H), 4.61-4.56 (m, 1H), 4.15-4.14 (m, 3H), 3.6-3.5 (m, 1H), 2.57-2.52 (m, 3H), 2.43 (s, 3H), 2.18-2.16 (m, 3H), 1.79-1.6 (m, 3H), 1.56 (s, 9H), 1.42 (s, 6H).

Step 10: Synthesis of Compound WX023

WX023-10 (130.00 mg, 249.70 μmol, 1.00 eq) was dissolved in anhydrous methanol (4.00 mL), HCl/methanol (4.75 mL, 4M) was added, and the reaction liquid was stirred at 25° C. for 2 h. After reaction, the reaction liquid was concentrated under vacuum. Water (5.00 mL) was added to the residue to dissolve the substrate, and the pH was adjusted with sodium bicarbonate to 8. The mixture was extracted with ethyl acetate (10 mL*5), combined with the organic phase, washed with saturated sodium chloride solution (10 mL), dried with anhydrous sodium sulfate, and filtered. The filtrate was concentrated under vacuum to obtain WX023. $^1$H NMR (400 MHz, CDCl$_3$) δ ppm: 8.36-8.27 (m, 1H), 7.81-7.79 (m, 1H), 7.60-7.57 (m, 1H), 7.36-7.34 (m, 1H), 7.08-6.99 (m, 2H), 4.80-4.74 (m, 1H), 3.68-3.66 (m, 1H), 3.38-3.36 (m, 1H), 3.12-3.10 (m, 1H), 2.68-2.81 (m, 1H), 2.43 (s, 3H), 2.06-2.07 (m, 3H), 1.79-1.77 (m, 2H), 1.70-1.65 (m, 2H), 1.43-1.41 (m, 1H), 1.34 (s, 6H).

Implementation 022: WX024

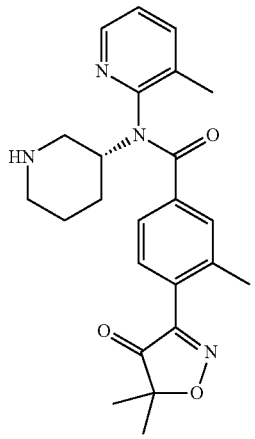 [SMILES: Cc1cc(C(=O)N(c2ncccc2C)[C@@H]2CCCNC2)ccc1C1=NOC(C)(C)C1=O]

Synthetic Route:

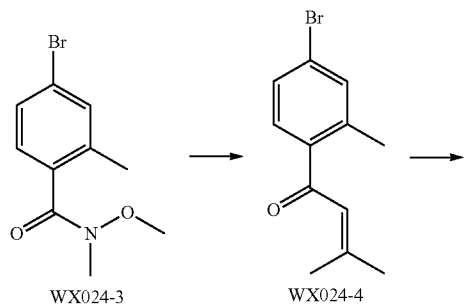

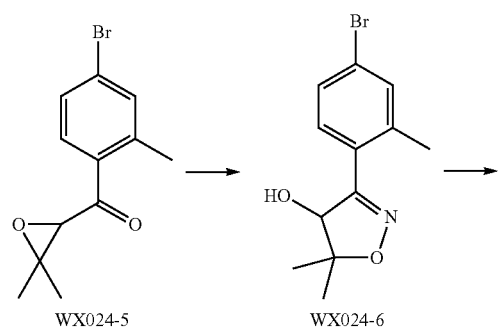

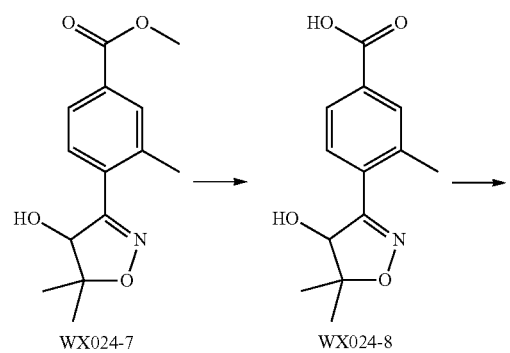

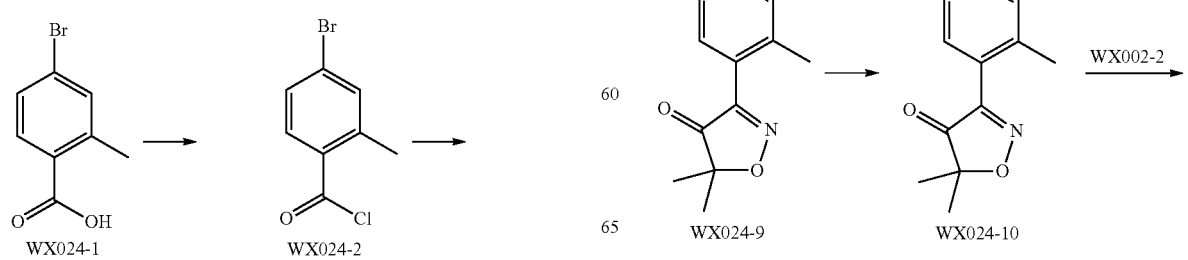

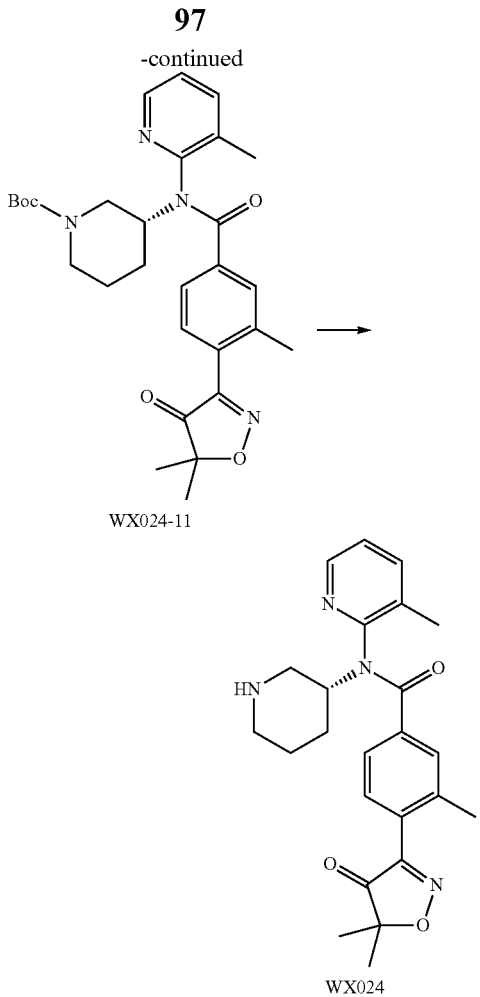

Step 1: Synthesis of Compound WX024-2

WX024-1 (5.00 g, 23.25 mmol, 1.00 eq) and (COCl)$_2$ (4.35 g, 34.27 mmol, 3.00 mL, 1.47 eq) were added to anhydrous dichloromethane (50.00 mL). The mixture was stirred, dripwise added with anhydrous DMF (50.00 μL), and then stirred at 25° C. for 1 h. After reaction, the solvent was spined out by rotary evaporation. Anhydrous dichloromethane (3*20 mL) was added to the crude and spined off to obtain WX024-2.

Step 2: Synthesis of Compound WX024-3

WX024-2 (5.40 g, 23.13 mmol, 1.00 eq) and N-methoxylamine hydrochloride (2.26 g, 23.13 mmol, 1.00 eq) were added to anhydrous dichloromethane (50.00 mL). The mixture was stirred, slowly dropwise added triethylamine (4.67 g, 46.17 mmol, 6.40 mL, 2.00 eq), and then stirred at 25° C. for 16 h. After reaction, the reaction liquid was washed with hydrochloric acid (0.5M, 50 mL), saturated sodium bicarbonate solution (50 mL), water (50 mL), and saturated sodium chloride solution (50 mL) in order; the organic phase was dried with anhydrous magnesium sulfate, filtered, and concentrated. The crude was purified by column chromatography (petroleum ether:ethyl acetate=1:0-4:1) to obtain WX024-3. $^1$H NMR (400 MHz, CDCl$_3$) δ ppm: 2.32 (s, 3H) 3.21-3.67 (m, 6H) 7.15 (d, J=8.28 Hz, 1H) 7.34-7.37 (m, 1H) 7.39 (s, 1H).

Step 3: Synthesis of Compound WX024-4

Under N$_2$ condition, WX024-3 (1.00 g, 3.87 mmol, 1.00 eq) was added to anhydrous tetrahydrofuran (10.00 mL), 2-methyl-1-propenylmagnesium bromide (0.5 M, 25.00 mL, 3.23 eq) was added at −10° C. The mixture was slowly warmed to 35° C. and stirred for 3 h. After reaction, The reaction liquid was cooled to 25° C., slowly added with saturated NH$_4$Cl solution (30 mL) to quench the reaction. The liquid was spined out the solvent by rotary evaporation, and dichloromethane (3*30 mL) was added for extraction. The organic phase was washed with saturated sodium chloride solution (30 mL), dried with anhydrous magnesium sulfate and filtered. The filtrate was concentrated to obtain WX024-4. $^1$H NMR (400 MHz, CDCl$_3$) δ ppm: 1.99 (s, 3H), 2.18 (s, 3H), 2.45 (s, 3H), 6.39 (s, 1H), 7.35-7.43 (m, 3H).

Step 4: Synthesis of Compound WX024-5

Under N$_2$ condition, WX024-4 (19.00 g, 75.06 mmol, 1.00 eq) was dissolved in anhydrous dichloromethane (300.00 mL). The mixture was stirred and cooled to 0° C., added with m-CPBA (50.00 g, 231.79 mmol, 80% purity, 3.09 eq), warmed to 25° C., and then stirred for 20 h. After reaction, Na$_2$SO$_3$ solution was slowly added to the reaction liquid until the potassium iodide-starch test paper had no blue change, and then extracted with dichloromethane (3*200 mL). The organic phase was washed with Na$_2$CO$_3$ solution (3*200 mL), and saturated sodium chloride solution (200 mL) in order, dried with anhydrous magnesium sulfate and filtered. The filtrate was concentrated under vacuum. The crude was purified by column chromatography (petroleum ether:ethyl acetate=1:0-5:1) to obtain WX024-5. $^1$H NMR (400 MHz, MeOD) δ ppm: 1.23 (s, 3H), 1.55 (s, 3H), 2.52 (s, 3H), 4.02-4.08 (m, 1H), 7.51-7.58 (m, 2H), 7.66-7.72 (m, 1H).

Step 5: Synthesis of Compound WX024-6

WX024-5 (18.00 g, 50.83 mmol, 1.00 eq) (purity 76%) and hydroxylamine hydrochloride (17.66 g, 254.15 mmol, 5.00 eq) were added to the mixed solvent of anhydrous methanol (300.00 mL) and pyridine (200.00 mL). The mixture was stirred at 80° C. for 20 h. After reaction, the solvent was spined out by rotary evaporation, water (200 mL) was added, pH was adjusted with hydrochloric acid (4M) to 5-6, and ethyl acetate (3*200 mL) was used for extraction. The organic phase was washed with saturated sodium chloride solution (200 mL), dried with anhydrous magnesium sulfate, and filtered. The filtrate was concentrated under vacuum, and the crude was purified by column chromatography (petroleum ether:ethyl acetate=1:0-4:1) to obtain WX024-6. $^1$H NMR (400 MHz, MeOD) δ ppm: 1.28-1.34 (m, 3H), 1.43 (s, 4H), 2.45-2.53 (m, 3H), 4.61 (br s, 1H), 7.39-7.56 (m, 4H).

Step 6: Synthesis of Compound WX024-7

Pd(PPh$_3$)$_4$ (1.12 g, 971.32 μmol, 0.10 eq) was added to the mixture of WX024-6 (3.00 g, 9.71 mmol, 1.00 eq) (purity 92%), triethylamine (2.92 g, 28.86 mmol, 4.00 mL, 2.97 eq), anhydrous DMF (10.00 mL) and methanol (30.00 mL). The mixture was stirred for 48 h at 80° C. under CO (50 psi) condition. After reaction, the solvent was spined out by rotary evaporation, water (50 mL) was added, and ethyl acetate (3*50 mL) was used for extraction. The organic phase was washed with saturated sodium chloride solution (50 mL), dried with anhydrous magnesium sulfate and filtered. The filtrate was concentrated under vacuum. The crude was purified by column chromatography (petroleum ether:ethyl acetate=1:0-4:1) to obtain WX024-7. $^1$H NMR (400 MHz, CDCl$_3$) δ ppm: 1.37 (s, 3H), 1.54 (s, 3H), 1.97 (d, J=9.03 Hz, 1H), 2.61 (s, 3H), 3.94 (s, 3H), 4.88 (d, J=9.29 Hz, 1H), 7.66-7.73 (m, 1H), 7.92 (d, J=8.28 Hz, 1H), 7.96 (s, 1H).

Step 7: Synthesis of Compound WX024-8

Monohydrate LiOH (1.31 g, 31.15 mmol, 5.00 eq) was added to the mixture of anhydrous tetrahydrofuran tetrahydrofuran (20.00 mL) and water (10.00 mL) of WX024-7 (1.64 g, 6.23 mmol, 1.00 eq). The mixture was stirred at 15° C. for 15 h. After reaction, the solvent was spined out by rotary evaporation, water (50 mL) was added, pH was adjusted with hydrochloric acid (4M) to 2-3, and ethyl acetate was used for extraction three times (50 mL each time). The organic phase was combined, washed with saturated sodium chloride solution (50 mL), dried with anhydrous sodium sulfate and filtered. The filtrate was concentrated under vacuum to obtain WX024-8. $^1$H NMR (400 MHz, MeOD) δ ppm: 1.33 (s, 3H), 1.44 (s, 3H), 2.56 (s, 3H), 4.92 (s, 1H), 7.72 (d, J=8.28 Hz, 1H), 7.88-7.92 (m, 1H), 7.94 (s, 1H).

Step 8: Synthesis of Compound WX024-9

$CrO_3$ (450.00 mg, 4.50 mmol, 166.67 μL, 0.99 eq), concentrated $H_2SO_4$ (1.05 g, 10.48 mmol, 570.00 μL, 98% purity, 2.31 eq) and water (2.00 mL) were added to the AcOH (20.00 mL) solution of WX024-8 (1.13 g, 4.53 mmol, 1.00 eq). The mixture was stirred at 100° C. for 10 min. After reaction, the reaction liquid was cooled to 20° C., poured into the water (50 mL) (the solution showed blue bluish, and there was white solid precipitated), and filtered. The filter cake was washed with water (3*50 mL). The filter cake was dissolved in dichloromethane/methanol (10:1)(50 mL), dried with anhydrous sodium sulfate, and filtered. The filtrate was concentrated under vacuum to obtain WX024-9. $^1$H NMR (400 MHz, MeOD) δ ppm: 1.48 (s, 6H), 2.48 (s, 3H), 7.66-7.76 (m, 1H), 7.94 (dd, J=8.16, 1.10 Hz, 1H), 8.00 (s, 1H).

Step 9: Synthesis of Compound WX024-10

Under $N_2$ condition, $(COCl)_2$ (210.25 mg, 1.66 mmol, 145.00 μL, 2.05 eq) was added to the anhydrous dichloromethane (3.00 mL) solution of WX024-9 (200.00 mg, 808.90 μmol, 1.00 eq), then anhydrous DMF (50.00 μL) was added. The mixture was stirred at 20° C. for 2 h. After reaction, the solvent was spined out by rotary evaporation. The crude was added with anhydrous methylbenzene (3*10 mL), and then concentrated with oil pump to obtain WX024-10.

Step 10: Synthesis of Compound WX024-11

WX002-2 (216.00 mg, 644.36 μmol, 0.80 eq) (87% purity) was added to tetrahydrofuran (3.00 mL). The mixture was cooled to 0° C., added with LiHMDS (1 M, 645.00 μL, 0.80 eq), and then stirred for 1 h. WX024-10 (214.00 mg, 805.45 μmol, 1.00 eq) was added, The mixture was warmed to 15° C. and stirred for 16 h, then warmed to 30° C. and continuously stirred for 5 h, After reaction, water (10 mL) was added to the reaction liquid. Ethyl acetate (3*12 mL) was used for extraction. The organic phase was washed with saturated sodium chloride solution (10 mL), dried with anhydrous sodium sulfate, and filtered. The filtrate was concentrated under vacuum. The crude was purified by column chromatography (petroleum ether:ethyl acetate=1:0-4:1) to obtain WX024-11. $^1$H NMR (400 MHz, MeOD) δ ppm: 1.41 (s, 6H), 1.43-1.53 (m, 9H), 1.54-1.84 (m, 3H), 2.03-2.16 (m, 3H), 2.28 (s, 3H), 2.43-2.75 (m, 2H), 3.73 (br t, J=6.65 Hz, 1H), 3.95-4.08 (m, 1H), 4.45-4.67 (m, 2H), 7.16 (br d, J=7.78 Hz, 1H), 7.25 (br s, 2H), 7.43 (br d, J=8.03 Hz, 1H), 7.52 (br d, J=7.53 Hz, 1H), 8.36-8.48 (m, 1H).

Step 11: Synthesis of Compound WX024

WX024-11 (105.00 mg, 179.50 μmol, 1.00 eq) (89% purity) was added to HCl/EtOAc (4 M, 2.40 mL, 53.48 eq). The mixture was stirred at 15° C. for 5 h. After reaction, pH was adjusted with saturated sodium bicarbonate to ≈7, and ethyl acetate (3*10 mL) was used for extraction, washed the organic phase with saturated sodium chloride solution (10 mL), dried with anhydrous magnesium sulfate, filtered. The filtrate was concentrated under vacuum. The crude was purified by prep-TLC (dichloromethane:methanol=10:1) to obtain WX024. $^1$H NMR (400 MHz, MeOD) δ ppm: 1.19-1.33 (m, 1H), 1.41 (s, 6H) 1.60-1.89 (m, 3H), 1.99-2.15 (m, 4H), 2.27 (s, 3H), 2.45-2.65 (m, 1H), 2.93-3.07 (m, 1H), 3.11-3.27 (m, 1H), 3.51 (br d, J=11.80 Hz, 1H), 4.47-4.82 (m, 1H), 7.15 (br d, J=8.03 Hz, 1H), 7.20-7.31 (m, 2H), 7.42 (br d, J=8.03 Hz, 1H), 7.48-7.59 (m, 1H), 8.34-8.49 (m, 1 H).

Implementation 023: WX025

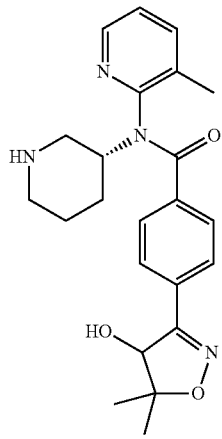 [SMILES: Cc1cccnc1N(C(=O)c1ccc(C2=NOC(C)(C)C2O)cc1)[C@@H]1CCCNC1]

Synthetic Route:

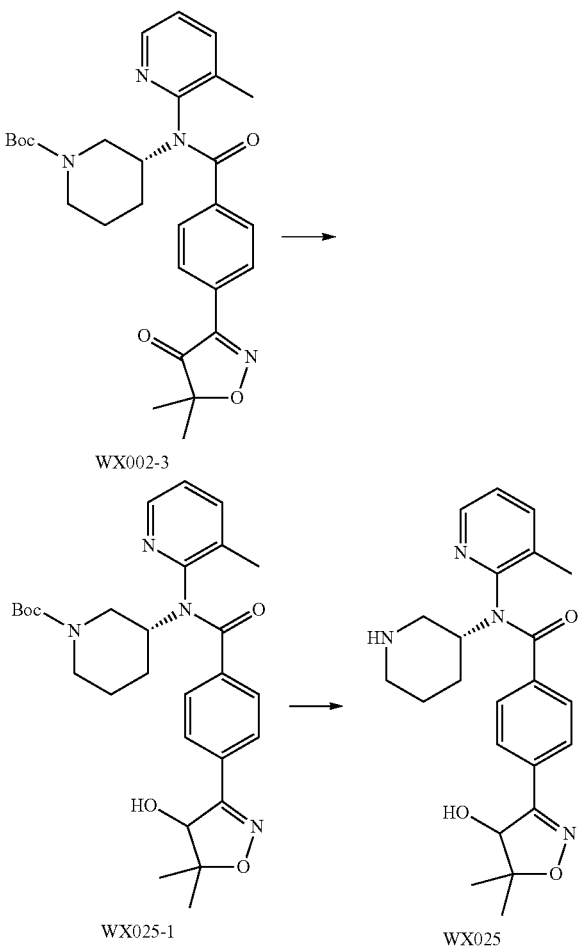

Step 1: Synthesis of Compound WX025-1

WX002-3 (30.00 mg, 59.22 μmol, 1.00 eq) and methanol (5.00 mL) were added in a 50 ml pre-dried three-mouth flask, and NaBH$_4$ (3.36 mg, 88.83 μmol, 1.50 eq) was added. The reaction liquid was stirred at 25° C. for 2 h. After reaction, 5 ml of water was added to the reaction system, and then the methanol was spined out by rotary evaporation. Ethyl acetate (10 mL*3) was added to the system to extract. The combined organic phase was washed with saturated sodium chloride solution (10 mL), dried with anhydrous sodium sulfate, and filtered. The filtrate was concentrated under vacuum to obtain WX025-1.

Step 2: Synthesis of Compound WX025

WX025-1 (20.00 mg, 39.32 μmol, 1.00 eq) was dissolved in methanol (5.00 mL), HCl/methanol (4 M, 1.00 mL) was added. The reaction liquid was stirred at 25° C. for 1 h. After reaction, the reaction liquid was concentrated under vacuum to obtain WX025. $^1$H NMR (400 MHz, MeOD) δ ppm: 8.53-8.41 (m, 1H), 7.70-7.55 (m, 3H), 7.38-7.29 (m, 3H), 5.16-5.02 (m, 1H), 4.85-4.82 (m, 1H), 3.84-3.74 (m, 1H), 3.70-3.56 (m, 1H), 3.42-3.35 (m, 1H), 2.97-2.83 (m, 1H), 2.37-2.16 (m, 1H), 2.05 (s, 3H), 2.02-1.85 (m, 2H), 1.48-1.36 (m, 4H), 1.29- 1.21 (s, 3H).

Implementation 024: WX026

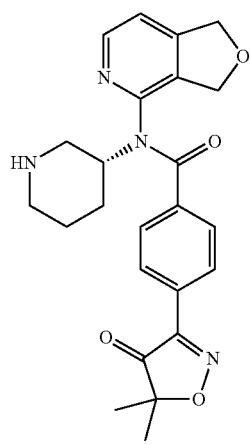 [SMILES: CC1(C)ON=C(c2ccc(C(=O)N(c3nccc4c3COC4)[C@@H]3CCCNC3)cc2)C1=O]

Synthetic Route:

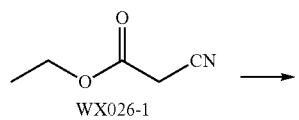

WX026-1

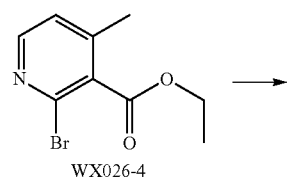

WX026-2

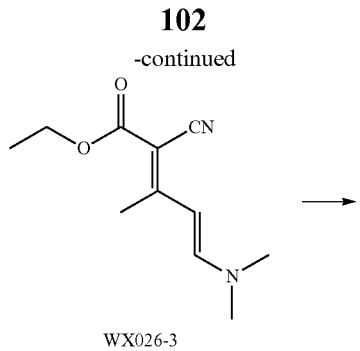

WX026-3

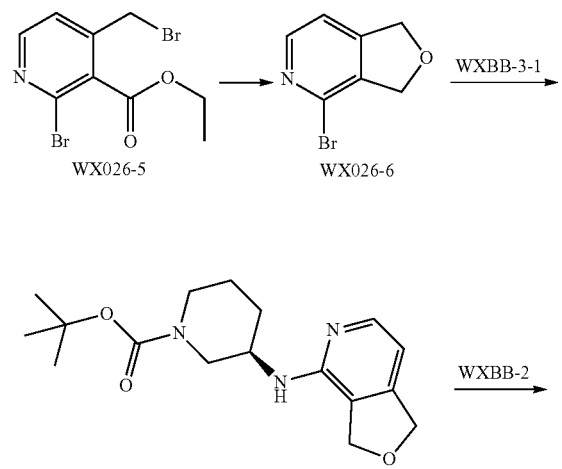

WX026-4

WX026-5  WX026-6

WX026-7

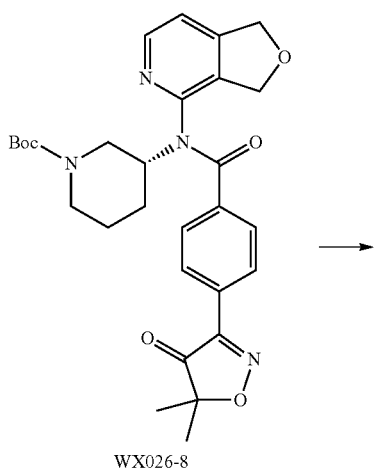

WX026-8

-continued

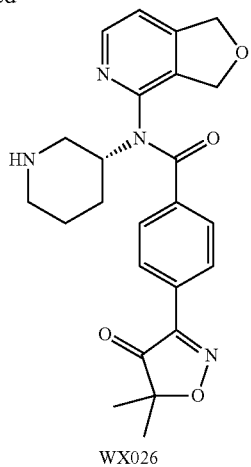

WX026

Step 1: Synthesis of Compound WX026-2

WX026-1 (100.00 g, 884.10 mmol, 94.34 mL, 1.00 eq) and acetone (102.70 g, 1.77 mol, 130.00 mL, 2.00 eq) were dissolved in glacial acetic acid (AcOH) (100.00 mL), and piperidine (8.28 g, 97.25 mmol, 9.63 mL, 0.11 eq) was added. The reaction liquid was stirred at 100° C. for 18 h. After reaction, the reaction liquid was dried by rotary evaporation under vacuum, and the crude was purified by chromatographic column (petroleum ether:ethyl acetate=100: 1-20:1) to obtain WX026-2. $^1$H NMR (400 MHz, CDCl$_3$) δ ppm: 1.36 (t, J=7.2 Hz, 3H), 2.32 (s, 3H), 2.42 (s, 3H), 4.28 (q, J=7.2 Hz, 2H).

Step 2: Synthesis of Compound WX026-3

DMFDMA (80.28 g, 673.72 mmol, 89.20 mL, 1.20 eq) was added to the mixture of anhydrous methylbenzene (100.00 mL) of WX026-2 (86.00 g, 561.43 mmol, 1.00 eq) and acetic anhydride (1.15 g, 11.23 mmol, 1.05 mL, 0.02 eq). The mixture was stirred at 50° C. for 18 h. After reaction, the reaction liquid was concentrated under vacuum to obtain WX026-3.

Step 3: Synthesis of Compound WX026-4

WX026-3 (120.00 g, 576.20 mmol, 1.00 eq) was dissolved in AcOH (1.00 L), and HBr/AcOH (1.83 kg, 5.76 mol, 1.00 L, 35% purity, 10.00 eq) was added. The reaction liquid was stirred at 55° C. for 18 h. After reaction, the reaction liquid was dried by rotary evaporation, and the crude was purified by chromatographic column (petroleum ether:ethyl acetate=50:1-1:1) to obtain WX026-4. H NMR (400 MHz, CDCl$_3$) δ ppm: 8.25 (1H, d, J=5.27 Hz), 7.13 (1H, dd, J=5.02, 0.75 Hz), 4.45 (2H, q, J=7.03 Hz), 2.35 (3H, s), 1.42 (3H, t, J=7.15 Hz).

Step 4: Synthesis of Compound WX026-5

NBS (50.03 g, 281.08 mmol, 1.10 eq) and benzoyl peroxide (12.50 g, 51.60 mmol, 0.20 eq) were added to the CCl$_4$ (660.00 mL) solution of WX026-4 (66.00 g, 255.53 mmol, 1.00 eq). The reaction liquid was stirred at 90° C. for 20 h. After reaction, the reaction liquid was dried by rotary evaporation. The residue was dissolved with dichloromethane (1 L), washed with water (1 L*2). The organic phase was dried with anhydrous Na$_2$SO$_4$, and filtered. The filtrate was concentrated under vacuum. The crude was purified by chromatographic column (petroleum ether:ethyl acetate=1: 0-10:1) to obtain WX026-5. $^1$H NMR (400 MHz, CDCl$_3$) δ ppm: 8.37 (1H, d, J=4.8 Hz), 7.11 (1H, d, J=4.8 Hz), 4.48-4.37 (4H, m), 1.39 (3H, t, J=7.2 Hz).

Step 5: Synthesis of Compound WX026-6

WX026-5 (5.00 g, 6.76 mmol, 1.00 eq) (43.65% purity) was dissolved in dichloromethane (100.00 mL), and the mixture was placed in a 500 mL three-mouth round-bottom flask, and then dropwise added with DIBAL-H (1 M, 45.00 mL, 6.66 eq) at −70° C. under nitrogen condition. The mixture was stirred at −70° C. for 1.5 h, and dropwise added with water (815.00 mg, 45.23 mmol, 6.69 eq). MeCN (50.00 mL) and K$_2$CO$_3$ (2.80 g, 20.27 mmol, 3.00 eq) were added. The mixture was naturally warmed to 20° C. The mixture was stirred for 48 h. After reaction, water (100 mL) was added to the reaction liquid. The organic phase was collected, dried with anhydrous sodium sulfate, and filtered. The filtrate was concentrated to obtain WX026-6. $^1$H NMR (400 MHz, CDCl$_3$) δ ppm: 8.29 (1H, d, J=4.8 Hz), 7.18 (1H, d, J=4.8 Hz), 5.20 (2H, d, J=2 Hz), 5.08 (2H, d, J=1.6 Hz).

Step 6: Synthesis of Compound WX026-7

WX026-6 (540.00 mg, 2.70 mmol, 1.00 eq) and WXBB-3-1 (551.57 mg, 2.75 mmol, 1.02 eq) were dissolved in methylbenzene (10.00 mL). t-BuOK (700.00 mg, 6.24 mmol, 2.31 eq), Pd$_2$(dba)$_3$ (247.24 mg, 270.00 μmol, 0.10 eq) and BINAP (252.18 mg, 405.00 μmol, 0.15 eq) were added. The mixture was stirred at 90° C. for 4 h under nitrogen condition. After reaction, the reaction liquid was concentrated, 50 mL of water was added to residue, dichloromethane (50 mL*2) was used for extraction. The organic phase was dried with anhydrous sodium sulfate, and filtered. The filtrate was dried by rotary evaporation. The crude was purified by chromatographic column (petroleum ether:ethyl acetate=20:1-3:1) to obtain WX026-7. $^1$H NMR (400 MHz, CDCl$_3$) δ ppm: 8.04 (1H, d, J=5.15 Hz), 6.55 (1H, d, J=5.14 Hz), 5.05 (2H, t, J=2.38 Hz), 4.94 (2H, br s), 4.03-4.22 (1H, m), 3.74 (1H, dd, J=13.11, 3.07 Hz), 3.27-3.47 (3H, m), 1.94 (1H, br s), 1.68-1.76 (2H, m), 1.54-1.62 (1H, m), 1.43 (9H, br s).

Step 7: Synthesis of Compound WX026-8

WX026-7 (100.00 mg, 313.09 μmol, 0.80 eq) was dissolved in anhydrous tetrahydrofuran (5.00 mL), and LiHMDS (1 M, 352.22 μL, 0.90 eq) was added to the reaction liquid at 0° C. The reaction liquid was stirred at 0° C. for 0.5 h, and then WXBB-2 (98.49 mg, 391.36 μmol, 1.00 eq) was added to the reaction liquid at 0° C. The reaction liquid was stirred at 25° C. for 2.5 h. After reaction, water (10 mL) was added to the reaction liquid to quench the reaction, the mixture was extracted with ethyl acetate (10 mL×2), and the organic phase was combined after liquid separation. The organic phase was washed with saturated sodium chloride solution (10 mL), dried with anhydrous sodium sulfate, and filtered. The filtrate was concentrated under vacuum, and the crude was purified by thin layer chromatography silica gel plate (petroleum ether:ethyl acetate=1:1) to obtain WX026-8. $^1$H NMR (400 MHz, MeOD) δ ppm: 8.47 (d, J=4.85 Hz, 1H), 7.95 (br d, J=8.38 Hz, 2H), 7.43 (d, J=8.38 Hz, 2H), 7.30 (d, J=5.07 Hz, 1H), 4.9-5.0 (m, 2H), 4.78-4.56 (m, 2H), 4.50-4.32 (m, 2H), 4.01 (br d, J=13.23 Hz, 1H), 3.35 (s, 1H), 2.60 (br s, 1H), 2.09-1.84 (m, 1H), 1.79-1.69 (m, 1H), 1.65-1.52 (m, 2H), 1.47 (s, 9H), 1.41 (s, 6H).

Step 8: Synthesis of Compound WX026

WX026-8 (20.00 mg, 37.41 μmol, 1.00 eq) was dissolved in anhydrous methanol (5.00 mL), and HCl/methanol (4 M, 5.00 mL) was added to the reaction liquid. The reaction liquid was stirred at 25° C. for 2 h. After reaction, the reaction liquid was concentrated under vacuum to obtain WX026. $^1$H NMR (400 MHz, MeOD) δ ppm: 8.54 (d, J=5.15 Hz, 1H), 8.01-7.94 (m, 2H), 7.48-7.41 (m, 2H), 7.36 (d, J=4.77 Hz, 1H), 4.96 (br s, 5H), 3.81-3.70 (m, 1H), 3.65-3.56 (m, 1H), 3.57-3.54 (m, 1H), 3.50 (br s, 1H), 2.90 (br s, 1H), 2.01 (br s, 2H), 1.93-1.80 (m, 1H), 1.43 (s, 7H).

Implementation 025: WX027
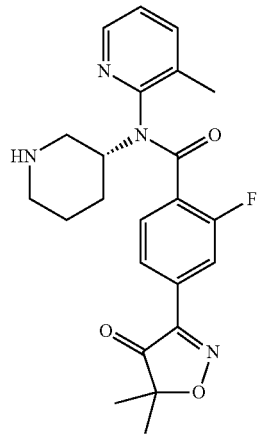 [SMILES: Cc1cccnc1N(C(=O)c1ccc(C2=NOC(C)(C)C2=O)cc1F)[C@@H]1CCCNC1]
Synthetic Route:
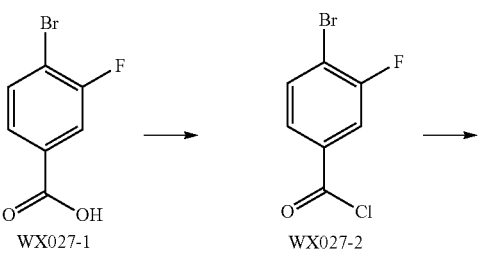
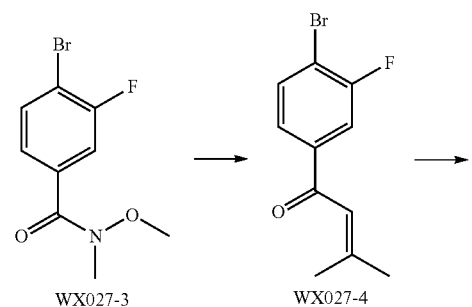
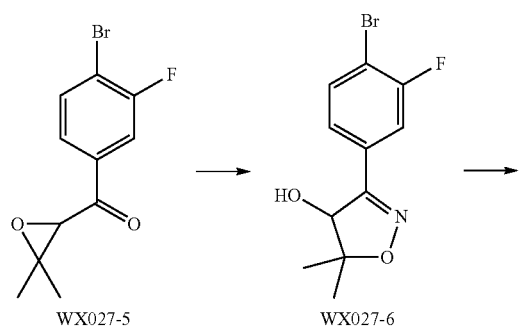
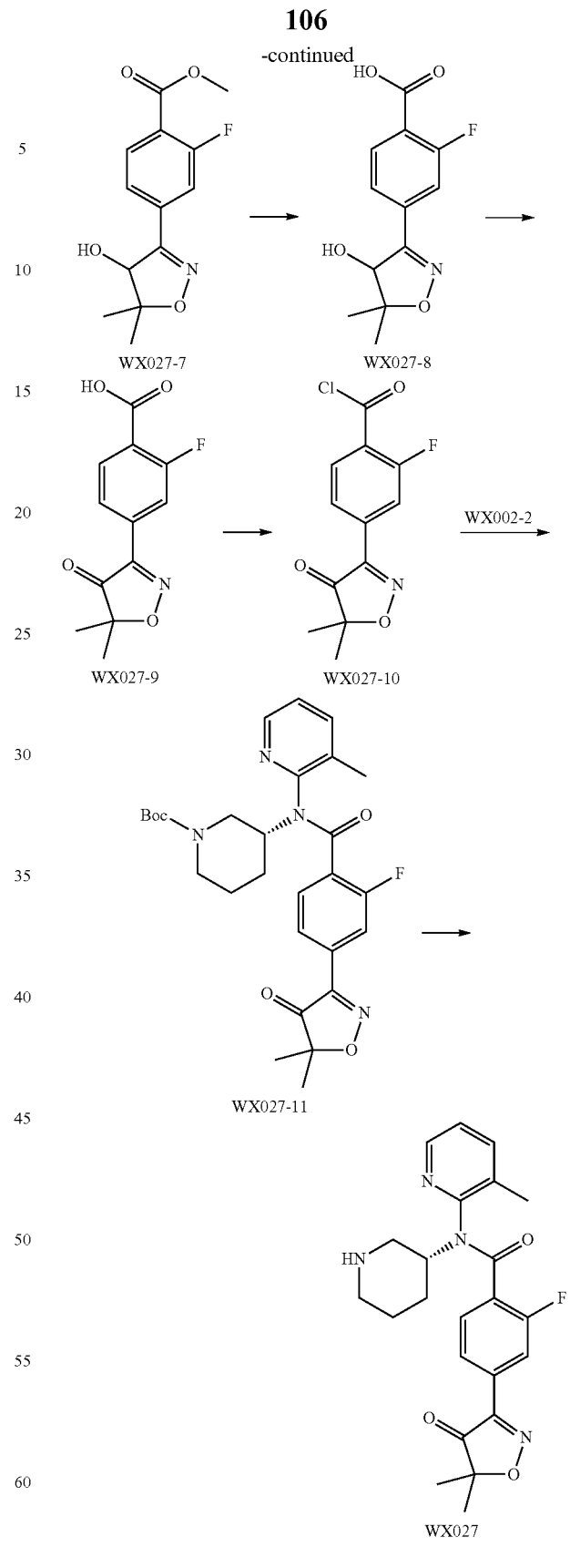
Step 1: Synthesis of Compound WX027-2
Under 0° C., (COCl)$_2$ (7.24 g, 57.08 mmol, 5.00 mL, 2.50 eq) was slowly dropwise added to the dichloromethane (50.00 mL) solution of WX027-1 (5.00 g, 22.83 mmol, 1.00 eq) and DMF (166.86 mg, 2.28 mmol, 175.64 µL, 0.10 eq). After the (COCl)$_2$ was completely added, the reaction liquid was stirred at 25° C. for 1 h. After reaction, the reaction liquid was concentrated to obtain the crude WX027-2.

Step 2: Synthesis of Compound WX027-3

Under 0° C., Et$_3$N (6.90 g, 68.22 mmol, 9.45 mL, 3.00 eq) was slowly dropwise added to the dichloromethane (54.00 mL) solution of WX027-2 (5.40 g, 22.74 mmol, 1.00 eq) and N-methoxylamine hydrochloride (3.33 g, 34.11 mmol, 1.50 eq). After Et$_3$N was completely added, the reaction liquid was stirred at 25° C. for 1 h. After reaction, the reaction liquid was cooled to room temperature, the reaction was quenched with water (50 mL), and then dichloromethane (100 mL*3) was used for extraction. The organic phase was combined, dried with anhydrous sodium sulfate, and concentrated to obtain the crude. The crude was purified by column chromatography (petroleum ether:ethyl acetate=2:1) to obtain WX027-3. $^1$H NMR (400 MHz, CDCl$_3$) δ ppm: 7.60 (dd, J=6.8, 8.2 Hz, 1H), 7.50 (dd, J=1.9, 9.2 Hz, 1H), 7.41 (dd, J=1.9, 8.3 Hz, 1H), 3.55 (s, 3H), 3.36 (s, 3H).

Step 3: Synthesis of Compound WX027-4

Under 0° C., 2-methyl-1-propenylmagnesium bromide (0.5 M, 129.36 mL, 3.00 eq) was slowly dropwise added to the tetrahydrofuran (56.00 mL) solution of WX027-3 (5.65 g, 21.56 mmol, 1.00 eq). After 2-methyl-1-propenylmagnesium bromide was completely added, the reaction liquid was stirred at 25° C. for 3 h. After reaction, the reaction liquid was cooled to room temperature, the reaction was quenched with water (8 mL). The liquid was dried with anhydrous magnesium sulfate, filtered to obtain the mother solution, and concentrated to obtain the crude. The crude was purified by column chromatography (petroleum ether:ethyl acetate=3:1) to obtain WX027-4. $^1$H NMR (400 MHz, CDCl$_3$) δ ppm: 7.83-7.56 (m, 3H), 6.67 (s, 1H), 2.23 (s, 3H), 2.04 (s, 3H).

Step 4: Synthesis of Compound WX027-5 m-CPBA (1.97 g, 9.72 mmol, 85% purity, 2.50 eq) was added to the dichloromethane (16.00 mL) solution of WX027-4 (1.00 g, 3.89 mmol, 1.00 eq). After charging, the reaction liquid was stirred at 35° C. for 12 h under nitrogen condition. After reaction, the reaction liquid was cooled to room temperature, the reaction was quenched with saturated Na$_2$SO$_3$ (10 mL), and then dichloromethane (10 mL*3) was used for extraction. The organic phase was combined, dried with anhydrous sodium sulfate, and concentrated to obtain the crude. The crude was purified by column chromatography (petroleum ether:ethyl acetate=15:1) to obtain WX027-5. $^1$H NMR (400 MHz, CDCl$_3$) δ ppm: 8.03 (s, 1H), 7.94 (d, J=7.7 Hz, 1H), 7.53-7.42 (m, 1H), 3.94 (s, 1H), 1.56 (s, 3H), 1.22 (s, 3H)

Step 5: Synthesis of Compound WX027-6

WX027-5 (2.10 g, 7.69 mmol, 1.00 eq) and NH$_2$OH.HCl (2.14 g, 30.76 mmol, 4.00 eq) were added to the reaction flask. Anhydrous methanol (34.00 mL) and pyridine (20.00 mL) were added to the reaction flask. The mixture was stirred at 80° C. for 12 h under N$_2$ condition. After reaction, the reaction liquid was dried by rotary evaporation under vacuum. The crude was dissolved in ethyl acetate, the organic phase was washed with saturated sodium chloride solution (20 mL), dried with anhydrous sodium sulfate, and filtered. The filtrate was concentrated under vacuum. The crude was purified by column chromatography (petroleum ether:ethyl acetate=1:0-10:1) to obtain WX027-6. $^1$H NMR (400 MHz, CDCl$_3$) δ ppm: 7.65-7.56 (m, 2H), 7.52-7.43 (m, 1H), 4.80 (s, 1H), 1.53 (s, 3H), 1.35 (s, 3H).

Step 6: Synthesis of Compound WX027-7

WX027-6 (600.00 mg, 2.08 mmol, 1.00 eq) was dissolved in DMF (10.00 mL) and methanol (30.00 mL), and triethylamine (632.20 mg, 6.25 mmol, 866.02 µL, 3.00 eq) and Pd(PPh$_3$)$_4$ (240.65 mg, 208.25 µmol, 0.10 eq) were added. Under CO (50 Psi) condition, the mixture was stirred at 80° C. for 12 h. After reaction, the reaction liquid was naturally cooled to room temperature, and filtered. The filtrate was concentrated under vacuum to obtain the crude. The crude was purified by column chromatography (petroleum ether: ethyl acetate=1:0-10:1) to obtain WX027-7.
$^1$H NMR (400 MHz, CDCl$_3$) δ ppm: 7.99-7.91 (m, 1H), 7.67-7.56 (m, 2H), 4.81 (s, 1H), 3.93 (s, 3H), 1.52 (s, 3H), 1.33 (s, 3H).

Step 7: Synthesis of Compound WX027-8

Anhydrous tetrahydrofuran (10.00 mL) and water (2.00 mL) were added to WX027-7 (500.00 mg, 1.87 mmol, 1.00 eq) and Monohydrate LiOH (235.51 mg, 5.61 mmol, 3.00 eq). The reaction liquid was stirred at 25° C. for 12 h. After reaction, anhydrous hydrochloric acid solution (6M) was slowly dropwise added to the reaction system to adjust the pH to 2-3. Ethyl acetate (10 mL*3) was added to the system for extraction. The organic phase was combined, washed with saturated sodium chloride solution (10 mL), dried with anhydrous sodium sulfate, and filtered. The filtrate was concentrated under vacuum to obtain WX027-8. $^1$H NMR (400 MHz, MeOD) δ ppm: 7.99-7.93 (m, 1H), 7.68 (d, J=8.16 Hz, 1H), 7.63-7.58 (m, 1H), 4.90 (s, 1H), 1.42 (s, 3H), 1.28 (s, 3H).

Step 8: Synthesis of Compound WX027-9

Concentrated H$_2$SO$_4$ (240.00 µL), water (800.00 µL) and AcOH (8.00 mL) were added to the mixture of WX027-8 (250.00 mg, 987.24 µmol, 1.00 eq) and CrO$_3$ (118.46 mg, 1.18 mmol, 43.87 µL, 1.20 eq). The reaction liquid was stirred at 100° C. for 0.5 h under nitrogen condition. After reaction, the reaction system was cooled to room temperature, and 10 ml of water was slowly added. Dichloromethane:methanol (8:1) (18 mL*3) was added to the system to extract, and the organic phase was combined after liquid separation. The organic phase was washed with saturated sodium chloride solution (10 mL), dried with anhydrous sodium sulfate, and filtered. The filtrate was concentrated under vacuum to obtain WX027-9. $^1$H NMR (400 MHz, MeOD) δ ppm: 8.05-7.95 (m, 2H), 7.93-7.88 (m, 1H), 1.47 (s, 6H).

Step 9: Synthesis of Compound WX027-10

Under 0° C., (COCl)$_2$ (45.47 mg, 358.27 µmol, 31.36 µL, 1.50 eq) and DMF (1.75 mg, 23.88 µmol, 1.84 µL, 0.10 eq) were slowly dropwise added to the anhydrous dichloromethane (10.00 mL) mixture of WX027-9 (60.00 mg, 238.84 µmol, 1.00 eq). The reaction liquid was stirred at 0° C. for 1 h. After reaction, the reaction liquid was concentrated under vacuum to obtain the crude. Crude was added with Methylbenzene (10 mL*3), and then spined dry under vacuum to obtain WX027-10.

Step 10: Synthesis of Compound WX027-11

Under nitrogen condition at 0° C., LiHMDS (1 M, 212.34 µL, 0.90 eq) was slowly dropwise added to the anhydrous tetrahydrofuran (10.00 mL) solution of WX002-2 (55.00 mg, 188.75 µmol, 0.80 eq), and the mixture was continuously stirred at 0° C. for 1 h, added with WX027-10 (63.62 mg, 235.94 µmol, 1.00 eq), naturally warmed to 25° C. and then stirred for 1 h. After reaction, 10 ml of water was slowly added to the reaction system. The mixture with ethyl acetate (10 mL*3) was extracted. The organic phase was combined, washed with saturated sodium chloride solution (10 mL), dried with anhydrous sodium sulfate, and filtered. The filtrate was concentrated under vacuum. The crude was purified by thin layer chromatography silica gel plate (petroleum ether:ethyl acetate=2:1) to obtain WX027-11. m/z=525.3 [M+1].

Step 10: Synthesis of Compound WX027

WX027-11 (35.00 mg, 66.72 μmol, 1.00 eq) was dissolved in methanol (5.00 mL), and HCl/methanol (4 M, 3.00 mL) was added to the solution. The reaction liquid was stirred at 25° C. for 1 h. After reaction, the reaction liquid was concentrated under vacuum to obtain WX027. $^1$H NMR (400 MHz, MeOD) δ ppm: 8.47-8.34 (m, 2H), 7.77-7.58 (m, 3H), 7.35-7.18 (m, 2H), 5.04-4.93 (m, 1H), 3.85-3.71 (m, 1H), 3.63-3.54 (m, 1H), 3.38- 3.31 (m, 1H), 2.99-2.82 (m, 1H), 2.41-2.25 (m, 1H), 2.19 (s, 3H), 2.10-1.85 (m, 2H), 1.52-1.42 (m, 1H), 1.38 (s, 6H).

Implementation 026: WX028, WX029, WX030

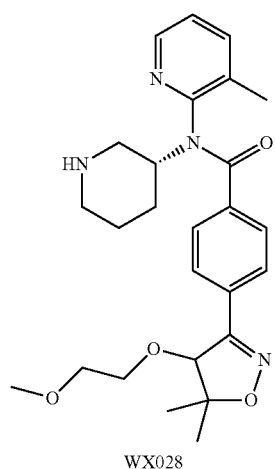

WX028

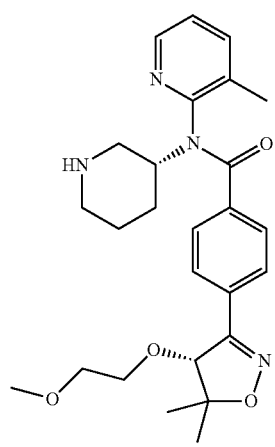

WX029 或 WX030

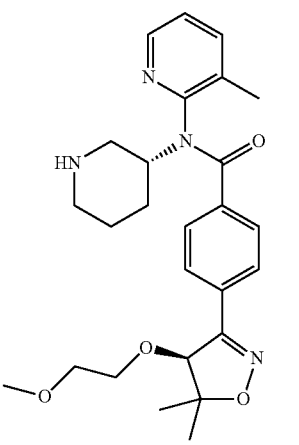

WX029 或 WX030

Synthetic Route:

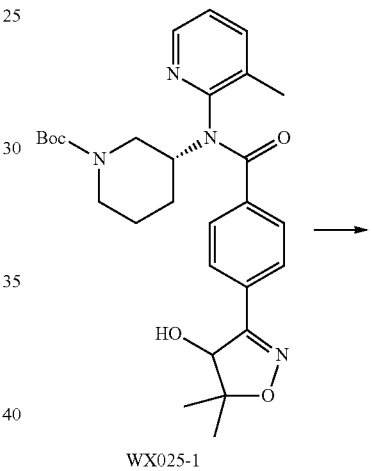

WX025-1

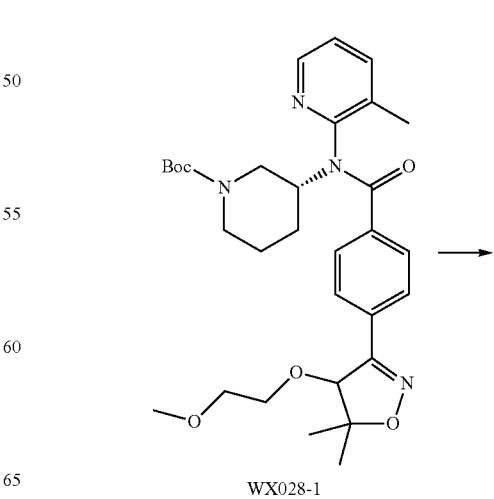

WX028-1

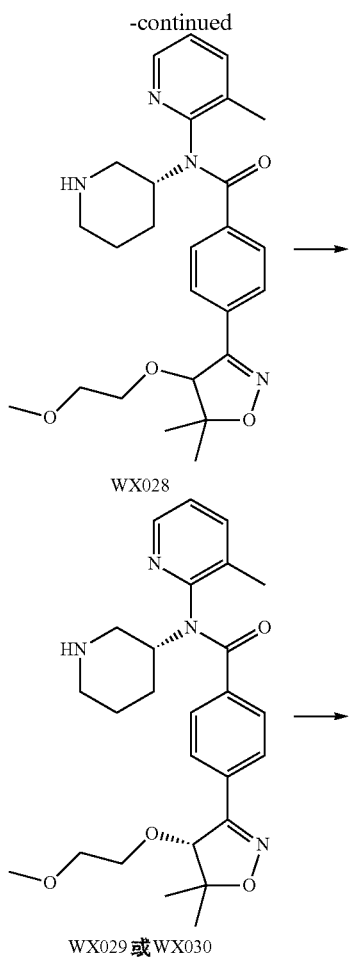

WX028

WX029 或 WX030 saturated sodium chloride solution (5 mL), dried with anhydrous sodium sulfate, and filtered. The filtrate was concentrated under vacuum. The crude was purified by thin layer chromatography silica gel plate (petroleum ether:ethyl acetate=0:1) to obtain WX028-1.

Step 2: Synthesis of Compound WX028

WX028-1 (20.00 mg, 35.29 μmol, 1.00 eq) was dissolved in anhydrous methanol (2.00 mL), and HCl/methanol (4 M, 1.00 mL) was added. The reaction liquid was stirred at 25° C. for 2 h. After reaction, the reaction liquid was dried by rotary evaporation under vacuum to obtain WX028.

$^1$H NMR (400 MHz, CDCl$_3$-d4) δ ppm: 8.48-8.37 (m, 1H), 7.65-7.49 (m, 3H), 7.34-7.23 (m, 3H), 5.21-4.96 (m, 1H), 4.74 (s, 1H), 3.81-3.37 (m, 6H), 3.27-3.25 (m, 3H), 3.22-3.07 (m, 1H), 2.90-2.76 (m, 1H), 2.33- 2.07 (m, 1H), 2.00 (s, 3H), 1.96-1.77 (m, 2H), 1.44 (s, 3H), 1.39-1.28 (m, 1H), 1.25 (s, 3H).

Step 3: Synthesis of compounds WX029 and WX030

WX028 was purified by chiral separation (column: AD (250 mm*30 mm, 5 μm); mobile phase: [0.1% NH$_3$ water ETOH]; B %: 35%-35%, min) to obtain WX029 and WX030.

WX029: Prepeak, SFC, Rt=3.493, $^1$H NMR (400 MHz, MeOD) δ ppm: 8.48-8.37 (m, 1H), 7.65-7.49 (m, 3H), 7.34-7.23 (m, 3H), 4.76 (s, 1H), 3.81-3.37 (m, 7H), 3.27-3.25 (m, 3H), 3.22-3.07 (m, 1H), 2.90-2.76 (m, 1H), 2.33-2.07 (m, 1H), 2.00 (s, 3H), 1.96-1.77 (m, 2H), 1.44 (s, 3H), 1.39-1.25 (m, 4H).

WX030: Postpeak, SFC, Rt=3.950, $^1$H NMR (400 MHz, MeOD) δ ppm: 8.48-8.37 (m, 1H), 7.65-7.49 (m, 3H), 7.34-7.23 (m, 3H), 5.21-4.96 (m, 1H), 4.74 (s, 1H), 3.81-3.75 (m, 4H), 3.70-3.44 (m, 3H), 3.43-3.31 (m, 3H), 2.88-2.86 (m, 1H), 2.33-2.07 (m, 1H), 2.00 (s, 3H), 1.96-1.77 (m, 2H), 1.39-1.28 (m, 1H), 1.31- 1.27 (m, 6H).

Implementation 027: WX031

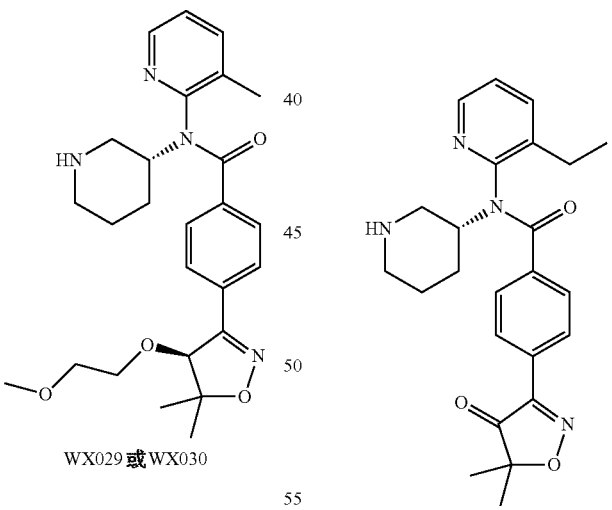

WX029 或 WX030

Step 1: Synthesis of Compound WX028-1

WX025-1 (30.00 mg, 58.98 μmol, 1.00 eq) was dissolved in anhydrous DMF (5.00 mL), and NaH (4.72 mg, 117.97 μmol, 60% purity, 2.00 eq) was added at 0° C. under nitrogen condition. The mixture was continuously stirred at 25° C. for 1 h. 1-bromine-2-methyloxyethane (16.40 mg, 117.96 μmol, 11.08 μL, 2.00 eq) was dropwise added. After 1-bromine-2-methyloxyethane was completely added, the mixture was warmed to 80° C. and stirred for 12 h. After reaction, 3 ml of water was slowly added to the reaction system at 0° C., the mixture was extracted with ethyl acetate (5 mL*3). The organic phase was combined, washed with Synthetic Route:

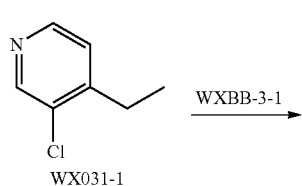

WX031-1

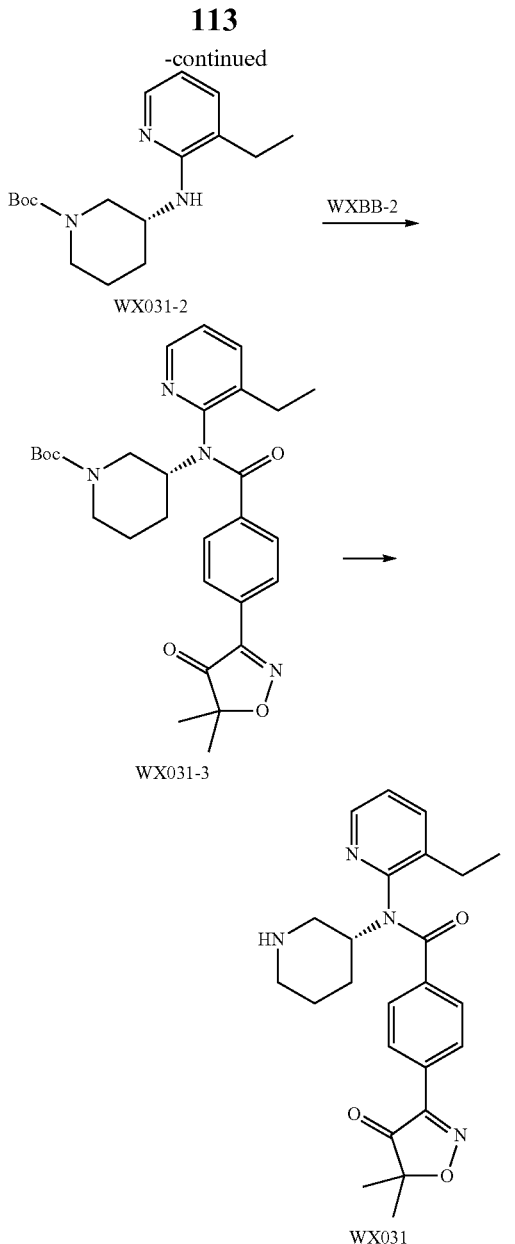

washed with saturated sodium chloride solution (10 mL), dried with anhydrous sodium sulfate, and filtered. The filtrate was concentrated under vacuum to obtain WX031-2. $^1$H NMR (400 MHz, MeOD) δ ppm: 7.87 (br d, J=3.6 Hz, 1H), 7.32 (br d, J=7.2 Hz, 1H), 6.59 (dd, J=7.0, 5.6 Hz, 1H), 4.03 (br s, 1H), 3.77 (br s, 1H), 3.59 (br s, 2H), 3.25 (br s, 1H), 2.48 (q, J=7.40 Hz, 2H), 2.08-1.96 (m, 1H), 1.54-1.84 (m, 2H), 1.48 (br s, 1H), 1.38 (br s, 9H), 1.24 (t, J=7.6 Hz, 3H).

Step 2: Synthesis of Compound WX031-3

Under nitrogen condition at 0° C., LiHMDS (1 M, 257.85 μL, 0.90 eq) was added to the anhydrous tetrahydrofuran (5.00 mL) solution of WX031-2 (70.00 mg, 229.20 μmol, 0.80 eq). The reaction liquid was stirred at 0° C. for 0.5 h. WXBB-2 (72.10 mg, 286.50 μmol, 1.00 eq) was added at 0° C. The reaction liquid was stirred at 25° C. for 2.5 h. After reaction, water (10 mL) was added to the reaction liquid, ethyl acetate (10 mL×3) was used for extraction. The combined organic phase was washed with saturated sodium chloride solution (10 mL), dried with anhydrous sodium sulfate, and filtered. The filtrate was concentrated under vacuum. The crude was purified by thin layer chromatography silica gel plate (petroleum ether:ethyl acetate=1:1) to obtain WX031-3. m/z=521.3 [M+1].

Step 3: Synthesis of Compound WX031

WX031-3 (30.00 mg, 57.62 μmol, 1.00 eq) was dissolved in anhydrous methanol (5.00 mL), and hydrochloric acid/methanol (4 M, 5.00 mL) was added to the reaction liquid. The reaction liquid was stirred at 25° C. for 2 h. After reaction, the reaction liquid was concentrated under vacuum with water pump at 40° C. to obtain WX031. $^1$H NMR (400 MHz, MeOD) δ ppm: 8.49-8.38 (m, 1H), 7.87 (br d, J=8.4 Hz, 2H), 7.63 (br d, J=7.2 Hz, 1H), 7.38-7.26 (m, 3H), 5.05 (br s, 1H), 3.77 (br d, J=11.0 Hz, 1H), 3.67-3.50 (m, 1H), 2.98-2.80 (m, 1H), 2.50 (br d, J=8.0 Hz, 1H), 2.40-2.24 (m, 1H), 2.17 (br d, J=8.0 Hz, 1H), 1.93 (br s, 1H), 1.85 (br s, 2H), 1.38 (s, 7H), 0.97 (t, 3H).

Implementation 028: WX032, WX033, WX034

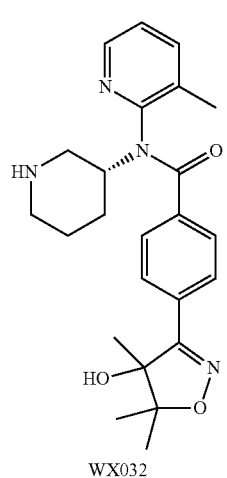

WX032

Step 1: Synthesis of Compound WX031-2

WX031-1 (100.00 mg, 706.21 μmol, 1.00 eq), WXBB-3-1 (141.44 mg, 706.21 μmol, 1.00 eq), t-BuONa (135.73 mg, 1.41 mmol, 2.00 eq), BINAP (87.95 mg, 141.24 μmol, 0.20 eq) and Pd$_2$(dba)$_3$ (64.67 mg, 70.62 μmol, 0.10 eq) were dissolved in anhydrous methylbenzene (4.00 mL). The mixture was stirred at 90° C. for 3 h under nitrogen condition. After reaction, the reaction liquid was cooled to room temperature, diluted with 10 ml of ethyl acetate, and filtered. The filter cake was washed with 20 ml of ethyl acetate. The organic phase was collected, and concentrated under vacuum. The crude was diluted with 10 mL of ethyl acetate and 10 mL of water. The pH of aqueous phase was adjusted with hydrochloric acid/aqueous solution (2M) to 1-2. The liquid was separated, and the aqueous phase was collected. The pH of aqueous phase was adjusted with solid sodium bicarbonate to 8. The mixture was extracted with ethyl acetate (10 mL*3). The organic phase was combined, 115
-continued

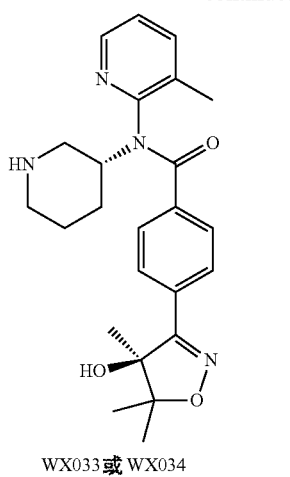

WX033或WX034

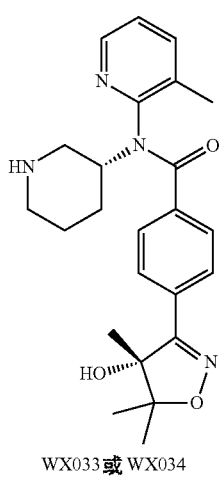

WX033或WX034

Synthetic Route:

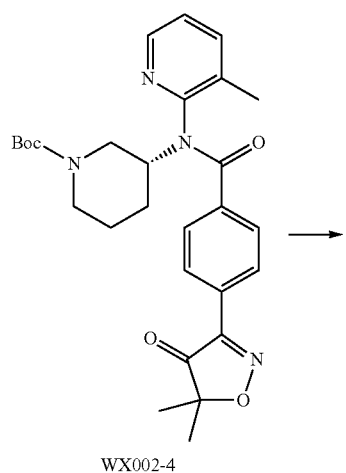

WX002-4

116
-continued

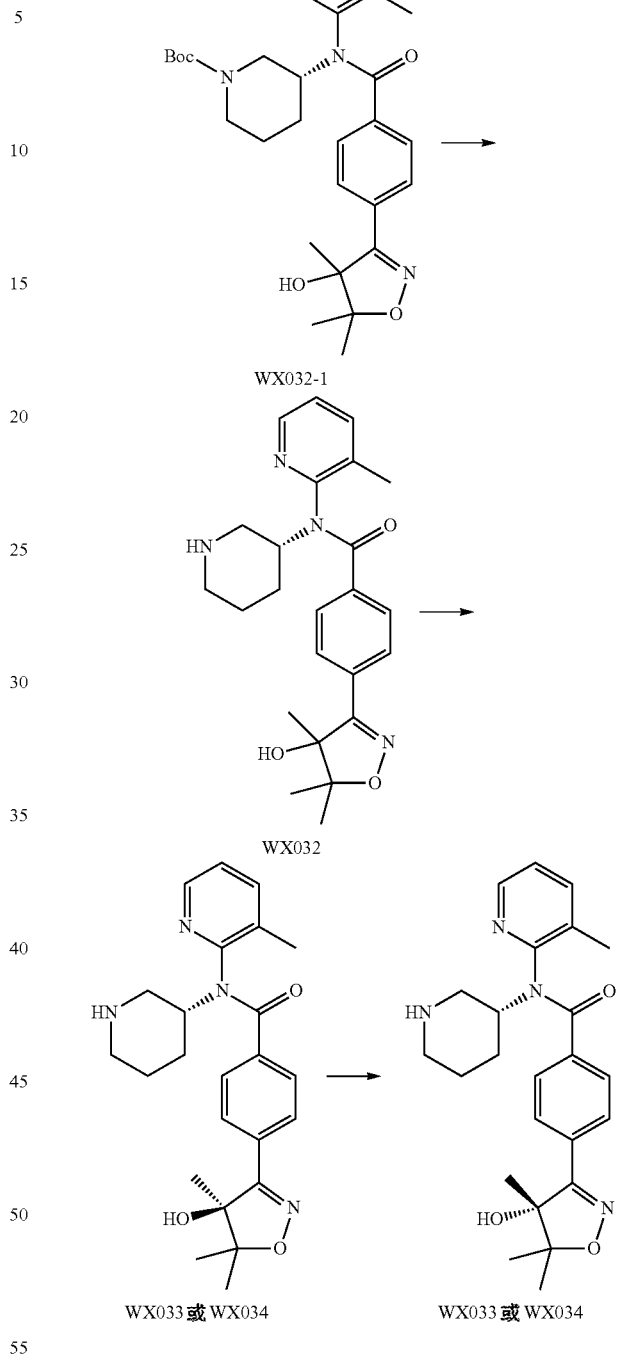

Step 1: Synthesis of Compound WX032-1

Under nitrogen condition at 0° C., MeMgBr (3 M, 157.92 μL, 4.00 eq) was slowly dropwise added to the anhydrous tetrahydrofuran (15.00 mL) solution of WX002-3 (60.00 mg, 118.44 μmol, 1.00 eq). After MeMgBr was completely added, the reaction liquid was stirred at 25° C. for 3 h. After reaction, 3 ml of water was slowly added to the reaction liquid at 0° C., and the mixture was extracted with ethyl acetate (10 mL*3). The combined organic phase was washed with saturated sodium chloride solution (10 mL), dried with anhydrous sodium sulfate, and filtered. The filtrate was concentrated under vacuum, and the crude was purified by thin layer chromatography silica gel plate (petroleum ether: ethyl acetate=1:1) to obtain WX032-1.

Step 2: Synthesis of Compound WX032

HCl/methanol (4 M, 1.00 mL) was added to the methanol (3.00 mL) solution of WX032-1 (90.00 mg, 172.21 µmol, 1.00 eq), and the reaction liquid was stirred at 25° C. for 0.5 h under nitrogen condition. After reaction, the reaction liquid was concentrated under vacuum to obtain WX032. $^1$H NMR (400 MHz, MeOD-d4) δ ppm: 8.49-8.38 (m, 1H), 7.66-7.51 (m, 3H), 7.36-7.25 (m, 3H), 5.12-4.97 (m, 1H), 3.81-3.70 (m, 1H), 3.68-3.54 (m, 1H), 3.38-3.32 (m, 1H), 2.95-2.77 (m, 1H), 2.36-2.09 (m, 1H), 2.01 (s, 3H), 1.97-1.81 (m, 2H), 1.44- 1.33 (m, 1H), 1.28 (s, 6H), 1.19 (s, 3H).

Step 3: Synthesis of compounds WX033 and WX034

WX032 was separated by SFC (column: AD (250 mm*30 mm, 10 µm); mobile phase: [0.1% NH$_3$ water ETOH]; B %: 30%-30%, min) to obtain a pair of enantiomers.

WX033: Prepeak, SFC Rt=4.187, $^1$H NMR (400 MHz, CDCl$_3$) δ ppm: 1.21 (s, 3H), 1.32 (br s, 3H), 1.38 (s, 3H), 1.49-1.81 (m, 3H), 1.86 (br s, 1H), 1.97 (br s, 2H), 2.19-2.57 (m, 3H), 2.83-3.04 (m, 1H), 3.10-3.46 (m, 1H), 4.43-4.79 (m, 1H), 7.03-7.15 (m, 1H), 7.27 (s, 4H), 7.55 (br d, J=8.03 Hz, 2H), 8.41 (br d, J=3.26 Hz, 1H).

WX034: Postpeak, SFC Rt=4.371, $^1$H NMR (400 MHz, CDCl$_3$) δ ppm: 1.11 (br d, J=8.03 Hz, 4H), 1.20-1.35 (m, 4H), 1.41 (br s, 3H), 1.66-1.91 (m, 4H), 2.03 (br s, 1H), 2.24 (br d, J=17.07 Hz, 1H), 2.82 (br t, J=11.80 Hz, 1H), 3.49 (br d, J=11.54 Hz, 1H), 3.62-3.94 (m, 2H), 4.15 (br d, J=11.04 Hz, 1H), 4.85-5.58 (m, 1H), 6.98 (br d, J=8.03 Hz, 1H), 7.03-7.20 (m, 3H), 7.27 (s, 2H), 8.38 (br d, J=3.01 Hz, 1H).

Implementation 029: WX035

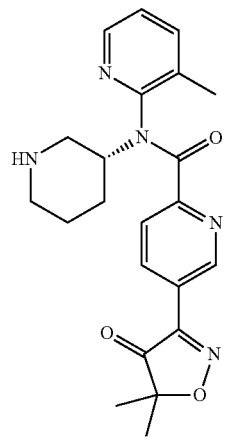 [SMILES: Cc1cccnc1N(C(=O)c1ccc(C2=NOC(C)(C)C2=O)cn1)[C@@H]1CCCNC1]

Synthetic Route:

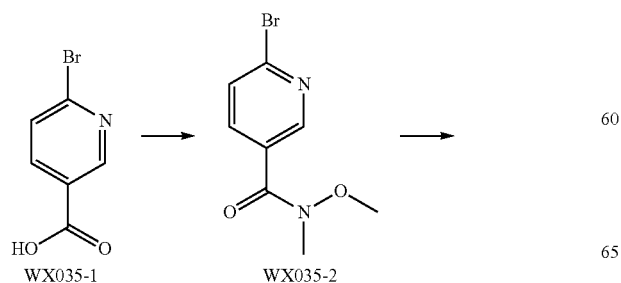

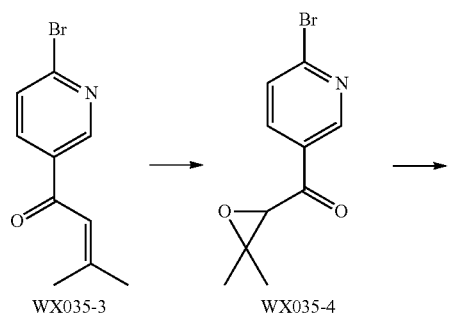

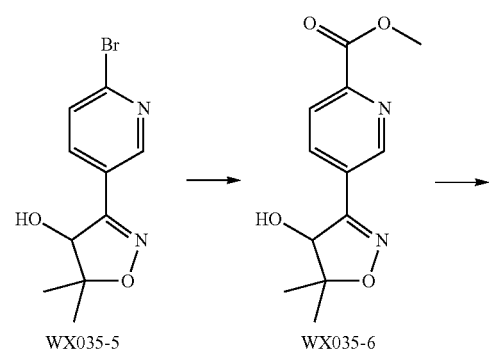

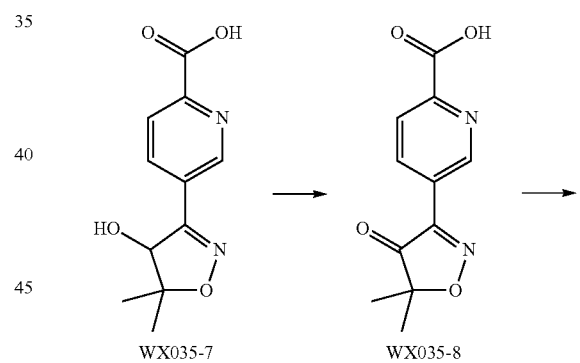

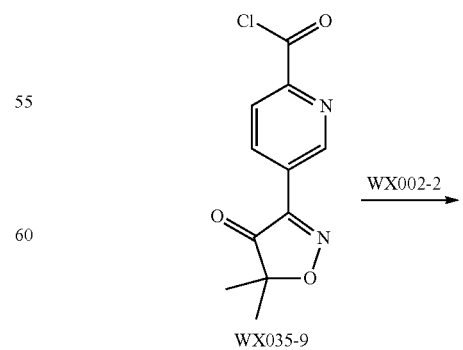

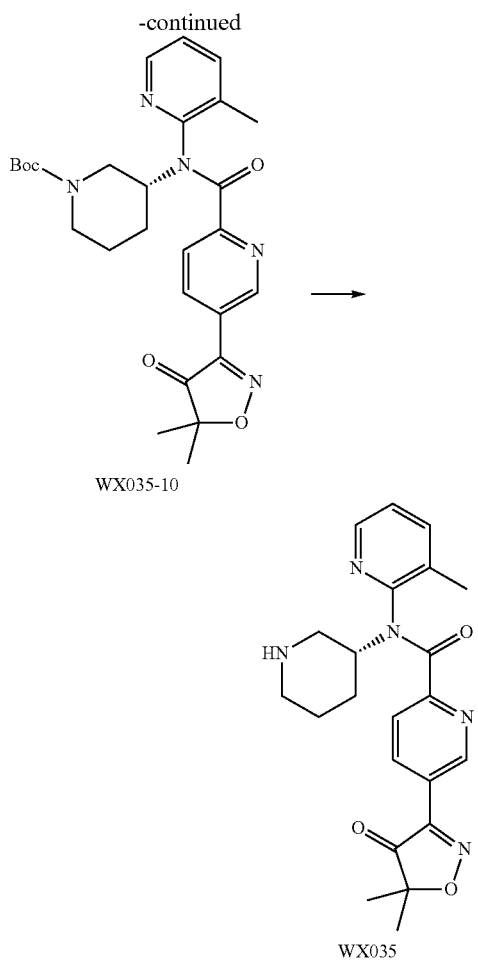

WX035-10

WX035

Step 1: Synthesis of Compound WX035-2

WX035-1 (45.00 g, 222.76 mmol, 1.00 eq) was dissolved in anhydrous dichloromethane (500.00 mL), and triethylamine (45.08 g, 445.52 mmol, 61.76 mL, 2.00 eq), EDCI (46.97 g, 245.04 mmol, 1.10 eq), HOBt (33.11 g, 245.04 mmol, 1.10 eq), and N-methoxymethylamine (26.07 g, 267.31 mmol, 1.20 eq) were added to the solution at 20° C. in order. The mixture was stirred at 20° C. for 3 h. After reaction, the reaction system was added with 100 mL of dichloromethane for dilution, then added with aq. HCl (200 mL, 0.5 N), and filtered. The filter cake was washed with dichloromethane (200 mL*2). The organic phase was separated from the filtrate, washed with saturated sodium bicarbonate (200 mL) and saturated sodium chloride solution (200 mL) in order, dried with anhydrous sodium sulfate. The filtrate was concentrated under vacuum to obtain WX035-2. $^1$H NMR (400 MHz, CDCl$_3$) δ ppm: 8.75-8.74 (d, J=2.4 Hz, 1H), 7.92-7.89 (m, 1H), 7.56-7.54 (m, 1H), 3.55 (s, 3H) 3.38 (s, 3H).

Step 2: Synthesis of Compound WX035-3

WX035-2 (10.00 g, 39.50 mmol, 16.32 mL, 1.00 eq) was dissolved in tetrahydrofuran (100.00 mL), and 2-methyl-1-propenylmagnesium bromide (0.5 M, 237.00 mL, 3.00 eq) was slowly dropwise added to the solution at −10° C. under nitrogen condition. The reaction liquid was continuously stirred at 20° C. for 1 h. After reaction, the reaction liquid was dropwise added with 200 mL of sat. NH$_4$Cl at 0° C., then extracted with ethyl acetate (200 mL*2). The organic phase was combined, dried with anhydrous sodium sulfate, and filtered. The filtrate was concentrated under vacuum to obtain WX035-3. $^1$H NMR (400 MHz, CDCl$_3$) δ ppm: 8.87-8.86 (d, J=2 Hz, 1H), 8.07-8.04 (d, J=8.4 Hz, 1H), 7.60-7.58 (d, J=8.4 Hz, 1H), 6.68 (s, 1H), 2.26 (s, 3H), 2.06 (s, 3H).

Step 3: Synthesis of Compound WX035-4

WX035-3 (9.50 g, 39.57 mmol, 1.00 eq) was dissolved in dried dichloromethane (30.00 mL), meta-chloroperoxybenzoic acid (38.16 g, 187.94 mmol, 4.75 eq, 85% purity) was added to the solution at 20° C. The reaction mixture was stirred at 20° C. for 12 h. After reaction, saturated Na$_2$SO$_3$ (200 mL) was dropwise added to the reaction system at 0° C. The mixture was stirred at room temperature for 30 min after dropwise adding, extracted with 200 mL of dichloromethane. The organic phase was dried with anhydrous sodium sulfate, and filtered. The filtrate was concentrated under vacuum. The crude was purified by rapid column chromatography (petroleum ether:ethyl acetate=20:1-10:1) to obtain WX035-4. $^1$H NMR (400 MHz, CDCl$_3$) δ ppm: 8.97 (s, 1H), 8.15-8.13 (m, 1H), 7.67-7.65 (d, J=8 Hz, 1H), 3.95 (s, 1H), 1.58 (s, 3H), 1.25 (s, 3H).

Step 4: Synthesis of Compound WX035-5

WX035-4 (3.60 g, 13.79 mmol, 1.00 eq) was dissolved in methanol (20.00 mL) and pyridine (12.00 mL), NH$_2$OH.HCl (3.83 g, 55.18 mmol, 4.00 eq) was added to the solution at 20° C. The reaction mixture was stirred at 80° C. for 12 h under nitrogen condition. After reaction, the reaction liquid was concentrated under vacuum, 50 ml of dichloromethane was added to the residue, and saturated sodium chloride solution (50 mL) was used for washing. The organic phase was dried with anhydrous sodium sulfate, and filtered. The filtrate was concentrated under vacuum. The crude was separated by rapid column chromatography (petroleum ether:ethyl acetate=20:1-10:1) to obtain WX035-5. $^1$H NMR (400 MHz, CDCl$_3$) δ ppm 8.74 (s, 1H), 8.04-8.02 (m, 1H) 7.56-7.54 (d, J=8.4 Hz, 1H) 4.89-4.87 (d, J=8.8 Hz, 1H), 2.42-2.39 (d, J=8.8 Hz, 1H), 1.53 (s, 3H), 1.36 (s, 3H).

Step 5: Synthesis of Compound WX035-6

WX035-5 (860.00 mg, 2.31 mmol, 1.00 eq), triethylamine (467.65 mg, 4.62 mmol, 640.62 μL, 2.00 eq) and methanol (10.00 mL) were added to the reaction flask in order, and Pd(dppf)Cl$_2$ (169.08 mg, 231.00 μmol, 0.10 eq) was added under nitrogen condition. Under CO (50 psi), the reaction liquid was stirred at 80° C. for 12 h. After reaction, the reaction liquid was filtered. The filtrate was concentrated under vacuum. The crude was purified by rapid column chromatography (petroleum ether:ethyl acetate=10:1-5:1) to obtain WX035-6. $^1$H NMR (400 MHz, MeOD) δ ppm: 9.11 (s, 1H), 8.31-8.29 (m, 1H), 8.13-8.11 (d, J=8 Hz, 1H), 5.00 (s, 1H), 4.02 (s, 3H), 1.56 (s, 3H), 1.36 (s, 3H).

Step 6: Synthesis of Compound WX035-7

WX035-6 (400.00 mg, 1.60 mmol, 1.00 eq) was dissolved in tetrahydrofuran (6.00 mL) and water (3.00 mL). Monohydrate LiOH (335.68 mg, 8.00 mmol, 5.00 eq) was added to the reaction system at 20° C. The mixture was stirred at 20° C. for 2 h. After reaction, the reaction system was added with 5 mL of water, washed with ethyl acetate (10 mL*2), adjusted aqueous phase with 2 N HCl to pH=6, and then extracted with ethyl acetate (20 mL*4). The organic phase was combined, dried with anhydrous sodium sulfate, and filtered. The filtrate was concentrated under vacuum to obtain WX035-7. $^1$H NMR (400 MHz, MeOD) δ ppm 13.28 (s, 1H), 9.03 (s, 1H), 8.29-8.26 (m, 1H), 8.12-8.10 (d, J=8 Hz, 1H), 6.11-6.08 (d, J=8.4 Hz, 1H), 5.02-5.01 (d, J=7.2 Hz, 1H), 1.35 (s, 3H), 1.24 (s, 3H).

Step 7: Synthesis of Compound WX035-8

CrO$_3$ (50.80 mg, 508.00 μmol, 18.81 μL, 1.20 eq) was added to the mixture of AcOH (6.00 mL), H$_2$SO$_4$ (52.35 μL), and water (2.00 mL) of WX035-7 (100.00 mg, 423.33 μmol, 1.00 eq). The mixture was stirred at 25° C. for 1 h, warmed to 100° C. for 10 min. After reaction, the reaction system was added with 50 mL of water was added to (there was precipitation generated), and filtered. The filtrate was extracted with dichloromethane (100 mL*3). The residue was dissolved with dichloromethane:methanol=10:1 (150 mL), washed with water (100 mL). The dichloromethane phase was combined, dried with anhydrous sodium sulfate, and filtered. The filtrate was concentrated under vacuum to obtain WX035-8. $^1$H NMR (400 MHz, MeOD) δ ppm 9.31 (br s, 1H), 8.63 (br s, 1H), 8.26 (br d, J=7.90 Hz, 1H), 1.49 (s, 6H)

Step 8: Synthesis of Compound WX035-9

Under 0° C., (COCl)$_2$ (40.65 mg, 320.23 μmol, 28.03 μL, 1.50 eq) and DMF (1.56 mg, 21.35 μmol, 1.64 μL, 0.10 eq) were added to the anhydrous dichloromethane (5.00 mL) solution of WX035-8 (50.00 mg, 213.48 μmol, 1.00 eq). The mixture was stirred for 2 h. After reaction, the reaction liquid was concentrated under vacuum to obtain the crude. Anhydrous methylbenzene (10 mL*3) was added to the crude, and concentrated under vacuum to obtain WX035-9.

Step 9: Synthesis of Compound WX035-10

Under nitrogen condition at 0° C., LiHMDS (1 M, 178.11 μL, 0.90 eq) was slowly dropwise added to the anhydrous tetrahydrofuran (5.00 mL) solution of WX002-2 (46.13 mg, 158.32 μmol, 0.80 eq), the mixture was continuously stirred at 0° C. for 1 hr, then WX035-9 (50.00 mg, 197.90 μmol, 1.00 eq) was slowly added. The mixture was stirred for 1 h. After reaction, 10 mL of water was slowly added to the reaction liquid at 0° C. The mixture was extracted with ethyl acetate (10 mL*3). The organic phase was combined, dried with anhydrous sodium sulfate, and filtered. The filtrate was concentrated under vacuum. The crude was purified by thin layer chromatography silica gel plate (petroleum ether:ethyl acetate=1:1) to obtain WX035-10. m/z=508.3[M+1].

Step 10: Synthesis of Compound WX035

HCl/methanol (4 M, 4.00 mL) was added to the anhydrous methanol (2.00 mL) solution of WX035-10 (12.00 mg, 23.64 μmol, 1.00 eq). The reaction liquid was stirred at 25° C. for 1 h under nitrogen condition. After reaction, the reaction liquid was concentrated under vacuum to obtain WX035.

$^1$H NMR (400 MHz, MeOD) δ ppm: 8.82-8.73 (m, 1H), 8.50-8.39 (m, 2H), 8.11-7.83 (m, 2H), 7.63-7.45 (m, 1H), 3.87-3.75 (m, 1H), 3.72-3.58 (m, 1H), 3.57-3.35 (m, 2H), 3.07-2.88 (m, 1H), 2.39 (s, 1H), 2.25 (s, 3H), 2.07-1.91 (m, 2H), 1.68-1.49 (m, 1H), 1.42 (s, 6H).

Implementation 030: WX036

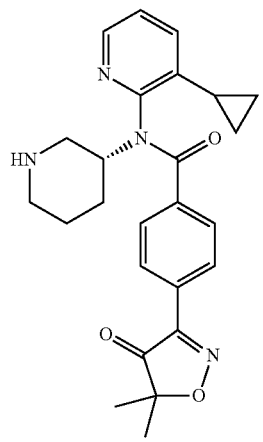 [SMILES: CC1(C)ON=C(c2ccc(C(=O)N(c3ncccc3C3CC3)[C@@H]3CCCNC3)cc2)C1=O]

Synthetic Route:

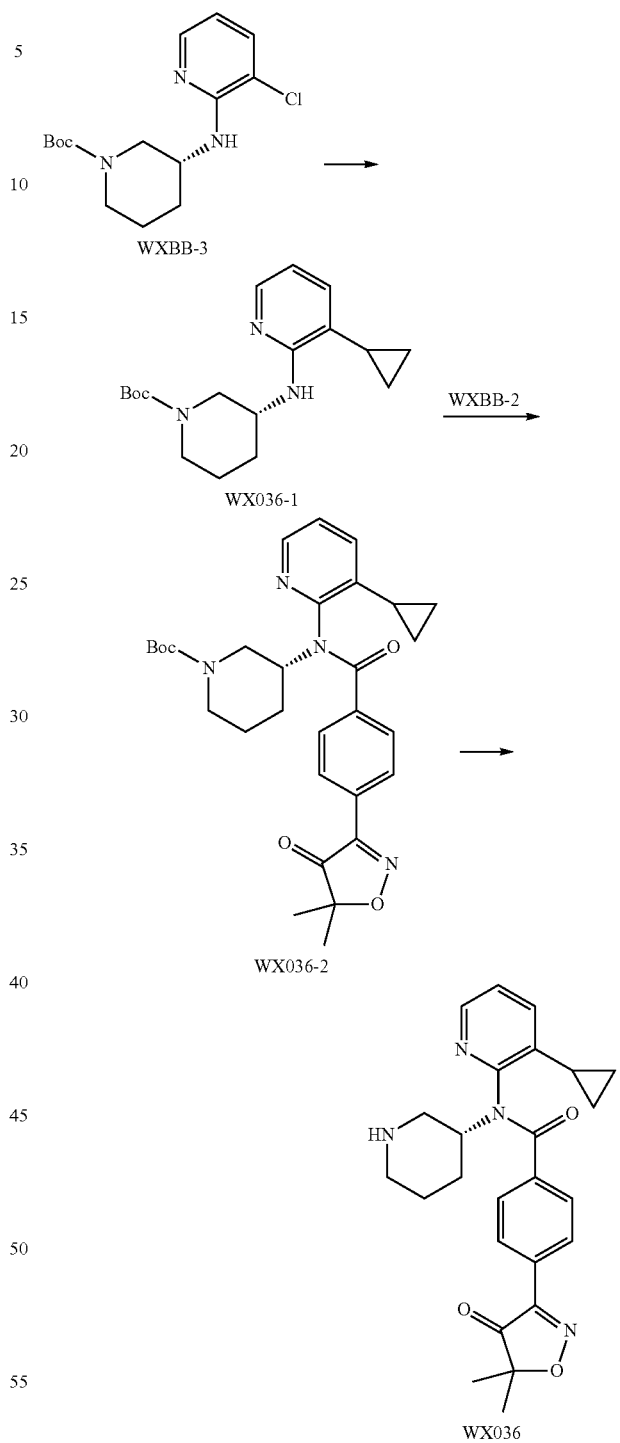

Step 1: Synthesis of Compound WX036-1

WXBB-3 (50.00 mg, 160.35 μmol, 1.00 eq), cyclopropylboronic acid (27.55 mg, 320.70 μmol, 2.00 eq), K$_2$CO$_3$ (66.49 mg, 481.05 μmol, 3.00 eq), Pd(OAc)$_2$ (3.60 mg, 16.04 μmol, 0.10 eq) and bis (1-adamantinyl)-butyl phosphine (11.50 mg, 32.07 μmol, 0.20 eq) were added in the reaction flask, then anhydrous methylbenzene (20.00 mL) and water (100.00 μL) were added. The reaction liquid was stirred at 90° C. for 2 h under nitrogen condition. After reaction, the reaction liquid was cooled to room temperature, and filtered. The filter cake was washed with 10 mL of ethyl acetate to collect the filtrate which was then concentrated under vacuum to obtain the crude. The crude was purified by thin layer chromatography silica gel plate (petroleum ether: ethyl acetate=3:1) to obtain WX036-1. $^1$H NMR (400 MHz, MeOD) δ ppm: 7.85 (br d, J=4.6 Hz, 1H), 7.27 (br d, J=7.0 Hz, 1H), 6.58-6.50 (m, 1H), 4.10-3.98 (m, 1H), 3.60 (br s, 2H), 3.41 (br s, 2H), 1.99 (br d, J=4.2 Hz, 1H), 1.76 (br s, 2H), 1.65-1.55 (m, 2H), 1.45-1.22 (m, 9H), 0.94 (br d, J=8.2 Hz, 2H), 0.53 (br s, 2H).

Step 2: Synthesis of Compound WX036-2

Under nitrogen condition at 0° C., LiHMDS (1 M, 70.89 μL, 0.90 eq) was added to the anhydrous tetrahydrofuran (5.00 mL) solution of WX036-1 (20.00 mg, 63.01 μmol, 0.80 eq). The reaction liquid was stirred at 0° C. for 0.5 h, added with WXBB-2 (19.82 mg, 78.76 μmol, 1.00 eq) at 0° C., and stirred at 25° C. for 2.5 h. After reaction, water (10 mL) was added to the reaction liquid, the mixture was extracted with ethyl acetate (10 mL×3), and combined with the organic phase. The organic phase was washed with saturated sodium chloride solution (10 mL), dried with anhydrous sodium sulfate, and filtered. The filtrate was concentrated under vacuum to obtain the crude. The crude was purified by thin layer chromatography silica gel plate (petroleum ether:ethyl acetate=3:1) to obtain WX036-2. m/z=533.3[M+1].

Step 3: Synthesis of Compound WX036

HCl/methanol (4 M, 5.00 mL) was added to the anhydrous methanol (5.00 mL) solution of WX036-2 (20.00 mg, 37.55 μmol, 1.00 eq). The reaction liquid was stirred at 25° C. for 2 h. After reaction, the reaction liquid was concentrated under vacuum to obtain WX036. $^1$H NMR (400 MHz, MeOD) δ ppm: 8.37 (d, J=3.8 Hz, 1H), 7.89 (br d, J=8.2 Hz, 2H), 7.35 (br d, J=8.4 Hz, 2H), 7.26 (dd, J=7.8, 4.8 Hz, 1H), 7.07 (br d, J=7.6 Hz, 1H), 5.18- 5.04 (m, 1H), 3.86-3.76 (m, 1H), 3.69 (s, 1H), 3.58 (br t, J=12.0 Hz, 1H), 2.99-2.83 (m, 1H), 2.39-2.11 (m, 1H), 2.07-1.93 (m, 2H), 1.92-1.76 (m, 2H), 1.40 (s, 6H), 0.89-1.18 (m, 2H), 0.70 (br d, J=4.2 Hz, 1H), 0.13-0.27 (m, 1H).

Implementation 031: WX037

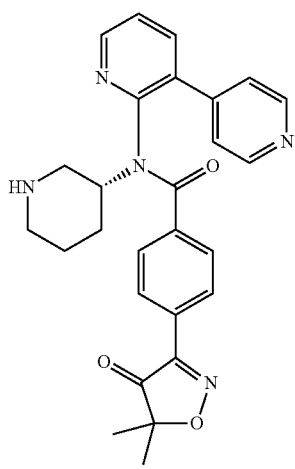 [SMILES: CC1(C)ON=C(c2ccc(C(=O)N(c3ncccc3-c3ccncc3)[C@@H]3CCCNC3)cc2)C1=O]

Synthetic Route:

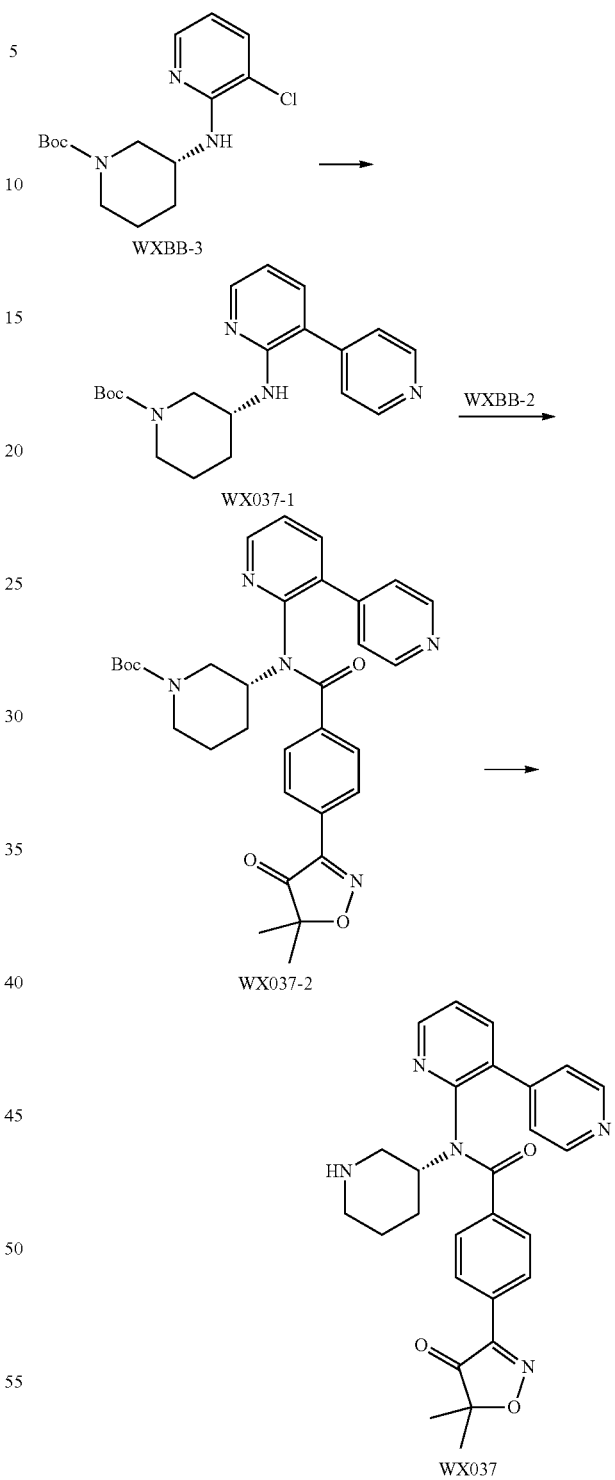

Step 1: Synthesis of Compound WX037-1

WXBB-3 (300.00 mg, 962.12 μmol, 1.00 eq), 4-pyridineboronic acid (473.06 mg, 3.85 mmol, 4.00 eq), K$_2$CO$_3$ (398.93 mg, 2.89 mmol, 3.00 eq), Pd(OAc)$_2$ (21.60 mg, 96.21 μmol, 0.10 eq), and bis (1-adamantinyl)-butyl phosphine (68.99 mg, 192.42 μmol, 0.20 eq) were added in the reaction flask, then 1,4-dioxane (6.00 mL) and water (1.20 mL) were added. The mixture was stirred at 90° C. for 20 h under nitrogen condition. After reaction, the filtrate was filtered, and then the filtered cake was washed with ethyl acetate (20 mL). The filtrate was collected, washed with water (30 mL), dried with anhydrous sodium sulfate, and filtered. The filtrate was concentrated under vacuum to obtain the crude. The crude was purified by thin layer chromatography silica gel plate (dichloromethane:methanol=10:1) to obtain WX037-1. m/z=355.3[M+1].

Step 2: Synthesis of Compound WX037-2

Under nitrogen condition at 0° C., LiHMDS (1 M, 174.57 μL, 0.90 eq) was slowly dropwise added to the anhydrous tetrahydrofuran (5.00 mL) solution of WX037-1 (55.00 mg, 155.17 μmol, 0.80 eq). The mixture was continuously stirred at 0° C. for 1 hr, then slowly added with WXBB-2 (48.81 mg, 193.96 μmol, 1.00 eq), and continuously stirred for 1 h. After reaction, the reaction system was cooled to 0° C., slowly added with 10 mL of water. The mixture was extracted with ethyl acetate (10 mL*3). The organic phase was combined, dried with anhydrous sodium sulfate, and filtered. The filtrate was concentrated under vacuum to obtain the crude. The crude was purified by thin layer chromatography silica gel plate (dichloromethane:methanol=10:1) to obtain WX037-2. m/z=570.4[M+1].

Step 3: Synthesis of Compound WX037

HCl/methanol (4 M, 4.00 mL) was added to the anhydrous methanol (4.00 mL) solution of WX037-2 (20.00 mg, 35.11 μmol, 1.00 eq). The reaction liquid was stirred at 25° C. for 1 h. After reaction, the reaction liquid was concentrated under vacuum to obtain WX037. $^1$H NMR (400 MHz, MeOD) δ ppm: 8.90-8.79 (m, 3H), 7.92-7.977 (m, 3H), 7.69-7.60 (m, 3H), 6.76 (br s, 2H), 5.26-5.23 (m, 1H), 3.97-3.93 (m, 1H), 3.83-3.80 (m, 1H), 3.47-3.43 (m, 1H), 3.08-3.03 (m 1H), 2.13-2.10 (m, 2H), 2.02-1.86 (m, 1H), 1.45-1.42 (m, 8H).

Implementation 032: WX038

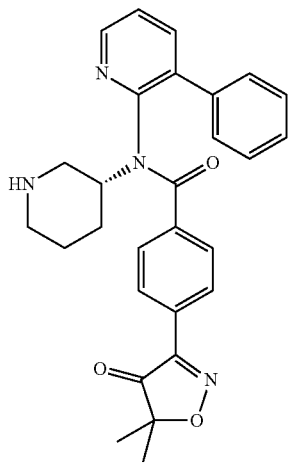 [SMILES: CC1(C)ON=C(c2ccc(C(=O)N(c3ncccc3-c3ccccc3)[C@@H]3CCCNC3)cc2)C1=O]

Synthetic Route:

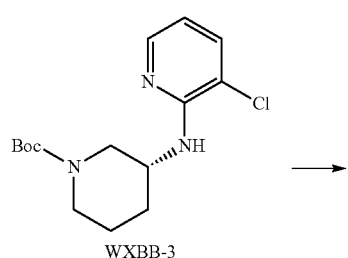

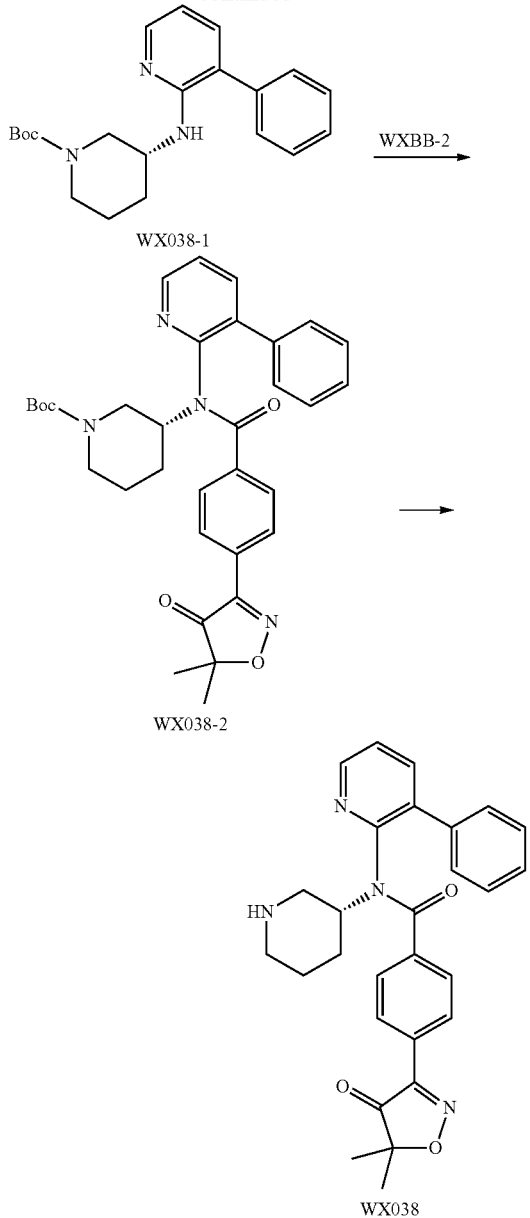

Step 1: Synthesis of Compound WX038-1

Borophenylic acid (78.21 mg, 641.42 μmol, 2.00 eq), WXBB-3 (100.00 mg, 320.71 μmol, 1.00 eq), Pd(OAc)$_2$ (7.20 mg, 32.07 μmol, 0.10 eq), K$_2$CO$_3$ (132.98 mg, 962.12 μmol, 3.00 eq) and bis (1-adamantinyl)-butyl phosphine (23.00 mg, 64.14 μmol, 0.20 eq) were added in the reaction flask, then water (100.00 μL) and 1,4-dioxane (5.00 mL) were added to the reaction flask. The reaction flask was bubbled with nitrogen for 1 min, placed at 100° C. in oil bath for 12 h. After reaction, the reaction liquid was naturally cooled to room temperature, then filtered through the five-hole funnel covered with diatomite. The filter cake was washed with ethyl acetateethyl acetate (20 mL). The filtrate was combined, and concentrated under vacuum to obtain the crude. The crude was diluted with 15 mL of ethyl acetate and 10 mL of water, adjusted aqueous phase with aqueous hydrochloric acid solution (2M) to pH=1-2. The liquid was separated. The aqueous phase was collected, adjusted with solid sodium bicarbonate to 8, and then extracted with ethyl acetate (10 mL*3). The organic phase was combined, washed with saturated sodium chloride solution (10 mL), dried with anhydrous sodium sulfate, and filtered. The filtrate was concentrated under vacuum to obtain WX038-1.

Step 2: Synthesis of Compound WX038-2

Under nitrogen condition at 0° C., LiHMDS (1 M, 127.31 μL, 0.80 eq) was slowly dropwise added to the anhydrous tetrahydrofuran (10.00 mL) of WX038-1 (45.00 mg, 127.31 μmol, 0.80 eq). The mixture was stirred at 0° C. for 1 h. WXBB-2 (40.05 mg, 159.14 μmol, 1.00 eq) was added. The reaction liquid was stirred at 25° C. for 2 h. After reaction, the reaction system was cooled to 0° C., and 5 mL of water was slowly added. The mixture was extracted with ethyl acetate (10 mL*3). The organic phase was combined, washed with saturated sodium chloride solution (10 mL), dried with anhydrous sodium sulfate, and filtered. The filtrate was concentrated under vacuum to obtain the crude. The crude was purified by thin layer chromatography silica gel plate (petroleum ether:ethyl acetate=2:1) to obtain WX038-2.

Step 3: Synthesis of Compound WX038

HCl/methanol (4 M, 1.00 mL) was added to the methanol (10.00 mL) solution of WX038-2 (65.00 mg, 114.30 μmol, 1.00 eq). The reaction liquid was stirred at 25° C. for 2 h under nitrogen condition. After reaction, the reaction liquid was concentrated under vacuum to obtain the crude. The crude was diluted with 20 mL of ethyl acetate and 10 mL of water. The aqueous phase was adjusted with solid sodium bicarbonate to pH=8. The mixture was extracted with ethyl acetate (10 mL*3). The organic phase was combined, washed with saturated sodium chloride solution (10 mL), dried with anhydrous sodium sulfate, and filtered. The filtrate was concentrated under vacuum to obtain WX038. $^1$H NMR (400 MHz, CDCl$_3$) δ ppm: 8.56-8.42 (m, 1H), 7.70-7.54 (m, 2H), 7.46-7.35 (m, 1H), 7.33-7.21 (m, 3H), 6.92-6.55 (m, 4H), 4.82-4.40 (m, 1H), 3.56-3.42 (m, 1H), 3.23-3.06 (m, 2H), 3.38-3.32 (m, 1H), 2.72-2.56 (m, 1H), 2.45-2.15 (m, 1H), 1.86-1.66 (m, 2H), 1.38 (s, 6H), 1.22-1.14 (m, 1H), 0.86-0.70 (m, 1H).

Implementation 033: WX039

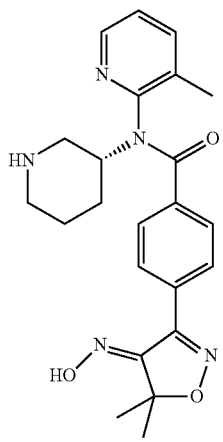

Synthetic Route:

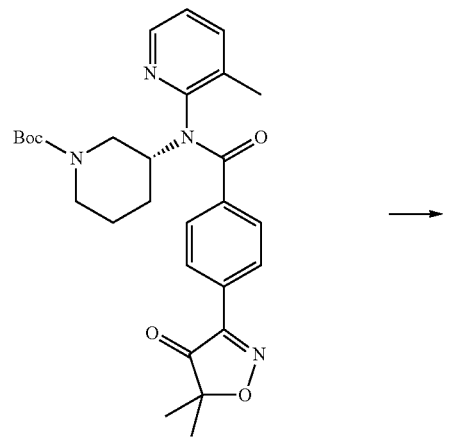

WX002-2

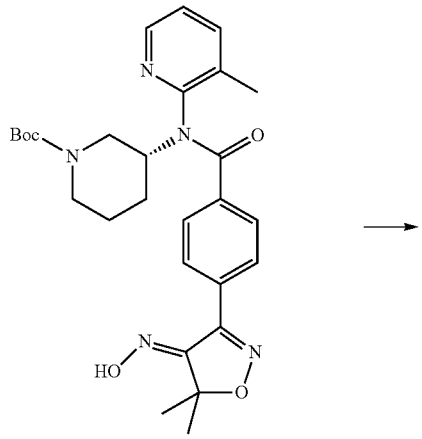

WX039-1

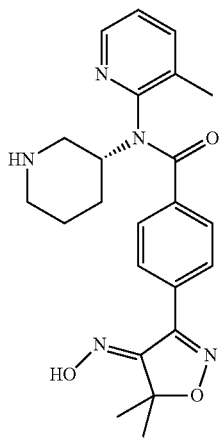

WX039

Step 1: Synthesis of Compound WX039-1

WX002-2 (40.00 mg, 66.22 μmol, 1.00 eq) (83.871% purity) was dissolved in pyridine (5.00 mL), hydroxylammonium chloride (5.30 mg, 76.27 μmol, 1.15 eq) was added. The mixture was heated to 65° C. and stirred for 2 h. After heated up to 80° C., the mixture was continuously reacted for 3 h, then heated up to 110° C., and continuously reacted for 2 h. After reaction, the reaction liquid was dried by rotary evaporation under vacuum to obtain the crude. The crude was separated by prep-TLC (petroleum ether:ethyl acetate-ethyl acetate=1:1) to obtain WX039-1.

$^1$H NMR (400 MHz, CDCl$_3$) δ ppm 1.47 (br d, J=16.56 Hz, 9H) 1.66 (br s, 2H) 1.68-1.76 (m, 6H) 1.79 (br s, 1H) 1.93-2.05 (m, 3H) 2.27-2.75 (m, 2H) 3.31-4.74 (m, 4H) 7.13 (br s, 1H) 7.35 (br d, J=8.28 Hz, 3H) 7.74-7.91 (m, 2H) 8.61-8.70 (m, 1H)

Step 2: Synthesis of WX039

WX039-1 (38.00 mg, 65.59 μmol, 1.00 eq) (90.032% purity) was dissolved in HCl/ethyl acetateethyl acetate (4 M, 500.00 μL, 30.49 eq). The mixture was stirred at 10° C. for 1 h. After reaction, the bottom solid was retained and the supernatant liquid was poured out. The solid was washed with ethyl acetate (3 mL*2), and the solid at the bottom of flask was concentrated under vacuum to obtain WX039.

$^1$H NMR (400 MHz, DMSO-d$_6$) δ ppm: 1.20 (br s, 1H), 1.60 (br s, 6H), 1.79 (br s, 2H), 1.93-2.09 (m, 3H), 2.10-2.36 (m, 1H), 2.63-3.40 (m, 4H), 4.49-5.12 (m, 1H), 7.26 (br d, J=7.28 Hz, 3H), 7.58 (br d, J=6.78 Hz, 1H), 7.75 (br d, J=7.28 Hz, 2H), 8.35-8.50 (m, 1H), 9.04 (br s, 1H), 9.35 (br s, 1H).

Implementation 034: WX040

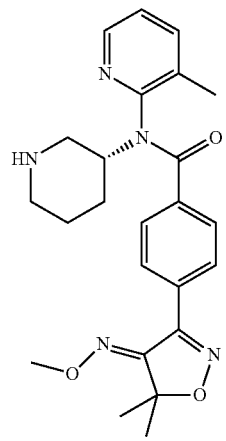

Synthetic Route:

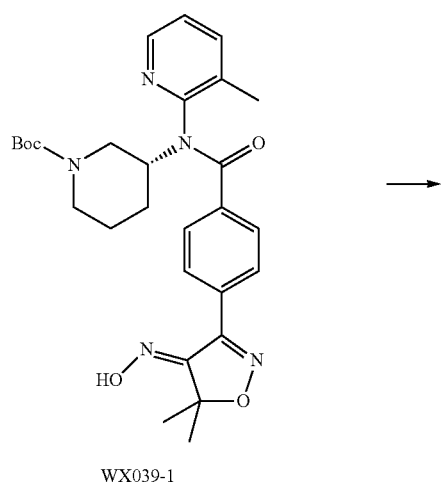

WX039-1

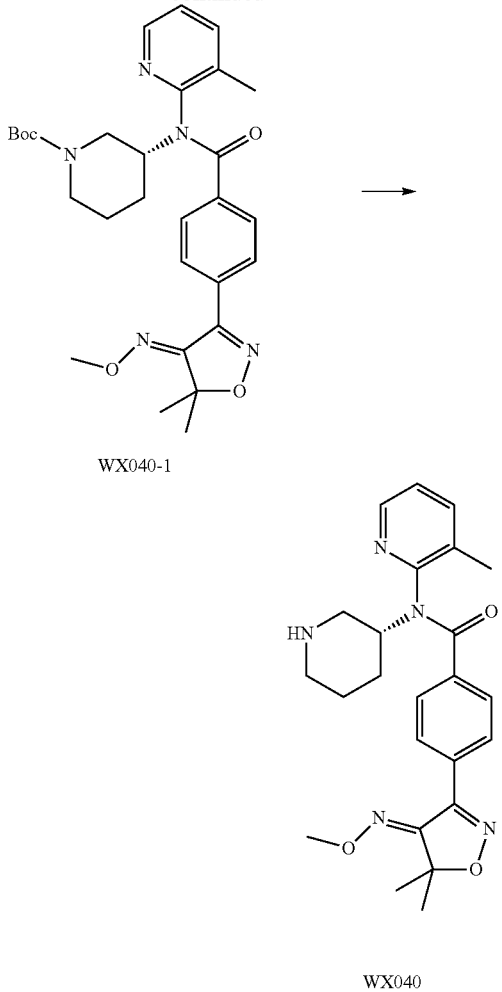

Step 1: Synthesis of Compound WX040-1

WX039-1 (200.00 mg, 373.83 μmol, 1.00 eq) (97.498% purity) was dissolved in anhydrous DMF (20.00 mL), K$_2$CO$_3$ (80.00 mg, 578.83 μmol, 1.55 eq) and iodomethane (114.00 mg, 803.73 μmol, 50.00 μL, 2.15 eq) were added. The mixture was stirred at 10° C. for 14 h. After reaction, the reaction liquid was added with 30 mL of water, extracted with ethyl acetate (30 mL*3). The organic phase was combined, washed with water (20 mL*3), and concentrated under vacuum to obtain WX040-1. $^1$H NMR (400 MHz, CDCl$_3$) δ ppm: 1.30-1.37 (m, 1H), 1.47 (br d, J=15.81 Hz, 9H), 1.65 (s, 6H), 1.70-1.85 (m, 1H), 2.02 (br d, J=13.30 Hz, 2H), 2.12-2.73 (m, 2H), 2.86-3.00 (m, 3H), 3.25-3.63 (m, 1H), 3.98 (s, 3H), 4.22-4.87 (m, 2H), 7.10 (br s, 1H) 7.32 (br s, 3H), 7.83 (br d, J=7.28 Hz, 2H), 8.42 (br s, 1H).

Step 2: Synthesis of Compound WX040

WX040-1 (200.00 mg, 365.79 μmol, 1.00 eq) (purity: 97.966%) was dissolved in HCl/EtOAc (4 M, 3.00 mL, 32.81 eq). The mixture was stirred at 10° C. for 2 h. After reaction, the reaction liquid was added with 20 mL of water and 20 mL of ethyl acetate, adjusted with saturated sodium bicarbonate to pH≈8. The organic phase was collected, dried with anhydrous sodium sulfate, and filtered. The filtrate was concentrated under vacuum to obtain WX040. $^1$H NMR (400 MHz, DMSO-d$_6$) δ ppm: 1.07 (br d, J=10.04 Hz, 1H), 1.43-1.68 (m, 8H), 1.90-2.05 (m, 3H), 2.08-2.37 (m, 3H), 2.73-3.09 (m, 2H), 3.94 (s, 3H), 4.31-4.65 (m, 1H), 7.25 (br d, J=7.03 Hz, 3H), 7.54 (br s, 1H), 7.74 (br d, J=8.03 Hz, 2H), 8.35-8.47 (m, 1H).

Implementation 035: WX041

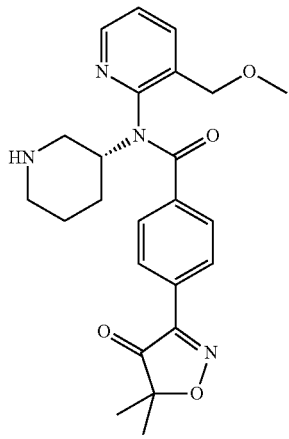

Synthetic Route:

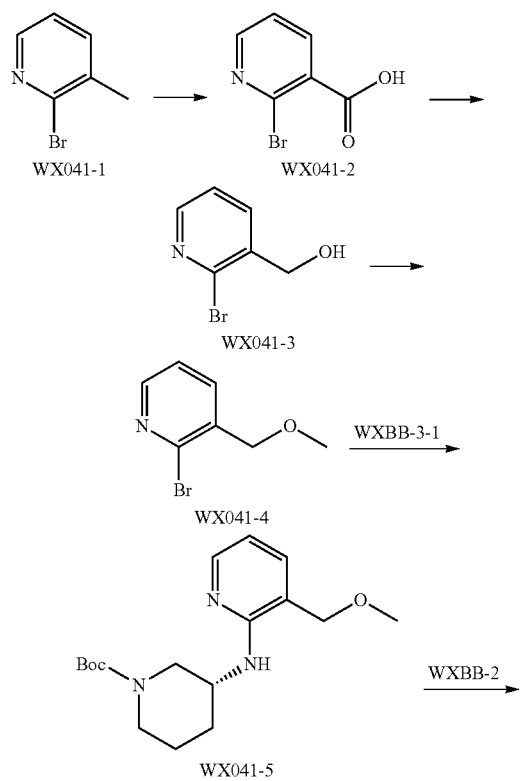

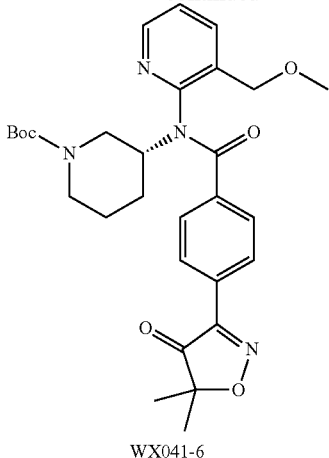

WX041-6

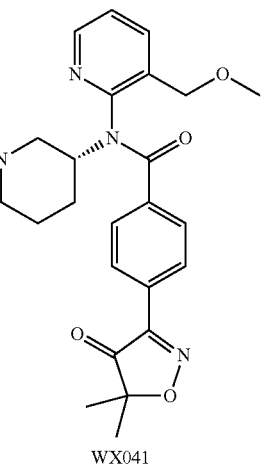

WX041

Step 1: Synthesis of Compound WX041-2

Under 20° C., potassium permanganate (9.46 g, 59.87 mmol, 1.03 eq) was added to the aqueous (200.00 mL) solution of WX041-1 (10.00 g, 58.13 mmol, 6.49 mL, 1.00 eq). The mixture was stirred for 1 h at 100° C., added with potassium permanganate (9.46 g, 59.87 mmol, 1.03 eq) and stirred for 16 h, then added with potassium permanganate (9.46 g, 59.87 mmol, 1.03 eq) again and continuously stirred for 6 h. After reaction, the reaction liquid was filtered to remove the undissolved substance, added with water (100 mL), adjusted with hydrochloric acid (4M) to pH=3~4, and extracted with ethyl acetate three times (200 mL each time). The organic phase was washed with saturated sodium chloride solution (200 mL), dried with anhydrous sodium sulfate, and filtered. The filtrate was concentrated under vacuum to obtain WX041-2.

$^1$H NMR (400 MHz, MeOD) δ ppm: 7.50 (dd, J=7.78, 4.77 Hz, 1H), 8.15-8.20 (m, 1H), 8.42-8.48 (m, 1H).

Step 2: Synthesis of Compound WX041-3

Under $N_2$ condition, borane-tetrahydrofuran solution (1 M, 60.00 mL, 1.52 eq) was added to the anhydrous tetrahydrofuran (20.00 mL) of WX041-2 (8.00 g, 39.60 mmol, 1.00 eq) at 0° C. The mixture was slowly warmed to 15° C. and stirred for 20 h. After reaction, water (100 mL) was slowly added to quench the reaction. The mixture was extracted with ethyl acetate (100 mL*3). The organic phase was washed with saturated sodium chloride solution (100 mL), dried with anhydrous sodium sulfate, and filtered. The filtrate was concentrated under vacuum. The crude was dissolved in ethyl acetate/water (1/1, 100 mL), adjusted with NaCO₃ to pH=10-11. The organic phase was taken, washed with saturated sodium chloride solution (50 mL), dried with anhydrous magnesium sulfate, and filtered. The filtrate was concentrated under vacuum to obtain WX041-3. ¹H NMR (400 MHz, CDCl₃) δ ppm: 4.76 (s, 2H), 7.33 (dd, J=6.78, 5.27 Hz, 1H), 7.81-7.90 (m, 1H), 8.26-8.34 (m, 1H).

Step 3: Synthesis of Compound WX041-4

Under N₂ condition, NaH (849.00 mg, 21.23 mmol, 60% purity, 3.99 eq) was added to the anhydrous tetrahydrofuran (40.00 mL) solution of WX041-3 (1.00 g, 5.32 mmol, 1.00 eq) at 0° C. The mixture was stirred for 0.5 h, then added with iodomethane (3.02 g, 21.28 mmol, 1.32 mL, 4.00 eq), warmed to 15° C. and stirred for 15.5 h. After reaction, water (30 mL) was slowly added to quench the reaction, and ethyl acetate (30 mL*3) was used for extraction. The organic phase was washed with saturated sodium chloride solution (30 mL), dried with anhydrous sodium sulfate, and filtered. The filtrate was concentrated under vacuum. The crude was purified by column chromatography (petroleum ether:ethyl acetate=1:0-5:1) to obtain WX041-4. ¹H NMR (400 MHz, CDCl₃) δ ppm: 3.51 (s, 3H), 4.50 (s, 2H), 7.30 (dd, J=7.53, 4.77 Hz, 1H), 7.79 (dt, J=7.53, 1.00 Hz, 1H), 8.29 (dd, J=4.64, 1.88 Hz, 1H).

Step 4: Synthesis of Compound WX041-5

Under N₂ condition, WX041-4 (550.00 mg, 2.72 mmol, 1.00 eq) and WXBB-3-1 (550.00 mg, 2.75 mmol, 1.01 eq) were added to the anhydrous methylbenzene (10.00 mL), then t-BuONa (525.00 mg, 5.47 mmol, 2.01 eq), BINAP (254.00 mg, 408.00 μmol, 0.15 eq) and Pd₂(dba)₃ (249.00 mg, 272.00 μmol, 0.10 eq) were added. The mixture was stirred at 90° C. for 6 h. After reaction, the reaction liquid was added with water (30 mL), extracted with ethyl acetate (30 mL*3). The combined organic phase was washed with saturated sodium chloride solution (30 mL), dried with anhydrous magnesium sulfate, filtered, and concentrated (rotary evaporator, vacuum by water pump, water bath at 40° C.). The crude was dissolved in water/ethyl acetate (1:1) (30 mL), and the pH was adjusted with hydrochloric acid (4M) to 2-3. The mixture was layered (the organic phase was discarded); the aqueous phase was adjusted with Na₂CO₃ to pH=9-10, extracted with ethyl acetate (3*30 mL), washed with saturated sodium chloride solution (30 mL), dried with anhydrous magnesium sulfate, and filtered. The filtrate was concentrated under vacuum to obtain WX041-5.

¹H NMR (400 MHz, CDCl₃) δ ppm: 1.40 (br s, 9H), 1.54-1.80 (m, 4H), 1.86-2.04 (m, 1H), 3.30 (s, 3H), 3.43 (br s, 2H), 3.72 (br s, 1H), 4.13 (br d, J=7.03 Hz, 1H), 4.32-4.44 (m, 2H), 5.42 (br d, J=7.03 Hz, 1H), 6.52 (dd, J=7.03, 5.27 Hz, 1H), 7.24 (br d, J=6.53 Hz, 1H), 8.09 (dd, J=5.02, 1.76 Hz, 1H).

Step 5: Synthesis of Compound WX041-6

Under N₂ condition, LiHMDS (1 M, 690.00 μL, 0.81 eq) was added to the anhydrous tetrahydrofuran (2.00 mL) solution of WX041-5 (220.00 mg, 684.48 μmol, 0.80 eq) at 0° C. The mixture was stirred for 1 h, added with WXBB-2 (215.00 mg, 854.29 μmol, 1.00 eq), then warmed to 15° C. and stirred for 16 h. After reaction, the reaction liquid was added with saturated NH₄Cl solution (10 mL), extracted with ethyl acetate (3*12 mL). The organic phase was washed with saturated sodium chloride solution (10 mL), dried with anhydrous sodium sulfate, and filtered. The filtrate was concentrated under vacuum. The crude was dissolved in water/ethyl acetate (1:1) (20 mL), and the pH was adjusted with hydrochloric acid (4M) to 2-3. The organic phase was washed with saturated sodium chloride solution (10 mL), dried with anhydrous magnesium sulfate, and filtered. The filtrate was concentrated under vacuum. The crude was purified by prep-TLC (petroleum ether:ethyl acetate=5:1) to obtain WX041-6. ¹H NMR (400 MHz, MeOD) δ ppm: 1.39-1.48 (m, 17H), 1.68-1.80 (m, 2H), 2.21-2.28 (m, 1H), 2.63 (br s, 1H), 3.36 (br d, J=11.80 Hz, 3H), 3.96-4.58 (m, 5H), 7.36 (br, 3H), 7.74 (br d, J=10.29 Hz, 1H), 7.88 (br d, J=7.28 Hz, 2H), 8.44-8.56 (m, 1H).

Step 6: Synthesis of Compound WX041

WX041-6 (120.00 mg, 223.62 μmol, 1.00 eq) was added to HCl/EtOAc (4 M, 2.00 mL, 35.77 eq). The mixture was stirred at 15° C. for 16 h. After reaction, the mixture was adjusted with saturated sodium bicarbonate to pH=7, extracted with ethyl acetate (3*10 mL). The organic phase was washed with saturated sodium chloride solution (10 mL), dried with anhydrous magnesium sulfate, and filtered. The filtrate was concentrated under vacuum. The crude was purified by prep-HPLC (column: Xtimate C18 150*25 mm*5 μm; mobile phase: [water (0.05% ammonia hydroxide v/v)-ACN]; B %: 38%-68%, 10 min) to obtain WX041. ¹H NMR (400 MHz, CDCl₃) δ ppm: 1.44 (s, 7H), 1.72 (br d, J=16.56 Hz, 2H), 2.27-2.73 (m, 4H), 2.96-3.24 (m, 1H), 3.31 (br s, 3H), 3.55 (br s, 1H), 3.91 (br s, 1H), 4.27 (br d, J=13.05 Hz, 1H), 4.45-4.89 (m, 1H), 7.23 (br s, 1H), 7.35 (br s, 2H), 7.64 (br s, 1H), 7.89 (br s, 2H), 8.52 (br s, 1H).

Implementation 036: WX042

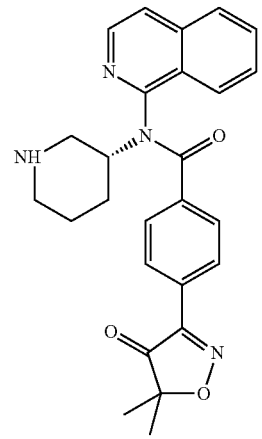 [SMILES: CC1(C)ON=C(c2ccc(C(=O)N(c3nccc4ccccc34)[C@@H]3CCCNC3)cc2)C1=O]

Synthetic Route:

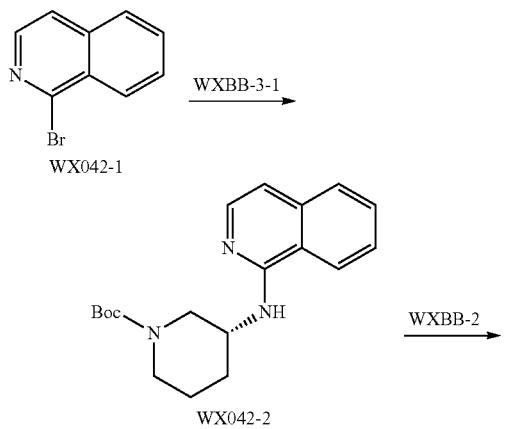

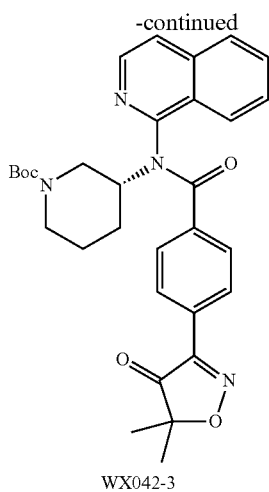

WX042-3

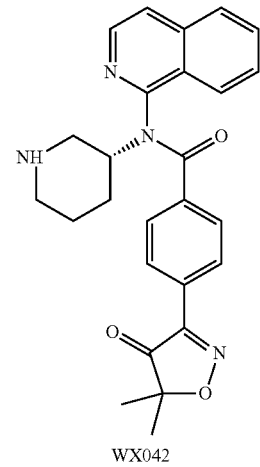

WX042

Step 1: Synthesis of Compound WX042-2

WX042-1 (50.00 mg, 240.33 μmol, 1.00 eq), WXBB-3-1 (52.95 mg, 264.36 μmol, 1.10 eq), $Pd_2(dba)_3$ (22.01 mg, 24.03 μmol, 0.10 eq), BINAP (29.93 mg, 48.07 μmol, 0.20 eq) and t-BuONa (46.19 mg, 480.65 μmol, 2.00 eq) were added in the reaction flask, then anhydrous methylbenzene (10.00 mL) was added to the reaction flask. Under the nitrogen condition, the reaction liquid was stirred at 100° C. for 12 h. After reaction, the reaction liquid was naturally cooled to room temperature, and filtered. The filtered cake was washed with ethyl acetate (20 mL). The filtrate was combined, concentrated under vacuum to obtain the crude. The crude was diluted with 20 mL of ethyl acetate and 20 mL of water. The pH of aqueous phase was adjusted with (2M) hydrochloric acid aqueous solution to 1~2. The mixture was layered, and then the aqueous phase was collected. The pH of aqueous phase was adjusted with solid sodium bicarbonate to 8, and ethyl acetate (20 mL*3) was added for extraction. The organic phase was combined, washed with saturated sodium chloride solution (10 mL), dried with anhydrous sodium sulfate, and filtered. The filtrate was concentrated under vacuum to obtain WX042-2.

Step 2: Synthesis of Compound WX042-3

Under nitrogen condition, LiHMDS (1 M, 207.41 μL, 0.90 eq) was slowly dropwise added to the anhydrous tetrahydrofuran (10.00 mL) solution of WX042-2 (60.00 mg, 183.25 μmol, 0.80 eq) at 0° C. The mixture was stirred at 0° C. for 1 h. WXBB-2 (58.00 mg, 230.46 μmol, 1.00 eq) was added. After charging, the mixture was naturally warmed to 25° C., and then stirred for 2 h. After reaction, the reaction system was cooled to 0° C., and 10 mL of water was slowly added. The mixture was extracted with ethyl acetate (10 mL*3). The organic phase was combined, washed with saturated sodium chloride solution (10 mL), dried with anhydrous sodium sulfate, and filtered. The filtrate was concentrated under vacuum to obtain the crude. The crude was purified by thin layer chromatography silica gel plate (petroleum ether:ethyl acetate=1:1) to obtain WX042-3. MS: m/z=543.3 [M+1]

Step 3: Synthesis of Compound WX042

WX042-3 (90.00 mg, 165.86 μmol, 1.00 eq), anhydrous methanol (5.00 mL) and HCl/methanol (4 M, 1.00 mL) were added to the reaction flask. Under nitrogen condition, the mixture was stirred for 2 h at 25° C. After reaction, the reaction liquid was concentrated under vacuum to obtain the crude, and then the crude was purified by prep-HPLC (column: Luna C8 100*30 5 μm; mobile phase: [water (0.1% TFA)-ACN]; B %: 20%-40%, 10 min) to obtain WX042. $^1$H NMR (400 MHz, MeOD-d4) δ ppm: 8.55-8.41 (m, 1H), 8.13-7.97 (m, 1H), 7.95-7.60 (m, 6H), 7.43-7.28 (m, 2H), 5.37-5.23 (m, 1H), 3.99-3.88 (m, 1H), 3.83-3.68 (m, 1H), 3.40-3.35 (m, 1H), 2.98-2.82 (m, 1H), 2.52-2.04 (m, 1H), 2.01-1.87 (m, 2H), 1.54-1.40 (m, 1H), 1.35 (s, 6H).

Bio-Activity Test

Example 1: In Vitro Screening Experiment

1. Reagent Preparation:

1) Preparation of 1× AlphaLISA test buffer solution:

2.5 ml of 10× AlphaLISA test buffer solution was added to 22.5 ml of Milli-Q water to produce the 1× AlphaLISA test buffer solution.

2) Preparation of mixture (25 μg/mL/2.5 nM) of 2.5× AlphaLISA Acceptor beads and Biotinylated Antibody Anti-PCSK9:

50 μL of 5 mg/mL Alpha LISA Anti-PCSK9 Acceptor beads and 50 μL of 500 nM Biotinylated Antibody Anti-PCSK9 were added to 9,900 μL of 1× AlphaLISA test buffer solution.

3) Preparation of 2× Streptavidin (SA) Donor beads (80 μg/mL):

200 μL of 5 mg/mL SA-Donor beads was added to 12,300 μL of 1× AlphaLISA test buffer solution.

2. Operation Steps:

1) DMSO was added to the test compound to produce the 50 μM stock solution, which was then serially diluted into 10 concentrations by 3-fold, and placed in the 384-pore plate;

2) PCSK9-Huh7 cells were added in the 384-pore plate, and the cell plate was cultured in the incubator for 20 h;

3) 20 μL/pore mixture of 2.5× AlphaLISA Acceptor beads and Biotinylated Antibody Anti-PCSK9 was added, and incubated at 23° C. for 60 min.

4) 25 μL/pore 2× Streptavidin (SA) Donor beads were added; and incubated for 30 min at 23° C. (kept in dark place).

5) EnVision-Alpha Reader reading:

Test condition: Total Measurement Time: 550 ms, Laser 680 nm Excitation Time: 180 ms, Mirror: D640as, Emission Filtered: M570w, Center Wavelength 570 nm, Bandwidth 100 nm, Transmittance 75%.

3. Data Analysis:

Date was analyzed with Prismsoftware (nonlinear regression (Sigmoidal dose-response-variable slope)

Inhibition ratio %=100*(Sample reading−LC reading)/(HC reading−LC reading)  Computational formula:

TABLE 1

In vitro screening result of the compound described in this disclosure

| Number | Compound | IC50 |
|---|---|---|
| 1 | WX001 | A |
| 2 | WX002 | A |
| 3 | WX003 | A |
| 4 | WX004 | A |
| 5 | WX005 | A |
| 6 | WX006 | A |
| 7 | WX008 | A |
| 8 | WX009 | A |
| 9 | WX011 | A |
| 10 | WX012 | A |
| 11 | WX013 | A |
| 12 | WX015 | A |
| 13 | WX021 | A |
| 14 | WX022 | A |
| 15 | WX023 | A |
| 16 | WX024 | A |
| 17 | WX025 | A |
| 18 | WX026 | A |
| 19 | WX027 | A |
| 20 | WX028 | A |
| 21 | WX029 | A |
| 22 | WX030 | A |
| 23 | WX031 | A |
| 24 | WX032 | A |
| 25 | WX033 | A |
| 26 | WX034 | A |
| 27 | WX035 | A |
| 28 | WX036 | A |
| 29 | WX037 | A |
| 30 | WX038 | A |
| 31 | WX039 | A |
| 32 | WX040 | A |
| 33 | WX041 | A |
| 34 | WX042 | A |

Note:
A ≤10 μM

Conclusions: the compounds described in this disclosure have significant inhibiting effect on PCSK9.

Example 2: Research of Pharmacokinetic Properties

Method:

Research of Pharmacokinetic Properties in SD Rats

This example was intended to evaluate the PK properties of test compound, and calculate the bioavailability in male SD rats. Each test compound used six male SD rats, Six male SD rats were randomly divided into two groups. Three rats were respectively administrated with the dose of 1 mg/kg by intravenous injection; the whole blood was collected at 0.0833, 0.25, 0.5, 1, 2, 4, 6, 8 and 24 h after administration and plasma samples were prepared. The other three rats were respectively administrated with the dose of 5 mg/kg by gavage, the whole blood was collected at 0.25, 0.5, 1, 2, 4, 6, 8 and 24 h after administration, and plasma samples were prepared. the concentration of the test compound in the plasma was tested by LC/MS/MS method, and relevant PK parameters was calculated with Phoenix WinNonlin 6.2.1.

The test results showed that the compound described in this disclosure had good PK properties in male SD rats. For the bioavailability data, see table 2.

TABLE 2

Bioavailability data

| | PF-06446846 | WX001 | WX002 | WX021 | WX027 | WX040 |
|---|---|---|---|---|---|---|
| F in rats (%) | 20% | 83.9% | 68.0% | 37.7% | 58.8% | 56.3% |

Conclusions: The compounds described in this disclosure had good pharmacokinetic properties.

The invention claimed is:
1. A compound of formula (I), and/or a pharmaceutically acceptable salt thereof,

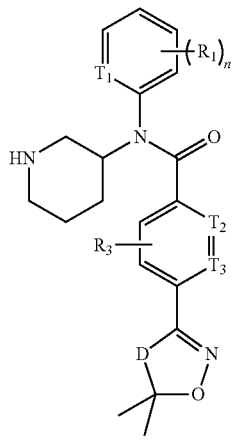

(I)

Wherein,
$T_1$ is chosen from N and CH;
$T_2$ is chosen from CH and N;
$T_3$ is chosen from CH and N;
D is chosen from

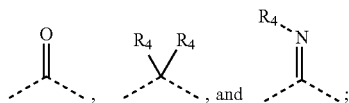

n is chosen from 0, 1, 2 and 3;
Each $R_1$ is independently chosen from halogen, OH and $NH_2$, or $C_{1-3}$ alkyl, $C_{1-3}$ heteroalkyl, $C_{3-6}$ cycloalkyl, phenyl, and 5 or 6 membered heteroaryl group, any of which is optionally substituted by one, two or three R groups;
or, two adjacent $R_1$ are connected together to form a nitrogen-containing 5-membered ring, an oxygen-containing 5-membered ring, or a benzene ring, any of which is optionally substituted by one, two or three R groups;
$R_3$ is chosen from H, halogen, OH and $NH_2$, or $C_{1-3}$ alkyl group, which is optionally substituted by one, two or three R groups;
Each $R_4$ is independently chosen from H and OH, or $C_{1-3}$ alkyl group and a $C_{1-3}$ alkoxy group, either of which is optionally substituted by one, two or three R groups;
R is chosen from F, Cl, Br, I, OH, $NH_2$, $NH(CH_3)$, $N(CH_3)_2$, Me and OMe;
wherein each of said $C_{1-3}$ heteroalkyl independently comprises 1, 2, or 3 heteroatoms groups independently chosen from —O—, —S—, and —NH—.

2. A compound of formula (I), and/or a pharmaceutically acceptable salt thereof,

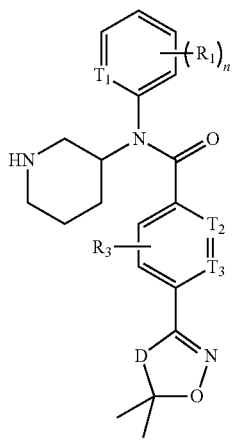
(I)

Wherein,
$T_1$ is chosen from N and CH;
$T_2$ is chosen from CH and N;
$T_3$ is chosen from CH and N;
D is chosen from

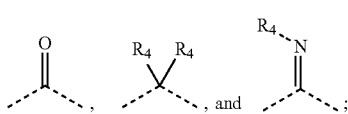

n is chosen from 0, 1, 2 and 3;
wherein each $R_1$ is independently chosen from F, Cl, Br, I, OH and $NH_2$, or is chosen from $C_{1-3}$ alkyl and $C_{1-3}$ alkoxy, either of which is optionally substituted by one, two or three R groups;
$R_3$ is chosen from H, halogen, OH and $NH_2$, or $C_{1-3}$ alkyl group, which is optionally substituted by one, two or three R groups;
Each $R_4$ is independently chosen from H and OH, or $C_{1-3}$ alkyl group and a $C_{1-3}$ alkoxy group, either of which is optionally substituted by one, two or three R groups;
R is chosen from F, Cl, Br, I, OH, $NH_2$, $NH(CH_3)$, $N(CH_3)_2$, Me and OMe.

3. The compound and/or the pharmaceutically acceptable salt A thereof according to claim 1, wherein each $R_1$ is independently chosen from F, Cl, Br, I, OH and $NH_2$, or is chosen from Me, Et, $OCH_3$,

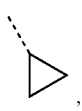

phenyl and pyridyl, any of which is optionally substituted by one, two or three R groups.

4. The compound and/or the pharmaceutically acceptable salt thereof according to claim 3, wherein each $R_1$ is independently chosen from F, Cl, Br, I, OH, $NH_2$, Me, Et, $OCH_3$, $CH_2N(CH_3)_2$, $OCH_2CH_3$, $CH_2OCH_3$,

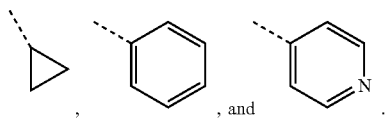

5. The compound and/or the pharmaceutically acceptable salt thereof according to claim 2, wherein the structural unit

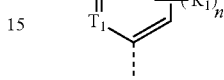

is chosen from

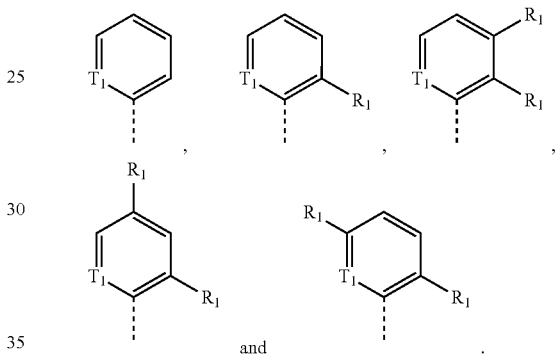

and

6. The compound and/or the pharmaceutically acceptable salt thereof according to claim 5, wherein the structural unit

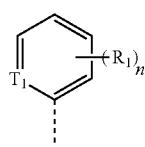

is chosen from

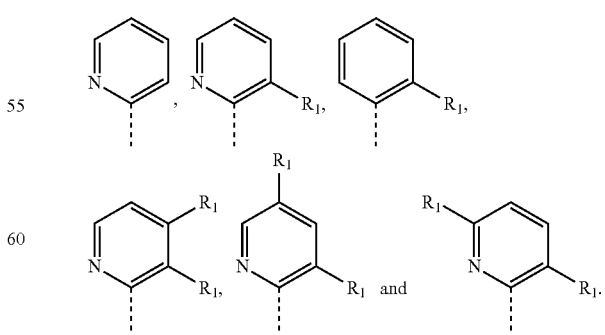

7. The compound and/or the pharmaceutically acceptable salt thereof according to claim 1, wherein the structural unit

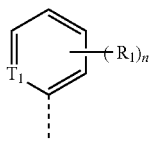

is chosen from

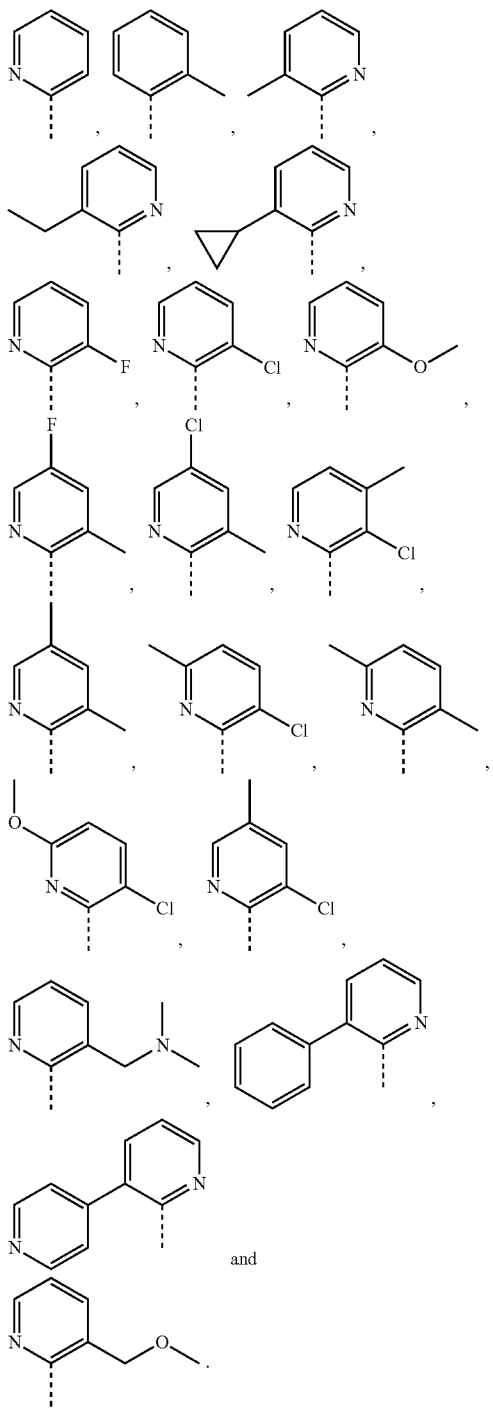

and

8. The compound and/or the pharmaceutically acceptable salt thereof according to claim 1, wherein the structural unit

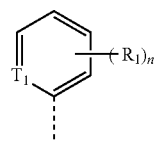

is chosen from

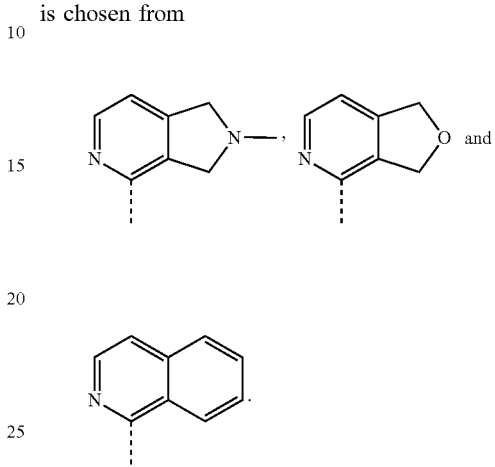

9. The compound and/or the pharmaceutically acceptable salt thereof according to claim 2, wherein $R_3$ is chosen from F, Cl, Br, I, OH and $NH_2$, or is chosen from Me and Et, either of which is optionally substituted by one, two or three R groups.

10. The compound and/or the pharmaceutically acceptable salt thereof according to claim 9, wherein $R_3$ is chosen from F, Cl, Br, I, OH, $NH_2$, Me and Et.

11. The compound and/or the pharmaceutically acceptable salt thereof according to claim 2, wherein the structural unit

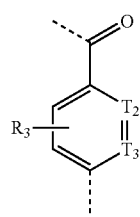

is chosen from

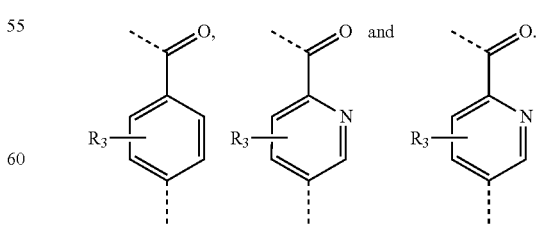

12. The compound and/or the pharmaceutically acceptable salt thereof according to claim 11, wherein the structural unit is chosen from

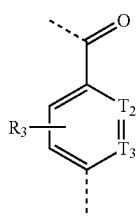

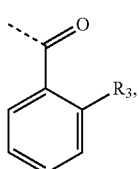

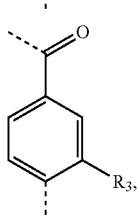

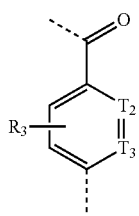

13. The compound and/or the pharmaceutically acceptable salt thereof according to claim 2, wherein the structural unit

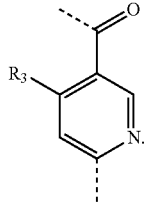

is chosen from

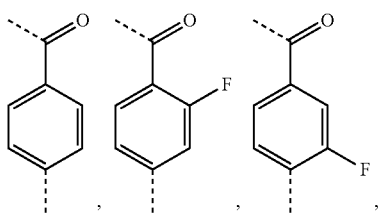

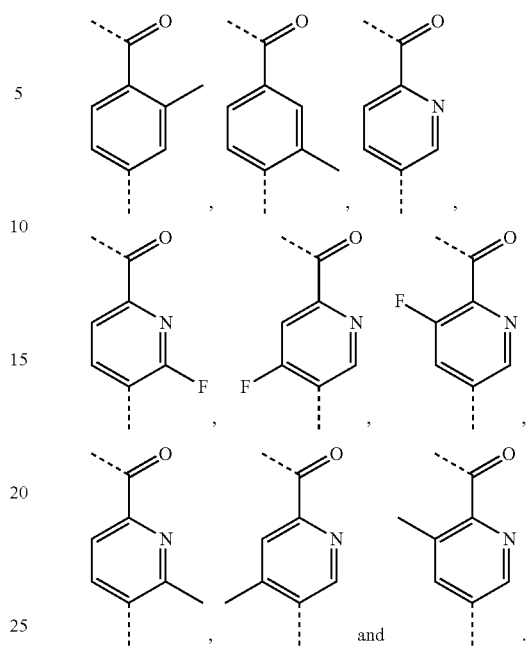

14. The compound and/or the pharmaceutically acceptable salt thereof according to claim 2, wherein each $R_4$ is independently chosen from H and OH or is chosen from Me, Et, $OCH_3$ and $OCH_2CH_3$, any one of which is optionally substituted by one, two or three R groups.

15. The compound and/or the pharmaceutically acceptable salt thereof according to claim 14, wherein each $R_4$ is independently chosen from H, OH, Me, $OCH_3$, and $OCH_2CH_2OCH_3$.

16. The compound and/or the pharmaceutically acceptable salt thereof according to claim 15, wherein the structural unit

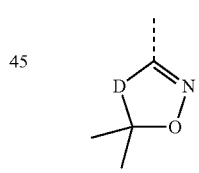

is chosen from

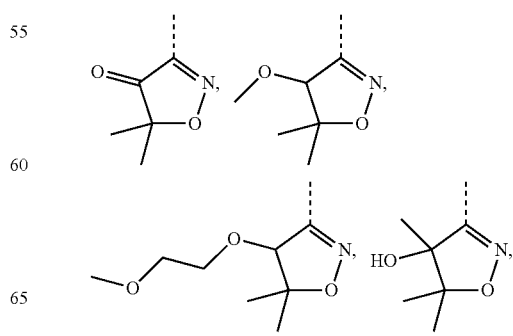

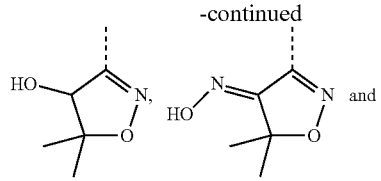 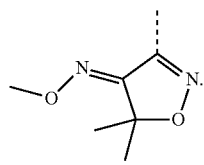
17. The compound and/or the pharmaceutically acceptable salt thereof according to claim 2, wherein the compound and/or pharmaceutically acceptable salt thereof is chosen from
(I-1)
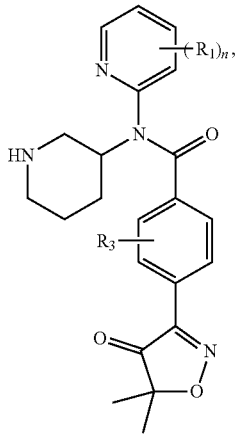
(I-2)
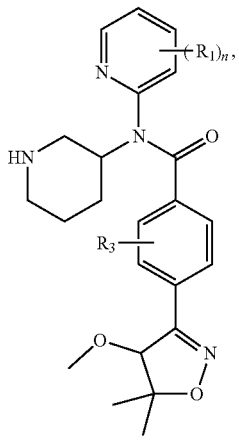
(I-3)
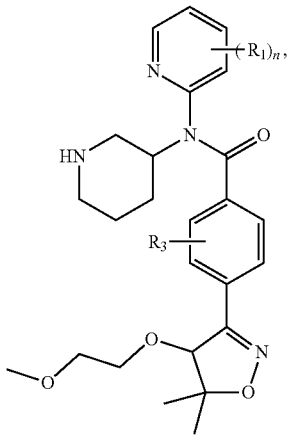
(I-4)
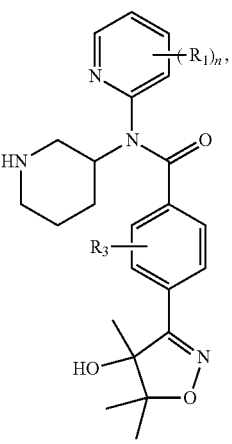
(I-5) and
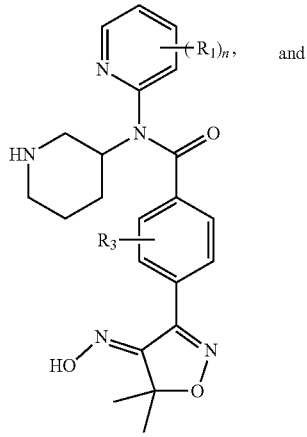

(I-6)
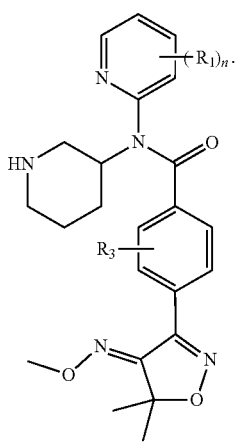
18. The compound and/or the pharmaceutically acceptable salt thereof according to claim 2, wherein the compound of formula (I) is chosen from structural formulas (IA) and (IB):
(IA)
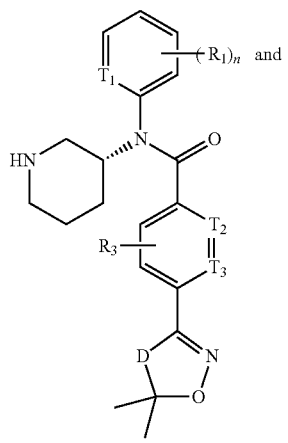
and
(IB)
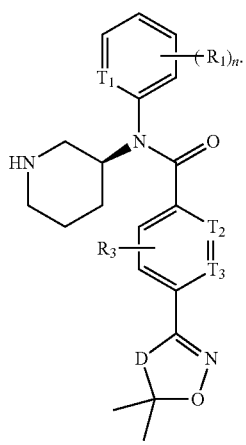
19. A compound chosen from:
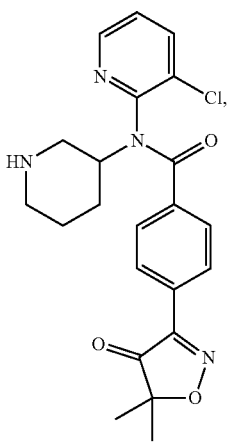
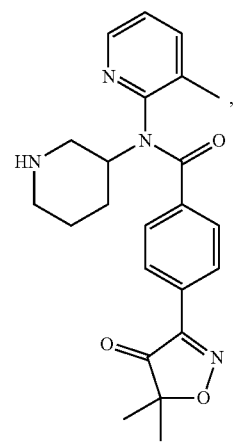
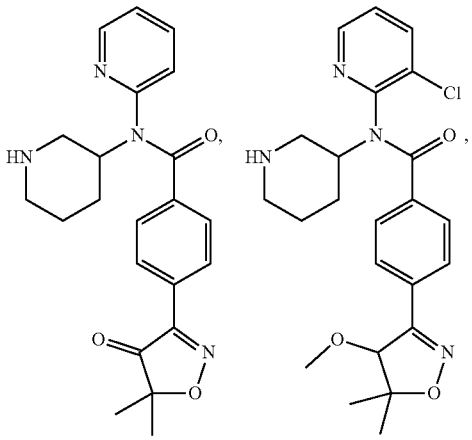
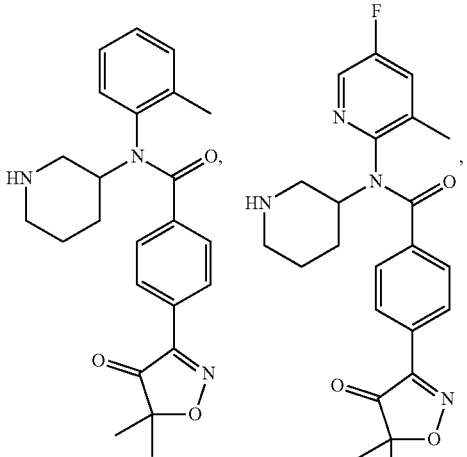

-continued
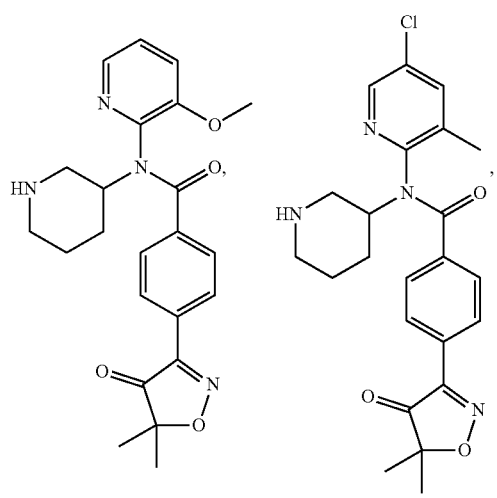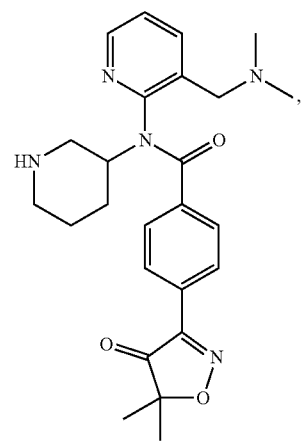
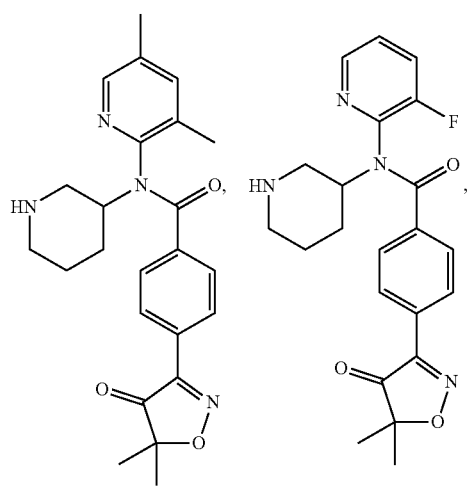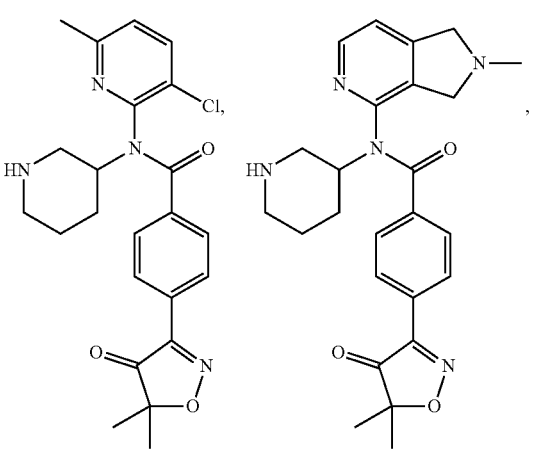
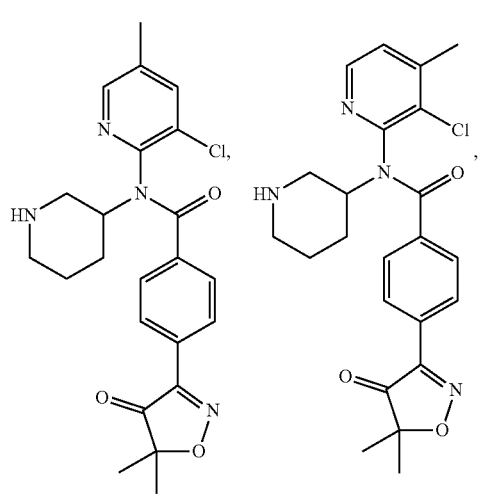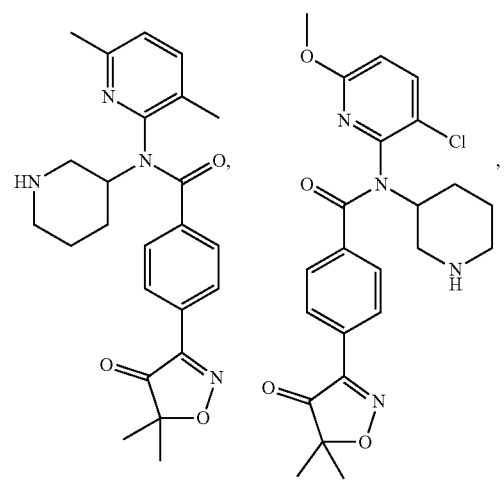

151
-continued
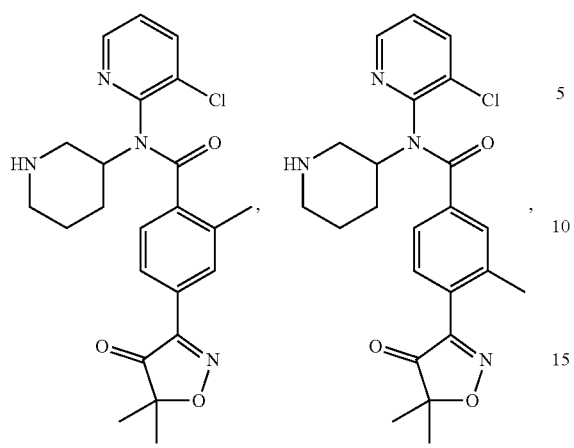
152
-continued
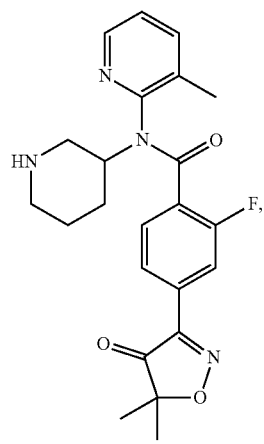
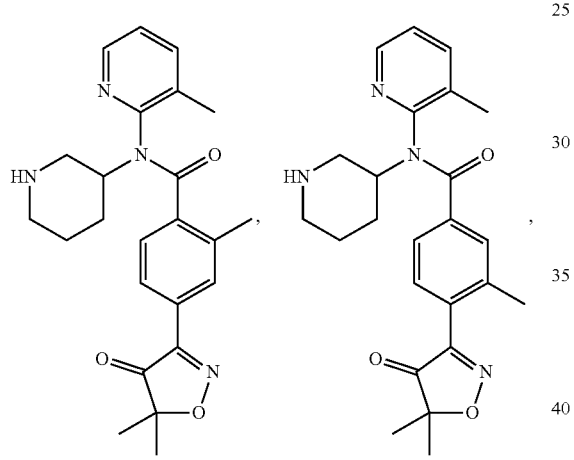
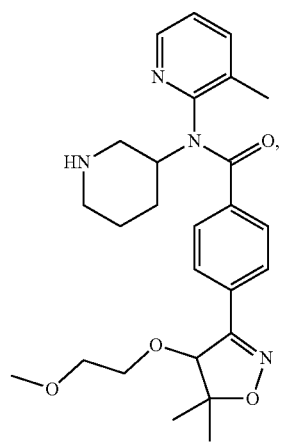
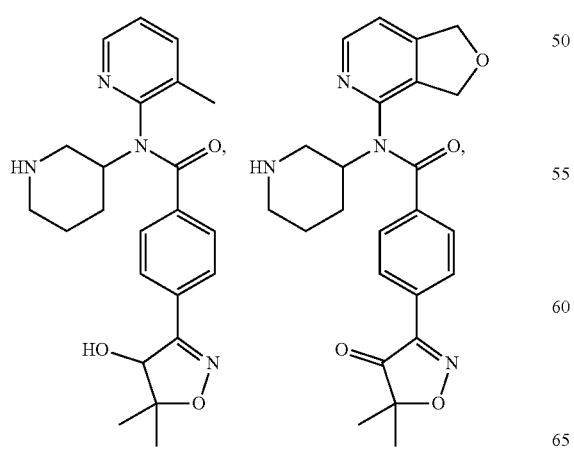
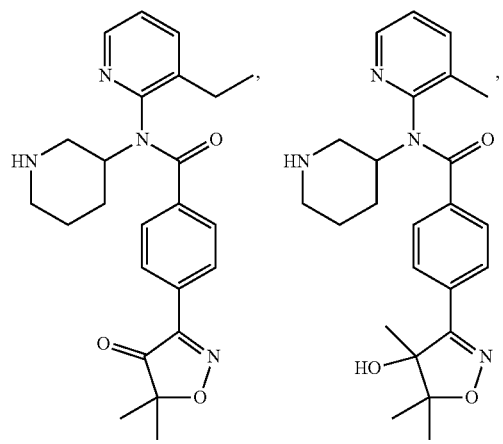

153
-continued
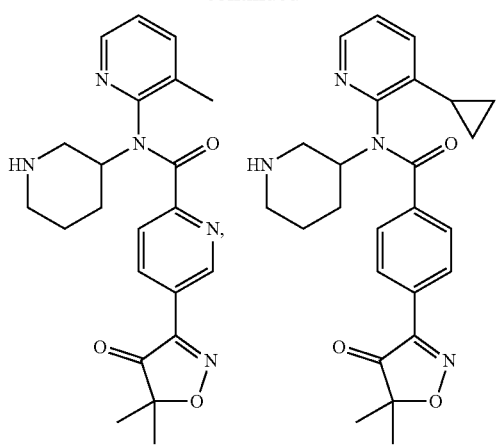
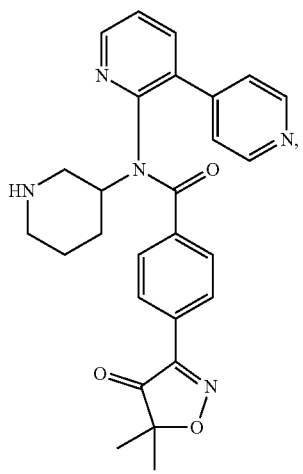
154
-continued
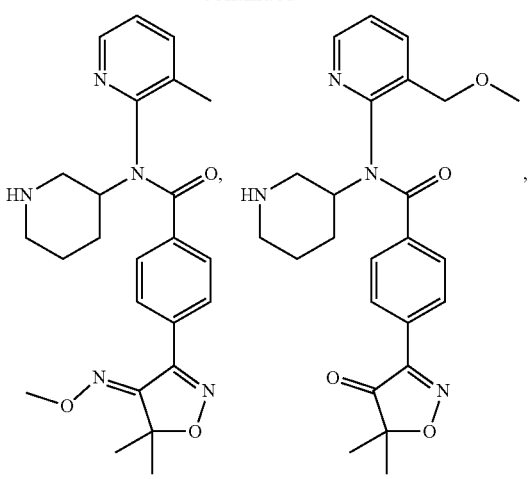
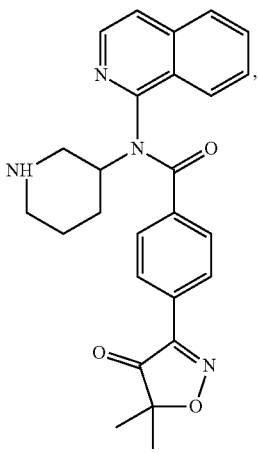 [SMILES: CC1(C)ON=C(c2ccc(C(=O)N(c3nccc4ccccc34)C3CCCNC3)cc2)C1=O]
and pharmaceutically acceptable salt forms thereof.
20. The compound according to claim 19, wherein the compound is chosen from:
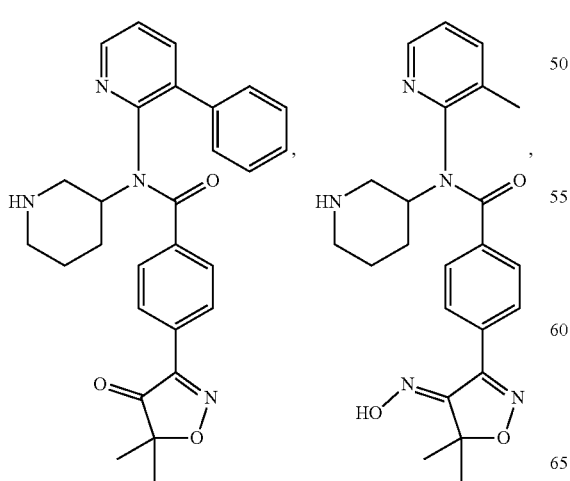
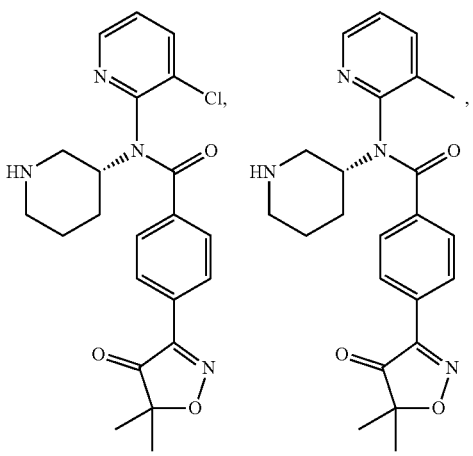

-continued
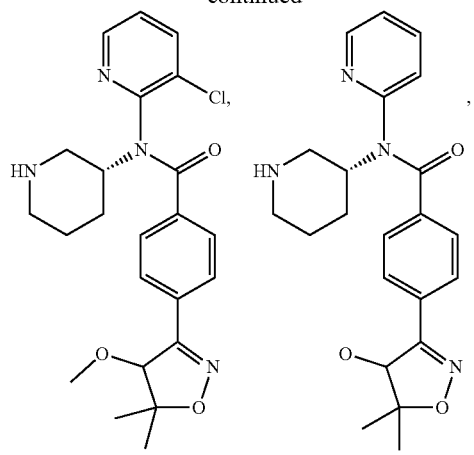
-continued
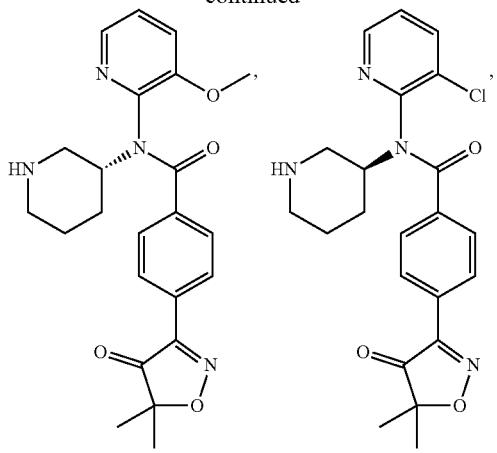
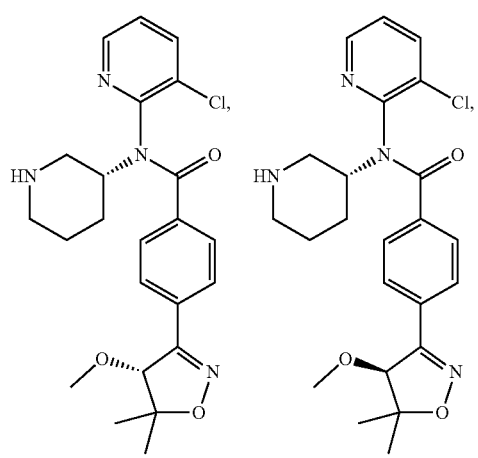
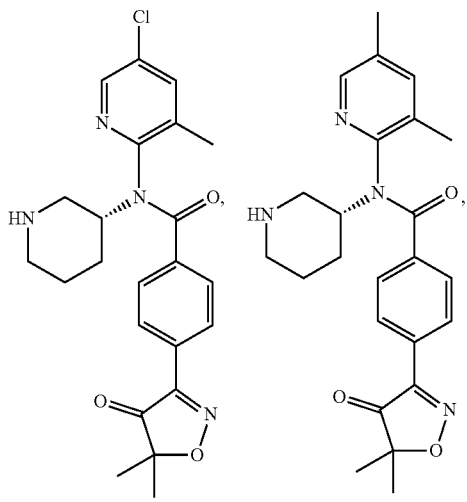
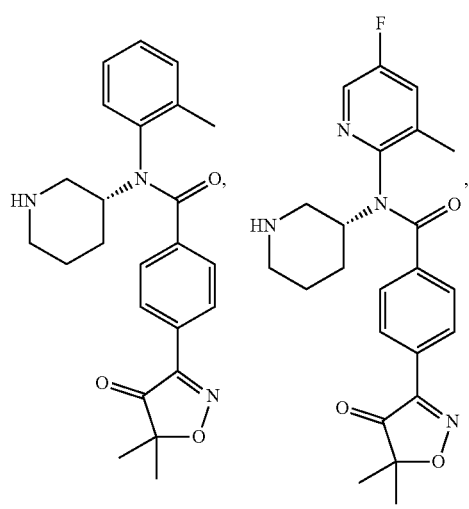
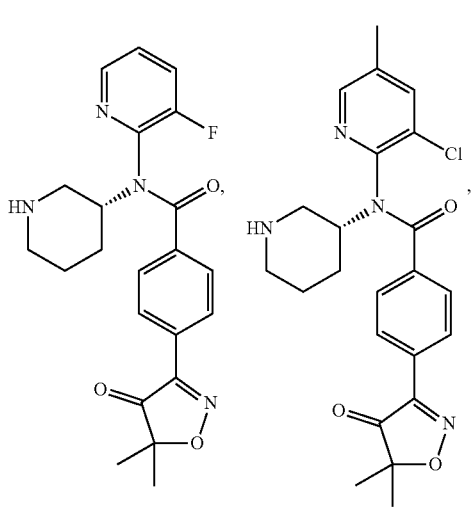

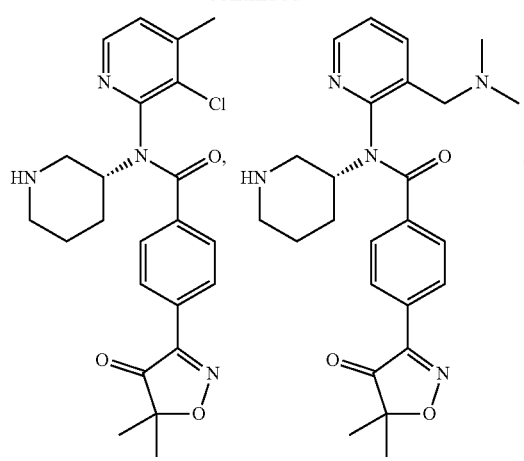
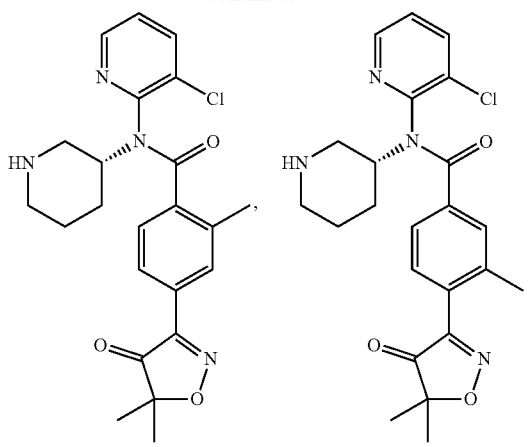
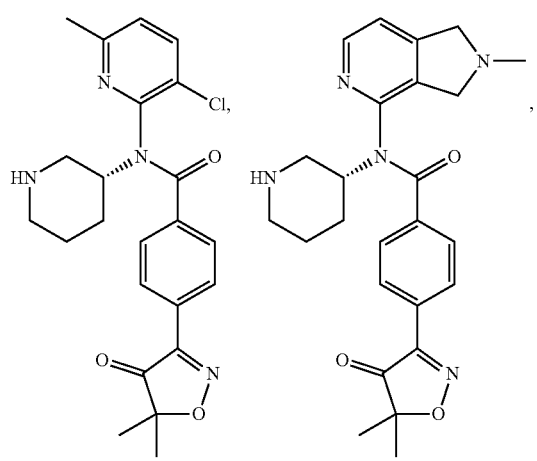
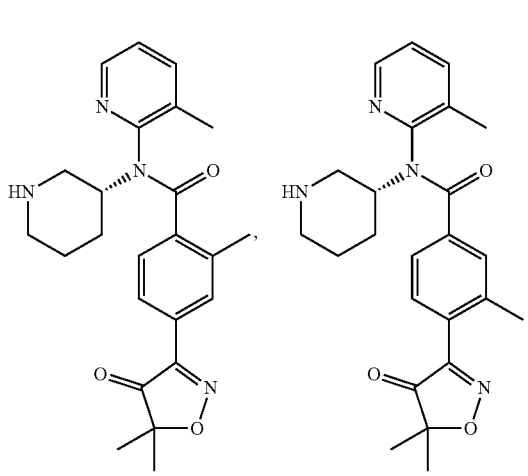
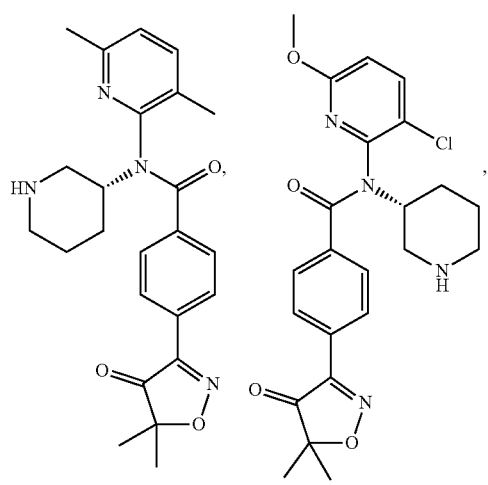
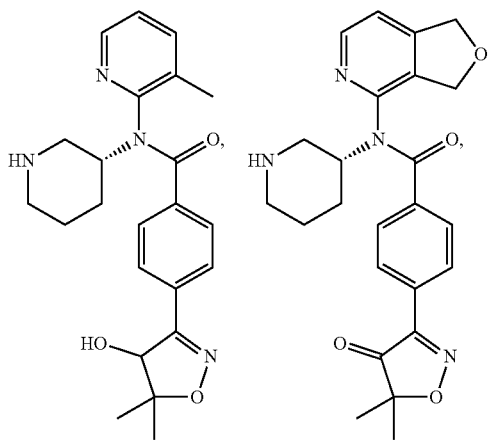

-continued
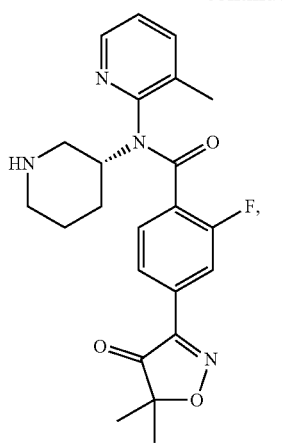
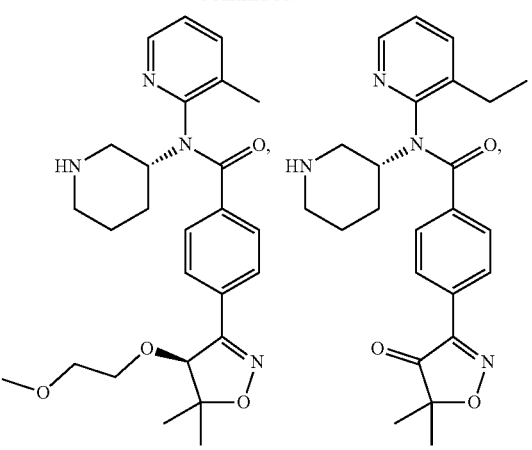
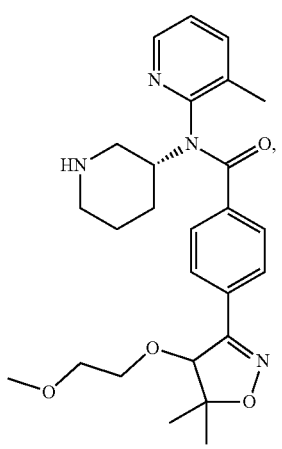
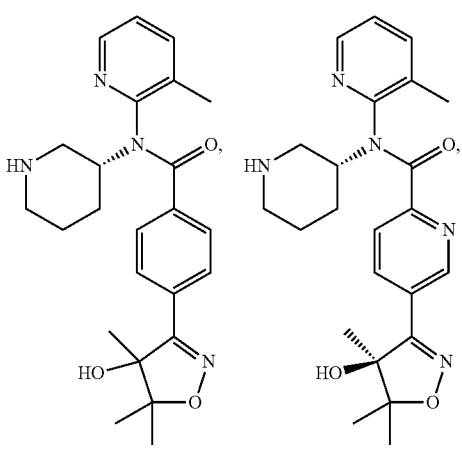
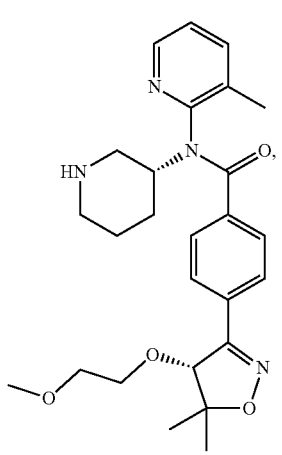
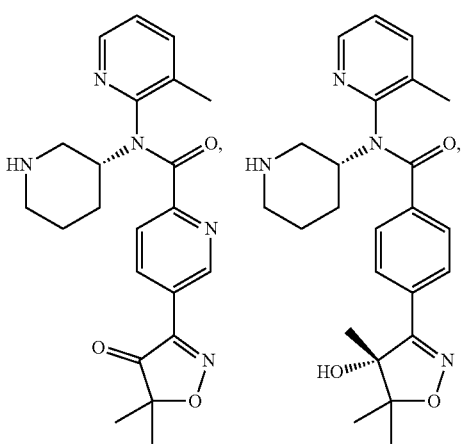

-continued

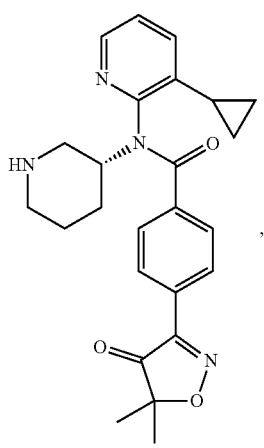

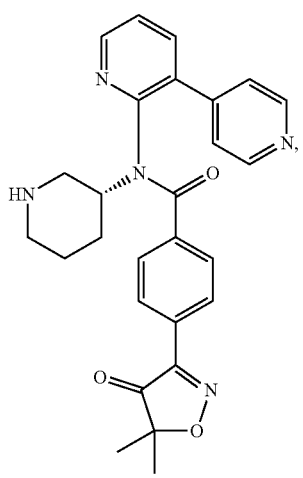

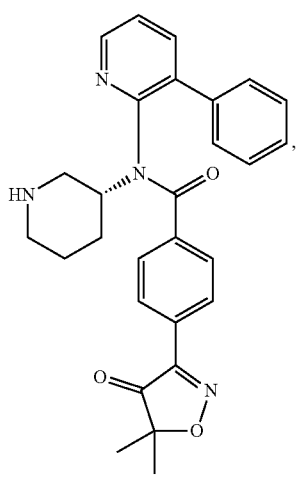

-continued

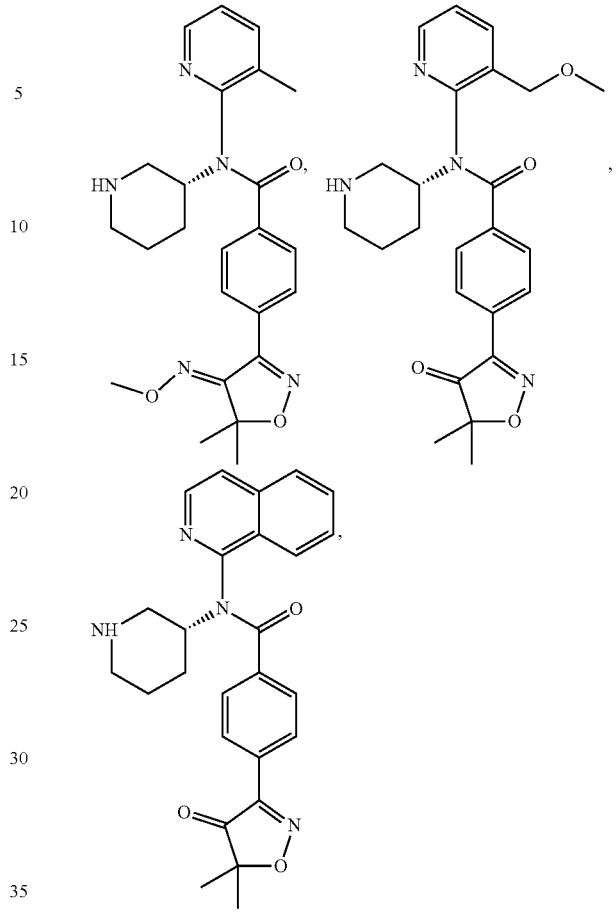

and pharmaceutically acceptable salt forms thereof.

21. A pharmaceutically acceptable salt of a compound according to claim 2, wherein the pharmaceutically acceptable salt is derived from the compound according to claim 2 and an acid selected from 2-acetoxybenzoic acid, acetic acid, ascorbic acid, benzenesulfonic acid, benzoic acid, hydrosulphuric acid, carbonic acid, citric acid, edetic acid, ethane disulfonic acid, ethane sulfonic acid, fumaric acid, glucoheptonic acid, gluconic acid, glutamic acid, glycolic acid, hydrobromic acid, hydrochloric acid, hydrohalic acid, hydroxyl naphthalic acid, isethionic acid, lactic acid, lactobionic acid, dodecyl sulfonic acid, maleic acid, malic acid, mandelic acid, methane sulfonic acid, nitric acid, oxalic acid, pamoic acid, pantothenic acid, phenylacetic acid, phosphoric acid, polygalacturonic acid, propionic acid, salicylic acid, stearic acid, acetic acid, succinic acid, sulfamic acid, sulfanilic acid, sulfuric acid, tannic acid, tartaric acid and p-toluenesulfonic acid.

22. A composition comprising a compound or pharmaceutically acceptable salt thereof according to claim 1 and a pharmaceutically acceptable carrier.

23. The composition according to claim 22, wherein the carrier is selected from water, oil, a vegetable or mineral substance, a cream base, a lotion base, and an ointment base.

24. A method of treating dyslipidemia in a patient in need thereof, comprising administering to the patient a compound or pharmaceutically acceptable salt thereof according to claim 1.

25. A composition comprising a compound or pharmaceutically acceptable salt thereof according to claim 2 and a pharmaceutically acceptable carrier.

26. A method of treating dyslipidemia in a patient in need thereof, comprising administering to the patient a compound or pharmaceutically acceptable salt thereof according to claim 2.

27. A method of treating dyslipidemia in a patient in need thereof, comprising administering to the patient a composition according to claim 22.

28. A method of treating dyslipidemia in a patient in need thereof, comprising administering to the patient a composition according to claim 25.

* * * * *